US006995178B2

(12) United States Patent
Lahm et al.

(10) Patent No.: US 6,995,178 B2

(45) Date of Patent: Feb. 7, 2006

(54) INSECTICIDAL ANTHRANILAMIDES

(75) Inventors: George P. Lahm, Wilmington, DE (US); Brian J. Myers, Oxford, PA (US); Thomas P. Selby, Wilmington, DE (US); Thomas M. Stevenson, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 57 days.

(21) Appl. No.: 10/698,643

(22) Filed: Oct. 31, 2003

(65) Prior Publication Data

US 2004/0142984 A1 Jul. 22, 2004

Related U.S. Application Data

(62) Division of application No. 10/220,450, filed as application No. PCT/US01/09338 on Mar. 20, 2001, now Pat. No. 6,747,047.

(60) Provisional application No. 60/262,015, filed on Jan. 17, 2001, provisional application No. 60/254,635, filed on Dec. 11, 2000, provisional application No. 60/220,232, filed on Jul. 24, 2000, and provisional application No. 60/191,242, filed on Mar. 22, 2000.

(51) Int. Cl.
*C07D 213/02* (2006.01)
*A61K 31/44* (2006.01)
*A61K 31/505* (2006.01)

(52) U.S. Cl. ....................... 514/354; 514/256; 544/242; 546/316; 546/323

(58) Field of Classification Search ................. 514/256, 514/354; 546/316, 323; 544/242
See application file for complete search history.

(56) References Cited

U.S. PATENT DOCUMENTS

| | | | | |
|---|---|---|---|---|
| 4,321,371 | A | 3/1982 | Parg et al. | |
| 5,602,126 | A | 2/1997 | Barnette et al. | |
| 5,728,693 | A | 3/1998 | Stevenson | |
| 6,747,047 | B2 * | 6/2004 | Lahm et al. ................ | 514/341 |

FOREIGN PATENT DOCUMENTS

| | | | | |
|---|---|---|---|---|
| DE | 4428380 | A | | 8/1994 |
| DE | 19840322 | A1 | | 9/1998 |
| EP | 0919542 | A2 | | 6/1999 |
| EP | 1193254 | A1 | | 1/2001 |
| NL | 9202078 | A | | 11/1992 |
| WO | WO 95/25723 | A1 | * | 9/1995 |
| WO | WO 96/38419 | | | 12/1996 |
| WO | WO 01/02354 | A1 | | 1/2001 |
| WO | WO 01/32628 | A1 | | 5/2001 |

OTHER PUBLICATIONS

XP002177117 Suto, Mark J. et al.: Tetrahedron Letters, vol. 36, No. 40, 1995, pp. 7213–7216, Elsevier Science Publishers, Amsterdam, NL.

Klaubert et al., J. Med. Chem., vol. 24, No. 6, pp. 748–752, 1981.

* cited by examiner

*Primary Examiner*—Zinna Northington Davis

(57) ABSTRACT

This invention provides compounds of Formula 1, their N-oxides and agriculturally suitable salts

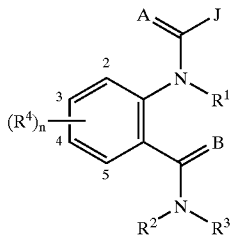

1 wherein

A, B, J, $R^1$, $R^2$, $R^3$ and $R^4$ and n are as defined in the disclosure.

Also disclosed are methods for controlling arthropods comprising contacting the arthropods or their environment with an arthropodicidally effective amount of a compound of Formula 1 and compositions containing the compounds of Formula 1.

25 Claims, No Drawings

INSECTICIDAL ANTHRANILAMIDES

CROSS-REFERENCE TO RELATED APPLICATIONS

This application is a divisional of U.S. application Ser. No. 10/220,450, filed Aug. 28, 2002, now U.S. Pat. No. 6,747,047, granted Jun. 8, 2004, which is a national filing under 35 U.S.C. 371 of International Application No. PCT/US01/09338, filed Mar. 20, 2001, which claims priority of U.S. Provisional Application No. 60/262,015, filed Jan. 17, 2001, U.S. Provisional Application No. 60/254,635, filed Dec. 11, 2000, U.S. Provisional Application No. 60/220,232, file Jul. 24, 2000, and U.S. Provisional Application No. 60/191,242, filed Mar. 22, 2000.

BACKGROUND OF THE INVENTION

This invention relates to certain anthranilamides, their N-oxides, agriculturally suitable salts and compositions, and methods of their use as anthropodicides in both agronomic and nonagronomic environments.

The control of arthropod pests is extremely important in achieving high crop efficiency. Arthropod damage to growing and stored agronomic crops can cause significant reduction in productivity and thereby result in increased costs to the consumer. The control of arthropod pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

NL 9202078 discloses N-acyl anthranilic acid derivatives of Formula i as insecticides i

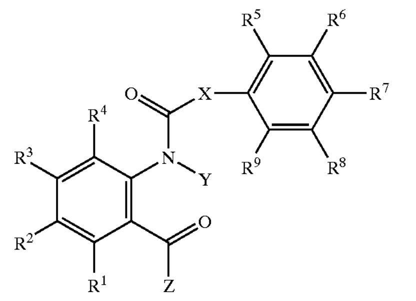

wherein, inter alia,

X is a direct bond;

Y is H or $C_1$–$C_6$ alkyl;

Z is $NH_2$, $NH(C_1$–$C_3$ alkyl) or $N(C_1$–$C_3$ alkyl$)_2$; and $R^1$ through $R^9$ are independently H, halogen, $C_1$–$C_6$ alkyl, phenyl, hydroxy, $C_1$–$C_6$ alkoxy or $C_1$–$C_7$ acyloxy.

SUMMARY OF THE INVENTION

This invention pertains to a method for controlling arthropods comprising contacting the arthropods or their environment with an arthropodicidally effective amount of a compound of Formula 1, its N-oxide or agriculturally suitable salts

1

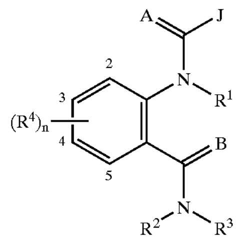

wherein

A and B are independently O or S;

each J is independently a phenyl or naphthyl group substituted with 1 to 2 $R^5$ and optionally substituted with 1 to 3 $R^6$;

or each J is independently a 5- or 6-membered heteroaromatic ring or an aromatic 8-, 9- or 10-membered fused heterobicyclic ring system wherein each ring or ring system is optionally substituted with 1 to 4 $R^7$;

n is 1 to 4;

$R^1$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or $R^1$ is $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl or C(=A)J;

$R^2$ is H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^3$ is H; G; $C_1$–$C_6$ alkyl, $C_2$–$C_6$ alkenyl, $C_2$–$C_6$ alkynyl, $C_3$–$C_6$ cycloalkyl, each optionally substituted with one or more substituents selected from the group consisting of halogen G, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_2$–$C_6$ alkoxycarbonyl, $C_2$–$C_6$ alkylcarbonyl, $C_3$–$C_6$ trialkylsilyl, and a phenyl, phenoxy or 5- or 6-membered heteroaromatic ring, each ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl and $C_3$–$C_6$ trialkylsilyl; $C_1$–$C_4$ alkoxy; $C_1$–$C_4$ alkylamino; $C_2$–$C_8$ dialkylamino; $C_3$–$C_6$ cycloalkylamino; $C_2$–$C_6$ alkoxycarbonyl or $C_2$–$C_6$ alkylcarbonyl;

$R^2$ and $R^3$ can be taken together with the nitrogen to which they are attached to form a ring containing 2 to 6 atoms of carbon and optionally one additional atom of nitrogen, sulfur or oxygen, said ring may be optionally substituted with 1 to 4 substituents selected from the group consisting of $C_1$–$C_2$ alkyl, halogen, CN, $NO_2$ and $C_1$–$C_2$ alkoxy;

G is a 5- or 6-membered nonaromatic carbocyclic or heterocyclic ring, optionally including one or two ring members selected from the group consisting of C(═O), SO or $S(O)_2$ and optionally substituted with 1 to 4 substituents selected from the group consisting of $C_1$–$C_2$ alkyl, halogen, CN, $NO_2$ and $C_1$–$C_2$ alkoxy;

each $R^4$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, or $C_3$–$C_6$ trialkylsilyl; or each $R^4$ is independently phenyl, benzyl or phenoxy, each optionally substituted with $C_1$–$C_4$ allyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

each $R^5$ is independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl $C_2$–$C_6$ haloalkynyl, $C_3$–$C_6$ halocycloalkyl, halogen, CN, $CO_2H$, $CONH_2$, $NO_2$, hydroxy, $C_1$–$C_6$ alkoxy, $C_1$–$C_6$ haloalkoxy, $C_1$–$C_6$ alkylthio, $C_1$–$C_6$ alkylsulfinyl, $C_1$–$C_6$ alkylsulfonyl, $C_1$–$C_6$ haloalkylthio, $C_1$–$C_6$ haloalkylsulfinyl, $C_1$–$C_6$ haloalkylsulfonyl, $C_1$–$C_6$ alkylamino, $C_2$–$C_{12}$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, or $C_3$–$C_6$ trialkylsilyl; or $(R^5)_2$ when attached to adjacent carbon atoms can be taken together as $—OCF_2O—$, $—CF_2CF_2O—$, or $—OCF_2CF_2O—$;

each $R^6$ is independently H, halogen, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy or $C_2$–$C_4$ alkoxycarbonyl; or each $R^6$ is independently a phenyl, benzyl, phenoxy, 5- or 6-membered heteroaromatic ring or an aromatic 8-, 9- or 10-membered fused heterobicyclic ring system, each ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl and $C_3$–$C_6$ trialkylsilyl;

each $R^7$ is independently, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, or $C_3$–$C_6$ trialkylsilyl; or each $R^7$ is independently a phenyl, benzyl, benzoyl, phenoxy, 5- or 6-membered heteroaromatic ring or an aromatic 8-, 9- or 10-membered fused heterobicyclic ring system, each ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl and $C_3$–$C_6$ trialkylsilyl;

provided that (1) when A and B are both O, $R^2$ is H or $C_1$–$C_3$ alkyl, $R^3$ is H or $C_1$–$C_3$ alkyl and $R^4$ is H, halogen, $C_1$–$C_6$ alkyl, phenyl, hydroxy or $C_1$–$C_6$ alkoxy, then one $R^5$ is other than halogen, $C_1$–$C_6$ alkyl, hydroxy or $C_1$–$C_6$ alkoxy; or (2) J is other than an optionally substituted 1,2,3-thiadiazole.

This invention also pertains to compounds of Formula 1, their N-oxides and agriculturally suitable salts

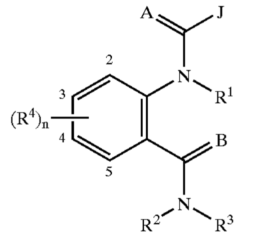

1 wherein

A and B are independently O or S;

each J is independently a phenyl or naphthyl group substituted with 1 to 2 $R^5$ and optionally substituted with 1 to 3 $R^6$;

or each J is independently a 5- or 6-membered heteroaromatic ring or an aromatic 8-, 9- or 10-membered fused heterobicyclic ring system wherein each ring or ring system is optionally substituted with 1 to 4 $R^7$;

n is 1 to 4;

$R^1$ is H; or $C_1$–$C_6$ allyl, $C_2$–$C_6$ alkenyl, $C_2$–$C_6$ alkynyl or $C_3$–$C_6$ cycloalkyl each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or $R^1$ is $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl or C(=A)J;

$R^2$ is H, $C_1$–$C_6$ alkyl, $C_2$–$C_6$ alkenyl, $C_2$–$C_6$ alkenyl, $C_3$–$C_6$-cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^3$ is H; $C_1$–$C_6$ alkyl, $C_2$–$C_6$ alkenyl, $C_2$–$C_6$ alkynyl, $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_2$–$C_6$ alkoxycarbonyl, $C_2$–$C_6$ alkylcarbonyl, $C_3$–$C_6$ trialkylsilyl, and a phenoxy ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl and $C_3$–$C_6$ trialkylsilyl; $C_1$–$C_4$ alkoxy; $C_1$–$C_4$ alkylamino; $C_2$–$C_8$ dialkylamino; $C_3$–$C_6$ cycloalkylamino; $C_2$–$C_6$ alkoxycarbonyl or $C_2$–$C_6$ alkylcarbonyl; or $R^2$ and $R^3$ can be taken together with the nitrogen to which they are attached to form a ring containing 2 to 6 atoms of carbon and optionally one additional atom of nitrogen, sulfur or oxygen, said ring may be optionally substituted with 1 to 4 substituents selected from the group consisting of $C_1$–$C_2$ alkyl, halogen, CN, $NO_2$ and $C_1$–$C_2$ alkoxy;

each $R^4$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, or $C_3$–$C_6$ trialkylsilyl; or each $R^4$ is independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

each $R^5$ is independently $C_1$–$C_6$ haloalkyl, $C_2$–$C_6$ haloalkenyl, $C_2$–$C_6$ haloalkynyl, $C_3$–$C_6$ halocycloalkyl, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, CN, $NO_2$, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, or $C_3$–$C_8$ dialkylaminocarbonyl; or $(R^5)_2$ attached to adjacent carbon atoms can be taken together as $—OCF_2O—$, $—CF_2CF_2O—$, or $—OCF_2CF_2O—$;

each $R^6$ is independently H, halogen, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy or $C_2$–$C_4$ alkoxycarbonyl; or each $R^6$ is independently a phenyl, benzyl, phenoxy, 5- or 6-membered heteroaromatic ring or an aromatic 8-, 9- or 10-membered fused heterobicyclic ring system, each ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfinyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl and $C_3$–$C_6$ trialkylsilyl;

each $R^7$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2H$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, or $C_3$–$C_6$ trialkylsilyl; or each $R^7$ is independently phenyl, benzyl, benzoyl, phenoxy or 5- or 6-membered heteroaromatic ring or an 8-, 9- or 10-membered fused heterobicyclic ring system, each ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfinyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl and $C_3$–$C_6$ trialkylsilyl;

provided that (i) at least one $R^4$ and at least one $R^7$ are other than H;

(ii) J is other than an optionally substituted 1,2,3-thiadiazole;

(iii) when J is an optionally substituted pyridine and $R^2$ is H, $R^3$ is other than H or $CH_3$;

(iv) when J is an optionally substituted pyridine, then $R^7$ cannot be $CONH_2$, $C_2$–$C_6$ alkylaminocarbonyl or $C_3$–$C_8$ dialkylaminocarbonyl;

(v) when J is an optionally substituted pyrazole, tetrazole or pyrimidine, then $R^2$ and $R^3$ cannot both be hydrogen.

This invention also pertains to arthropodicidal compositions comprising an arthropodicidally effective amount of a compound of Formula 1 and at least one additional component selected from the group consisting of surfactants, solid diluents and liquid diluents.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1–2 alkyl" indicates that one or two of the available positions for that substituent may be alkyl. "Alkenyl" includes straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Cycloalkyl" includes, for example, cyclopropyl, cyclobutyl, cyclopentyl and cyclohexyl.

The term "heterocyclic ring" or heterocyclic ring system" denotes rings or ring systems in which at least one ring atom is not carbon and comprises 1 to 4 heteroatoms independently selected from the group consisting of nitrogen, oxygen and sulfur, provided that each heterocyclic ring contains no more than 4 nitrogens, no more than 2 oxygens and no more than 2 sulfurs. The heterocyclic ring can be attached through any available carbon or nitrogen by replacement of hydrogen on said carbon or nitrogen. The term "aromatic ring system" denotes fully unsaturated carbocycles and heterocycles in which the polycyclic ring system is aromatic (where aromatic indicates that the Hückel rule is satisfied for the ring system). The term "heteroaromatic ring" denotes fully aromatic rings in which at least one ring atom is not carbon and comprises 1 to 4 heteroatoms independently selected from the group consisting of nitrogen, oxygen and sulfur, provided that each heterocyclic ring contains no more than 4 nitrogens, no more than 2 oxygens and no more than 2 sulfurs (where aromatic indicates that the Hückel rule is satisfied). The heterocyclic ring can be attached through any available carbon or nitrogen by replacement of hydrogen on said carbon or nitrogen. The term "aromatic heterocyclic ring system" includes fully aromatic heterocycles and heterocycles in which at least one ring of a polycyclic ring system is aromatic (where aromatic indicates that the Hückel rule is satisfied). The term "fused heterobicyclic ring system" includes a ring system comprised of two fused rings in which at least one ring atom is not carbon and can be aromatic or non aromatic, as defined above.

The term "halogen", either alone or in compound words such as "haloalkyl", includes fluorine, chlorine, bromine, or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C{=}CHCH_2$ and $CF_3CH_2CH{=}CHCH_2$. Examples of "haloalkynyl" include $HC{\equiv}CCHCl$, $CF_3C{\equiv}C$, $CCl_3C{\equiv}C$ and $FCH_2C{\equiv}CCH_2$. Examples of "haloalkoxy" include $CF_3O$, $CCl_3CH_2O$, $HCF_2CH_2CH_2O$ and $CF_3CH_2O$.

The total number of carbon atoms in a substituent group is indicated by the "$C_i$–$C_j$" prefix where i and j are numbers from 1 to 6. For example, $C_1$–$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of Formula 1 contains a heterocyclic ring, all substituents are attached to this ring through any available carbon or nitrogen by replacement of a hydrogen on said carbon or nitrogen.

When a group contains a substituent which can be hydrogen, for example $R^3$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the compounds of the invention may be present as a mixture of stereoisomers, individual stereoisomers, or as an optically active form.

The present invention comprises compounds selected from Formula 1, N-oxides and agriculturally suitable salts thereof. One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748–750, S. V. Ley, Ed., Pergamon Press; M. Tisler and B. Stanovnik in *Comprehensive Heterocyclic Chemistry*, vol. 3, pp 18–19, A. J. Boulton and A. McKillop, Eds., Pergamon Press; M. R. Grimmett and B. R. T. Keene in *Advances in Heterocyclic Chemistry*, vol. 43, pp 139–151, A. R. Katritzky, Ed., Academic Press; M. Tisler and B. Stanovnik in *Advances in Heterocyclic Chemistry*, vol. 9, pp 285–291, A. R. Katritzky and A. J. Boulton, Eds., Academic Press; and G. W. H. Cheeseman and E. S. G. Werstiuk in *Advances in Heterocyclic Chemistry*, vol. 22, pp 390–392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Of note are certain compounds of Formula II

II

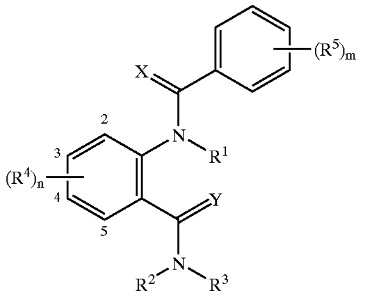

wherein

X and Y are O;

m is 1 to 5;

n is 1 to 4;

$R^1$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or $R^1$ is $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl;

$R^2$ is H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^3$ is i-propyl or t-butyl; and each $R^4$ and $R^5$ are independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkoxycarbonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or each $R^4$ and $R^5$ are independently phenyl optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl $C_1$–$C_4$ alkoxycarbonyl, $C_1$–$C_4$ alkylamino, $C_2$–$C_8$ dialkylamino, $C_3$–$C_6$ cycloalkylamino, $C_3$–$C_6$ (alkyl) cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

Also of note are methods for controlling arthropods comprising contacting the arthropods or their environment with an arthropodicidally effective amount of a compound of Formula II and insecticidal compositions thereof.

Also of note are certain compounds of Formula III

III

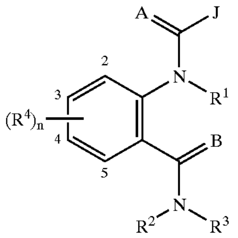

wherein

A and B are independently O or S;

J is a phenyl group substituted with 1 to 2 $R^5$ and optionally substituted with 1 to 3 $R^6$, or a 5- or 6-membered heteroaromatic ring optionally substituted with 1 to 4 $R^7$;

n is 1 to 4;

$R^1$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or $R^1$ is $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl;

$R^2$ is H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^3$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl and $C_1$–$C_4$ alkylsulfonyl; or $R^2$ and $R^3$ can be taken together with the nitrogen to which they are attached to form a ring containing 2 to 6 atoms of carbon and optionally one additional atom of nitrogen, sulfur or oxygen, said ring may be optionally substituted with 1 to 4 substituents selected from the group consisting of $C_1$–$C_2$ alkyl, halogen, CN, $NO_2$ and $C_1$–$C_2$ alkoxy;

each $R^4$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or each $R^4$ is independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

each $R^5$ is independently $C_1$–$C_6$ haloalkyl, $C_2$–$C_6$ haloalkenyl, $C_2$–$C_6$ haloalkynyl, $C_3$–$C_6$ halocycloalkyl, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, CN, $NO_2$, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, or $C_3$–$C_8$ dialkylaminocarbonyl; or $(R^5)_2$ when attached to adjacent carbon atoms can be taken together as $—OCF_2O—$, $—CF_2CF_2O—$, or $—OCF_2CF_2O—$;

each $R^6$ is independently H, halogen, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy; or each $R^6$ is independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

each $R^7$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or each $R^7$ is independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl $C_1$–$C_4$ alkoxycarbonyl, $C_1$–$C_4$ alkylamino, $C_2$–$C_8$ dialkylamino, $C_3$–$C_6$ cycloalkylamino, $C_3$–$C_6$ (alkyl) cycloalkylamino, $C_2$–$C_4$ alkylcarbonyl, $C_2$–$C_6$ alkoxycarbonyl, $C_2$–$C_6$alkylaminocarbonyl, $C_3$–$C_8$ dialkylaminocarbonyl or $C_3$–$C_6$ trialkylsilyl.

Also of note are methods for controlling arthropods comprising contacting the arthropods or their environment with an arthropodicidally effective amount of a compound of Formula III and insecticidal compositions thereof.

Also of note are certain compounds of Formula IV

IV

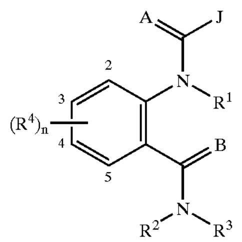

wherein

A and B are independently O or S;

J is a phenyl group substituted with 1 to 2 $R^5$ and optionally substituted with 1 to 3 $R^6$, or a 5- or 6-membered heteroaromatic ring optionally substituted with 1 to 4 $R^7$;

n is 1 to 4;

$R^1$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or $R^1$ is $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl;

$R^2$ is H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^3$ is H; $C_1$–$C_6$ alkyl, $C_2$–$C_6$ alkenyl, $C_2$–$C_6$ alkynyl, $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl and $C_1$–$C_4$ alkylsulfonyl; $C_1$–$C_4$ alkoxy; $C_1$–$C_4$ alkylamino; $C_2$–$C_8$ dialkylamino; $C_3$–$C_6$ cycloalkylamino; $C_2$–$C_6$ alkoxycarbonyl or $C_2$–$C_6$ alkylcarbonyl; or $R^2$ and $R^3$ can be taken together with the nitrogen to which they are attached to form a ring containing 2 to 6 atoms of carbon and optionally one additional atom of nitrogen, sulfur or oxygen, said ring may be optionally substituted with 1 to 4 substituents selected from the group consisting of $C_1$–$C_2$ alkyl, halogen, CN, $NO_2$ and $C_1$–$C_2$ alkoxy;

each $R^4$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or each $R^4$ is independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

each $R^5$ is independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or $(R^5)_2$ when attached to adjacent carbon atoms can be taken together as $—OCF_2O—$, $—CF_2CF_2O—$, or $—OCF_2CF_2O—$;

each $R^6$ is independently H, halogen, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy; or each $R^6$ is independently a phenyl, benzyl, phenoxy or a 5- or 6-membered heteroaromatic ring, each ring optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$dialkylaminocarbonyl or $C_3$–$C_6$ trialkylsilyl;

each $R^7$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; or each $R^7$ is independently a phenyl, benzyl, benzoyl, phenoxy or a 5- or 6-membered heteroaromatic ring, each ring optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

provided that when A and B are both O, $R^2$ is H or $C_1$–$C_3$ alkyl, $R^3$ is H or $C_1$–$C_3$ alkyl and $R^4$ is H, halogen, $C_1$–$C_6$ alkyl, phenyl, hydroxy or $C_1$–$C_6$ alkoxy, then one $R^5$ is other than halogen, $C_1$–$C_6$ alkyl, hydroxy or $C_1$–$C_6$ alkoxy.

Also of note are methods for controlling arthropods comprising contacting the arthropods or their environment with an arthropodicidally effective amount of a compound of Formula IV and insecticidal compositions thereof.

Preferred methods for reasons of better activity are:

Preferred 1. Methods comprising compounds of Formula 1 wherein J is a phenyl group substituted with 1 to 2 $R^5$ and optionally substituted with 1 to 3 $R^6$.

Preferred 2. Methods of Preferred 1 wherein

A and B are both O;

n is 1 to 2;

$R^1$ is H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;

$R^2$ is H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;

$R^3$ is $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $C_1$–$C_2$ alkoxy, $C_1$–$C_2$ alkylthio, $C_1$–$C_2$ alkylsulfinyl and $C_1$–$C_2$ alkylsulfonyl;

one of the $R^4$ groups is attached to the phenyl ring at the 2-position or 5-position, and said $R^4$ is $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl or $C_1$–$C_4$ haloalkylsulfonyl;

each $R^5$ is independently $C_1$–$C_4$ haloalkyl, CN, $NO_2$, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl or $C_2$–$C_4$ alkoxycarbonyl; or $(R^5)_2$ when attached to adjacent carbon atoms can be taken together as $—OCF_2O—$, $—CF_2CF_2O—$ or $—OCF_2CF_2O—$; and each $R^6$ is independently H, halogen, $C_1$–$C_4$ alkyl, $C_1$–$C_2$ alkoxy or $C_2$–$C_4$ alkoxycarbonyl, or each $R^6$ is independently a phenyl or a 5- or 6-membered heteroaromatic ring, each ring optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

Preferred 3. Methods of Preferred 2 wherein $R^1$ and $R^2$ are both H;

$R^3$ is $C_1$–$C_4$ alkyl optionally substituted with halogen, CN, $OCH_3$, or $S(O)_pCH_3$;

each $R^4$ is independently H, $CH_3$, $CF_3$, $OCF_3$, $OCHF_2$, $S(O)_pCF_3$, $S(O)_pCHF_2$, CN or halogen;

each $R^5$ is independently $CF_3$, $OCF_3$, $OCHF_2$, $S(O)_pCF_3$, $S(O)_pCHF_2$, $OCH_2CF_3$, $OCF_2CHF_2$, $S(O)_pCH_2CF_3$ or $S(O)_pCF_2CHF_2$;

each $R^6$ is independently H, halogen or methyl; or phenyl, pyrazole, imidazole, triazole, pyridine or pyrimidine, each ring optionally substituted with $C_1$–$C_4$ alkyl, $C_1$–$C_4$ haloalkyl, halogen or CN; and p is 0, 1 or 2.

Preferred 4. Methods of Preferred 3 wherein $R^3$ is i-propyl or t-butyl.

Preferred 5. Methods comprising compounds of Formula 1 wherein J is a 5- or 6-membered heteroaromatic ring optionally substituted with 1 to 4 $R^7$.

Preferred 6. Methods of Preferred 5 wherein

J is a 5- or 6-membered heteroaromatic ring selected from the group consisting of J-1, J-2, J-3, J-4 and J-5, each J optionally substituted with 1 to 3 $R^7$

J-1

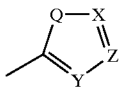

J-2

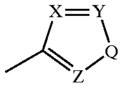

J-3

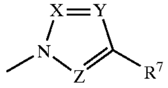

J-4

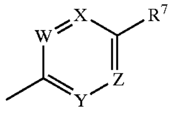

J-5

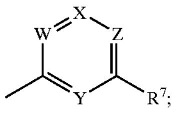

Q is O, S or $NR^7$; and

W, X, Y and Z are independently N or $CR^7$, provided that in J-4 and J-5 at least one of W, X, Y or Z is N.

Preferred 7. Methods of Preferred 5 or Preferred 6 wherein

A and B are O;

n is 1 to 2;

$R^1$ is H, $C_1$–$C_4$ alkyl, $C_2$–$C_4$ alkenyl, $C_2$–$C_4$ alkynyl, $C_2$–$C_6$ alkylcarbonyl or $C_2$–$C_6$ alkoxycarbonyl;

$R^2$ is H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;

$R^3$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $C_1$–$C_2$ alkoxy, $C_1$–$C_2$ alkylthio, $C_1$–$C_2$ alkylsulfinyl and $C_1$–$C_2$ alkylsulfonyl;

one of the $R^4$ groups is attached to the phenyl ring at the 2-position, and said $R^4$ is $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, or $C_1$–$C_4$ haloalkylsulfonyl; and each $R^7$ is independently H, $C_1$–$C_4$ alkyl, $C_1$–$C_4$ haloalkyl, halogen, CN, $NO_2$, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl or $C_2$–$C_4$ alkoxycarbonyl; or a phenyl or a 5- or 6-membered heteroaromatic ring, each ring optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

Preferred 8. Methods of Preferred 7 wherein

J is selected from the group consisting of pyridine, pyrimidine, pyrazole, imidazole, triazole, thiophene, thiazole and oxazole, furan, isothiazole and isoxazole, each optionally substituted with 1 to 3 $R^7$.

Preferred 9. Methods of Preferred 8 wherein

J is selected from the group consisting of pyridine, and pyrimidine, pyrazole, thiophene and thiazole, each optionally substituted with 1 to 3 $R^7$;

$R^1$ and $R^2$ are both H;

$R^3$ is $C_1$–$C_4$ alkyl optionally substituted with halogen, CN, $OCH_3$, or $S(O)_pCH_3$;

each $R^4$ is independently H, $CH_3$, $CF_3$, $OCF_3$, $OCHF_2$, $S(O)_pCF_3$, $S(O)_pCHF_2$, CN or halogen;

each $R^7$ is independently H, halogen, $CH_3$, $CF_3$, $OCHF_2$, $S(O)_pCF_3$, $S(O)_pCHF_2$, $OCH_2CF_3$, $OCF_2CHF_2$, $S(O)_pCH_2CF_3$, $S(O)_pCF_2CHF_2$; or phenyl, pyrazole, imidazole, triazole, pyridine or pyrimidine, each ring optionally substituted with $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, halogen or CN; and p is 0, 1 or 2.

Preferred 10. Methods of Preferred 9 wherein J is a pyridine optionally substituted with 1 to 3 $R^7$.

Preferred 11. Methods of Preferred 10 wherein one $R^7$ is a phenyl optionally substituted with $C_1$–$C_4$ alkyl, $C_1$–$C_4$ haloalkyl, halogen or CN.

Preferred 12. Methods of Preferred 10 wherein one $R^7$ is a pyrazole, imidazole, triazole, pyridine or pyrimidine, each ring optionally substituted with $C_1$–$C_4$ alkyl, $C_1$–$C_4$ haloalkyl, halogen or CN.

Preferred 13. Methods of Preferred 9 wherein J is a pyrimidine optionally substituted with 1 to 3 $R^7$.

Preferred 14. Methods of Preferred 13 wherein one $R^7$ is a phenyl optionally substituted with $C_1$–$C_4$ alkyl, $C_1$–$C_4$ haloalkyl, halogen or CN.

Preferred 15. Methods of Preferred 13 wherein one $R^7$ is a pyrazole, imidazole, triazole, pyridine or pyrimidine, each ring optionally substituted with $C_1$–$C_4$ alkyl, $C_1$–$C_4$ haloalkyl, halogen or CN.

Preferred 16. Methods of Preferred 9 wherein J is a pyrazole optionally substituted with 1 to 3 $R^7$.

Preferred 17. Methods of Preferred 16 wherein one $R^7$ is a phenyl optionally substituted with $C_1$–$C_4$ alkyl, $C_1$–$C_4$ haloalkyl, halogen or CN.

Preferred 18. Methods of Preferred 16 wherein one $R^7$ is a pyrazole, imidazole, triazole, pyridine or pyrimidine, each ring optionally substituted with $C_1$–$C_4$ alkyl, $C_1$–$C_4$ haloalkyl, halogen or CN.

Preferred 19. Methods of Preferred 18 wherein $R^7$ is a pyridine optionally substituted with $C_1$–$C_4$ alkyl, $C_1$–$C_4$ haloalkyl, halogen or CN.

Most preferred is the method comprising a compound of Formula 1 selected from the group consisting of:

3-methyl-N-(1-methylethyl)-2-[[4-(trifluoromethyl)benzoyl]amino]-benzamide, 2-methyl-N-[2-methyl-6-[[(1-methylethyl)amino]carbonyl]phenyl]-4-(trifluoromethyl)benzamide, 2-methyl-N-[2-methyl-6-[[(1-methylethyl)amino]carbonyl]phenyl]-6-(trifluoromethyl)-3-pyridinecarboxamide, 1-ethyl-N-[2-methyl-6-[[(1-methylethyl)amino]carbonyl]phenyl]-3-(trifluoromethyl)-1H-pyrazole-5-carboxamide, 1-(2-fluorophenyl)-N-[2-methyl-6-[[(1-methylethyl)amino)carbonyl]phenyl]-3-(trifluoromethyl)-1H-pyrazole-5-carboxamide, 1-(3-chloro-2-pyridinyl)-N-[2-methyl-6-[[(1-methylethyl)amino]carbonyl]phenyl]3-(trifluoromethyl)-1H-pyrazole-5-carboxamide, N-[2-chloro-6-[[(1-methylethyl)amino]carbonyl]phenyl]-1-(3-chloro-2-pyridinyl)-3-(trifluoromethyl)-1H-pyrazole-5-carboxamide, 3-bromo-1-(2-chlorophenyl)-N-[2-methyl-6-[[(1-methylethyl)amino]carbonyl]phenyl]-1H-pyrazole-5-carboxamide, and 3-bromo-N-[2-chloro-6-[[(1-methylethyl)amino]carbonyl]phenyl]-1-(2-chlorophenyl)-1H-pyrazole-5-carboxamide.

Preferred compounds for reasons of better activity and/or ease of synthesis are:

Preferred A. Compounds of Formula 1 wherein J is a phenyl group substituted with 1 to 2 $R^5$ and optionally substituted with 1 to 3 $R^6$.

Preferred B. Compounds of Preferred A wherein
- A and B are both O;
- n is 1 to 2;
- $R^1$ is H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;
- $R^2$ is H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;
- $R^3$ is $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $C_1$–$C_2$ alkoxy, $C_1$–$C_2$ alkylthio, $C_1$–$C_2$ alkylsulfinyl and $C_1$–$C_2$ alkylsulfonyl;
- one of the $R^4$ groups is attached to the phenyl ring at the 2-position or 5-position, and said $R^4$ is $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl or $C_1$–$C_4$ haloalkylsulfonyl;
- each $R^5$ is independently $C_1$–$C_4$ haloalkyl, CN, $NO_2$, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl or $C_2$–$C_4$ alkoxycarbonyl; or
- $(R^5)_2$ when attached to adjacent carbon atoms can be taken together as —$OCF_2O$—, —$CF_2CF_2O$— or —$OCF_2CF_2O$—; and
- each $R^6$ is independently H, halogen, $C_1$–$C_4$ alkyl, $C_1$–$C_2$ alkoxy or $C_2$–$C_4$ alkoxycarbonyl, or
- each $R^6$ is independently a phenyl or a 5- or 6-membered heteroaromatic ring, each ring optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

Preferred C. Compounds of Preferred B wherein
- $R^1$ and $R^2$ are both H;
- $R^3$ is $C_1$–$C_4$ alkyl optionally substituted with halogen, CN, $OCH_3$, $S(O)_pCH_3$;
- each $R^4$ is independently H, $CH_3$, $CF_3$, $OCF_3$, $OCHF_2$, $S(O)_pCF_3$, $S(O)_pCHF_2$, CN or halogen;
- each $R^5$ is independently $CF_3$, $OCF_3$, $OCHF_2$, $S(O)_pCF_3$, $S(O)_pCHF_2$, $OCH_2CF_3$, $OCF_2CHF_2$, $S(O)_pCH_2CF_3$ or $S(O)_pCF_2CHF_2$;
- each $R^6$ is independently H, halogen or methyl; or phenyl, pyrazole, imidazole, triazole, pyridine or pyrimidine, each ring optionally substituted with $C_1$–$C_4$ alkyl, $C_1$–$C_4$ haloalkyl, halogen or CN; and
- p is 0, 1 or 2.

Preferred D. Compounds of Preferred C wherein $R^3$ is i-propyl or t-butyl.

Preferred E. Compounds of Formula 1 wherein J is a 5- or 6-membered heteroaromatic ring optionally substituted with 1 to 4 $R^7$.

Preferred F. Compounds of Preferred E wherein
- J is a 5- or 6-membered heteroaromatic ring selected from the group consisting of J-1, J-2, J-3, J-4 and J-5, each J optionally substituted with 1 to 3 $R^7$

J-1

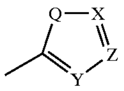

J-2

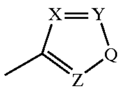

J-3

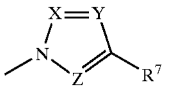

J-4

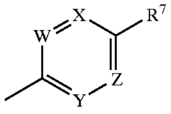

J-5

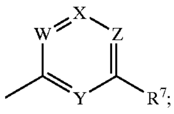

;

- Q is O, S or $NR^7$; and
- W, X, Y and Z are independently N or $CR^7$, provided that in J-4 and J-5 at least one of W, X, Y or Z is N.

Preferred G. Compounds of Preferred E or Preferred F wherein
- A and B are O;
- n is 1 to 2;
- $R^1$ is H, $C_1$–$C_4$ alkyl, $C_2$–$C_4$ alkenyl, $C_2$–$C_4$ alkynyl, $C_2$–$C_6$ alkylcarbonyl or $C_2$–$C_6$ alkoxycarbonyl;
- $R^2$ is H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;

$R^3$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $C_1$–$C_2$ alkoxy, $C_1$–$C_2$ alkylthio, $C_1$–$C_2$ alkylsulfinyl and $C_1$–$C_2$ alkylsulfonyl;

one of the $R^4$ groups is attached to the phenyl ring at the 2-position, and said $R^4$ is $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl or $C_1$–$C_4$ haloalkylsulfonyl; and each $R^7$ is independently H, $C_1$–$C_4$ alkyl, $C_1$–$C_4$ haloalkyl, halogen, CN, $NO_2$, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl or $C_2$–$C_4$ alkoxycarbonyl; or a phenyl or a 5- or 6-membered heteroaromatic ring, each ring optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

Preferred H. Compounds of Preferred G wherein

J is selected from the group consisting of pyridine, pyrimidine, pyrazole, imidazole, triazole, thiophene, thiazole and oxazole, furan, isothiazole and isoxazole, each optionally substituted with 1 to 3 $R^7$.

Preferred I. Compounds of Preferred H wherein

J is selected from the group consisting of pyridine, pyrimidine, pyrazole, thiophene and thiazole, each optionally substituted with 1 to 3 $R^7$;

$R^1$ and $R^2$ are both H;

$R^3$ is $C_1$–$C_4$ alkyl optionally substituted with halogen, CN, $OCH_3$, or $S(O)_pCH_3$;

each $R^4$ is independently H,$CH_3$, $CF_3$, $OCF_3$, $OCHF_2$, $S(O)_pCF_3$, $S(O)_pCHF_2$, CN or halogen;

each $R^7$ is independently H, halogen, $CH_3$, $CF_3$, $OCHF_2$, $S(O)_pCF_3$, $S(O)_pCHF_2$, $OCH_2CF_3$, $OCF_2CHF_2$, $S(O)_pCH_2CF_3$, or $S(O)_pCF_2CHF_2$; or phenyl, pyrazole, imidazole, triazole, pyridine or pyrimidine, each ring optionally substituted with $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, halogen or CN; and p is 0, 1 or 2.

Preferred J. Compounds of Preferred I wherein J is a pyridine optionally substituted with 1 to 3 $R^7$.

Preferred K. Compounds of Preferred J wherein one $R^7$ is a phenyl optionally substituted with $C_1$–$C_4$ alkyl, $C_1$–$C_4$ haloalkyl, halogen or CN.

Preferred L. Compounds of Preferred J wherein one $R^7$ is a pyrazole, imidazole, triazole, pyridine or pyrimidine, each ring optionally substituted with $C_1$–$C_4$ alkyl, $C_1$–$C_4$ haloalkyl, halogen or CN.

Preferred M. Compounds of Preferred I wherein J is a pyrimidine optionally substituted with 1 to 3 $R^7$.

Preferred N. Compounds of Preferred M wherein one $R^7$ is a phenyl optionally substituted with $C_1$–$C_4$ alkyl, $C_1$–$C_4$ haloalkyl, halogen or CN.

Preferred O. Compounds of Preferred M wherein one $R^7$ is a pyrazole, imidazole, triazole, pyridine or pyrimidine, each ring optionally substituted with $C_1$–$C_4$ alkyl, $C_1$–$C_4$ haloalkyl, halogen or CN.

Preferred P. Compounds of Preferred I wherein J is a pyrazole optionally substituted with 1 to 3 $R^7$.

Preferred Q. Compounds of Preferred P wherein one $R^7$ is a phenyl optionally substituted with $C_1$–$C_4$ alkyl, $C_1$–$C_4$ haloalkyl, halogen or CN.

Preferred R. Compounds of Preferred P wherein one $R^7$ is a pyrazole, imidazole, triazole, pyridine or pyrimidine, each ring optionally substituted with $C_1$–$C_4$ alkyl, $C_1$–$C_4$ haloalkyl, halogen or CN.

Preferred S. Compounds of Preferred R wherein $R^7$ is a pyridine optionally substituted with $C_1$–$C_4$ alkyl, $C_1$–$C_4$ haloalkyl, halogen or CN.

Most preferred is the compound of Formula 1 selected from the group consisting of:

3-methyl-N-(1-methylethyl)-2-[[4-(trifluoromethyl)benzoyl]amino]-benzamide, 2-methyl-N-[2-methyl-6-[[(1-methylethyl)amino]carbonyl]phenyl]-4-(trifluoromethyl)benzamide, 2-methyl-N-[2-methyl-6-[[(1-methylethyl)amino]carbonyl]phenyl]-6-(trifluoromethyl)-3-pyridinecarboxamide, 1-ethyl-N-[2-methyl-6-[[(1-methylethyl)amino]carbonyl]phenyl]-3-(trifluoromethyl)-1H-pyrazole-5-carboxamide, 1-(2-fluorophenyl)N-[2-methyl-6-[[(1-methylethyl)amino)carbonyl]phenyl]-3-(trifluoromethyl)-1H-pyrazole-5-carboxamide, 1-(3-chloro-2-pyridinyl)-N-[2-methyl-6-[[(1-methylethyl)amino]carbonyl]phenyl]3-(trifluoromethyl)-1H-pyrazole-5-carboxamide, N-[2-chloro-6-[[(1-methylethyl)amino]carbonyl]phenyl]-1-(3-chloro-2-pyridinyl)-3-(trifluoromethyl)-1H-pyrazole-5-carboxamide, 3-bromo-1-(2-chlorophenyl)-N-[2-methyl-6-[[(1-methylethyl)amino]carbonyl]phenyl]-1H-pyrazole-5-carboxamide, and 3-bromo-N-[2-chloro-6-[[(1-methylethyl)amino]carbonyl]phenyl]-1-(2-chlorophenyl)-1H-pyrazole-5-carboxamide.

Preferred compositions are those comprising compounds of formula 1 as preferred in Preferred 1 through 19, and the specifically preferred compounds above.

As noted above, each J is independently a phenyl group or a naphthyl group substituted with 1 to 2 $R^5$ and optionally substituted with 1 to 3 $R^6$; or each J is independently a 5- or 6-membered heteroaromatic ring or an aromatic 8-, 9- or 10-membered fused heterobicyclic ring system wherein each ring or ring system is optionally substituted with 1 to 4 $R^7$. The term "optionally substituted" in connection with these J groups refers to groups which are unsubstituted or have at least one non-hydrogen substituent that does not extinguish the arthropodicidal activity possessed by the unsubstituted analog. Note also that J-1 through J-5 above denote 5- or 6-membered heteroaromatic rings. An example of phenyl substituted with 1 to 2 $R^5$ and optionally substituted with 1 to 3 $R^6$ is the ring illustrated as J-6 in Exhibit 1, wherein m is an integer from 1–2 and q is an integer from 1 to 3. Note that at least one $R^5$ must be present in J-6.

Although $R^6$ groups are shown in the structure J-6, it is noted that they do not need to be present since they are optional substituents. An example of a naphthyl group substituted with 1 to 2 $R^5$ and optionally substituted with 1 to 3 $R^6$ is J-59 illustrated in Exhibit 1, wherein m is an integer from 1–2 and q is an integer from 1 to 3. Note that at least one $R^5$ must be present in J-59. Although $R^6$ groups are shown in the structure J-59, it is noted that they do not need to be present since they are optional substituents. Examples of 5- or 6-membered heteroaromatic ring optionally substituted with 1 to 4 $R^7$ include the rings J-7 through J-58 illustrated in Exhibit 1 wherein r is an integer from 1 to 4. Note that J-7 through J-26 are examples of J-1, J-27 through J-41 are examples of J-2, J-42 through J-44 are examples of J-3, J-46 through J-53 are examples of J-4 and J-54 through J-58 are examples of J-5. The nitrogen atoms that require substitution to fill their valence are substituted with $R^7$. Note that some J groups can only be substituted with less than 4 $R^7$ groups (e.g. J-19, J-20, J-23 through J-26 and J-37 through J-40 can only be substituted with one $R^7$). Examples of aromatic 8-, 9- or 10-membered fused heterobicyclic ring systems optionally substituted with 1 to 4 $R^7$ include J-60 through J-90 illustrated in Exhibit 1 wherein r is an integer from 1 to 4. Although $R^7$ groups are shown in the structures J-7 through J-58 and J-60 through J-90, it is noted that they do not need to be present since they are optional substituents. Note that when $R^5$, R6 and/or $R^7$ are H when attached to an atom, this is the same as if said atom is unsubstituted Note that when the attachment point between $(R^5)_m$, $(R^6)_q$ or $(R^7)_r$ and the J group is illustrated as floating, $(R^5)_m$, $(R^6)_q$ or $(R^7)_r$ can be attached to any available carbon atom of the J group. Note that when the attachment point on the J group is illustrated as floating, the J group can be attached to the remainder of Formula 1 through any available carbon of the J group by replacement of a hydrogen atom.

Exhibit 1

J-6

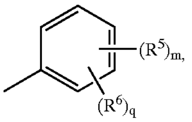

J-7

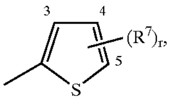

J-8

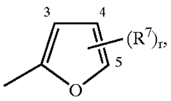

J-9

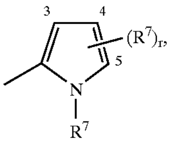

J-10

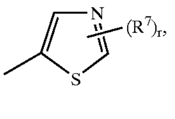

-continued

J-11

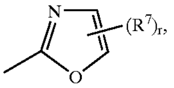

J-12

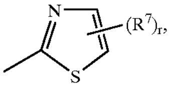

J-13

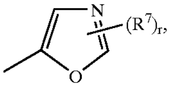

J-14

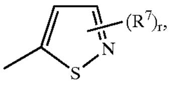

J-15

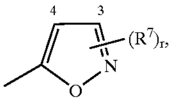

J-16

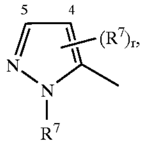

J-17

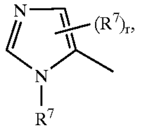

J-18

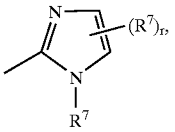

J-19

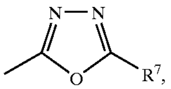

J-20

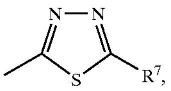

J-21

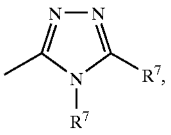

J-22

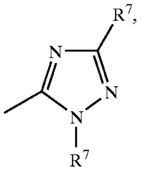

J-23

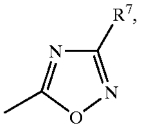

-continued
J-24
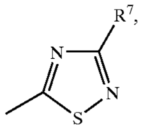
J-25
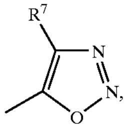
J-26
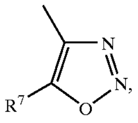
J-27
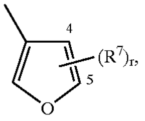
J-28
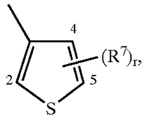
J-29
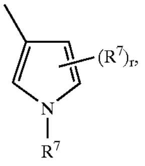
J-30
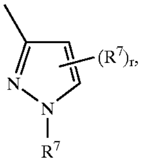
J-31
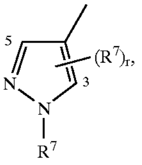
J-32
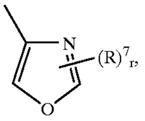
J-33
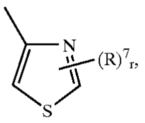
J-34
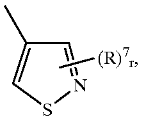
-continued
J-35
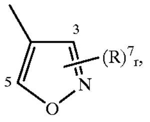
J-36
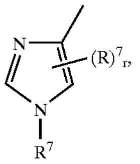
J-37
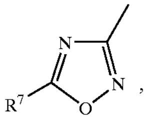
J-38
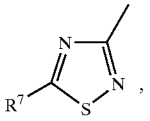
J-39
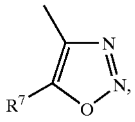
J-40
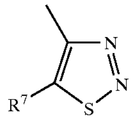
J-41
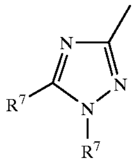
J-42
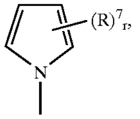
J-43
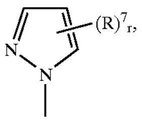
J-44
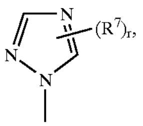
J-45
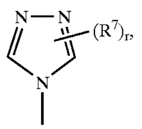
J-46
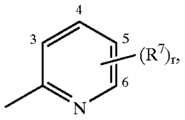

-continued
J-47
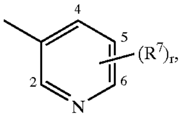
J-48
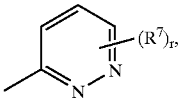
J-49
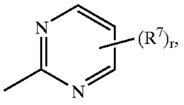
J-50
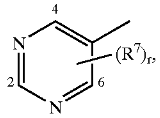
J-51
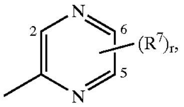
J-52
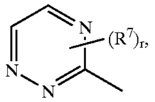
J-53
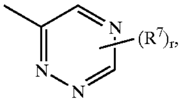
J-54
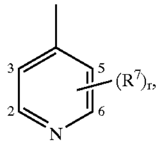
J-55
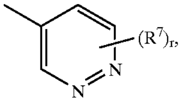
J-56
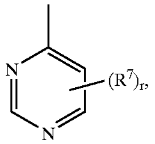
J-57
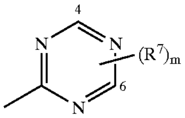
J-58
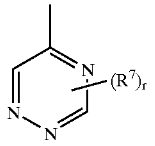
-continued
J-59
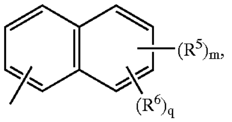
J-60
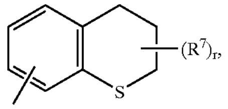
J-61
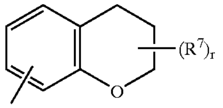
J-62
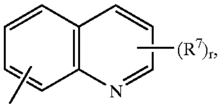
J-63
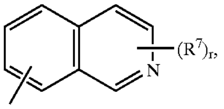
J-64
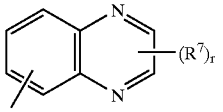
J-65
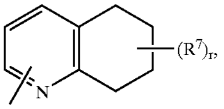
J-66
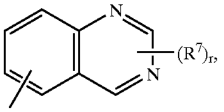
J-67
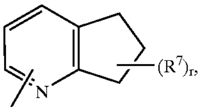
J-68
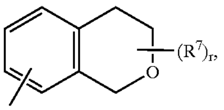
J-69
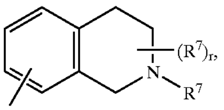
J-70
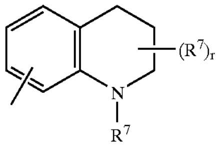
J-71
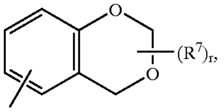

-continued

J-72

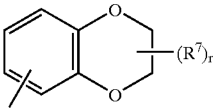

J-73

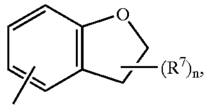

J-74

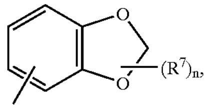

J-75

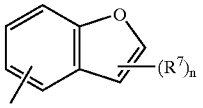

J-76

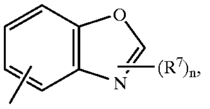

J-77

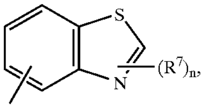

J-78

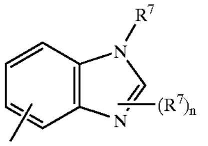

J-79

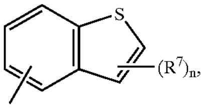

J-80

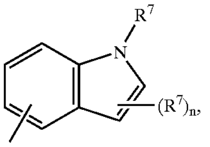

J-81

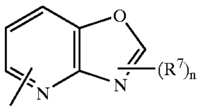

J-82

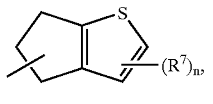

J-83

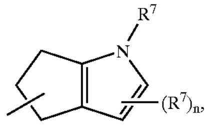

J-84

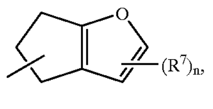

-continued

J-85

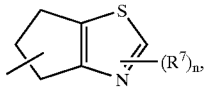

J-86

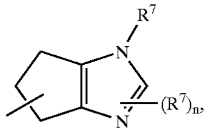

J-87

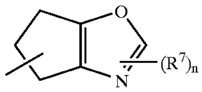

J-88

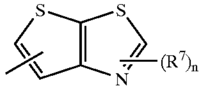

J-89

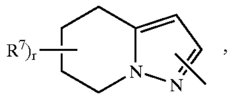

J-90

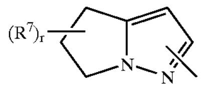

As noted above, G is a 5- or 6-membered nonaromatic carbocyclic or heterocyclic ring, optionally including one or two ring members selected from the group consisting of C(=O), SO or $S(O)_2$ and optionally substituted with 1 to 4 substituents selected from the group consisting of $C_1$–$C_2$ alkyl, halogen, CN, $NO_2$ and $C_1$–$C_2$ alkoxy. The term "optionally substituted" in connection with these G groups refers to groups which are unsubstituted or have at least one non-hydrogen substituent that does not extinguish the arthropodicidal activity possessed by the unsubstituted analog. Note that when the attachment point on the G group is illustrated as floating, the G group can be attached to the remainder of Formula 1 through any available carbon of the G group by replacement of a hydrogen atom. The optional substituents can be attached to any available carbon by replacing a hydrogen atom. Examples of 5- or 6-membered nonaromatic carbocyclic rings as G include the rings illustrated as G-1 through G-8 of Exhibit 2, wherein such rings are optionally substituted with 1 to 4 substituents selected from the group consisting of $C_1$–$C_2$ allyl, halogen, CN, $NO_2$ and $C_1$–$C_2$ alkoxy. Examples of 5- or 6-membered nonaromatic heterocyclic rings as G include the rings illustrated as G-9 through G-48 of Exhibit 2, wherein such rings are optionally substituted with 1 to 4 substituents selected from the group consisting of $C_1$–$C_2$ alkyl, halogen, CN, $NO_2$ and $C_1$–$C_2$ alkoxy. Note that when G comprises a ring selected from G-31 through G-34, G-37 and G-38, $Q^1$ is selected from O, S or N. Note that when G is G-11, G-13, G-14, G16, G-23, G-24, G-30 through G-34, G-37 and G-38 and $Q^1$ is N, the nitrogen atom can complete its valence by substitution with either H or $C_1$–$C_2$ alkyl.

Exhibit 2

G-1

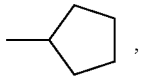

-continued
G-2
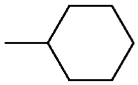,
G-3
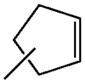,
G-4
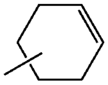,
G-5
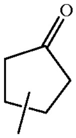,
G-6
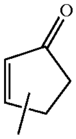,
G-7
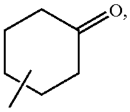
G-8
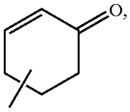
G-9
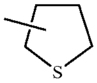,
G-10
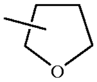,
G-11
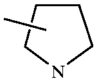,
G-12
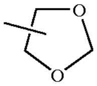,
G-13
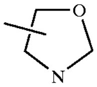,
G-14
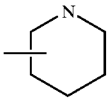,
G-15
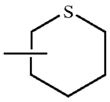,
-continued
G-16
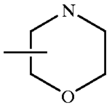,
G-17
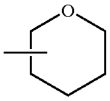,
G-18
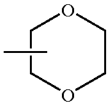,
G-19
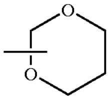,
G-20
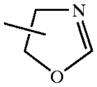,
G-21
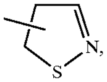
G-22
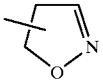
G-23
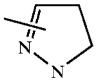,
G-24
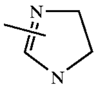,
G-25
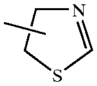,
G-26
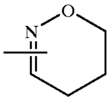,
G-27
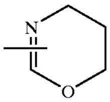,
G-28
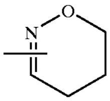,
G-29
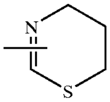,
G-30
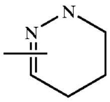, -continued

G-31

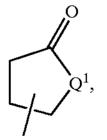

G-32

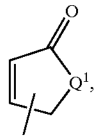

G-33

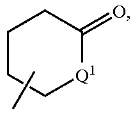

G-34

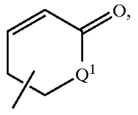

G-35

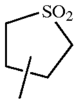

,

G-36

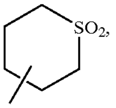

G-37

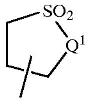

or

G-38

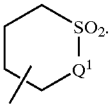

As noted above, each $R^6$ and each $R^7$ can be independently (among others) 5- or 6-membered heteroaromatic rings or aromatic 8-, 9- or 10-membered fused heterobicyclic ring systems, each ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl. Examples of such $R^6$ and $R^7$ groups include the rings or ring systems illustrated as rings J-7 through J-58 and J-60 through J-90 illustrated in Exhibit 1, except that such rings are optionally substituted with 1 to 3 substituents selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl) cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl rather than $(R^7)_r$. Note that these substituents can be attached to any available carbon atom of the J group by replacement of a hydrogen atom. Note that when the attachment point on the J group is illustrated as floating, the J group can be attached to the remainder of Formula 1 through any available carbon of the J group by replacement of a hydrogen atom.

One or more of the following methods and variations as described in Schemes 1–17 can be used to prepare the compounds of Formula 1. The definitions of A, B, J, $R^1$, $R^2$, $R^3$, $R^4$, $R^5$, $R^6$, $R^7$, m and n in the compounds of Formulae 1–34 below are as defined above in the Summary of the Invention. Compounds of Formulae 1a–c, 2a–b, 4a–g, 5a–b are various subsets of the compounds of Formula 1, 2, 4 and 5.

Compounds of Formula 1 can be prepared by procedures outlined in Schemes 1–17. A typical procedure is detailed in Scheme 1 and involves coupling of an anthranilic amide of Formula 2 with an acid chloride of Formula 3 in the presence of an acid scavenger to provide the compound of Formula 1a. Typical acid scavengers include amine bases such as triethylamine, diisopropylethylamine and pyridine; other scavengers include hydroxides such as sodium and potassium hydroxide and carbonates such as sodium carbonate and potassium carbonate. In certain instances it is useful to use polymer-supported acid scavengers such as polymer-bound diisopropylethylamine and polymer-bound dimethylaminopyridine. In a subsequent step, amides of Formula 1a can be converted to thioamides of Formula 1b using a variety of standard thio transfer reagents including phosphorus pentasulfide and Lawesson's reagent.

Scheme 1

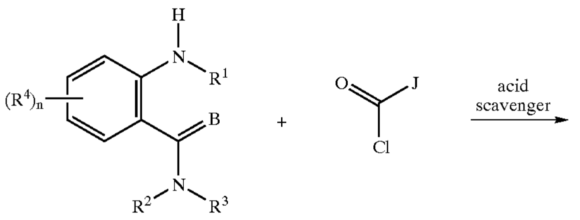

2

3

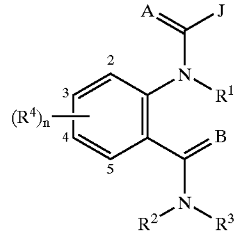

1a (A is O)
1b (A is S)

An alternate procedure for the preparation of compounds of Formula 1a involves coupling of an anthranilic amide of Formula 2 with an acid of Formula 4 in the presence of a dehydrating agent such as dicyclohexylcarbodiimide (DCC). Polymer supported reagents are again useful here, such as polymer-bound cyclohexylcarbodiimide. Synthetic procedures of Schemes 1 and 2 are only representative examples of useful methods for the preparation of Formula 1 compounds as the synthetic literature is extensive for this type of reaction.

Scheme 2

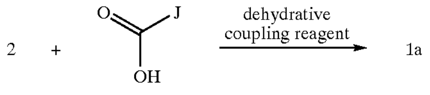

4

One skilled in the art will also realize that acid chlorides of Formula 3 may be prepared from acids of Formula 4 by numerous well-known methods.

Anthranilic amides of Formula 2a are typically available from the corresponding 2-nitrobenzamides of Formula 5 via catalytic hydrogenation of the nitro group. Typical procedures involve reduction with hydrogen in the presence of a metal catalyst such as palladium on carbon or platinum oxide and in hydroxylic solvents such as ethanol and isopropanol. These procedures are well documented in the chemical literature. $R^1$ substituents such as alkyl, substituted alkyl and the like can generally be introduced at this stage through known procedures including either direct alkylation or through the generally preferred method of reductive alkylation of the amine. A commonly employed procedure is to combine the aniline 2a with an aldehyde in the presence of a reducing agent such as sodium cyanoborohydride to produce the Formula 2b compounds where $R^1$ is alkyl, alkenyl, alkynyl or substituted derivatives thereof.

Scheme 3

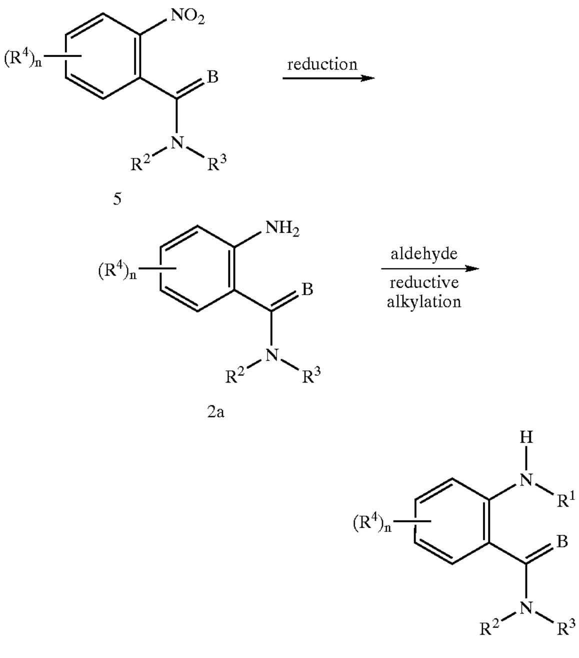

5

2a 2b ($R^1$ is other than H)

The intermediate amides of Formula 5a are readily prepared from commercially available 2-nitrobenzoic acids. Typical methods for amide formation can be applied here. These include direct dehydrative coupling of acids of Formula 6 with amines of Formula 7 using for example DCC, and conversion of the acids to an activated form such as the acid chlorides or anhydrides and subsequent coupling with amines to form amides of Formula 5a. We have found ethylchloroformate to be an especially useful reagent for this type of reaction involving activation of the acid. The chemical literature is extensive on this type of reaction. Amides of Formula 5a are readily converted to thioamides of Formula 5b by using commercially available thio transfer reagents such as phosphorus pentasulfide and Lawesson's reagent.

Scheme 4

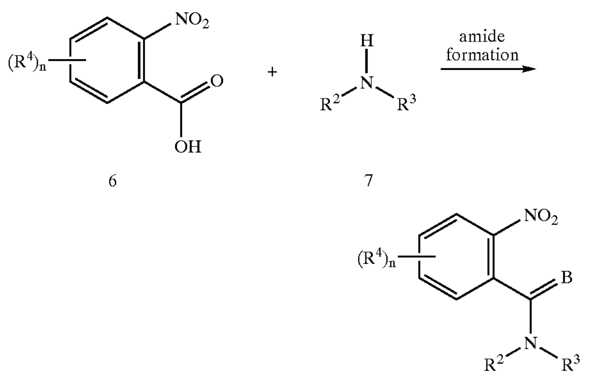

6

7

5a (B is O)
5b (B is S)

Benzoic acids of Formula 4 (J is optionally substituted phenyl) are generally well know in the art as are procedures for their preparation. One particularly useful subset of benzoic acids of this invention are 2-methylperfluoroalkyl benzoic acids of Formula 4a ($R^5$ equals e.g. $CF_3$, $C_2F_5$, $C_3F_7$). The synthesis for these compounds is outlined in Schemes 5–9. Benzoic acids of Formula 4a may be prepared from the benzonitriles of Formula 8 by hydrolysis. The conditions used may involve the use of a base such as an alkaline metal hydroxide or alkoxide (e.g. potassium or sodium hydroxide) in a solvent such as water, ethanol or ethylene glycol (e.g. *J. Chem. Soc.* 1948, 1025). Alternatively, the hydrolysis may be carried out using an acid such as sulfuric acid or phosphoric acid in a suitable solvent such as water (e.g. *Org. Synth.* 1955, Coll vol. 3, 557). The choice of the conditions is contingent on the stability of $R^5$ to the reaction conditions and elevated temperatures are usually employed to achieve this transformation.

Scheme 5

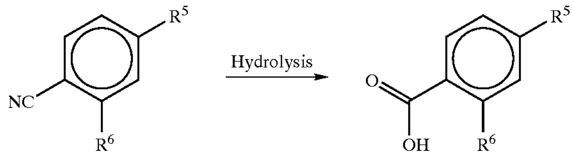

8

4a $R^6$ is Me

Nitriles of Formula 8 may be prepared from anilines of Formula 9 by the classical sequence involving diazotization and treatment of the intermediate diazonium salt with a copper cyanide salt (e.g. *J. Amer. Chem. Soc.* 1902, 24, 1035).

Scheme 6

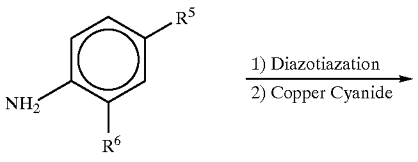

8

9 $R^6$ is Me

Anilines of Formula 9 may be prepared from compounds of Formula 10. This transformation may be achieved by a well-known procedure that employs Raney Nickel (Org. Synth. Coll. Vol VI, 581). Alternatively, the same transformation may be effected by the use of a suitable catalyst such as palladium in the presence of hydrogen. The reaction is usually conducted at pressures of $10^2$ to $10^5$ kPa in a suitable organic solvent such as, but not limited to, toluene. Elevated temperatures of 80–110° C. are usually required to achieve the transformation. As one skilled in the art will realize, numerous chemical modifications of the thioether moiety are possible, and may be employed when necessary to facilitate this transformation.

Scheme 7

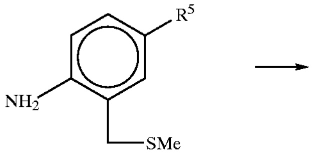

9

10

Compounds of Formula 10 may be prepared from iminosulfuranes of Formula 11. The transformation may be achieved in a protic solvent such as methanol or water, in a non-protic solvent such as dichloromethane or toluene in the presence of a suitable base such as triethylamine (e.g. Org. Syth. Coll. Vol. VI, 581) or sodium methoxide, or in a combination of a protic solvent, a non-protic solvent and a base. The temperature at which the reaction is conducted is usually in the range 40–110° C. As one skilled in the art will realize, suitable salts of compounds of Formula 11 such as, but not limited to a hydrochloride, a sulfate or a bisulfate may also be employed, provided that the appropriate amount of base is first used to generate the free base 11. This may be done as a separate step or as an integral part of the step involving the transformation of compounds of Formula 11 to compounds of Formula 10.

Scheme 8

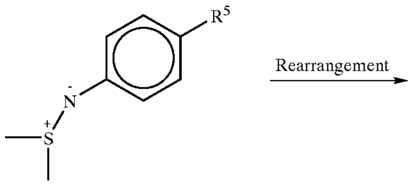

10

11
or salt

Compounds of Formula 11 may be prepared from anilines of Formula 12 by reaction with dimethyl sulfide and a suitable chlorinating agent such as, but not limited to N-chlorosuccinimide (e.g. Org. Synth. Coll. Vol. VI, 581), chlorine or N-chlorobenzotriazole. Alternatively, anilines of Formula 12 may be treated with dimethyl sulfoxide which has been "activated" by treatment with an agent such as acetic anhydride, trifluoroacetic, anhydride, trifluoromethanesulfonic anhydride, cyclohexylcarbodiimide, sulfur trioxide, or phosphorus pentoxide. The reaction is conducted in a suitable organic solvent such as dichloromethane or dimethyl sulfoxide. The reaction is conducted at a temperature of −70° C. to 25° C. and is dependent on the solvent and reagent used.

Scheme 9

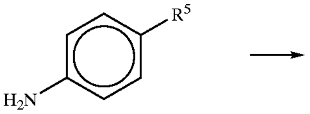

11

12

Intermediate anthranilic amides of Formula 2a and 2b may also be prepared from isatoic anhydrides of Formula 13 and 14 (Scheme 10). Typical procedures involve combination of equimolar amounts of the amine 7 with the isatoic anhydride in polar aprotic solvents such as pyridine and dimethylformamide at temperatures ranging from room temperature to 100° C. $R^1$ substituents such as alkyl and substituted alkyl may be introduced by the base catalyzed alkylation of isatoic anhydride 13 with known alkylating reagents $R^1$-Lg (wherein Lg is a leaving group such as halogen, all or aryl suphonates or alkyl sulfates) to provide the alkyl substituted intermediates 14. Isatoic anhydrides of Formula 13 may be made by methods described in Coppola, Synthesis 505–36 (1980).

Scheme 10

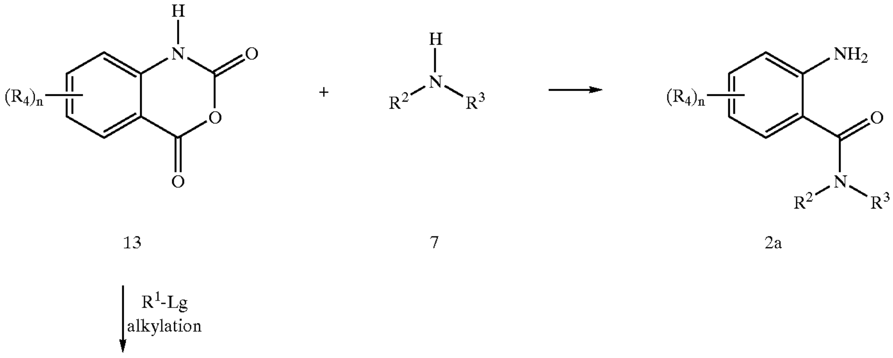

13 7 2a

-continued

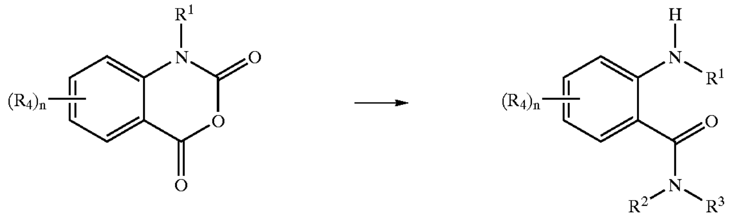

14

2b ($R^1$ is other than H)

An alternate procedure for the preparation of specific compounds of Formula 1 (where A is O, B is O and $R^1$ is H) involves reaction of an amine 7 with a benzoxazinone of Formula 15. Typical procedures involve combination of the amine with the benzoxazinone in solvents such as tetrahydrofuran or pyridine at temperatures ranging from room temperature to the reflux temperature of the solvent. Benzoxazinones are well documented in the chemical literature and are available via known methods that involve the coupling of either an anthranilic acid or an isatoic anhydride with an acid chloride. For references to the synthesis and chemistry of Benzoxazinones see Jakobsen et al, *Biorganic and Medicinal Chemistry*, 2000, 8, 2095–2103 and references cited within. See also Coppola, *J. Heterocyclic Chemistry*, 1999, 36, 563–588.

Scheme 11

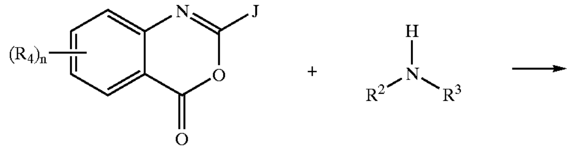

15

7

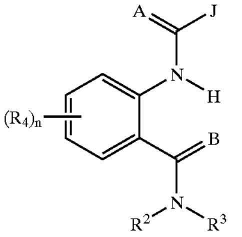

1c (A is O, B is O, $R^1$ is H)

Heterocyclic acids 4, where J is equal to an optionally substituted heterocycle, can be prepared by procedures outlined in Schemes 12–17. Both general and specific references to a wide variety of heterocyclic acids including thiophenes, furans, pyridines, pyrimidines, triazoles, imidazoles, pyrazoles, thiazoles, oxazoles, isothiazoles, thiadiazoles, oxadiazoles, triazines, pyrazines, pyridazines, and isoxazoles can be found in the following compendia: *Rodd's Chemistry of Chemistry of Carbon Compounds*, Vol. IVa. to IVl., S. Coffey editor, Elsevier Scientific Publishing, New York, 1973; *Comprehensive Heterocyclic Chemistry*, Vol. 1–7, A. R. Katritzky and C. W. Rees editors, Pergamon Press, New York, 1984; *Comprehensive Heterocyclic Chemistry II*, Vol. 1–9, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York Particularly useful heterocyclic acids of this invention include pyridine acids, pyrimidine acids and pyrazole acids. Procedures for the synthesis of representative examples of each are detailed in Schemes 12–17. A variety of heterocyclic acids and general methods for their synthesis may be found in World Patent Application WO 98/57397.

The synthesis of representative pyridine acids (4b) is depicted in Scheme 12. This procedure involves the known synthesis of pyridines from β-ketoesters and 4-aminobutenones (19). Substituent groups $R^7$(a) and $R^7$(b) include e.g. alkyl and haloalkyl.

Scheme 12

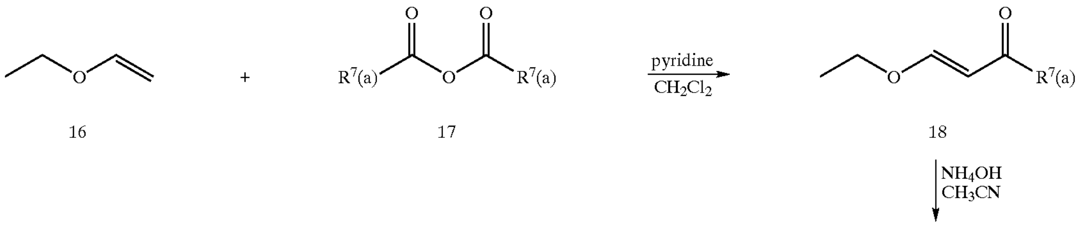

16

17

18

-continued

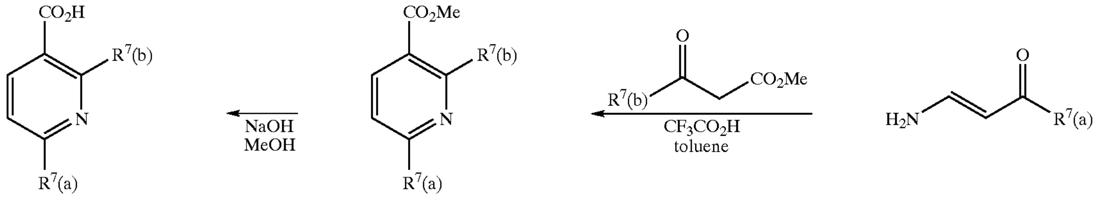

4b 20 19

The synthesis of representative pyrimidine acids (4c) is depicted in Scheme 13. This procedure involves the known synthesis of pyrimidines from vinylidene-β-ketoesters (22) and amidines. Substituent groups $R^7$(a) and $R^7$(b) include e.g. alkyl and haloalkyl.

Scheme 13

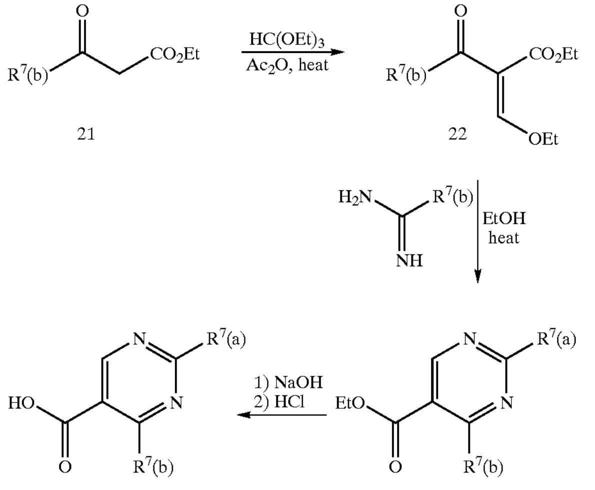

21 22 23 4c

The synthesis of representative pyrazole acids (4d–4g) is depicted in Schemes 14–17. Pyrazoles 4d are described in Scheme 14. The synthesis of Scheme 14 involves as the key step introduction of the $R^7$(b) substituent via alklylation of the pyrazole. The alkylating agent $R^7$(b)-Lg (wherein Lg is a leaving group such as Cl, Br, I, sulfonates such as p-toluenesulfonate or methanesulfonate or sulfates such as $-SO_2OR^7$(b)) includes $R^7$(b) groups such as $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, $C_2$–$C_6$ alkylcarbonyl, $C_2$–$C_6$ alkoxycarbonyl, $C_3$–$C_8$ dialkylaminocarbonyl, $C_3$–$C_6$ trialkylsilyl; or phenyl, benzyl, benzoyl, 5- or 6-membered heteroaromatic ring or an aromatic 8-, 9- or 10-membered fused heterobicyclic ring system, each ring or ring system optionally substituted. Oxidation of the methyl group affords the pyrazole carboxylic acid. Some of the more preferred $R^7$(a) groups include haloalkyl.

Scheme 14

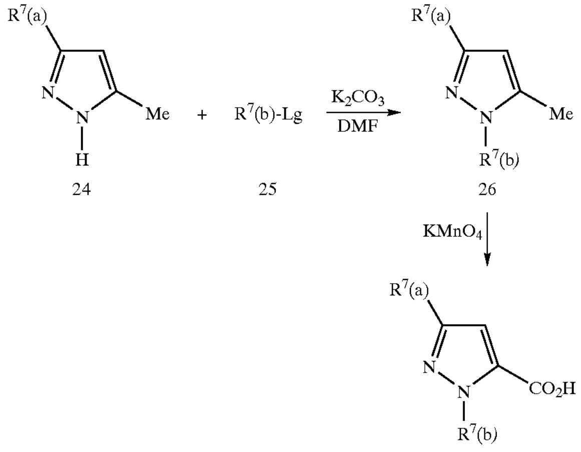

24 25 26 4d

Lg is a leaving group

Pyrazoles 4e are described in Scheme 15. These pyrazole acids may be prepared via metallation and carboxylation of pyrazoles of formula 28 as the key step. The $R^7$(b) group is introduced in a manner similar to that of Scheme 14, i.e. via alkylation with a $R^7$(b) alkylating agent. Representative $R^7$(a) groups include e.g. cyano, and haloalkyl.

Scheme 15

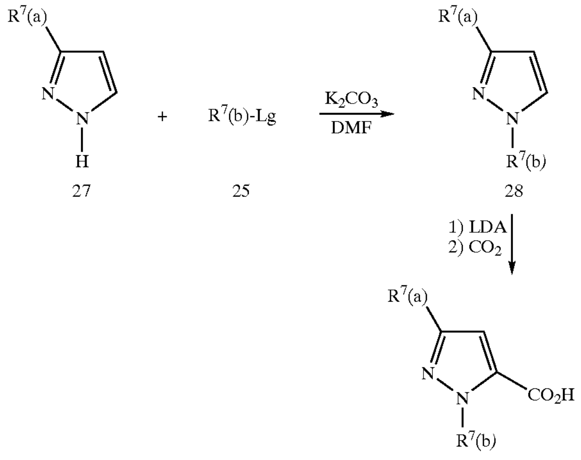

27 25 28 4e

Lg is a leaving group

Pyrazoles 4f are described in Scheme 16. These can be prepared via reaction of an optionally substituted phenyl hydrazine 29 with a pyruvate 30 to yield pyrazole esters 31. Hydrolysis of the ester affords the pyrazole acids 4f. This procedure is particularly useful for the preparation of compounds where $R^7$(b) is optionally substituted phenyl and $R^7$(a) is haloalkyl.

Scheme 16

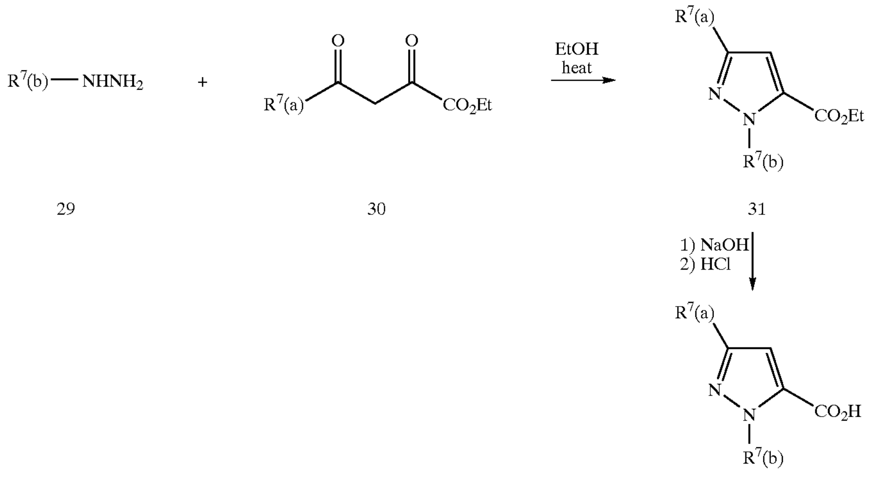

29 30 31 4f

Pyrazoles acids of Formula 4g are described in Scheme 17. These can be prepared via 3+2 cycloaddition of an appropriately substituted nitrilimine with either substituted propiolates (33) or acrylates (36). Cycloaddition with acrylates requires additional oxidation of the intermediate pyrazoline to the pyrazole. Hydrolysis of the ester affords the pyrazole acids 4g. Preferred iminohalides for this reaction include the trifluoromethyl iminochloride (38) and the iminodibromide (39). Compounds such as 38 are known (*J. Heterocycl. Chem.* 1985, 22(2), 565–8). Compounds such as 39 are available by known methods (*Tetrahedron Letters* 1999, 40, 2605). These procedures are particularly useful for the preparation of compounds where $R^7$(b) is optionally substituted phenyl and $R^7$(a) is haloalkyl or bromo.

Scheme 17

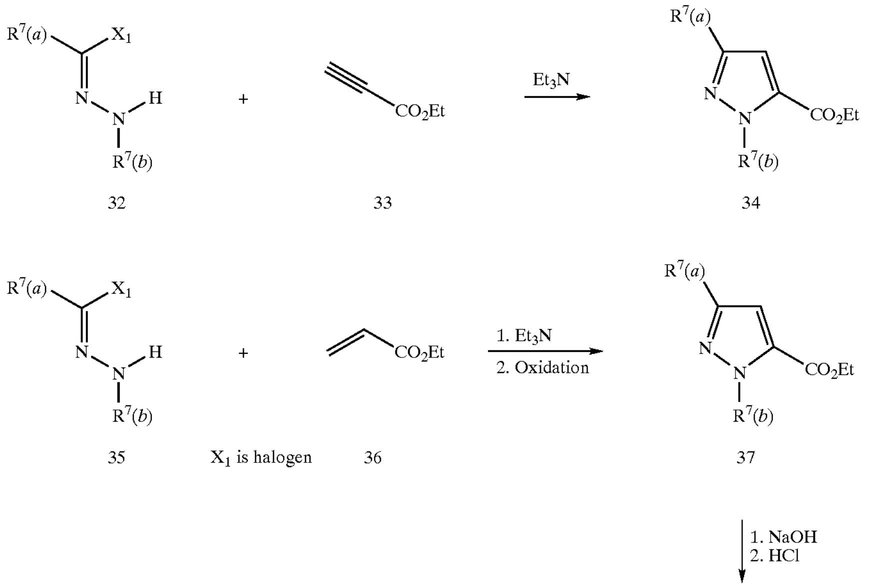

32 33 34

35 $X_1$ is halogen 36 37

-continued

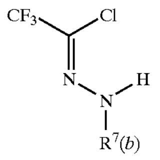

38

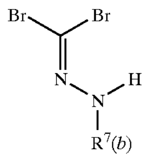

39

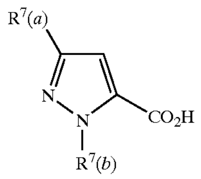

4g

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Orgaizic Synthesis*, 2nd ed,; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1H$ NMR spectra are reported in ppm downfield from tetramethylsilane; s is singlet, d is doublet, t is triplet, q is quartet, in is multiplet, dd is doublet of doublets, dt is doublet of triplets, br s is broad singlet.

EXAMPLE 1

Step A: Preparation of 3-methyl-N-(1-methylethyl)-2-nitrobenzamide

A solution of 3-methyl-2-nitrobenzoic acid (2.00 g, 11.0 mmol) and triethylamine (1.22 g, 12.1 mmol) in 25 mL of methylene chloride was cooled to 10° C. Ethyl chloroformate was carefully added and a solid precipitate formed. After stirring for 30 minutes isopropylamine (0.94 g, 16.0 mmol) was added and a homogeneous solution resulted. The reaction was stirred for an additional hour, poured into water and extracted with ethyl acetate. The organic enacts were washed with water, dried over magnesium sulfate and evaporated under reduced pressure to afford 1.96 g of the desired intermediate as a white solid melting at 126–128° C.

$^1H$ NMR ($CDCl_3$) δ 1.24 (d, 6H), 2.38 (s, 3H), 4.22 (m, 1H), 5.80 (br s, 1H), 7.4 (m, 3H).

Step B: Preparation of 2-amino-3-methyl-N-(1-methylethyl)benzamide

The 2-nitrobenzamide of Step A (1.70 g, 7.6 mmol) was hydrogenated over 5% Pd/C in 40 mL of ethanol at 50 psi. When the uptake of hydrogen ceased the reaction was filtered through celite and the celite was washed with ether. The filtrate was evaporated under reduced pressure to afford 1.41 g of the title compound as a solid melting at 149–151° C.

$^1H$ NMR ($CDCl_3$) δ 1.24 (dd, 6H), 2.16 (s, 3H), 4.25 (m, 1H), 5.54 (br s, 2H), 5.8 (br s, 1H), 6.59 (t, 1H), 7.13 (d, 1H), 7.17 (d, 1H).

Step C: Preparation of 3-methyl-N-(1-methylethyl)-2-[[4-(trifluoromethoxy)benzoyl]amino]benzamide 4-(trifluoromethoxy)benzoyl chloride (0.29 g, 1.3 mmol) was added dropwise to a mixture of the aniline from Step B (0.25 g, 1.3 mmol) and triethylamine (0.13 g, 1.3 mmol) in 5 mL of methylene chloride at room temperature. After string for one hour the reaction was poured into water and extracted with ethyl acetate. The combined extracts were dried over magnesium sulfate and evaporated under reduced pressure. The resulting solids were washed with hexane/ether and filtered to afford 0.41 g of the title compound, a compound of the present invention, as a solid melting at 207–209° C.

$^1H$ NMR ($CDCl_3$) δ 1.19 (d, 6H), 2.33 (s, 3H), 4.15 (m, 1H), 5.97 (br d, 1H), 7.2–7.4 (m, 6H), 8.04 (d, 1H), 10.11 (br s, 1H).

EXAMPLE 2

Step A: Preparation of 1-Ethyl-3-trifluoromethylpyrazol-5-yl Carboxylic acid

To a mixture of 3-trifluoromethylpyrazol (5 g, 37 mmol) and powdered potassium carbonate (10 g, 72 mmol) stirring in 30 mL of N,N-dimethylformamide, iodoethane (8 g, 51 mmol) was added dropwise. After a mild exotherm, the reaction was stirred overnight at room temperature. The reaction mixture was partitioned between 100 mL of diethyl ether and 100 mL of water. The ether layer was separated, washed with water (3×) and brine, and dried over magnesium sulfate. Evaporation of solvent in vacuo gave 4 g of oil.

To 3.8 g of this oil stirring in 40 mL of tetrahydrofuran under nitrogen in a dry ice/acetone bath, 17 mL of a 2.5 M solution of n-butyl lithium in tetrahydrofuran (43 mmol) was added dropwise and the solution stirred for 20 minutes at −78° C. An excess of gaseous carbon dioxide was bubbled into the stirred solution at a moderate rate for 10 minutes. After addition of carbon dioxide, the reaction was allowed to slowly reach room temperature and stirred overnight. The reaction mixture was partitioned between diethyl ether (100 mL) and 0.5 N aqueous sodium hydroxide (100 mL). The basic layer was separated and acidified with concentrated hydrochloric acid to a pH of 2–3. The aqueous mixture was extracted with ethyl acetate (100 mL) and the organic extract washed with water and brine and dried over magnesium sulfate. The oily residue, which remained after evaporating the solvent in vacuo, was triturated to a solid from a small amount of n-butyl chloride. After filtering and drying, a slightly impure, sample of 1-ethyl-3-trifluoromethyl-pyrazol-5-yl carboxylic acid (1.4 g) was obtained as a broad-melting solid.

$^1$H NMR ($CDCl_3$): 9.85 (br s, 1H), 7.23 (s, 1H), 4.68 (q, 2H), 1.51 (t, 3H) ppm.

Step B: Preparation of 2-[1-Ethyl-3-trifuoromethylpyrazol-5-yl carbamoyl]-3-methyl-N-(1-methylethyl)benzamide To a solution of 1-ethyl-3-trifluoromethyl-pyrazol-5-yl carboxylic acid (0.5 g, 2.4 mmol) stirring in 20 mL of methylene chloride, oxalyl chloride (1.2 mL, 14 mmol) was added. Upon addition of 2 drops of N,N-dimethylformamide, foaming and bubbling occurred. The reaction mixture was heated at reflux for 1 hr as a yellow solution. After cooling, the solvent was removed in vacuo and the resulting residue dissolved in 20 mL of tetrahydrofuran. To the stirred solution, 2-amino-3-methyl-N-(1-methylethyl)benzamide (0.7 g, 3.6 mmol) was added followed by the dropwise addition of N,N-diisopropylethylamine (3 mL, 17 mmol). After stirring at room temperature overnight, the reaction mixture was partitioned between ethyl acetate (100 mL) and 1N aqueous hydrochloric acid (75 mL). The separated organic layer was washed with water and brine and dried over magnesium sulfate. Evaporating in vacuo gave a white solid residue, which on purification by flash column chromatography on silica gel (2:1 hexanes/ethyl acetate) afforded 0.5 g of the title compound, a compound of the present invention, melting at 223–226° C.

$^1$H NMR (DMSO-$D_6$): 10.15 (s, 1H), 8.05 (d, 1H), 7.45 (s, 1H), 7.43–7.25 (m, 3H), 4.58 (q, 2H), 3.97 (m, 1H), 2.45 (s, 3H), 1.36 (t, 3H), 1.06 (d, 6H) ppm.

EXAMPLE 3

Step A: Preparation of S,S-dimethyl-N-[4-(trifluoromethyl) phenyl]sulfilimine

A solution of N-chlorosuccinimide (12–43 g, 93.1 mmol) in ~170 mL of dichloromethane was added to a mixture of 4-(trifluoromethyl) aniline (15 g, 93.1 mmol) and dimethyl sulfide (6.35 g, 102 mmol) in 230 mL of dichloromethane at −5–0° C. After the addition was complete, the mixture was stirred at 0–5° C. for 1 h, and N-chlorosuccinimide (0.02 g, 4.64 mmol) was added. After a further 30 minutes, the mixture was washed with 500 mL of 1N sodium hydroxide.

The organic phase was dried and evaporated to give the product as a solid 19–72 g melting at 101–103° C. (after crystallization from ethyl acetate/hexanes).

IR (Nujol) 1603, 1562, 1532, 1502, 1428, 1402, 1335, 1300, 1270, 1185, 1150, 1103, 1067, 1000, 972, 940, 906, 837, 817 $cm^{-1}$.

$^1$H NMR ($CDCl_3$) δ 7.35 (d, J=8.8 Hz, 2H), 6.84 (d, J=8.8 Hz, 2H), 2.67 (5, 3H).

Step B: 2-[(methylthio)methyl]-4-(trifluoromethyl) benzenamine

Sodium methoxide in methanol (1.95 g, 9.02 mmol, 25%) was added to S,S-dimethyl-N-[4-(trifluoromethyl)phenyl] sulfilimine from Step A (2 g, 9.04 mmol) in 15 mL of toluene. The mixture was warmed to ~80° C. for ~1 h. The mixture was allowed to cool to 25° C. and was poured into 100 mL of water. The mixture was extracted with 2×100 mL of ethyl acetate and the combined extracts were dried and evaporated to give 1.8 g of the product as a solid melting at 65.5–67.5° C. (after crystallization from hexanes).

IR (nujol) 3419, 3333, 1629, 1584, 1512, 1440, 1334, 1302, 1235, 1193, 1139, 1098, 1078, 979, 904, 832 $cm^{-1}$.

$^1$H NMR ($CDCl_3$) δ 7.35 (dd, J=1.5 Hz×8.2 Hz, 1H) 6.72 (d, J=8.4 Hz) 4.39 (br. 5, 2H, 3.69 (5, 2H), 1.99 (5, 3H).

Step C: Preparation of 2-methyl-4-(trifluoromethyl) benzenamine

Activated Raney nickel (500 g wet paste, ~50μ) was added portionwise to a solution of 2-[(methylthio)methyl]-4-(trifluoromethyl)benzenamine (55.3 g, 0.25 mole) in 1 L of ethanol over 30 minutes at 25–30° C. The heterogeneous mixture was stirred vigorously for 30 minutes after the addition. The stirring was stopped, and the solids were allowed to settle over one hour. The liquid was decanted from the solids and poured through filter paper. The filtrate was evaporated under reduced pressure, and the residue was taken up in dichloromethane. The organic phase was separated from a small volume of water, dried over magnesium sulfate and evaporated under reduced pressure to afford 37.6 g of the title compound as amber oil.

$^1$H NMR ($CDCl_3$) δ 7.28 (m, 2H), 6.68 (d, 1H), 3.87 (br s, 2H), 2.19 (s, 3H).

Step D: Preparation of 2-methyl-4-(trifluoromethyl) benzonitrile

Concentrated hydrochloric acid (16 mL) was added dropwise at a moderate rate to a heterogeneous mixture of 2-methyl-4-(trifluoromethyl)benzenamine (14 g, 80 mmol) and 120 mL of water while stirring vigorously. A thick suspension resulted which was stirred for 20 minutes, diluted with 280 mL of water and cooled to 5° C. A solution of sodium nitrite (5.5 g, 80 mmol) and 25 mL of water was added slowly to the reaction suspension. After stirring for 30 minutes at 5° C. a solution resulted which was stirred cold for 30 more minutes and then neutralized with potassium carbonate. This diazonium salt solution was then added portionwise via cannula to a stirred, 95° C. mixture of potassium cyanide (22 g, 0.34 mole), copper sulfate pentahydrate (20 g, 80 mmol) and 140 mL of water. After the addition the mixture was stirred for 30 minutes at 95° C. and then allowed to cool to room temperature. Ether was added and the heterogeneous mixture was filtered through celite. The solids were washed with ether, and the filtrate was partitioned. The aqueous phase was extracted with ether, and the combined organic extracts were dried over magnesium sulfate and concentrated under reduced pressure to afford 13.1 g of the title compound as brown oil.

$^1$H NMR ($CDCl_3$) δ 7.74 (d, 1H), 7.60 (s, 1H), 7.55 (d, 1H), 2.64 (s, 3H).

Step E: Preparation of 2-methyl-4-trifluoromethyl benzoic acid

Potassium hydroxide (15.7 g, 0.28 mole) and 15 mL of water were added as a solution to a stirred, heterogeneous mixture of 2-methyl-4-(trifluoromethyl)benzonitrile (13 g, 70 mmol) and 135 mL of ethylene glycol. The reaction mixture was heated at 120–130° C. for 20 hours and allowed to cool to room temperature. The dark solution was poured into 800 mL of water and filtered through celite. The filtrate was washed with ether and then the aqueous was acidified with concentrated hydrochloric acid. This aqueous phase was extracted three times with ethyl acetate, the organic extracts were combined, dried over magnesium sulfate and evaporated under reduced pressure to afford the title compound as a tan solid.

$^1$H NMR ($CDCl_3$) δ 7.98 (d, 1H), 7.70 (s, 1H), 7.65 (d, 1H), 2.60 (s, 3H).

Step F: Preparation of 2-methyl-4-(trifluoromethoxy) benzoyl chloride

Thionyl chloride (0.42 g, 3.5 mmol) was added to a solution of the benzoic acid from Step E (0.50 g, 2.4 mmol) in 10 mL of toluene at room temperature. The reaction was refluxed for three hours then cooled to room temperature. The solvent was evaporated under reduced pressure and excess thionyl chloride was removed by azeotroping with toluene. The benzoyl chloride obtained was used directly in Step G.

Step G: Preparation of 2-methyl-N-[2-methyl-6-[[(1-methylethyl)amino]-carbonyl]phenyl]-4-(trifluoromethyl) benzamide The benzoyl chloride of Step F (0.29 g, 1.3 mmol) was added to a mixture of the aniline from Example 1, Step B (0.36 g, 1.9 mmol) and diisopropylethylamine (0.26 g, 2.0 mmol) in 10 mL of chloroform at room temperature. The reaction was allowed to stir overnight. The solid precipitate was filtered and dried to afford 0.38 g of the title compound, a compound of the present invention, as a solid melting at 247–248° C.

$^1$H NMR ($CDCl_3$) α 1.24 (d, 6H), 2.41 (s, 3H), 2.58 (s, 3H), 4.20 (m, 1H), 5.94 (br d, 1H), 7.2–7.3 (m, 2H), 7.40 (d, 1H), 7.52 (s, 1H), 7.53 (d, 1H), 7.70 (d, 1H), 9.36 (br s, 1H).

EXAMPLE 4

Step A: Preparation of 2-Methyl-6-(trifluoromethyl)-3-pyridinecarbonyl chloride

Thionyl chloride (4.35 g, 36.5 mmol) was added to a mixture of 2-methyl-6-trifluoromethyl nicotinic acid (5.00 g, 24.4 mmol) in 75 mL of toluene and the mixture was heated at reflux for 3 hours. The reaction was cooled to room temperature and the solvent was removed under reduced pressure. Excess thionyl chloride was removed by azeotrope with toluene. The resultant acid chloride was used as is in Example 4, Step B.

Step B: Preparation of 8-Methyl-2-[2-methyl-6-(trifluoromethyl)-3-pyridinyl]-4H-3,1-benzoxazine A mixture of the 6-methyl isatoic anhydride (3.92 g, 22.1 mmol) and the acid chloride from Step A (5.45 g, 24.3 mmol) was heated at reflux in pyridine for 16 hours. The dark brown solution was cooled to room temperature and the solvent was removed under reduced pressure. Excess pyridine was removed by azeotrope with toluene. Ether was added and the resulting brown solid was removed by filtration. The solid was taken up in a mixture of aqueous sodium bicarbonate and chloroform, the chloroform extracts were dried over magnesium sulfate and evaporated. Excess pyridine was again removed by azeotrope with toluene to afford 5.1 g of the title compound as a brown solid.

$^1$H NMR ($CDCl_3$) d 2.65 (s, 3H), 3.11 (s, 3H), 7.49 (t, 1H) 7.40 (m, 1H), 7.68–7.73 (m, 2H), 1.11 (d, 1H), 8.58 (d, 1H).

Step C: Preparation of 2-Methyl-N-[2-methyl-6-[[(1-methylethyl)amino]carbonyl]phenyl]-6-(trifluoromethyl)-3-pyridine Isopropylamine (7.37 g, 0.125 mmol) was added to a mixture of the benzoxazinone of Step B (4.00 g, 12.5 mmol) in 30 mL of tetrahydrofuran. A homogeneous solution formed. The mixture was heated briefly after which a thick white precipitate formed. The solvent was removed under reduced pressure and the resultant solid was washed with ether and filtered to afford 4.48 g of the title compound as a solid melting at 247–248° C.

$^1$H NMR ($CDCl_3$) d 1.24 (d, 6H, 2.41 (s, 3H), 2.77 (s, 3H), 4.17 (m, 1H), 5.96 (bd, 1H), 7.21 (m, 2H) 7.40 (m, 1H), 7.53 (d, 1H), 7.97 (d, 1H), 9.80 (bs, 1H).

EXAMPLE 5

Step A: Preparation of 4-Methyl-N-[2-methyl-6-[[(1-methylethyl)amino]carbonyl]phenyl]-2-(trifluoromethyl)-5-pyrimidinecarboxamide To a solution 0.8 g (4 mmol) of 4-methyl-2-tritluoromethylpyrimidine-5-carboxylic acid [made by the method of Palanki et al, *J. Med. Chem.* 2000, 43, 3995] stirring in 15 mL of methylene chloride, oxalyl chloride (2 mL, 23 mmol) was added. Upon addition of 2 drops of N,N-dimethylformamide, foaming and bubbling occurred. The reaction mixture was heated at reflux for 1 hr as a yellow solution. After cooling, the solvent was removed in vacuo and the resulting residue dissolved in 20 mL of tetrahydrofuran. To the stirred solution, 2-amino-3-methyl-N-(1-methylethyl)benzamide (1 g, 5 mmol) was added followed by the dropwise addition of N,N-diisopropylethylamine (3 ml, 17 mmol). After stirring at room temperature overnight, the reaction mixture was partitioned between ethyl acetate (200 mL) and 1N aqueous hydrochloric acid (75 mL). The separated organic layer was washed with water and brine and dried over magnesium sulfate. Evaporating in vacuo gave a white solid, which was suspended in a small amount of ethyl acetate and filtered to afford (after drying) 650 mg of the title compound, a compound of the present invention, melting at 248–251° C.

$^1$H NMR (DMSO-$D_6$): 10.3 (s, NH, 9.07 (s, 1H), 8.25 (d, NH), 7.43–7.25 (m, 3H), 4.03 (m, 1H), 2.73 (s, 3H), 2.32 (s, 3H), 1.12 (d, 6H) ppm.

EXAMPLE 6

Step A: Preparation of 2-Methyl-1-phenyl-4-(trifluoromethyl)-1H-pyrazole

A solution of 1,1,1-trifluoropentane-2,4-dione (20.0 g, 0.130 mole) in glacial acetic acid (60 mL) was cooled to 7° C. using an ice/water bath. Phenylhydrazine (14.1 g, 0.130 mole) was added dropwise over a period of 60 minutes. The reaction mass temperature increased to 15° C. during the addition. The resulting orange solution was held under ambient conditions for 60 minutes. The bulk of the acetic acid was removed by stripping on a rotary evaporator at a bath temperature of 65° C. The residue was dissolved in methylene chloride (150 mL). The solution was washed with aqueous sodium bicarbonate (3 g in 50 mL water). The purple-red organic layer was separated, treated with activated charcoal (2 g) and $MgSO_4$, then filtered. Volatiles were removed on a rotary evaporator. The crude product consisted of 28.0 g of a rose-colored oil, which contained ~89% the desired product and 11% 1-phenyl-5-(trifluoromethyl)-3-methylpyrazole.

$^1$H NMR (DMSO-$D_6$) δ 2.35 (s, 3H), 6.76 (s, 1H), 7.6–7.5 (m, 5H).

Step B: Preparation of 1-Phenyl-3-(trifluoromethyl)-1H-pyrazole-5-carboxylic acid A sample of crude 1-phenyl-3-(trifluoromethyl)-5-methylpyrazole (~89%, 50.0 g, 0.221 mole) was mixed with water (400 mL) and cetyltrimethylammonium chloride (4.00 g, 0.011 mole). The mixture was heated to 95° C. Potassium permanganate was added in 10 equal portions, spaced at ~8 minute intervals. The reaction mass was maintained at 95–100° C. during this period. After the last portion was added, the mixture was held for ~15 minutes at 95–100° C., whereupon the purple, permanganate color had been discharged. The reaction mass was filtered while hot (~75° C.) through a 1 cm thick bed of Celite® on a 150 ml, coarse, glass frit. The filter cake was washed with warm (~50° C.) water (3×100 mL). The combined filtrate and washings were extracted with ether (2×100 mL) to remove a small amount of yellow, water-insoluble material. The aqueous layer was purged with nitrogen to remove residual ether. The clear, colorless alkaline solution was acidified by adding concentrated hydrochloric acid dropwise until the pH reached ~1.3 (28 g, 0.28 mole). Gas evolution was vigorous during the first two-thirds of the addition. The product was collected via filtration, washed with water (3×40 mL), then dried overnight at 55° C. in vacuo. The product consisted of 11.7 g of a white, crystalline powder, which was essentially pure based upon $^1H$ NMR.

$^1H$ NMR ($CDCl_3$) δ 7.33 (s, 1H), 7.4–7.5 (m, 5H).

Step C: Preparation of 1-Phenyl-3-(trifluoromethyl)-1H-pyrazole-5-carbonyl chloride A sample of crude 1-phenyl-3-(trifluoromethyl)pyrazole-5-carboxylic acid (4.13 g, 16.1 mmol) was dissolved in methylene chloride (45 mL). The solution was treated with oxalyl chloride (1.80 mL, 20.6 mmol), followed by N,N-dimethylformamide (0.010 mL, 0.13 mmol). Off-gassing began shortly after adding the N,N-dimethylformamide catalyst. The reaction mixture was stirred for ~20 minutes under ambient conditions, then was heated to reflux for a period of 35 minutes. Volatiles were removed by stripping the reaction mixture on a rotary evaporator at a bath temperature of 55° C. The product consisted of 4.43 g of a light-yellow oil. The only impurity observed by $^1H$ NMR was N,N-dimethylformamide.

$^1H$ NMR ($CDCl_3$) δ 7.40 (m, 1H), 7.42 (s, 1H), 7.50–7.53 (m, 4H).

Step D: Preparation of N-[2-Methyl-6-[[(1-methylethyl)amino]carbonyl]phenyl]-1-phenyl-3-(trifluoromethyl)-1H-pyrazole-5-carboxamide A sample of 3-methylisatoic anhydride (0.30 g, 1.7 mmol) partially dissolved in pyridine (4.0 mL) was treated with 1-phenyl-3-(trifluoromethylpyrazole)-5-carboxyl chloride (0.55 g, 1.9 mmol). The mixture was heated to ~95° C. for a period of 2 hours. The resulting orange solution was cooled to 29° C., then was treated with isopropylamine (1.00 g, 16.9 mmol). The reaction mass self-heated to 39° C. It was further heated to 55° C. for a period of 30 minutes, whereupon much precipitate formed. The reaction mass was dissolved in methylene chloride (150 mL). The solution was washed with aqueous acid (5 mL conc. HCl in 45 mL water), then with aqueous base (2 g sodium carbonate in 50 mL water). The organic layer was dried over $MgSO_4$, filtered, then concentrated on a rotary evaporator. Upon reduction to ~4 mL, product crystals had formed. The slurry was diluted with ~10 mL of ether, whereupon more product precipitated. The product was isolated by filtration, washed with ether (2×10 mL), then washed with water (2×50 mL). The wet cake was dried for 30 minutes at 70° C. in vacuo. The product consisted of 0.52 g of an off-white powder melting at 260–262° C.

$^1H$ NMR (DMSO-$D_6$) δ 1.07 (d, 6H), 2.21 (s, 3H), 4.02 (octet, 1H), 7.2–7.4 (m, 3H), 7.45–7.6 (m, 6H), 8.10 (d, 1H), 10.31 (s, 1H).

EXAMPLE 7

Step A: Preparation of 3-Trifluoromethyl-2-[3-(trifluoromethyl-1H-pyrazol-1-yl]pyridine A mixture of 2-chloro-3-trifluoromethylpyridine (3.62 g, 21 mmol), 3-trifluoromethylpyrazole (2.7 g, 20 mmol ), and potassium carbonate (6.0 g, 43 mmol) were heated at 100° C. for 18 h. The cooled reaction mixture was added to ice/water (100 mL). The mixture was extracted twice with ether (100 mL) and the combined ether extracts were washed twice with water (100 mL). The organic layer was dried with magnesium sulfate and concentrated to an oil. Chromatography on silica gel with hexanes:ethyl acetate 8:1 to 4:1 as eluent gave the title compound (3.5 g) as an oil. $^1H$ NMR ($CDCl_3$) δ 6.75 (m, 1H), 7.5 (m, 1H), 8.2 (m, 2H), 8.7 (m, 1H).

Step B: Preparation of 3-(Trifluoromethyl)-1-[3-(trifluoromethyl)-2-pyridinyl]-1H-pyrazole-5-carboxylic acid A mixture of the title compound of Example 5, Step A (3.4 g, 13 mmol) was dissolved in tetrahydrofuran (30 mL) and cooled to −70° C. Lithium diisopropylamide (2N in heptane/tetrahydrofuran, (Aldrich) 9.5 mL, 19 mmol) was added and the resulting dark mixture was stirred for 10 minutes. Dry carbon dioxide was bubbled through the mixture for 15 minutes. The mixture was allowed to warm to 23° C. and treated with water (50 mL) and 1 N sodium hydroxide (10 mL). The aqueous mixture was extracted with ether (100 mL) and then ethyl acetate (100 mL). The aqueous layer was acidified with 6N hydrochloric acid to pH 1–2 and extracted twice with dichloromethane. The organic layer was dried with magnesium sulfate and concentrated to give the title compound (1.5 g). $^1H$ NMR ($CDCl_3$) δ 7.6 (m, 1H), 7.95 (m, 1H), 8.56 (m, 1H), 8.9 (m, 1H), 14.2 (br, 1H)

Step C: Preparation of N-[2-Methyl-6-[[(1-methylethyl)amino]carbonyl]phenyl]-3-(trifluoromethyl)-1-[3-(trifluoromethyl)-2-pyridinyl]-1H-pyrazole-5-carboxamide A mixture of the title compound of Example 5, Step B (0.54 g, 1.1 mmol), the title compound from Example 1, Step B (0.44 g, 2.4 mmol) and bop chloride (bis(2-oxo-oxazolidinyl)phosphinyl chloride, 0.54 g, 2.1 mmol) in acetonitrile (13 mL) was treated with triethylamine (0.9 mL). The mixture was shaken in a closed scintillation vial for 18 h. The reaction was partitioned between ethyl acetate (100 mL) and 1N hydrochloric acid. The ethyl acetate layer was washed successively with 1N hydrochloric acid (50 mL), 1N sodium hydroxide (50 mL) and saturated sodium chloride solution (50 mL). The organic layer was dried over magnesium sulfate and concentrated. The residue was subjected to column chromatography on silica gel with hexanes/ethyl acetate (5:1 to 3:1) as eluent. The title compound (0.43 g) was isolated as a white solid. m.p. 227–230° C. $^1H$ NMR ($CDCl_3$) δ 1.2 (m, 6H), 4.15 (m, 1H), 5.9 (br d, 1H), 7.1 (m, 1H), 7.2 (m, 2H), 7.4 (s, 1H), 7.6 (m, 1H), 8.15 (m, 1H), 8.74 (m, 1H), 10.4 (br, 1H).

By the procedures described herein together with methods known in the art, the following compounds of Tables 1 to 17 can be prepared. The following abbreviations are used in the Tables: t is tertiary, s is secondary, n is normal, i is iso, c is cyclo, Me is methyl, Et is ethyl, Pr is propyl, i-Pr is isopropyl, t-Bu is tert butyl, Ph is phenyl, OMe is methoxy, OEt is ethoxy, SMe is methylthio, SEt is ethylthio, CN is cyano, $NO_2$ is nitro, TMS is trimethylsilyl, S(O)Me is methylsulfinyl, and $S(O)_2Me$ is methylsulfonyl.

TABLE 1

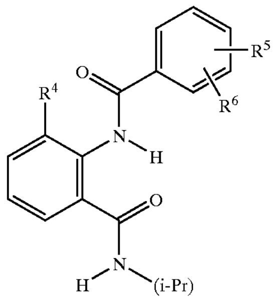

| $R^4$ | $R^5$ and/or $R^6$ | $R^4$ | $R^5$ and/or $R^6$ | $R^4$ | $R^5$ and/or $R^6$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| Cl | 2-$CF_3$ | Cl | 3-$CF_3$ | Cl | 4-$CF_3$ |
| Cl | 2-$OCF_3$ | Cl | 3-$OCF_3$ | Cl | 4-$OCF_3$ |
| Cl | 2-$OCF_2H$ | Cl | 3-$OCF_2H$ | Cl | 4-$OCF_2H$ |
| Cl | 2-$OCF_2CF_2H$ | Cl | 3-$OCF_2CF_2H$ | Cl | 4-$OCF_2CF_2H$ |
| Cl | 2-$OCH_2CF_3$ | Cl | 3-$OCH_2CF_3$ | Cl | 4-$OCF_2CF_3$ |
| Cl | 2-$SCF_3$ | Cl | 3-$SCF_3$ | Cl | 4-$SCF_3$ |
| Cl | 2-$SOCF_3$ | Cl | 3-$SOCF_3$ | Cl | 4-$SOCF_3$ |
| Cl | 2-$SO_2CF_3$ | Cl | 3-$SO_2CF_3$ | Cl | 4-$SO_2CF_3$ |
| Cl | 2-$SCF_2H$ | Cl | 3-$SCF_2H$ | Cl | 4-$SCF_2H$ |
| Cl | 2-$SOCF_2H$ | Cl | 3-$SOCF_2H$ | Cl | 4-$SOCF_2H$ |
| Cl | 2-$SO_2CF_2H$ | Cl | 3-$SO_2CF_2H$ | Cl | 4-$SO_2CF_2H$ |
| F | 2-$CF_3$ | F | 3-$CF_3$ | F | 4-$CF_3$ |
| F | 2-$OCF_3$ | F | 3-$OCF_3$ | F | 4-$OCF_3$ |
| F | 2-$OCF_2H$ | F | 3-$OCF_2H$ | F | 4-$OCF_2H$ |
| F | 2-$OCF_2CF_2H$ | F | 3-$OCF_2CF_2H$ | F | 4-$OCF_2CF_2H$ |
| F | 2-$OCH_2CF_3$ | F | 3-$OCH_2CF_3$ | F | 4-$OCH_2CF_3$ |
| F | 2-$SCF_3$ | F | 3-$SCF_3$ | F | 4-$SCF_3$ |
| F | 2-$SOCF_3$ | F | 3-$SOCF_3$ | F | 4-$SOCF_3$ |
| F | 2-$SO_2CF_3$ | F | 3-$SO_2CF_3$ | F | 4-$SO_2CF_3$ |
| F | 2-$SCF_2H$ | F | 3-$SCF_2H$ | F | 4-$SCF_2H$ |
| F | 2-$SOCF_2H$ | F | 3-$SOCF_2H$ | F | 4-$SOCF_2H$ |
| F | 2-$SO_2CF_2H$ | F | 3-$SO_2CF_2H$ | F | 4-$SO_2CF_2H$ |
| Br | 2-$CF_3$ | Br | 3-$CF_3$ | Br | 4-$CF_3$ |
| Br | 2-$OCF_3$ | Br | 3-$OCF_3$ | Br | 4-$OCF_3$ |
| Br | 2-$OCF_2H$ | Br | 3-$OCF_2H$ | Br | 4-$OCF_2H$ |
| Br | 2-$OCF_2CF_2H$ | Br | 3-$OCF_2CF_2H$ | Br | 4-$OCF_2CF_2H$ |
| Br | 2-$OCH_2CF_3$ | Br | 3-$OCH_2CF_3$ | Br | 4-$OCH_2CF_3$ |
| Br | 2-$SCF_3$ | Br | 3-$SCF_3$ | Br | 4-$SCF_3$ |
| Br | 2-$SOCF_3$ | Br | 3-$SOCF_3$ | Br | 4-$SOCF_3$ |
| Br | 2-$SO_2CF_3$ | Br | 3-$SO_2CF_3$ | Br | 4-$SO_2CF_3$ |
| Br | 2-$SCF_2H$ | Br | 3-$SCF_2H$ | Br | 4-$SCF_2H$ |
| Br | 2-$SOCF_2H$ | Br | 3-$SOCF_2H$ | Br | 4-$SOCF_2H$ |
| Br | 2-$SO_2CF_2H$ | Br | 3-$SO_2CF_2H$ | Br | 4-$SO_2CF_2H$ |
| I | 2-$CF_3$ | I | 3-$CF_3$ | I | 4-$CF_3$ |
| I | 2-$OCF_3$ | I | 3-$OCF_3$ | I | 4-$OCF_3$ |
| I | 2-$OCF_2H$ | I | 3-$OCF_2H$ | I | 4-$OCF_2H$ |
| I | 2-$OCF_2CF_2H$ | I | 3-$OCF_2CF_2H$ | I | 4-$OCF_2CF_2H$ |
| I | 2-$OCH_2CF_3$ | I | 3-$OCH_2CF_3$ | I | 4-$OCH_2CF_3$ |
| I | 2-$SCF_3$ | I | 3-$SCF_3$ | I | 4-$SCF_3$ |
| I | 2-$SOCF_3$ | I | 3-$SOCF_3$ | I | 4-$SOCF_3$ |
| I | 2-$SO_2CF_3$ | I | 3-$SO_2CF_3$ | I | 4-$SO_2CF_3$ |
| I | 2-$SCF_2H$ | I | 3-$SCF_2H$ | I | 4-$SCF_2H$ |
| I | 2-$SOCF_2H$ | I | 3-$SOCF_2H$ | I | 4-$SOCF_2H$ |
| I | 2-$SO_2CF_2H$ | I | 3-$SO_2CF_2H$ | I | 4-$SO_2CF_2H$ |
| OMe | 2-$CF_3$ | OMe | 3-$CF_3$ | OMe | 4-$CF_3$ |
| OMe | 2-$OCF_3$ | OMe | 3-$OCF_3$ | OMe | 4-$OCF_3$ |
| OMe | 2-$OCF_2H$ | OMe | 3-$OCF_2H$ | OMe | 4-$OCF_2H$ |
| OMe | 2-$OCF_2CF_2H$ | OMe | 3-$OCF_2CF_2H$ | OMe | 4-$OCF_2CF_2H$ |
| OMe | 2-$OCH_2CF_3$ | OMe | 3-$OCH_2CF_3$ | OMe | 4-$OCH_2CF_3$ |
| OMe | 2-$SCF_3$ | OMe | 3-$SCF_3$ | OMe | 4-$SCF_3$ |
| OMe | 2-$SOCF_3$ | OMe | 3-$SOCF_3$ | OMe | 4-$SOCF_3$ |

TABLE 1-continued

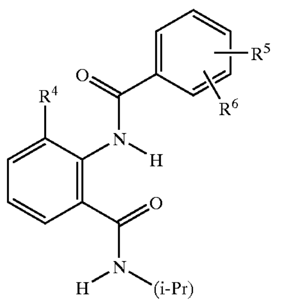

| $R^4$ | $R^5$ and/or $R^6$ | $R^4$ | $R^5$ and/or $R^6$ | $R^4$ | $R^5$ and/or $R^6$ |
|---|---|---|---|---|---|
| OMe | 2-$SO_2CF_3$ | OMe | 3-$SO_2CF_3$ | OMe | 4-$SO_2CF_3$ |
| OMe | 2-$SCF_2H$ | OMe | 3-$SCF_2H$ | OMe | 4-$SCF_2H$ |
| OMe | 2-$SOCF_2H$ | OMe | 3-$SOCF_2H$ | OMe | 4-$SOCF_2H$ |
| OMe | 2-$SO_2CF_2H$ | OMe | 3-$SO_2CF_2H$ | OMe | 4-$SO_2CF_2H$ |
| $CF_3$ | 2-$CF_3$ | $CF_3$ | 3-$CF_3$ | $CF_3$ | 4-$CF_3$ |
| $CF_3$ | 2-$OCF_3$ | $CF_3$ | 3-$OCF_3$ | $CF_3$ | 4-$OCF_3$ |
| $CF_3$ | 2-$OCF_2H$ | $CF_3$ | 3-$OCF_2H$ | $CF_3$ | 4-$OCF_2H$ |
| $CF_3$ | 2-$OCF_2CF_2H$ | $CF_3$ | 3-$OCF_2CF_2H$ | $CF_3$ | 4-$OCF_2CF_2H$ |
| $CF_3$ | 2-$OCH_2CF_3$ | $CF_3$ | 3-$OCH_2CF_3$ | $CF_3$ | 4-$OCH_2CF_3$ |
| $CF_3$ | 2-$SCF_3$ | $CF_3$ | 3-$SCF_3$ | $CF_3$ | 4-$SCF_3$ |
| $CF_3$ | 2-$SOCF_3$ | $CF_3$ | 3-$SOCF_3$ | $CF_3$ | 4-$SOCF_3$ |
| $CF_3$ | 2-$SO_2CF_3$ | $CF_3$ | 3-$SO_2CF_3$ | $CF_3$ | 4-$SO_2CF_3$ |
| $CF_3$ | 2-$SCF_2H$ | $CF_3$ | 3-$SCF_2H$ | $CF_3$ | 4-$SCF_2H$ |
| $CF_3$ | 2-$SOCF_2H$ | $CF_3$ | 3-$SOCF_2H$ | $CF_3$ | 4-$SOCF_2H$ |
| $CF_3$ | 2-$SO_2CF_2H$ | $CF_3$ | 3-$SO_2CF_2H$ | $CF_3$ | 4-$SO_2CF_2H$ |
| $OCF_2H$ | 2-$CF_3$ | $OCF_2H$ | 3-$CF_3$ | $OCF_2H$ | 4-$CF_3$ |
| $OCF_2H$ | 2-$OCF_3$ | $OCF_2H$ | 3-$OCF_3$ | $OCF_2H$ | 4-$OCF_3$ |
| $OCF_2H$ | 2-$OCF_2H$ | $OCF_2H$ | 3-$OCF_2H$ | $OCF_2H$ | 4-$OCF_2H$ |
| $OCF_2H$ | 2-$OCF_2CF_2H$ | $OCF_2H$ | 3-$OCF_2CF_2H$ | $OCF_2H$ | 4-$OCF_2CF_2H$ |
| $OCF_2H$ | 2-$OCH_2CF_3$ | $OCF_2H$ | 3-$OCH_2CF_3$ | $OCF_2H$ | 4-$OCH_2CF_3$ |
| $OCF_2H$ | 2-$SCF_3$ | $OCF_2H$ | 3-$SCF_3$ | $OCF_2H$ | 4-$SCF_3$ |
| $OCF_2H$ | 2-$SOCF_3$ | $OCF_2H$ | 3-$SOCF_3$ | $OCF_2H$ | 4-$SOCF_3$ |
| $OCF_2H$ | 2-$SO_2CF_3$ | $OCF_2H$ | 3-$SO_2CF_3$ | $OCF_2H$ | 4-$SO_2CF_3$ |
| $OCF_2H$ | 2-$SCF_2H$ | $OCF_2H$ | 3-$SCF_2H$ | $OCF_2H$ | 4-$SCF_2H$ |
| $OCF_2H$ | 2-$SOCF_2H$ | $OCF_2H$ | 3-$SOCF_2H$ | $OCF_2H$ | 4-$SOCF_2H$ |
| $OCF_2H$ | 2-$SO_2CF_2H$ | $OCF_2H$ | 3-$SO_2CF_2H$ | $OCF_2H$ | 4-$SO_2CF_2H$ |
| Me | 2-Me-4-$CF_3$ | F | 2-Me-4-$CF_3$ | Cl | 2-Me-4-$CF_3$ |
| Me | 2-Me-4-$OCF_3$ | F | 2-Me-4-$OCF_3$ | Cl | 2-Me-4-$OCF_3$ |
| Me | 2-Me-4-$OCF_2H$ | F | 2-Me-4-$OCF_2H$ | Cl | 2-Me-4-$OCF_2H$ |
| Me | 2-Me-4-$OCH_2CF_3$ | F | 2-Me-4-$OCH_2CF_3$ | Cl | 2-Me-4-$OCH_2CF_3$ |
| Me | 2-Me-4-$SCF_3$ | F | 2-Me-4-$SCF_3$ | Cl | 2-Me-4-$SCF_3$ |
| Me | 2-Me-4-$SOCF_3$ | F | 2-Me-4-$SOCF_3$ | Cl | 2-Me-4-$SOCF_3$ |
| Me | 2-Me-4-$SO_2CF_3$ | F | 2-Me-4-$SO_2CF_3$ | Cl | 2-Me-4-$SO_2CF_3$ |
| Me | 2-Me-4-$SCF_2H$ | F | 2-Me-4-$SCF_2H$ | Cl | 2-Me-4-$SCF_2H$ |
| Me | 2-Me-4-$SOCF_2H$ | F | 2-Me-4-$SOCF_2H$ | Cl | 2-Me-4-$SOCF_2H$ |
| Me | 2-Me-4-$SO_2CF_2H$ | F | 2-Me-4-$SO_2CF_2H$ | Cl | 2-Me-4-$SO_2CF_2H$ |
| Br | 2-Me-4-$CF_3$ | I | 2-Me-4-$CF_3$ | OMe | 2-Me-4-$CF_3$ |
| Br | 2-Me-4-$OCF_3$ | I | 2-Me-4-$OCF_3$ | OMe | 2-Me-4-$OCF_3$ |
| Br | 2-Me-4-$OCF_2H$ | I | 2-Me-4-$OCF_2H$ | OMe | 2-Me-4-$OCF_2H$ |
| Br | 2-Me-4-$OCH_2CF_3$ | I | 2-Me-4-$OCH_2CF_3$ | OMe | 2-Me-4-$OCH_2CF_3$ |
| Br | 2-Me-4-$SCF_3$ | I | 2-Me-4-$SCF_3$ | OMe | 2-Me-4-$SCF_3$ |
| Br | 2-Me-4-$SOCF_3$ | I | 2-Me-4-$SOCF_3$ | OMe | 2-Me-4-$SOCF_3$ |
| Br | 2-Me-4-$SO_2CF_3$ | I | 2-Me-4-$SO_2CF_3$ | OMe | 2-Me-4-$SO_2CF_3$ |
| Br | 2-Me-4-$SCF_2H$ | I | 2-Me-4-$SCF_2H$ | OMe | 2-Me-4-$SCF_2H$ |
| Br | 2-Me-4-$SOCF_2H$ | I | 2-Me-4-$SOCF_2H$ | OMe | 2-Me-4-$SOCF_2H$ |
| Br | 2-Me-4-$SO_2CF_2H$ | I | 2-Me-4-$SO_2CF_2H$ | OMe | 2-Me-4-$SO_2CF_2H$ |
| $CF_3$ | 2-Me-4-$CF_3$ | $NO_2$ | 2-Me-4-$CF_3$ | SMe | 2-Me-4-$CF_3$ |
| $CF_3$ | 2-Me-4-$OCF_3$ | $NO_2$ | 2-Me-4-$OCF_3$ | SMe | 2-Me-4-$OCF_3$ |
| $CF_3$ | 2-Me-4-$OCF_2H$ | $NO_2$ | 2-Me-4-$OCF_2H$ | SMe | 2-Me-4-$OCF_2H$ |
| $CF_3$ | 2-Me-4-$OCH_2CF_3$ | $NO_2$ | 2-Me-4-$OCH_2CF_3$ | SMe | 2-Me-4-$OCH_2CF_3$ |
| $CF_3$ | 2-Me-4-$SCF_3$ | $NO_2$ | 2-Me-4-$SCF_3$ | SMe | 2-Me-4-$SCF_3$ |
| $CF_3$ | 2-Me-4-$SOCF_3$ | $NO_2$ | 2-Me-4-$SOCF_3$ | SMe | 2-Me-4-$SOCF_3$ |
| $CF_3$ | 2-Me-4-$SO_2CF_3$ | $NO_2$ | 2-Me-4-$SO_2CF_3$ | SMe | 2-Me-4-$SO_2CF_3$ |
| $CF_3$ | 2-Me-4-$SCF_2H$ | $NO_2$ | 2-Me-4-$SCF_2H$ | SMe | 2-Me-4-$SCF_2H$ |
| $CF_3$ | 2-Me-4-$SOCF_2H$ | $NO_2$ | 2-Me-4-$SOCF_2H$ | SMe | 2-Me-4-$SOCF_2H$ |
| $CF_3$ | 2-Me-4-$SO_2CF_2H$ | $NO_2$ | 2-Me-4-$SO_2CF_2H$ | SMe | 2-Me-4-$SO_2CF_2H$ |

TABLE 2

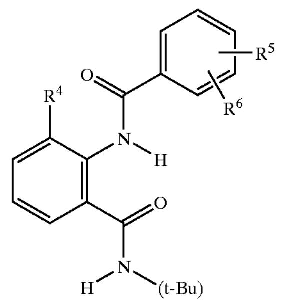

| $R^4$ | $R^5$ and/or $R^6$ | $R^4$ | $R^5$ and/or $R^6$ | $R^4$ | $R^5$ and/or $R^6$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| Cl | 2-$CF_3$ | Cl | 3-$CF_3$ | Cl | 4-$CF_3$ |
| Cl | 2-$OCF_3$ | Cl | 3-$OCF_3$ | Cl | 4-$OCF_3$ |
| Cl | 2-$OCF_2H$ | Cl | 3-$OCF_2H$ | Cl | 4-$OCF_2H$ |
| Cl | 2-$OCF_2CF_2H$ | Cl | 3-$OCF_2CF_2H$ | Cl | 4-$OCF_2CF_2H$ |
| Cl | 2-$OCH_2CF_3$ | Cl | 3-$OCH_2CF_3$ | Cl | 4-$OCH_2CF_3$ |
| Cl | 2-$SCF_3$ | Cl | 3-$SCF_3$ | Cl | 4-$SCF_3$ |
| Cl | 2-$SOCF_3$ | Cl | 3-$SOCF_3$ | Cl | 4-$SOCF_3$ |
| Cl | 2-$SO_2CF_3$ | Cl | 3-$SO_2CF_3$ | Cl | 4-$SO_2CF_3$ |
| Cl | 2-$SCF_2H$ | Cl | 3-$SCF_2H$ | Cl | 4-$SCF_2H$ |
| Cl | 2-$SOCF_2H$ | Cl | 3-$SOCF_2H$ | Cl | 4-$SOCF_2H$ |
| Cl | 2-$SO_2CF_2H$ | Cl | 3-$SO_2CF_2H$ | Cl | 4-$SO_2CF_2H$ |
| F | 2-$CF_3$ | F | 3-$CF_3$ | F | 4-$CF_3$ |
| F | 2-$OCF_3$ | F | 3-$OCF_3$ | F | 4-$OCF_3$ |
| F | 2-$OCF_2H$ | F | 3-$OCF_2H$ | F | 4-$OCF_2H$ |
| F | 2-$OCF_2CF_2H$ | F | 3-$OCF_2CF_2H$ | F | 4-$OCF_2CF_2H$ |
| F | 2-$OCH_2CF_3$ | F | 3-$OCH_2CF_3$ | F | 4-$OCH_2CF_3$ |
| F | 2-$SCF_3$ | F | 3-$SCF_3$ | F | 4-$SCF_3$ |
| F | 2-$SOCF_3$ | F | 3-$SOCF_3$ | F | 4-$SOCF_3$ |
| F | 2-$SO_2CF_3$ | F | 3-$SO_2CF_3$ | F | 4-$SO_2CF_3$ |
| F | 2-$SCF_2H$ | F | 3-$SCF_2H$ | F | 4-$SCF_2H$ |
| F | 2-$SOCF_2H$ | F | 3-$SOCF_2H$ | F | 4-$SOCF_2H$ |
| F | 2-$SO_2CF_2H$ | F | 3-$SO_2CF_2H$ | F | 4-$SO_2CF_2H$ |
| Br | 2-$CF_3$ | Br | 3-$CF_3$ | Br | 4-$CF_3$ |
| Br | 2-$OCF_3$ | Br | 3-$OCF_3$ | Br | 4-$OCF_3$ |
| Br | 2-$OCF_2H$ | Br | 3-$OCF_2H$ | Br | 4-$OCF_2H$ |
| Br | 2-$OCF_2CF_2H$ | Br | 3-$OCF_2CF_2H$ | Br | 4-$OCF_2CF_2H$ |
| Br | 2-$OCH_2CF_3$ | Br | 3-$OCH_2CF_3$ | Br | 4-$OCH_2CF_3$ |
| Br | 2-$SCF_3$ | Br | 3-$SCF_3$ | Br | 4-$SCF_3$ |
| Br | 2-$SOCF_3$ | Br | 3-$SOCF_3$ | Br | 4-$SOCF_3$ |
| Br | 2-$SO_2CF_3$ | Br | 3-$SO_2CF_3$ | Br | 4-$SO_2CF_3$ |
| Br | 2-$SCF_2H$ | Br | 3-$SCF_2H$ | Br | 4-$SCF_2H$ |
| Br | 2-$SOCF_2H$ | Br | 3-$SOCF_2H$ | Br | 4-$SOCF_2H$ |
| Br | 2-$SO_2CF_2H$ | Br | 3-$SO_2CF_2H$ | Br | 4-$SO_2CF_2H$ |
| I | 2-$CF_3$ | I | 3-$CF_3$ | I | 4-$CF_3$ |
| I | 2-$OCF_3$ | I | 3-$OCF_3$ | I | 4-$OCF_3$ |
| I | 2-$OCF_2H$ | I | 3-$OCF_2H$ | I | 4-$OCF_2H$ |
| I | 2-$OCF_2CF_2H$ | I | 3-$OCF_2CF_2H$ | I | 4-$OCF_2CF_2H$ |
| I | 2-$OCH_2CF_3$ | I | 3-$OCH_2CF_3$ | I | 4-$OCH_2CF_3$ |
| I | 2-$SCF_3$ | I | 3-$SCF_3$ | I | 4-$SCF_3$ |
| I | 2-$SOCF_3$ | I | 3-$SOCF_3$ | I | 4-$SOCF_3$ |
| I | 2-$SO_2CF_3$ | I | 3-$SO_2CF_3$ | I | 4-$SO_2CF_3$ |
| I | 2-$SCF_2H$ | I | 3-$SCF_2H$ | I | 4-$SCF_2H$ |
| I | 2-$SOCF_2H$ | I | 3-$SOCF_2H$ | I | 4-$SOCF_2H$ |
| I | 2-$SO_2CF_2H$ | I | 3-$SO_2CF_2H$ | I | 4-$SO_2CF_2H$ |
| OMe | 2-$CF_3$ | OMe | 3-$CF_3$ | OMe | 4-$CF_3$ |
| OMe | 2-$OCF_3$ | OMe | 3-$OCF_3$ | OMe | 4-$OCF_3$ |
| OMe | 2-$OCF_2H$ | OMe | 3-$OCF_2H$ | OMe | 4-$OCF_2H$ |
| OMe | 2-$OCF_2CF_2H$ | OMe | 3-$OCF_2CF_2H$ | OMe | 4-$OCF_2CF_2H$ |
| OMe | 2-$OCH_2CF_3$ | OMe | 3-$OCH_2CF_3$ | OMe | 4-$OCH_2CF_3$ |
| OMe | 2-$SCF_3$ | OMe | 3-$SCF_3$ | OMe | 4-$SCF_3$ |
| OMe | 2-$SOCF_3$ | OMe | 3-$SOCF_3$ | OMe | 4-$SOCF_3$ |

TABLE 2-continued

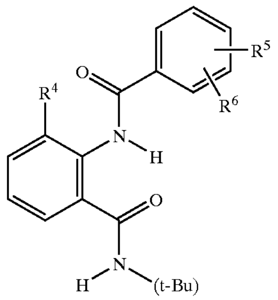

| $R^4$ | $R^5$ and/or $R^6$ | $R^4$ | $R^5$ and/or $R^6$ | $R^4$ | $R^5$ and/or $R^6$ |
|---|---|---|---|---|---|
| OMe | 2-$SO_2CF_3$ | OMe | 3-$SO_2CF_3$ | OMe | 4-$SO_2CF_3$ |
| OMe | 2-$SCF_2H$ | OMe | 3-$SCF_2H$ | OMe | 4-$SCF_2H$ |
| OMe | 2-$SOCF_2H$ | OMe | 3-$SOCF_2H$ | OMe | 4-$SOCF_2H$ |
| OMe | 2-$SO_2CF_2H$ | OMe | 3-$SO_2CF_2H$ | OMe | 4-$SO_2CF_2H$ |
| $CF_3$ | 2-$CF_3$ | $CF_3$ | 3-$CF_3$ | $CF_3$ | 4-$CF_3$ |
| $CF_3$ | 2-$OCF_3$ | $CF_3$ | 3-$OCF_3$ | $CF_3$ | 4-$OCF_3$ |
| $CF_3$ | 2-$OCF_2H$ | $CF_3$ | 3-$OCF_2H$ | $CF_3$ | 4-$OCF_2H$ |
| $CF_3$ | 2-$OCF_2CF_2H$ | $CF_3$ | 3-$OCF_2CF_2H$ | $CF_3$ | 4-$OCF_2CF_2H$ |
| $CF_3$ | 2-$OCH_2CF_3$ | $CF_3$ | 3-$OCH_2CF_3$ | $CF_3$ | 4-$OCH_2CF_3$ |
| $CF_3$ | 2-$SCF_3$ | $CF_3$ | 3-$SCF_3$ | $CF_3$ | 4-$SCF_3$ |
| $CF_3$ | 2-$SOCF_3$ | $CF_3$ | 3-$SOCF_3$ | $CF_3$ | 4-$SOCF_3$ |
| $CF_3$ | 2-$SO_2CF_3$ | $CF_3$ | 3-$SO_2CF_3$ | $CF_3$ | 4-$SO_2CF_3$ |
| $CF_3$ | 2-$SCF_2H$ | $CF_3$ | 3-$SCF_2H$ | $CF_3$ | 4-$SCF_2H$ |
| $CF_3$ | 2-$SOCF_2H$ | $CF_3$ | 3-$SOCF_2H$ | $CF_3$ | 4-$SOCF_2H$ |
| $CF_3$ | 2-$SO_2CF_2H$ | $CF_3$ | 3-$SO_2CF_2H$ | $CF_3$ | 4-$SO_2CF_2H$ |
| $OCF_2H$ | 2-$CF_3$ | $OCF_2H$ | 3-$CF_3$ | $OCF_2H$ | 4-$CF_3$ |
| $OCF_2H$ | 2-$OCF_3$ | $OCF_2H$ | 3-$OCF_3$ | $OCF_2H$ | 4-$OCF_3$ |
| $OCF_2H$ | 2-$OCF_2H$ | $OCF_2H$ | 3-$OCF_2H$ | $OCF_2H$ | 4-$OCF_2H$ |
| $OCF_2H$ | 2-$OCF_2CF_2H$ | $OCF_2H$ | 3-$OCF_2CF_2H$ | $OCF_2H$ | 4-$OCF_2CF_2H$ |
| $OCF_2H$ | 2-$OCH_2CF_3$ | $OCF_2H$ | 3-$OCH_2CF_3$ | $OCF_2H$ | 4-$OCH_2CF_3$ |
| $OCF_2H$ | 2-$SCF_3$ | $OCF_2H$ | 3-$SCF_3$ | $OCF_2H$ | 4-$SCF_3$ |
| $OCF_2H$ | 2-$SOCF_3$ | $OCF_2H$ | 3-$SOCF_3$ | $OCF_2H$ | 4-$SOCF_3$ |
| $OCF_2H$ | 2-$SO_2CF_3$ | $OCF_2H$ | 3-$SO_2CF_3$ | $OCF_2H$ | 4-$SO_2CF_3$ |
| $OCF_2H$ | 2-$SCF_2H$ | $OCF_2H$ | 3-$SCF_2H$ | $OCF_2H$ | 4-$SCF_2H$ |
| $OCF_2H$ | 2-$SOCF_2H$ | $OCF_2H$ | 3-$SOCF_2H$ | $OCF_2H$ | 4-$SOCF_2H$ |
| $OCF_2H$ | 2-$SO_2CF_2H$ | $OCF_2H$ | 3-$SO_2CF_2H$ | $OCF_2H$ | 4-$SO_2CF_2H$ |
| Me | 2-Me-4-$CF_3$ | F | 2-Me-4-$CF_3$ | Cl | 2-Me-4-$CF_3$ |
| Me | 2-Me-4-$OCF_3$ | F | 2-Me-4-$OCF_3$ | Cl | 2-Me-4-$OCF_3$ |
| Me | 2-Me-4-$OCF_2H$ | F | 2-Me-4-$OCF_2H$ | Cl | 2-Me-4-$OCF_2H$ |
| Me | 2-Me-4-$OCH_2CF_3$ | F | 2-Me-4-$OCH_2CF_3$ | Cl | 2-Me-4-$OCF_2CF_3$ |
| Me | 2-Me-4-$SCF_3$ | F | 2-Me-4-$SCF_3$ | Cl | 2-Me-4-$SCF_3$ |
| Me | 2-Me-4-$SOCF_3$ | F | 2-Me-4-$SOCF_3$ | Cl | 2-Me-4-$SOCF_3$ |
| Me | 2-Me-4-$SO_2CF_3$ | F | 2-Me-4-$SO_2CF_3$ | Cl | 2-Me-4-$SO_2CF_3$ |
| Me | 2-Me-4-$SCF_2H$ | F | 2-Me-4-$SCF_2H$ | Cl | 2-Me-4-$SCF_2H$ |
| Me | 2-Me-4-$SOCF_2H$ | F | 2-Me-4-$SOCF_2H$ | Cl | 2-Me-4-$SOCF_2H$ |
| Me | 2-Me-4-$SO_2CF_2H$ | F | 2-Me-4-$SO_2CF_2H$ | Cl | 2-Me-4-$SO_2CF_2H$ |
| Br | 2-Me-4-$CF_3$ | I | 2-Me-4-$CF_3$ | OMe | 2-Me-4-$CF_3$ |
| Br | 2-Me-4-$OCF_3$ | I | 2-Me-4-$OCF_3$ | OMe | 2-Me-4-$OCF_3$ |
| Br | 2-Me-4-$OCF_2H$ | I | 2-Me-4-$OCF_2H$ | OMe | 2-Me-4-$OCF_2H$ |
| Br | 2-Me-4-$OCH_2CF_3$ | I | 2-Me-4-$OCH_2CF_3$ | OMe | 2-Me-4-$OCH_2CF_3$ |
| Br | 2-Me-4-$SCF_3$ | I | 2-Me-4-$SCF_3$ | OMe | 2-Me-4-$SCF_3$ |
| Br | 2-Me-4-$SOCF_3$ | I | 2-Me-4-$SOCF_3$ | OMe | 2-Me-4-$SOCF_3$ |
| Br | 2-Me-4-$SO_2CF_3$ | I | 2-Me-4-$SO_2CF_3$ | OMe | 2-Me-4-$SO_2CF_3$ |
| Br | 2-Me-4-$SCF_2H$ | I | 2-Me-4-$SCF_2H$ | OMe | 2-Me-4-$SCF_2H$ |
| Br | 2-Me-4-$SOCF_2H$ | I | 2-Me-4-$SOCF_2H$ | OMe | 2-Me-4-$SOCF_2H$ |
| Br | 2-Me-4-$SO_2CF_2H$ | I | 2-Me-4-$SO_2CF_2H$ | OMe | 2-Me-4-$SO_2CF_2H$ |
| $CF_3$ | 2-Me-4-$CF_3$ | $NO_2$ | 2-Me-4-$CF_3$ | SMe | 2-Me-4-$CF_3$ |
| $CF_3$ | 2-Me-4-$OCF_3$ | $NO_2$ | 2-Me-4-$OCF_3$ | SMe | 2-Me-4-$OCF_3$ |
| $CF_3$ | 2-Me-4-$OCF_2H$ | $NO_2$ | 2-Me-4-$OCF_2H$ | SMe | 2-Me-4-$OCF_2H$ |
| $CF_3$ | 2-Me-4-$OCH_2CF_3$ | $NO_2$ | 2-Me-4-$OCH_2CF_3$ | SMe | 2-Me-4-$OCH_2CF_3$ |
| $CF_3$ | 2-Me-4-$SCF_3$ | $NO_2$ | 2-Me-4-$SCF_3$ | SMe | 2-Me-4-$SCF_3$ |
| $CF_3$ | 2-Me-4-$SOCF_3$ | $NO_2$ | 2-Me-4-$SOCF_3$ | SMe | 2-Me-4-$SOCF_3$ |
| $CF_3$ | 2-Me-4-$SO_2CF_3$ | $NO_2$ | 2-Me-4-$SO_2CF_3$ | SMe | 2-Me-4-$SO_2CF_3$ |
| $CF_3$ | 2-Me-4-$SCF_2H$ | $NO_2$ | 2-Me-4-$SCF_2H$ | SMe | 2-Me-4-$SCF_2H$ |
| $CF_3$ | 2-Me-4-$SOCF_2H$ | $NO_2$ | 2-Me-4-$SOCF_2H$ | SMe | 2-Me-4-$SOCF_2H$ |
| $CF_3$ | 2-Me-4-$SO_2CF_2H$ | $NO_2$ | 2-Me-4-$SO_2CF_2H$ | SMe | 2-Me-4-$SO_2CF_2H$ |

TABLE 3

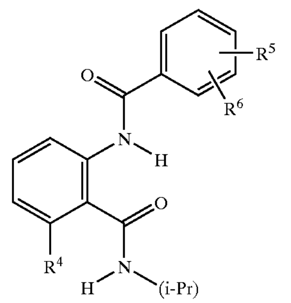

| $R^4$ | $R^5$ and/or $R^6$ | $R^4$ | $R^5$ and/or $R^6$ | $R^4$ | $R^5$ and/or $R^6$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| Cl | 2-$CF_3$ | Cl | 3-$CF_3$ | Cl | 4-$CF_3$ |
| Cl | 2-$OCF_3$ | Cl | 3-$OCF_3$ | Cl | 4-$OCF_3$ |
| Cl | 2-$OCF_2H$ | Cl | 3-$OCF_2H$ | Cl | 4-$OCF_2H$ |
| Cl | 2-$OCF_2CF_2H$ | Cl | 3-$OCF_2CF_2H$ | Cl | 4-$OCF_2CF_2H$ |
| Cl | 2-$OCH_2CF_3$ | Cl | 3-$OCH_2CF_3$ | Cl | 4-$OCH_2CF_3$ |
| Cl | 2-$SCF_3$ | Cl | 3-$SCF_3$ | Cl | 4-$SCF_3$ |
| Cl | 2-$SOCF_3$ | Cl | 3-$SOCF_3$ | Cl | 4-$SOCF_3$ |
| Cl | 2-$SO_2CF_3$ | Cl | 3-$SO_2CF_3$ | Cl | 4-$SO_2CF_3$ |
| Cl | 2-$SCF_2H$ | Cl | 3-$SCF_2H$ | Cl | 4-$SCF_2H$ |
| Cl | 2-$SOCF_2H$ | Cl | 3-$SOCF_2H$ | Cl | 4-$SOCF_2H$ |
| Cl | 2-$SO_2CF_2H$ | Cl | 3-$SO_2CF_2H$ | Cl | 4-$SO_2CF_2H$ |
| F | 2-$CF_3$ | F | 3-$CF_3$ | F | 4-$CF_3$ |
| F | 2-$OCF_3$ | F | 3-$OCF_3$ | F | 4-$OCF_3$ |
| F | 2-$OCF_2H$ | F | 3-$OCF_2H$ | F | 4-$OCF_2H$ |
| F | 2-$OCF_2CF_2H$ | F | 3-$OCF_2CF_2H$ | F | 4-$OCF_2CF_2H$ |
| F | 2-$OCH_2CF_3$ | F | 3-$OCH_2CF_3$ | F | 4-$OCH_2CF_3$ |
| F | 2-$SCF_3$ | F | 3-$SCF_3$ | F | 4-$SCF_3$ |
| F | 2-$SOCF_3$ | F | 3-$SOCF_3$ | F | 4-$SOCF_3$ |
| F | 2-$SO_2CF_3$ | F | 3-$SO_2CF_3$ | F | 4-$SO_2CF_3$ |
| F | 2-$SCF_2H$ | F | 3-$SCF_2H$ | F | 4-$SCF_2H$ |
| F | 2-$SOCF_2H$ | F | 3-$SOCF_2H$ | F | 4-$SOCF_2H$ |
| F | 2-$SO_2CF_2H$ | F | 3-$SO_2CF_2H$ | F | 4-$SO_2CF_2H$ |
| Br | 2-$CF_3$ | Br | 3-$CF_3$ | Br | 4-$CF_3$ |
| Br | 2-$OCF_3$ | Br | 3-$OCF_3$ | Br | 4-$OCF_3$ |
| Br | 2-$OCF_2H$ | Br | 3-$OCF_2H$ | Br | 4-$OCF_2H$ |
| Br | 2-$OCF_2CF_2H$ | Br | 3-$OCF_2CF_2H$ | Br | 4-$OCF_2CF_2H$ |
| Br | 2-$OCH_2CF_3$ | Br | 3-$OCH_2CF_3$ | Br | 4-$OCH_2CF_3$ |
| Br | 2-$SCF_3$ | Br | 3-$SCF_3$ | Br | 4-$SCF_3$ |
| Br | 2-$SOCF_3$ | Br | 3-$SOCF_3$ | Br | 4-$SOCF_3$ |
| Br | 2-$SO_2CF_3$ | Br | 3-$SO_2CF_3$ | Br | 4-$SO_2CF_3$ |
| Br | 2-$SCF_2H$ | Br | 3-$SCF_2H$ | Br | 4-$SCF_2H$ |
| Br | 2-$SOCF_2H$ | Br | 3-$SOCF_2H$ | Br | 4-$SOCF_2H$ |
| Br | 2-$SO_2CF_2H$ | Br | 3-$SO_2CF_2H$ | Br | 4-$SO_2CF_2H$ |
| I | 2-$CF_3$ | I | 3-$CF_3$ | I | 4-$CF_3$ |
| I | 2-$OCF_3$ | I | 3-$OCF_3$ | I | 4-$OCF_3$ |
| I | 2-$OCF_2H$ | I | 3-$OCF_2H$ | I | 4-$OCF_2H$ |
| I | 2-$OCF_2CF_2H$ | I | 3-$OCF_2CF_2H$ | I | 4-$OCF_2CF_2H$ |
| I | 2-$OCH_2CF_3$ | I | 3-$OCH_2CF_3$ | I | 4-$OCH_2CF_3$ |
| I | 2-$SCF_3$ | I | 3-$SCF_3$ | I | 4-$SCF_3$ |
| I | 2-$SOCF_3$ | I | 3-$SOCF_3$ | I | 4-$SOCF_3$ |
| I | 2-$SO_2CF_3$ | I | 3-$SO_2CF_3$ | I | 4-$SO_2CF_3$ |
| I | 2-$SCF_2H$ | I | 3-$SCF_2H$ | I | 4-$SCF_2H$ |
| I | 2-$SOCF_2H$ | I | 3-$SOCF_2H$ | I | 4-$SOCF_2H$ |
| I | 2-$SO_2CF_2H$ | I | 3-$SO_2CF_2H$ | I | 4-$SO_2CF_2H$ |
| OMe | 2-$CF_3$ | OMe | 3-$CF_3$ | OMe | 4-$CF_3$ |
| OMe | 2-$OCF_3$ | OMe | 3-$OCF_3$ | OMe | 4-$OCF_3$ |
| OMe | 2-$OCF_2H$ | OMe | 3-$OCF_2H$ | OMe | 4-$OCF_2H$ |
| OMe | 2-$OCF_2CF_2H$ | OMe | 3-$OCF_2CF_2H$ | OMe | 4-$OCF_2CF_2H$ |
| OMe | 2-$OCH_2CF_3$ | OMe | 3-$OCH_2CF_3$ | OMe | 4-$OCH_2CF_3$ |
| OMe | 2-$SCF_3$ | OMe | 3-$SCF_3$ | OMe | 4-$SCF_3$ |
| OMe | 2-$SOCF_3$ | OMe | 3-$SOCF_3$ | OMe | 4-$SOCF_3$ |

TABLE 3-continued

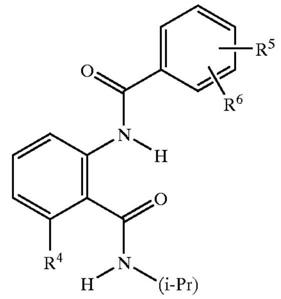

| $R^4$ | $R^5$ and/or $R^6$ | $R^4$ | $R^5$ and/or $R^6$ | $R^4$ | $R^5$ and/or $R^6$ |
|---|---|---|---|---|---|
| OMe | 2-$SO_2CF_3$ | OMe | 3-$SO_2CF_3$ | OMe | 4-$SO_2CF_3$ |
| OMe | 2-$SCF_2H$ | OMe | 3-$SCF_2H$ | OMe | 4-$SCF_2H$ |
| OMe | 2-$SOCF_2H$ | OMe | 3-$SOCF_2H$ | OMe | 4-$SOCF_2H$ |
| OMe | 2-$SO_2CF_2H$ | OMe | 3-$SO_2CF_2H$ | OMe | 4-$SO_2CF_2H$ |
| $CF_3$ | 2-$CF_3$ | $CF_3$ | 3-$CF_3$ | $CF_3$ | 4-$CF_3$ |
| $CF_3$ | 2-$OCF_3$ | $CF_3$ | 3-$OCF_3$ | $CF_3$ | 4-$OCF_3$ |
| $CF_3$ | 2-$OCF_2H$ | $CF_3$ | 3-$OCF_2H$ | $CF_3$ | 4-$OCF_2H$ |
| $CF_3$ | 2-$OCF_2CF_2H$ | $CF_3$ | 3-$OCF_2CF_2H$ | $CF_3$ | 4-$OCF_2CF_2H$ |
| $CF_3$ | 2-$OCH_2CF_3$ | $CF_3$ | 3-$OCH_2CF_3$ | $CF_3$ | 4-$OCH_2CF_3$ |
| $CF_3$ | 2-$SCF_3$ | $CF_3$ | 3-$SCF_3$ | $CF_3$ | 4-$SCF_3$ |
| $CF_3$ | 2-$SOCF_3$ | $CF_3$ | 3-$SOCF_3$ | $CF_3$ | 4-$SOCF_3$ |
| $CF_3$ | 2-$SO_2CF_3$ | $CF_3$ | 3-$SO_2CF_3$ | $CF_3$ | 4-$SO_2CF_3$ |
| $CF_3$ | 2-$SCF_2H$ | $CF_3$ | 3-$SCF_2H$ | $CF_3$ | 4-$SCF_2H$ |
| $CF_3$ | 2-$SOCF_2H$ | $CF_3$ | 3-$SOCF_2H$ | $CF_3$ | 4-$SOCF_2H$ |
| $CF_3$ | 2-$SO_2CF_2H$ | $CF_3$ | 3-$SO_2CF_2H$ | $CF_3$ | 4-$SO_2CF_2H$ |
| $OCF_2H$ | 2-$CF_3$ | $OCF_2H$ | 3-$CF_3$ | $OCF_2H$ | 4-$CF_3$ |
| $OCF_2H$ | 2-$OCF_3$ | $OCF_2H$ | 3-$OCF_3$ | $OCF_2H$ | 4-$OCF_3$ |
| $OCF_2H$ | 2-$OCF_2H$ | $OCF_2H$ | 3-$OCF_2H$ | $OCF_2H$ | 4-$OCF_2H$ |
| $OCF_2H$ | 2-$OCF_2CF_2H$ | $OCF_2H$ | 3-$OCF_2CF_2H$ | $OCF_2H$ | 4-$OCF_2CF_2H$ |
| $OCF_2H$ | 2-$OCH_2CF_3$ | $OCF_2H$ | 3-$OCH_2CF_3$ | $OCF_2H$ | 4-$OCH_2CF_3$ |
| $OCF_2H$ | 2-$SCF_3$ | $OCF_2H$ | 3-$SCF_3$ | $OCF_2H$ | 4-$SCF_3$ |
| $OCF_2H$ | 2-$SOCF_3$ | $OCF_2H$ | 3-$SOCF_3$ | $OCF_2H$ | 4-$SOCF_3$ |
| $OCF_2H$ | 2-$SO_2CF_3$ | $OCF_2H$ | 3-$SO_2CF_3$ | $OCF_2H$ | 4-$SO_2CF_3$ |
| $OCF_2H$ | 2-$SCF_2H$ | $OCF_2H$ | 3-$SCF_2H$ | $OCF_2H$ | 4-$SCF_2H$ |
| $OCF_2H$ | 2-$SOCF_2H$ | $OCF_2H$ | 3-$SOCF_2H$ | $OCF_2H$ | 4-$SOCF_2H$ |
| $OCF_2H$ | 2-$SO_2CF_2H$ | $OCF_2H$ | 3-$SO_2CF_2H$ | $OCF_2H$ | 4-$SO_2CF_2H$ |
| Me | 2-Me-4-$CF_3$ | F | 2-Me-4-$CF_3$ | Cl | 2-Me-4-$CF_3$ |
| Me | 2-Me-4-$OCF_3$ | F | 2-Me-4-$OCF_3$ | Cl | 2-Me-4-$OCF_3$ |
| Me | 2-Me-4-$OCF_2H$ | F | 2-Me-4-$OCF_2H$ | Cl | 2-Me-4-$OCF_2H$ |
| Me | 2-Me-4-$OCH_2CF_3$ | F | 2-Me-4-$OCH_2CF_3$ | Cl | 2-Me-4-$OCH_2CF_3$ |
| Me | 2-Me-4-$SCF_3$ | F | 2-Me-4-$SCF_3$ | Cl | 2-Me-4-$SCF_3$ |
| Me | 2-Me-4-$SOCF_3$ | F | 2-Me-4-$SOCF_3$ | Cl | 2-Me-4-$SOCF_3$ |
| Me | 2-Me-4-$SO_2CF_3$ | F | 2-Me-4-$SO_2CF_3$ | Cl | 2-Me-4-$SO_2CF_3$ |
| Me | 2-Me-4-$SCF_2H$ | F | 2-Me-4-$SCF_2H$ | Cl | 2-Me-4-$SCF_2H$ |
| Me | 2-Me-4-$SOCF_2H$ | F | 2-Me-4-$SOCF_2H$ | Cl | 2-Me-4-$SOCF_2H$ |
| Me | 2-Me-4-$SO_2CF_2H$ | F | 2-Me-4-$SO_2CF_2H$ | Cl | 2-Me-4-$SO_2CF_2H$ |
| Br | 2-Me-4-$CF_3$ | I | 2-Me-4-$CF_3$ | OMe | 2-Me-4-$CF_3$ |
| Br | 2-Me-4-$OCF_3$ | I | 2-Me-4-$OCF_3$ | OMe | 2-Me-4-$OCF_3$ |
| Br | 2-Me-4-$OCF_2H$ | I | 2-Me-4-$OCF_2H$ | OMe | 2-Me-4-$OCF_2H$ |
| Br | 2-Me-4-$OCH_2CF_3$ | I | 2-Me-4-$OCH_2CF_3$ | OMe | 2-Me-4-$OCH_2CF_3$ |
| Br | 2-Me-4-$SCF_3$ | I | 2-Me-4-$SCF_3$ | OMe | 2-Me-4-$SCF_3$ |
| Br | 2-Me-4-$SOCF_3$ | I | 2-Me-4-$SOCF_3$ | OMe | 2-Me-4-$SOCF_3$ |
| Br | 2-Me-4-$SO_2CF_3$ | I | 2-Me-4-$SO_2CF_3$ | OMe | 2-Me-4-$SO_2CF_3$ |
| Br | 2-Me-4-$SCF_2H$ | I | 2-Me-4-$SCF_2H$ | OMe | 2-Me-4-$SCF_2H$ |
| Br | 2-Me-4-$SOCF_2H$ | I | 2-Me-4-$SOCF_2H$ | OMe | 2-Me-4-$SOCF_2H$ |
| Br | 2-Me-4-$SO_2CF_2H$ | I | 2-Me-4-$SO_2CF_2H$ | OMe | 2-Me-4-$SO_2CF_2H$ |
| $CF_3$ | 2-Me-4-$CF_3$ | $NO_2$ | 2-Me-4-$CF_3$ | SMe | 2-Me-4-$CF_3$ |
| $CF_3$ | 2-Me-4-$OCF_3$ | $NO_2$ | 2-Me-4-$OCF_3$ | SMe | 2-Me-4-$OCF_3$ |
| $CF_3$ | 2-Me-4-$OCF_2H$ | $NO_2$ | 2-Me-4-$OCF_2H$ | SMe | 2-Me-4-$OCF_2H$ |
| $CF_3$ | 2-Me-4-$OCH_2CF_3$ | $NO_2$ | 2-Me-4-$OCH_2CF_3$ | SMe | 2-Me-4-$OCH_2CF_3$ |
| $CF_3$ | 2-Me-4-$SCF_3$ | $NO_2$ | 2-Me-4-$SCF_3$ | SMe | 2-Me-4-$SCF_3$ |
| $CF_3$ | 2-Me-4-$SOCF_3$ | $NO_2$ | 2-Me-4-$SOCF_3$ | SMe | 2-Me-4-$SOCF_3$ |
| $CF_3$ | 2-Me-4-$SO_2CF_3$ | $NO_2$ | 2-Me-4-$SO_2CF_3$ | SMe | 2-Me-4-$SO_2CF_3$ |
| $CF_3$ | 2-Me-4-$SCF_2H$ | $NO_2$ | 2-Me-4-$SCF_2H$ | SMe | 2-Me-4-$SCF_2H$ |
| $CF_3$ | 2-Me-4-$SOCF_2H$ | $NO_2$ | 2-Me-4-$SOCF_2H$ | SMe | 2-Me-4-$SOCF_2H$ |
| $CF_3$ | 2-Me-4-$SO_2CF_2H$ | $NO_2$ | 2-Me-4-$SO_2CF_2H$ | SM | 2-Me-4-$SO_2CF_2H$ |

TABLE 4

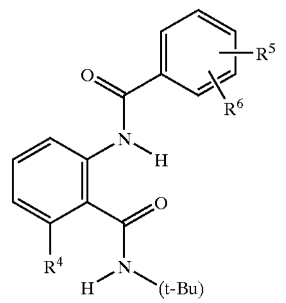

| $R^4$ | $R^5$ and/or $R^6$ | $R^4$ | $R^5$ and/or $R^6$ | $R^4$ | $R^5$ and/or $R^6$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| Cl | 2-$CF_3$ | Cl | 3-$CF_3$ | Cl | 4-$CF_3$ |
| Cl | 2-$OCF_3$ | Cl | 3-$OCF_3$ | Cl | 4-$OCF_3$ |
| Cl | 2-$OCF_2H$ | Cl | 3-$OCF_2H$ | Cl | 4-$OCF_2H$ |
| Cl | 2-$OCF_2CF_2H$ | Cl | 3-$OCF_2CF_2H$ | Cl | 4-$OCF_2CF_2H$ |
| Cl | 2-$OCH_2CF_3$ | Cl | 3-$OCH_2CF_3$ | Cl | 4-$OCH_2CF_3$ |
| Cl | 2-$SCF_3$ | Cl | 3-$SCF_3$ | Cl | 4-$SCF_3$ |
| Cl | 2-$SOCF_3$ | Cl | 3-$SOCF_3$ | Cl | 4-$SOCF_3$ |
| Cl | 2-$SO_2CF_3$ | Cl | 3-$SO_2CF_3$ | Cl | 4-$SO_2CF_3$ |
| Cl | 2-$SCF_2H$ | Cl | 3-$SCF_2H$ | Cl | 4-$SCF_2H$ |
| Cl | 2-$SOCF_2H$ | Cl | 3-$SOCF_2H$ | Cl | 4-$SOCF_2H$ |
| Cl | 2-$SO_2CF_2H$ | Cl | 3-$SO_2CF_2H$ | Cl | 4-$SO_2CF_2H$ |
| F | 2-$CF_3$ | F | 3-$CF_3$ | F | 4-$CF_3$ |
| F | 2-$OCF_3$ | F | 3-$OCF_3$ | F | 4-$OCF_3$ |
| F | 2-$OCF_2H$ | F | 3-$OCF_2H$ | F | 4-$OCF_2H$ |
| F | 2-$OCF_2CF_2H$ | F | 3-$OCF_2CF_2H$ | F | 4-$OCF_2CF_2H$ |
| F | 2-$OCH_2CF_3$ | F | 3-$OCH_2CF_3$ | F | 4-$OCH_2CF_3$ |
| F | 2-$SCF_3$ | F | 3-$SCF_3$ | F | 4-$SCF_3$ |
| F | 2-$SOCF_3$ | F | 3-$SOCF_3$ | F | 4-$SOCF_3$ |
| F | 2-$SO_2CF_3$ | F | 3-$SO_2CF_3$ | F | 4-$SO_2CF_3$ |
| F | 2-$SCF_2H$ | F | 3-$SCF_2H$ | F | 4-$SCF_2H$ |
| F | 2-$SOCF_2H$ | F | 3-$SOCF_2H$ | F | 4-$SOCF_2H$ |
| F | 2-$SO_2CF_2H$ | F | 3-$SO_2CF_2H$ | F | 4-$SO_2CF_2H$ |
| Br | 2-$CF_3$ | Br | 3-$CF_3$ | Br | 4-$CF_3$ |
| Br | 2-$OCF_3$ | Br | 3-$OCF_3$ | Br | 4-$OCF_3$ |
| Br | 2-$OCF_2H$ | Br | 3-$OCF_2H$ | Br | 4-$OCF_2H$ |
| Br | 2-$OCF_2CF_2H$ | Br | 3-$OCF_2CF_2H$ | Br | 4-$OCF_2CF_2H$ |
| Br | 2-$OCH_2CF_3$ | Br | 3-$OCH_2CF_3$ | Br | 4-$OCH_2CF_3$ |
| Br | 2-$SCF_3$ | Br | 3-$SCF_3$ | Br | 4-$SCF_3$ |
| Br | 2-$SOCF_3$ | Br | 3-$SOCF_3$ | Br | 4-$SOCF_3$ |
| Br | 2-$SO_2CF_3$ | Br | 3-$SO_2CF_3$ | Br | 4-$SO_2CF_3$ |
| Br | 2-$SCF_2H$ | Br | 3-$SCF_2H$ | Br | 4-$SCF_2H$ |
| Br | 2-$SOCF_2H$ | Br | 3-$SOCF_2H$ | Br | 4-$SOCF_2H$ |
| Br | 2-$SO_2CF_2H$ | Br | 3-$SO_2CF_2H$ | Br | 4-$SO_2CF_2H$ |
| I | 2-$CF_3$ | I | 3-$CF_3$ | I | 4-$CF_3$ |
| I | 2-$OCF_3$ | I | 3-$OCF_3$ | I | 4-$OCF_3$ |
| I | 2-$OCF_2H$ | I | 3-$OCF_2H$ | I | 4-$OCF_2H$ |
| I | 2-$OCF_2CF_2H$ | I | 3-$OCF_2CF_2H$ | I | 4-$OCF_2CF_2H$ |
| I | 2-$OCH_2CF_3$ | I | 3-$OCH_2CF_3$ | I | 4-$OCH_2CF_3$ |
| I | 2-$SCF_3$ | I | 3-$SCF_3$ | I | 4-$SCF_3$ |
| I | 2-$SOCF_3$ | I | 3-$SOCF_3$ | I | 4-$SOCF_3$ |
| I | 2-$SO_2CF_3$ | I | 3-$SO_2CF_3$ | I | 4-$SO_2CF_3$ |
| I | 2-$SCF_2H$ | I | 3-$SCF_2H$ | I | 4-$SCF_2H$ |
| I | 2-$SOCF_2H$ | I | 3-$SOCF_2H$ | I | 4-$SOCF_2H$ |
| I | 2-$SO_2CF_2H$ | I | 3-$SO_2CF_2H$ | I | 4-$SO_2CF_2H$ |
| OMe | 2-$CF_3$ | OMe | 3-$CF_3$ | OMe | 4-$CF_3$ |
| OMe | 2-$OCF_3$ | OMe | 3-$OCF_3$ | OMe | 4-$OCF_3$ |
| OMe | 2-$OCF_2H$ | OMe | 3-$OCF_2H$ | OMe | 4-$OCF_2H$ |
| OMe | 2-$OCF_2CF_2H$ | OMe | 3-$OCF_2CF_2H$ | OMe | 4-$OCF_2CF_2H$ |
| OMe | 2-$OCH_2CF_3$ | OMe | 3-$OCH_2CF_3$ | OMe | 4-$OCH_2CF_3$ |
| OMe | 2-$SCF_3$ | OMe | 3-$SCF_3$ | OMe | 4-$SCF_3$ |
| OMe | 2-$SOCF_3$ | OMe | 3-$SOCF_3$ | OMe | 4-$SOCF_3$ |

TABLE 4-continued

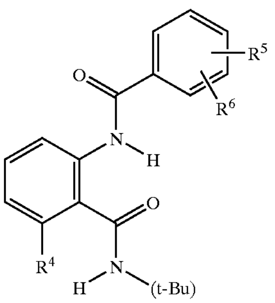

| R$^4$ | R$^5$ and/or R$^6$ | R$^4$ | R$^5$ and/or R$^6$ | R$^4$ | R$^5$ and/or R$^6$ |
|---|---|---|---|---|---|
| OMe | 2-SO$_2$CF$_3$ | OMe | 3-SO$_2$CF$_3$ | OMe | 4-SO$_2$CF$_3$ |
| OMe | 2-SCF$_2$H | OMe | 3-SCF$_2$H | OMe | 4-SCF$_2$H |
| OMe | 2-SOCF$_2$H | OMe | 3-SOCF$_2$H | OMe | 4-SOCF$_2$H |
| OMe | 2-SO$_2$CF$_2$H | OMe | 3-SO$_2$CF$_2$H | OMe | 4-SO$_2$CF$_2$H |
| CF$_3$ | 2-CF$_3$ | CF$_3$ | 3-CF$_3$ | CF$_3$ | 4-CF$_3$ |
| CF$_3$ | 2-OCF$_3$ | CF$_3$ | 3-OCF$_3$ | CF$_3$ | 4-OCF$_3$ |
| CF$_3$ | 2-OCF$_2$H | CF$_3$ | 3-OCF$_2$H | CF$_3$ | 4-OCF$_2$H |
| CF$_3$ | 2-OCF$_2$CF$_2$H | CF$_3$ | 3-OCF$_2$CF$_2$H | CF$_3$ | 4-OCF$_2$CF$_2$H |
| CF$_3$ | 2-OCH$_2$CF$_3$ | CF$_3$ | 3-OCH$_2$CF$_3$ | CF$_3$ | 4-OCH$_2$CF$_3$ |
| CF$_3$ | 2-SCF$_3$ | CF$_3$ | 3-SCF$_3$ | CF$_3$ | 4-SCF$_3$ |
| CF$_3$ | 2-SOCF$_3$ | CF$_3$ | 3-SOCF$_3$ | CF$_3$ | 4-SOCF$_3$ |
| CF$_3$ | 2-SO$_2$CF$_3$ | CF$_3$ | 3-SO$_2$CF$_3$ | CF$_3$ | 4-SO$_2$CF$_3$ |
| CF$_3$ | 2-SCF$_2$H | CF$_3$ | 3-SCF$_2$H | CF$_3$ | 4-SCF$_2$H |
| CF$_3$ | 2-SOCF$_2$H | CF$_3$ | 3-SOCF$_2$H | CF$_3$ | 4-SOCF$_2$H |
| CF$_3$ | 2-SO$_2$CF$_2$H | CF$_3$ | 3-SO$_2$CF$_2$H | CF$_3$ | 4-SO$_2$CF$_2$H |
| OCF$_2$H | 2-CF$_3$ | OCF$_2$H | 3-CF$_3$ | OCF$_2$H | 4-CF$_3$ |
| OCF$_2$H | 2-OCF$_3$ | OCF$_2$H | 3-OCF$_3$ | OCF$_2$H | 4-OCF$_3$ |
| OCF$_2$H | 2-OCF$_2$H | OCF$_2$H | 3-OCF$_2$H | OCF$_2$H | 4-OCF$_2$H |
| OCF$_2$H | 2-OCF$_2$CF$_2$H | OCF$_2$H | 3-OCF$_2$CF$_2$H | OCF$_2$H | 4-OCF$_2$CF$_2$H |
| OCF$_2$H | 2-OCH$_2$CF$_3$ | OCF$_2$H | 3-OCH$_2$CF$_3$ | OCF$_2$H | 4-OCH$_2$CF$_3$ |
| OCF$_2$H | 2-SCF$_3$ | OCF$_2$H | 3-SCF$_3$ | OCF$_2$H | 4-SCF$_3$ |
| OCF$_2$H | 2-SOCF$_3$ | OCF$_2$H | 3-SOCF$_3$ | OCF$_2$H | 4-SOCF$_3$ |
| OCF$_2$H | 2-SO$_2$CF$_3$ | OCF$_2$H | 3-SO$_2$CF$_3$ | OCF$_2$H | 4-SO$_2$CF$_3$ |
| OCF$_2$H | 2-SCF$_2$H | OCF$_2$H | 3-SCF$_2$H | OCF$_2$H | 4-SCF$_2$H |
| OCF$_2$H | 2-SOCF$_2$H | OCF$_2$H | 3-SOCF$_2$H | OCF$_2$H | 4-SOCF$_2$H |
| OCF$_2$H | 2-SO$_2$CF$_2$H | OCF$_2$H | 3-SO$_2$CF$_2$H | OCF$_2$H | 4-SO$_2$CF$_2$H |
| Me | 2-Me-4-CF$_3$ | F | 2-Me-4-CF$_3$ | Cl | 2-Me-4-CF$_3$ |
| Me | 2-Me-4-OCF$_3$ | F | 2-Me-4-OCF$_3$ | Cl | 2-Me-4-OCF$_3$ |
| Me | 2-Me-4-OCF$_2$H | F | 2-Me-4-OCF$_2$H | Cl | 2-Me-4-OCF$_2$H |
| Me | 2-Me-4-OCH$_2$CF$_3$ | F | 2-Me-4-OCH$_2$CF$_3$ | Cl | 2-Me-4-OCH$_2$CF$_3$ |
| Me | 2-Me-4-SCF$_3$ | F | 2-Me-4-SCF$_3$ | Cl | 2-Me-4-SCF$_3$ |
| Me | 2-Me-4-SOCF$_3$ | F | 2-Me-4-SOCF$_3$ | Cl | 2-Me-4-SOCF$_3$ |
| Me | 2-Me-4-SO$_2$CF$_3$ | F | 2-Me-4-SO$_2$CF$_3$ | Cl | 2-Me-4-SO$_2$CF$_3$ |
| Me | 2-Me-4-SCF$_2$H | F | 2-Me-4-SCF$_2$H | Cl | 2-Me-4-SCF$_2$H |
| Me | 2-Me-4-SOCF$_2$H | F | 2-Me-4-SOCF$_2$H | Cl | 2-Me-4-SOCF$_2$H |
| Me | 2-Me-4-SO$_2$CF$_2$H | F | 2-Me-4-SO$_2$CF$_2$H | Cl | 2-Me-4-SO$_2$CF$_2$H |
| Br | 2-Me-4-CF$_3$ | I | 2-Me-4-CF$_3$ | OMe | 2-Me-4-CF$_3$ |
| Br | 2-Me-4-OCF$_3$ | I | 2-Me-4-OCF$_3$ | OMe | 2-Me-4-OCF$_3$ |
| Br | 2-Me-4-OCF$_2$H | I | 2-Me-4-OCF$_2$H | OMe | 2-Me-4-OCF$_2$H |
| Br | 2-Me-4-OCH$_2$CF$_3$ | I | 2-Me-4-OCH$_2$CF$_3$ | OMe | 2-Me-4-OCH$_2$CF$_3$ |
| Br | 2-Me-4-SCF$_3$ | I | 2-Me-4-SCF$_3$ | OMe | 2-Me-4-SCF$_3$ |
| Br | 2-Me-4-SOCF$_3$ | I | 2-Me-4-SOCF$_3$ | OMe | 2-Me-4-SOCF$_3$ |
| Br | 2-Me-4-SO$_2$CF$_3$ | I | 2-Me-4-SO$_2$CF$_3$ | OMe | 2-Me-4-SO$_2$CF$_3$ |
| Br | 2-Me-4-SCF$_2$H | I | 2-Me-4-SCF$_2$H | OMe | 2-Me-4-SCF$_2$H |
| Br | 2-Me-4-SOCF$_2$H | I | 2-Me-4-SOCF$_2$H | OMe | 2-Me-4-SOCF$_2$H |
| Br | 2-Me-4-SO$_2$CF$_2$H | I | 2-Me-4-SO$_2$CF$_2$H | OMe | 2-Me-4-SO$_2$CF$_2$H |
| CF$_3$ | 2-Me-4-CF$_3$ | NO$_2$ | 2-Me-4-CF$_3$ | SMe | 2-Me-4-CF$_3$ |
| CF$_3$ | 2-Me-4-OCF$_3$ | NO$_2$ | 2-Me-4-CF$_3$ | SMe | 2-Me-4-OCF$_3$ |
| CF$_3$ | 2-Me-4-OCF$_2$H | NO$_2$ | 2-Me-4-OCF$_2$H | SMe | 2-Me-4-OCF$_2$H |
| CF$_3$ | 2-Me-4-OCH$_2$CF$_3$ | NO$_2$ | 2-Me-4-OCH$_2$CF$_3$ | SMe | 2-Me-4-OCH$_2$CF$_3$ |
| CF$_3$ | 2-Me-4-SCF$_3$ | NO$_2$ | 2-Me-4-SCF$_3$ | SMe | 2-Me-4-SCF$_3$ |
| CF$_3$ | 2-Me-4-SOCF$_3$ | NO$_2$ | 2-Me-4-SOCF$_3$ | SMe | 2-Me-4-SOCF$_3$ |
| CF$_3$ | 2-Me-4-SO$_2$CF$_3$ | NO$_2$ | 2-Me-4-SO$_2$CF$_3$ | SMe | 2-Me-4-SO$_2$CF$_3$ |
| CF$_3$ | 2-Me-4-SCF$_2$H | NO$_2$ | 2-Me-4-SCF$_2$H | SMe | 2-Me-4-SCF$_2$H |
| CF$_3$ | 2-Me-4-SOCF$_2$H | NO$_2$ | 2-Me-4-SOCF$_2$H | SMe | 2-Me-4-SOCF$_2$H |
| CF$_3$ | 2-Me-4-SO$_2$CF$_2$H | NO$_2$ | 2-Me-4-SO$_2$CF$_2$H | SMe | 2-Me-4-SO$_2$CF$_2$H |

TABLE 5

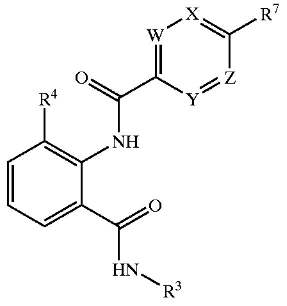

| $R^3$ | $R^4$ | $R^7$ | W | X | Y | Z |
|---|---|---|---|---|---|---|
| i-Pr | Me | $CF_3$ | CMe | N | CH | CH |
| i-Pr | Cl | $CF_3$ | CMe | N | CH | CH |
| i-Pr | Br | $CF_3$ | CMe | N | CH | CH |
| i-Pr | I | $CF_3$ | CMe | N | CH | CH |
| i-Pr | F | $CF_3$ | CMe | N | CH | CH |
| i-Pr | H | $CF_3$ | CMe | N | CH | CH |
| i-Pr | Et | $CF_3$ | CMe | N | CH | CH |
| i-Pr | Me | $CF_3$ | CMe | CH | N | CH |
| i-Pr | Cl | $CF_3$ | CMe | CH | N | CH |
| i-Pr | Br | $CF_3$ | CMe | CH | N | CH |
| i-Pr | I | $CF_3$ | CMe | CH | N | CH |
| i-Pr | F | $CF_3$ | CMe | CH | N | CH |
| i-Pr | H | $CF_3$ | CMe | CH | N | CH |
| i-Pr | Et | $CF_3$ | CMe | CH | N | CH |
| i-Pr | Me | $CF_3$ | CMe | CH | CH | N |
| i-Pr | Cl | $CF_3$ | CMe | CH | CH | N |
| i-Pr | Br | $CF_3$ | CMe | CH | CH | N |
| i-Pr | I | $CF_3$ | CMe | CH | CH | N |
| i-Pr | F | $CF_3$ | CMe | CH | CH | N |
| i-Pr | H | $CF_3$ | CMe | CH | CH | N |
| i-Pr | Et | $CF_3$ | CMe | CH | CH | N |
| i-Pr | Me | $CF_3$ | CMe | N | CH | N |
| i-Pr | Cl | $CF_3$ | CMe | N | CH | N |
| i-Pr | Br | $CF_3$ | CMe | N | CH | N |
| i-Pr | I | $CF_3$ | CMe | N | CH | N |
| i-Pr | F | $CF_3$ | CMe | N | CH | N |
| i-Pr | H | $CF_3$ | CMe | N | CH | N |
| i-Pr | Et | $CF_3$ | CMe | N | CH | N |
| t-Bu | Me | $CF_3$ | CMe | N | CH | CH |
| t-Bu | Cl | $CF_3$ | CMe | N | CH | CH |
| t-Bu | Br | $CF_3$ | CMe | N | CH | CH |
| t-Bu | I | $CF_3$ | CMe | N | CH | CH |
| t-Bu | F | $CF_3$ | CMe | N | CH | CH |
| t-Bu | H | $CF_3$ | CMe | N | CH | CH |
| t-Bu | Et | $CF_3$ | CMe | N | CH | CH |
| t-Bu | Me | $CF_3$ | CMe | CH | N | CH |
| t-Bu | Cl | $CF_3$ | CMe | CH | N | CH |
| t-Bu | Br | $CF_3$ | CMe | CH | N | CH |
| t-Bu | I | $CF_3$ | CMe | CH | N | CH |
| t-Bu | F | $CF_3$ | CMe | CH | N | CH |
| t-Bu | H | $CF_3$ | CMe | CH | N | CH |
| t-Bu | Et | $CF_3$ | CMe | CH | N | CH |
| t-Bu | Me | $CF_3$ | CMe | CH | CH | N |
| t-Bu | Cl | $CF_3$ | CMe | CH | CH | N |
| t-Bu | Br | $CF_3$ | CMe | CH | CH | N |
| t-Bu | I | $CF_3$ | CMe | CH | CH | N |
| t-Bu | F | $CF_3$ | CMe | CH | CH | N |
| t-Bu | H | $OF_3$ | CMe | CH | CH | N |
| t-Bu | Et | $CF_3$ | CMe | CH | CH | N |
| i-Pr | Me | $OCF_3$ | CMe | N | CH | CH |
| i-Pr | Cl | $OCF_3$ | CMe | N | CH | CH |
| i-Pr | Br | $OCF_3$ | CMe | N | CH | CH |
| i-Pr | I | $OCF_3$ | CMe | N | CH | CH |
| i-Pr | F | $OCF_3$ | CMe | N | CH | CH |
| i-Pr | H | $OCF_3$ | CMe | N | CH | CH |
| i-Pr | Et | $OCF_3$ | CMe | N | CH | CH |
| i-Pr | Me | $CF_3$ | CH | N | CH | CH |
| i-Pr | Cl | $CF_3$ | CH | N | CH | CH |
| i-Pr | Br | $CF_3$ | CH | N | CH | CH |
| i-Pr | I | $CF_3$ | CH | N | CH | CH |
| i-Pr | F | $CF_3$ | CH | N | CH | CH |

TABLE 5-continued

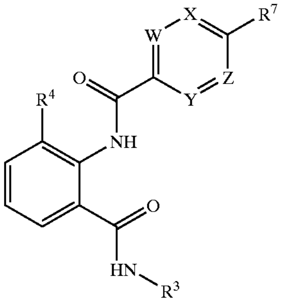

| $R^3$ | $R^4$ | $R^7$ | W | X | Y | Z |
|---|---|---|---|---|---|---|
| i-Pr | H | $CF_3$ | CH | N | CH | CH |
| i-Pr | Et | $CF_3$ | CH | N | CH | CH |
| i-Pr | Me | Cl | CMe | CH | CH | N |
| i-Pr | Cl | Cl | CMe | CH | CH | N |
| i-Pr | Br | Cl | CMe | CH | CH | N |
| i-Pr | I | Cl | CMe | CH | CH | N |
| i-Pr | F | Cl | CMe | CH | CH | N |
| i-Pr | H | Cl | CMe | CH | CH | N |
| i-Pr | Et | Cl | CMe | CH | CH | N |

TABLE 6

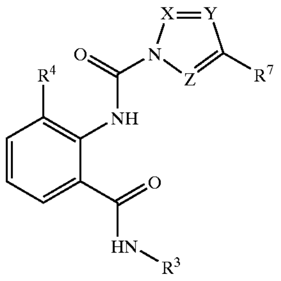

| $R^3$ | $R^4$ | $R^7$ | X | Y | Z |
|---|---|---|---|---|---|
| i-Pr | Me | $CF_3$ | CMe | N | CH |
| i-Pr | Cl | $CF_3$ | CMe | N | CH |
| i-Pr | Br | $CF_3$ | CMe | N | CH |
| i-Pr | I | $CF_3$ | CMe | N | CH |
| i-Pr | F | $CF_3$ | CMe | N | CH |
| i-Pr | H | $CF_3$ | CMe | N | CH |
| i-Pr | Et | $CF_3$ | CMe | N | CH |
| i-Pr | Me | $CF_3$ | CMe | CH | N |
| i-Pr | Cl | $CF_3$ | CMe | CH | N |
| i-Pr | Br | $CF_3$ | CMe | CH | N |
| i-Pr | I | $CF_3$ | CMe | CH | N |
| i-Pr | F | $CF_3$ | CMe | CH | N |
| i-Pr | H | $CF_3$ | CMe | CH | N |
| i-Pr | Et | $CF_3$ | CMe | CH | N |
| i-Pr | Me | $CF_3$ | CMe | N | N |
| i-Pr | Cl | $CF_3$ | CMe | N | N |
| i-Pr | Br | $CF_3$ | CMe | N | N |
| i-Pr | I | $CF_3$ | CMe | N | N |
| i-Pr | F | $CF_3$ | CMe | N | N |
| i-Pr | H | $CF_3$ | CMe | N | N |
| i-Pr | Et | $CF_3$ | CMe | N | N |
| i-Pr | Me | $CF_3$ | CEt | CH | N |
| i-Pr | Cl | $CF_3$ | CEt | CH | N |
| i-Pr | Br | $CF_3$ | CEt | CH | N |
| i-Pr | I | $CF_3$ | CEt | CH | N |
| i-Pr | F | $CF_3$ | CEt | CH | N |
| i-Pr | H | $CF_3$ | CEt | CH | N |
| i-Pr | Et | $CF_3$ | CEt | CH | N |
| t-Bu | Me | $CF_3$ | CMe | N | CH |
| t-Bu | Cl | $CF_3$ | CMe | N | CH |
| t-Bu | Br | $CF_3$ | CMe | N | CH |

TABLE 6-continued

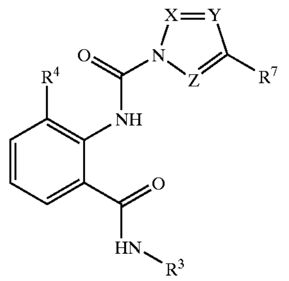

| $R^3$ | $R^4$ | $R^7$ | X | Y | Z |
|---|---|---|---|---|---|
| t-Bu | I | $CF_3$ | CMe | N | CH |
| t-Bu | F | $CF_3$ | CMe | N | CH |
| t-Bu | H | $CF_3$ | CMe | N | CH |
| t-Bu | Et | $CF_3$ | CMe | N | CH |
| t-Bu | Me | $CF_3$ | CMe | CH | N |
| t-Bu | Cl | $CF_3$ | CMe | CH | N |
| t-Bu | Br | $CF_3$ | CMe | CH | N |
| t-Bu | I | $CF_3$ | CMe | CH | N |
| t-Bu | F | $CF_3$ | CMe | CH | N |
| t-Bu | H | $CF_3$ | CMe | CH | N |
| t-Bu | Et | $CF_3$ | CMe | CH | N |
| t-Bu | Me | $CF_3$ | CMe | N | N |
| t-Bu | Cl | $CF_3$ | CMe | N | N |
| t-Bu | Br | $CF_3$ | CMe | N | N |
| t-Bu | I | $CF_3$ | CMe | N | N |
| t-Bu | F | $CF_3$ | CMe | N | N |
| t-Bu | H | $CF_3$ | CMe | N | N |
| t-Bu | Et | $CF_3$ | CMe | N | N |
| i-Pr | Me | $OCF_3$ | CMe | CH | N |
| i-Pr | Cl | $OCF_3$ | CMe | CH | N |
| i-Pr | Br | $OCF_3$ | CMe | CH | N |
| i-Pr | I | $OCF_3$ | CMe | CH | N |
| i-Pr | F | $OCF_3$ | CMe | CH | N |
| i-Pr | H | $OCF_3$ | CMe | CH | N |
| i-Pr | Et | $OCF_3$ | CMe | CH | N |
| i-Pr | Me | $CF_3$ | CH | CH | N |
| i-Pr | Cl | $CF_3$ | CH | CH | N |
| i-Pr | Br | $CF_3$ | CH | CH | N |
| i-Pr | I | $CF_3$ | CH | CH | N |
| i-Pr | F | $CF_3$ | CH | CH | N |
| i-Pr | H | $CF_3$ | CH | CH | N |
| i-Pr | Et | $CF_3$ | CH | CH | N |
| i-Pr | Me | Cl | CMe | CH | N |
| i-Pr | Cl | Cl | CMe | CH | N |
| i-Pr | Br | Cl | CMe | CH | N |
| i-Pr | I | Cl | CMe | CH | N |
| i-Pr | F | Cl | CMe | CH | N |
| i-Pr | H | Cl | CMe | CH | N |
| i-Pr | Et | Cl | CMe | CH | N |

TABLE 7

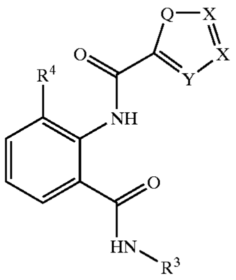

| $R^3$ | $R^4$ | Q | X | Y | Z |
|---|---|---|---|---|---|
| i-Pr | Me | S | $CCF_3$ | CH | CH |
| i-Pr | Cl | S | $CCF_3$ | CH | CH |

TABLE 7-continued

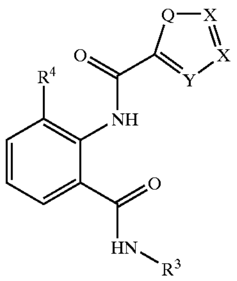

| $R^3$ | $R^4$ | Q | X | Y | Z |
|---|---|---|---|---|---|
| i-Pr | Br | S | $CCF_3$ | CH | CH |
| i-Pr | I | S | $CCF_3$ | CH | CH |
| i-Pr | F | S | $CCF_3$ | CH | CH |
| i-Pr | H | S | $CCF_3$ | CH | CH |
| i-Pr | Et | S | $CCF_3$ | CH | CH |
| i-Pr | Me | S | $CCF_3$ | CMe | CH |
| i-Pr | Cl | S | $CCF_3$ | CMe | CH |
| i-Pr | Br | S | $CCF_3$ | CMe | CH |
| i-Pr | I | S | $CCF_3$ | CMe | CH |
| i-Pr | F | S | $CCF_3$ | CMe | CH |
| i-Pr | H | S | $CCF_3$ | CMe | CH |
| i-Pr | Et | S | $CCF_3$ | CMe | CH |
| t-Bu | Me | S | $CCF_3$ | CMe | CH |
| t-Bu | Cl | S | $CCF_3$ | CMe | CH |
| t-Bu | Br | S | $CCF_3$ | CMe | CH |
| t-Bu | I | S | $CCF_3$ | CMe | CH |
| t-Bu | F | S | $CCF_3$ | CMe | CH |
| t-Bu | H | S | $CCF_3$ | CMe | CH |
| t-Bu | Et | S | $CCF_3$ | CMe | CH |
| i-Pr | Me | S | $CCF_3$ | CMe | N |
| i-Pr | Cl | S | $CCF_3$ | CMe | N |
| i-Pr | Br | S | $CCF_3$ | CMe | N |
| i-Pr | I | S | $CCF_3$ | CMe | N |
| i-Pr | F | S | $CCF_3$ | CMe | N |
| i-Pr | H | S | $CCF_3$ | CMe | N |
| i-Pr | Et | S | $CCF_3$ | CMe | N |
| i-Pr | Me | S | $COCH_2CF_3$ | CMe | N |
| i-Pr | Cl | S | $COCH_2CF_3$ | CMe | N |
| i-Pr | Br | S | $COCH_2CF_3$ | CMe | N |
| i-Pr | I | S | $COCH_2CF_3$ | CMe | N |
| i-Pr | F | S | $COCH_2CF_3$ | CMe | N |
| i-Pr | H | S | $COCH_2CF_3$ | CMe | N |
| i-Pr | Et | S | $COCH_2CF_3$ | CMe | N |
| i-Pr | Me | S | $COCHF_2$ | CMe | N |
| i-Pr | Cl | S | $COCHF_2$ | CMe | N |
| i-Pr | Br | S | $COCHF_2$ | CMe | N |
| i-Pr | I | S | $COCHF_2$ | CMe | N |
| i-Pr | F | S | $COCHF_2$ | CMe | N |
| i-Pr | H | S | $COCHF_2$ | CMe | N |
| i-Pr | Et | S | $COCHF_2$ | CMe | N |
| i-Pr | Me | O | $CCF_3$ | CMe | N |
| i-Pr | Cl | O | $CCF_3$ | CMe | N |
| i-Pr | Br | O | $CCF_3$ | CMe | N |
| i-Pr | I | O | $CCF_3$ | CMe | N |
| i-Pr | F | O | $CCF_3$ | CMe | N |
| i-Pr | H | O | $CCF_3$ | CMe | N |
| i-Pr | Et | O | $CCF_3$ | CMe | N |
| i-Pr | Me | NMe | N | CH | $CCF_3$ |
| i-Pr | Cl | NMe | N | CH | $CCF_3$ |
| i-Pr | Br | NMe | N | CH | $CCF_3$ |
| i-Pr | I | NMe | N | CH | $CCF_3$ |
| i-Pr | F | NMe | N | CH | $CCF_3$ |
| i-Pr | H | NMe | N | CH | $CCF_3$ |
| i-Pr | Et | NMe | N | CH | $CCF_3$ |
| i-Pr | Me | NEt | N | CH | $CCF_3$ |
| i-Pr | Cl | NEt | N | CH | $CCF_3$ |
| i-Pr | Br | NEt | N | CH | $CCF_3$ |
| i-Pr | I | NEt | N | CH | $CCF_3$ |
| i-Pr | F | NEt | N | CH | $CCF_3$ |
| i-Pr | H | NEt | N | CH | $CCF_3$ |
| i-Pr | Et | NEt | N | CH | $CCF_3$ |
| i-Pr | Me | NMe | N | CH | $CC_2F_3$ |
| i-Pr | Cl | NMe | N | CH | $CC_2F_3$ |

TABLE 7-continued

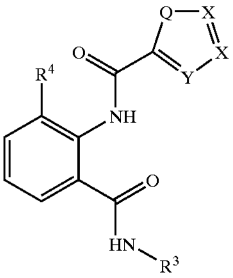

| $R^3$ | $R^4$ | Q | X | Y | Z |
|---|---|---|---|---|---|
| i-Pr | Br | NMe | N | CH | $CCF_3$ |
| i-Pr | I | NMe | N | CH | $CCF_3$ |
| i-Pr | F | NMe | N | CH | $CCF_3$ |
| i-Pr | H | NMe | N | CH | $CCF_3$ |
| i-Pr | Et | NMe | N | CH | $CCF_3$ |
| t-Bu | Me | NMe | N | CH | $CCF_3$ |
| t-Bu | Cl | NMe | N | CH | $CCF_3$ |
| t-Bu | Br | NMe | N | CH | $CCF_3$ |
| t-Bu | I | NMe | N | CH | $CCF_3$ |
| t-Bu | F | NMe | N | CH | $CCF_3$ |
| t-Bu | H | NMe | N | CH | $CCF_3$ |
| t-Bu | Et | NMe | N | CH | $CCF_3$ |
| i-Pr | Me | NMe | CH | N | $CCF_3$ |
| i-Pr | Cl | NMe | CH | N | $CCF_3$ |
| i-Pr | Br | NMe | CH | N | $CCF_3$ |
| i-Pr | I | NMe | CH | N | $CCF_3$ |
| i-Pr | F | NMe | CH | N | $CCF_3$ |
| i-Pr | H | NMe | CH | N | $CCF_3$ |
| i-Pr | Et | NMe | CH | N | $CCF_3$ |
| i-Pr | Me | NMe | N | N | $CCF_3$ |
| i-Pr | Cl | NMe | N | N | $CCF_3$ |
| i-Pr | Br | NMe | N | N | $CCF_3$ |
| i-Pr | I | NMe | N | N | $CCF_3$ |
| i-Pr | F | NMe | N | N | $CCF_3$ |
| i-Pr | H | NMe | N | N | $CCF_3$ |
| i-Pr | Et | NMe | N | N | $CCF_3$ |

TABLE 8

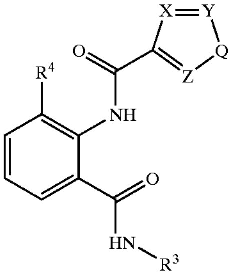

| $R^3$ | $R^4$ | Q | X | Y | Z |
|---|---|---|---|---|---|
| i-Pr | Me | $NCHF_2$ | CMe | N | CH |
| i-Pr | Cl | $NCHF_2$ | CMe | N | CH |
| i-Pr | Br | $NCHF_2$ | CMe | N | CH |
| i-Pr | I | $NCHF_2$ | CMe | N | CH |
| i-Pr | F | $NCHF_2$ | CMe | N | CH |
| i-Pr | H | $NCHF_2$ | CMe | N | CH |
| i-Pr | Et | $NCHF_2$ | CMe | N | CH |
| i-Pr | Me | $NCHF_2$ | CH | N | CMe |
| i-Pr | Cl | $NCHF_2$ | CH | N | CMe |
| i-Pr | Br | $NCHF_2$ | CH | N | CMe |
| i-Pr | I | $NCHF_2$ | CH | N | CMe |
| i-Pr | F | $NCHF_2$ | CH | N | CMe |
| i-Pr | H | $NCHF_2$ | CH | N | CMe |
| i-Pr | Et | $NCHF_2$ | CH | N | CMe |
| i-Pr | Me | $NCF_2CHF_2$ | CMe | N | CH |

TABLE 8-continued

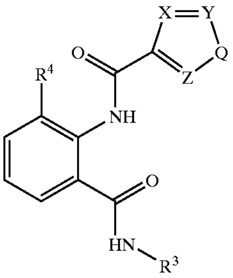

| $R^3$ | $R^4$ | Q | X | Y | Z |
|---|---|---|---|---|---|
| i-Pr | Cl | $NCF_2CHF_2$ | CMe | N | CH |
| i-Pr | Br | $NCF_2CHF_2$ | CMe | N | CH |
| i-Pr | I | $NCF_2CHF_2$ | CMe | N | CH |
| i-Pr | F | $NCF_2CHF_2$ | CMe | N | CH |
| i-Pr | H | $NCF_2CHF_2$ | CMe | N | CH |
| i-Pr | Et | $NCF_2CHF_2$ | CMe | N | CH |
| i-Pr | Me | $NCF_2CHF_2$ | CH | N | CMe |
| i-Pr | Cl | $NCF_2CHF_2$ | CH | N | CMe |
| i-Pr | Br | $NCF_2CHF_2$ | CH | N | CMe |
| i-Pr | I | $NCF_2CHF_2$ | CH | N | CMe |
| i-Pr | F | $NCF_2CHF_2$ | CH | N | CMe |
| i-Pr | H | $NCF_2CHF_2$ | CH | N | CMe |
| i-Pr | Et | $NCF_2CHF_2$ | CH | N | CMe |
| i-Pr | Me | $NCH_2CF_3$ | CMe | N | CH |
| i-Pr | Cl | $NCH_2CF_3$ | CMe | N | CH |
| i-Pr | Br | $NCH_2CF_3$ | CMe | N | CH |
| i-Pr | I | $NCH_2CF_3$ | CMe | N | CH |
| i-Pr | F | $NCH_2CF_3$ | CMe | N | CH |
| i-Pr | H | $NCH_2CF_3$ | CMe | N | CH |
| i-Pr | Et | $NCH_2CF_3$ | CMe | N | CH |
| i-Pr | Me | $NCH_2CF_3$ | CH | N | CMe |
| i-Pr | Cl | $NCH_2CF_3$ | CH | N | CMe |
| i-Pr | Br | $NCH_2CF_3$ | CH | N | CMe |
| i-Pr | I | $NCH_2CF_3$ | CH | N | CMe |
| i-Pr | F | $NCH_2CF_3$ | CH | N | CMe |
| i-Pr | H | $NCH_2CF_3$ | CH | N | CMe |
| i-Pr | Et | $NCH_2CF_3$ | CH | N | CMe |
| i-Pr | Me | $NCF_2CHF_2$ | N | CH | CMe |
| i-Pr | Cl | $NCF_2CHF_2$ | N | CH | CMe |
| i-Pr | Br | $NCF_2CHF_2$ | N | CH | CMe |
| i-Pr | I | $NCF_2CHF_2$ | N | CH | CMe |
| i-Pr | F | $NCF_2CHF_2$ | N | CH | CMe |
| i-Pr | H | $NCF_2CHF_2$ | N | CH | CMe |
| i-Pr | Et | $NCF_2CHF_2$ | N | CH | CMe |

TABLE 9

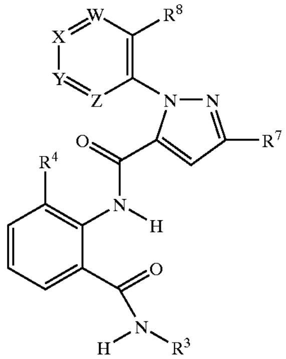

| W | X | Y | Z | $R^3$ | $R^4$ | $R^7$ | $R^8$ |
|---|---|---|---|---|---|---|---|
| CH | CH | CH | CH | i-Pr | Me | $CF_3$ | Me |
| CH | CH | CH | CH | t-Bu | Me | $CF_3$ | Me |
| CH | CH | CH | CH | i-Pr | Cl | $CF_3$ | Me |

TABLE 9-continued

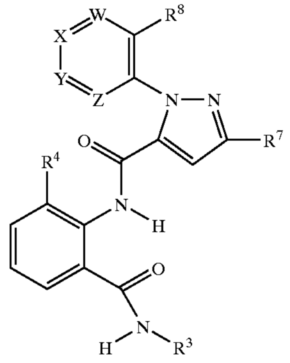

| W | X | Y | Z | $R^3$ | $R^4$ | $R^7$ | $R^8$ |
|---|---|---|---|---|---|---|---|
| CH | CH | CH | CH | t-Bu | Cl | $CF_3$ | Me |
| CH | CH | CH | CH | i-Pr | Br | $CF_3$ | Me |
| CH | CH | CH | CH | t-Bu | Br | $CF_3$ | Me |
| CH | CH | CH | CH | i-Pr | Me | Cl | Me |
| CH | CH | CH | CH | t-Bu | Me | Cl | Me |
| CH | CH | CH | CH | i-Pr | Cl | Cl | Me |
| CH | CH | CH | CH | t-Bu | Cl | Cl | Me |
| CH | CH | CH | CH | i-Pr | Br | Cl | Me |
| CH | CH | CH | CH | t-Bu | Br | Cl | Me |
| CH | CH | CH | CH | i-Pr | Me | Br | Me |
| CH | CH | CH | CH | t-Bu | Me | Br | Me |
| CH | CH | CH | CH | i-Pr | Cl | Br | Me |
| CH | CH | CH | CH | t-Bu | Cl | Br | Me |
| CH | CH | CH | CH | i-Pr | Br | Br | Me |
| CH | CH | CH | CH | t-Bu | Br | Br | Me |
| CH | CH | CH | CH | i-Pr | Me | CN | Me |
| CH | CH | CH | CH | t-Bu | Me | CN | Me |
| CH | CH | CH | CH | i-Pr | Cl | CN | Me |
| CH | CH | CH | CH | t-Bu | Cl | CN | Me |
| CH | CH | CH | CH | i-Pr | Br | CN | Me |
| CH | CH | CH | CH | t-Bu | Br | CN | Me |
| CH | CH | CH | CH | i-Pr | Me | $CF_3$ | F |
| CH | CH | CH | CH | t-Bu | Me | $CF_3$ | F |
| CH | CH | CH | CH | i-Pr | Cl | $CF_3$ | F |
| CH | CH | CH | CH | t-Bu | Cl | $CF_3$ | F |
| CH | CH | CH | CH | i-Pr | Br | $CF_3$ | F |
| CH | CH | CH | CH | t-Bu | Br | $CF_3$ | F |
| CH | CH | CH | CH | i-Pr | Me | Cl | F |
| CH | CH | CH | CH | t-Bu | Me | Cl | F |
| CH | CH | CH | CH | i-Pr | Cl | Cl | F |
| CH | CH | CH | CH | t-Bu | Cl | Cl | F |
| CH | CH | CH | CH | i-Pr | Br | Cl | F |
| CH | CH | CH | CH | t-Bu | Br | Cl | F |
| CH | CH | CH | CH | i-Pr | Me | Br | F |
| CH | CH | CH | CH | t-Bu | Me | Br | F |
| CH | CH | CH | CH | i-Pr | Cl | Br | F |
| CH | CH | CH | CH | t-Bu | Cl | Br | F |
| CH | CH | CH | CH | i-Pr | Br | Br | F |
| CH | CH | CH | CH | t-Bu | Br | Br | F |
| CH | CH | CH | CH | i-Pr | Me | CN | F |
| CH | CH | CH | CH | t-Bu | Me | CN | F |
| CH | CH | CH | CH | i-Pr | Cl | CN | F |
| CH | CH | CH | CH | t-Bu | Cl | CN | F |
| CH | CH | CH | CH | i-Pr | Br | CN | F |
| CH | CH | CH | CH | t-Bu | Br | CN | F |
| CH | CH | CH | CH | i-Pr | Me | $CF_3$ | Cl |
| CH | CH | CH | CH | t-Bu | Me | $CF_3$ | Cl |
| CH | CH | CH | CH | i-Pr | Cl | $CF_3$ | Cl |
| CH | CH | CH | CH | t-Bu | Cl | $CF_3$ | Cl |
| CH | CH | CH | CH | i-Pr | Br | $CF_3$ | Cl |
| CH | CH | CH | CH | t-Bu | Br | $CF_3$ | Cl |
| CH | CH | CH | CH | i-Pr | Me | Cl | Cl |
| CH | CH | CH | CH | t-Bu | Me | Cl | Cl |
| CH | CH | CH | CH | i-Pr | Cl | Cl | Cl |
| CH | CH | CH | CH | t-Bu | Cl | Cl | Cl |
| CH | CH | CH | CH | i-Pr | Br | Cl | Cl |
| CH | CH | CH | CH | t-Bu | Br | Cl | Cl |
| CH | CH | CH | CH | i-Pr | Me | Br | Cl |
| CH | CH | CH | CH | t-Bu | Me | Br | Cl |

TABLE 9-continued

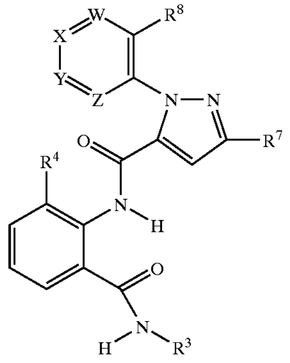

| W | X | Y | Z | $R^3$ | $R^4$ | $R^7$ | $R^8$ |
|---|---|---|---|---|---|---|---|
| CH | CH | CH | CH | i-Pr | Cl | Br | Cl |
| CH | CH | CH | CH | t-Bu | Cl | Br | Cl |
| CH | CH | CH | CH | i-Pr | Br | Br | Cl |
| CH | CH | CH | CH | t-Bu | Br | Br | Cl |
| CH | CH | CH | CH | i-Pr | Me | CN | Cl |
| CH | CH | CH | CH | t-Bu | Me | CN | Cl |
| CH | CH | CH | CH | i-Pr | Cl | CN | Cl |
| CH | CH | CH | CH | t-Bu | Cl | CN | Cl |
| CH | CH | CH | CH | i-Pr | Br | CN | Cl |
| CH | CH | CH | CH | t-Bu | Br | CN | Cl |
| CH | CH | CH | CH | i-Pr | Me | $CF_3$ | Br |
| CH | CH | CH | CH | t-Bu | Me | $CF_3$ | Br |
| CH | CH | CH | CH | i-Pr | Cl | $CF_3$ | Br |
| CH | CH | CH | CH | t-Bu | Cl | $CF_3$ | Br |
| CH | CH | CH | CH | i-Pr | Br | $CF_3$ | Br |
| CH | CH | CH | CH | t-Bu | Br | $CF_3$ | Br |
| CH | CH | CH | CH | i-Pr | Me | Cl | Br |
| CH | CH | CH | CH | t-Bu | Me | Cl | Br |
| CH | CH | CH | CH | i-Pr | Cl | Cl | Br |
| CH | CH | CH | CH | t-Bu | Cl | Cl | Br |
| CH | CH | CH | CH | i-Pr | Br | Cl | Br |
| CH | CH | CH | CH | t-Bu | Br | Cl | Br |
| CH | CH | CH | CH | i-Pr | Me | Br | Br |
| CH | CH | CH | CH | t-Bu | Me | Br | Br |
| CH | CH | CH | CH | i-Pr | Cl | Br | Br |
| CH | CH | CH | CH | t-Bu | Cl | Br | Br |
| CH | CH | CH | CH | i-Pr | Br | Br | Br |
| CH | CH | CH | CH | t-Bu | Br | Br | Br |
| CH | CH | CH | CH | i-Pr | Me | CN | Br |
| CH | CH | CH | CH | t-Bu | Me | CN | Br |
| CH | CH | CH | CH | i-Pr | Cl | CN | Br |
| CH | CH | CH | CH | t-Bu | Cl | CN | Br |
| CH | CH | CH | CH | i-Pr | Br | CN | Br |
| CH | CH | CH | CH | t-Bu | Br | CH | Br |
| CH | CH | CH | CH | i-Pr | Me | $CF_3$ | CN |
| CH | CH | CH | CH | t-Bu | Me | $CF_3$ | CN |
| CH | CH | CH | CH | i-Pr | Cl | $CF_3$ | CN |
| CH | CH | CH | CH | t-Bu | Cl | $CF_3$ | CN |
| CH | CH | CH | CH | i-Pr | Br | $CF_3$ | CN |
| CH | CH | CH | CH | t-Bu | Br | $CF_3$ | CN |
| CH | CH | CH | CH | i-Pr | Me | Cl | CN |
| CH | CH | CH | CH | t-Bu | Me | Cl | CN |
| CH | CH | CH | CH | i-Pr | Cl | Cl | CN |
| CH | CH | CH | CH | t-Bu | Cl | Cl | CN |
| CH | CH | CH | CH | i-Pr | Br | Cl | CN |
| CH | CH | CH | CH | t-Bu | Br | Cl | CN |
| CH | CH | CH | CH | i-Pr | Me | Br | CN |
| CH | CH | CH | CH | t-Bu | Me | Br | CN |
| CH | CH | CH | CH | i-Pr | Cl | Br | CN |
| CH | CH | CH | CH | t-Bu | Cl | Br | CN |
| CH | CH | CH | CH | i-Pr | Br | Br | CN |
| CH | CH | CH | CH | t-Bu | Br | Br | CN |
| CH | CH | CH | CH | i-Pr | Me | CN | CN |
| CH | CH | CH | CH | t-Bu | Me | CN | CN |
| CH | CH | CH | CH | i-Pr | Cl | CN | CN |
| CH | CH | CH | CH | t-Bu | Cl | CN | CN |
| CH | CH | CH | CH | i-Pr | Br | CN | CN |
| CH | CH | CH | CH | t-Bu | Br | CN | CN |
| CH | CH | CH | N | i-Pr | Me | $CF_3$ | Me |

TABLE 9-continued

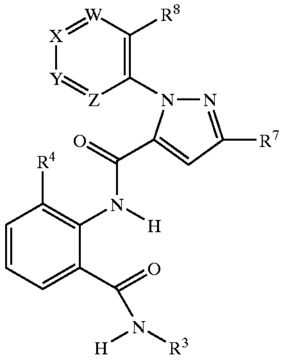

| W | X | Y | Z | $R^3$ | $R^4$ | $R^7$ | $R^8$ |
|---|---|---|---|---|---|---|---|
| CH | CH | CH | N | t-Bu | Me | $CF_3$ | Me |
| CH | CH | CH | N | i-Pr | Cl | $CF_3$ | Me |
| CH | CH | CH | N | t-Bu | Cl | $CF_3$ | Me |
| CH | CH | CH | N | i-Pr | Br | $CF_3$ | Me |
| CH | CH | CH | N | t-Bu | Br | $CF_3$ | Me |
| CH | CH | CH | N | i-Pr | Me | Cl | Me |
| CH | CH | CH | N | t-Bu | Me | Cl | Me |
| CH | CH | CH | N | i-Pr | Cl | Cl | Me |
| CH | CH | CH | N | t-Bu | Cl | Cl | Me |
| CH | CH | CH | N | i-Pr | Br | Cl | Me |
| CH | CH | CH | N | t-Bu | Br | Cl | Me |
| CH | CH | CH | N | i-Pr | Me | Br | Me |
| CH | CH | CH | N | t-Bu | Me | Br | Me |
| CH | CH | CH | N | i-Pr | Cl | Br | Me |
| CH | CH | CH | N | t-Bu | Cl | Br | Me |
| CH | CH | CH | N | i-Pr | Br | Br | Me |
| CH | CH | CH | N | t-Bu | Br | Br | Me |
| CH | CH | CH | N | i-Pr | Me | CN | Me |
| CH | CH | CH | N | t-Bu | Me | CN | Me |
| CH | CH | CH | N | i-Pr | Cl | CN | Me |
| CH | CH | CH | N | t-Bu | Cl | CN | Me |
| CH | CH | CH | N | i-Pr | Br | CN | Me |
| CH | CH | CH | N | t-Bu | Br | CN | Me |
| CH | CH | CH | N | i-Pr | Me | $CF_3$ | F |
| CH | CH | CH | N | t-Bu | Me | $CF_3$ | F |
| CH | CH | CH | N | i-Pr | Cl | $CF_3$ | F |
| CH | CH | CH | N | t-Bu | Cl | $CF_3$ | F |
| CH | CH | CH | N | i-Pr | Br | $CF_3$ | F |
| CH | CH | CH | N | t-Bu | Br | $CF_3$ | F |
| CH | CH | CH | N | i-Pr | Me | Cl | F |
| CH | CH | CH | N | t-Bu | Me | Cl | F |
| CH | CH | CH | N | i-Pr | Cl | Cl | F |
| CH | CH | CH | N | t-Bu | Cl | Cl | F |
| CH | CH | CH | N | i-Pr | Br | Cl | F |
| CH | CH | CH | N | t-Bu | Br | Cl | F |
| CH | CH | CH | N | i-Pr | Me | Br | F |
| CH | CH | CH | N | t-Bu | Me | Br | F |
| CH | CH | CH | N | i-Pr | Cl | Br | F |
| CH | CH | CH | N | t-Bu | Cl | Br | F |
| CH | CH | CH | N | i-Pr | Br | Br | F |
| CH | CH | CH | N | t-Bu | Br | Br | F |
| CH | CH | CH | N | i-Pr | Me | CN | F |
| CH | CH | CH | N | t-Bu | Me | CN | F |
| CH | CH | CH | N | i-Pr | Cl | CN | F |
| CH | CH | CH | N | t-Bu | Cl | CN | F |
| CH | CH | CH | N | i-Pr | Br | CN | F |
| CH | CH | CH | N | t-Bu | Br | CN | F |
| CH | CH | CH | N | i-Pr | Me | $CF_3$ | Cl |
| CH | CH | CH | N | t-Bu | Me | $CF_3$ | Cl |
| CH | CH | CH | N | i-Pr | Cl | $CF_3$ | Cl |
| CH | CH | CH | N | t-Bu | Cl | $CF_3$ | Cl |
| CH | CH | CH | N | i-Pr | Br | $CF_3$ | Cl |
| CH | CH | CH | N | t-Bu | Br | $CF_3$ | Cl |
| CH | CH | CH | N | i-Pr | Me | Cl | Cl |
| CH | CH | CH | N | t-Bu | Me | Cl | Cl |
| CH | CH | CH | N | i-Pr | Cl | Cl | Cl |
| CH | CH | CH | N | t-Bu | Cl | Cl | Cl |
| CH | CH | CH | N | i-Pr | Br | Cl | Cl |
| CH | CH | CH | N | t-Bu | Br | Cl | Cl |

TABLE 9-continued

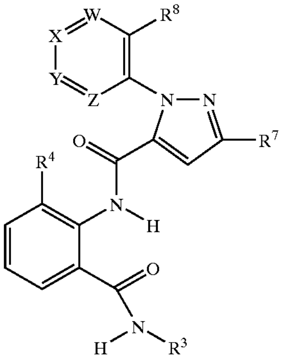

| W | X | Y | Z | $R^3$ | $R^4$ | $R^7$ | $R^8$ |
|---|---|---|---|---|---|---|---|
| CH | CH | CH | N | i-Pr | Me | Br | Cl |
| CH | CH | CH | N | t-Bu | Me | Br | Cl |
| CH | CH | CH | N | i-Pr | Cl | Br | Cl |
| CH | CH | CH | N | t-Bu | Cl | Br | Cl |
| CH | CH | CH | N | i-Pr | Br | Br | Cl |
| CH | CH | CH | N | t-Bu | Br | Br | Cl |
| CH | CH | CH | N | i-Pr | Me | CN | Cl |
| CH | CH | CH | N | t-Bu | Me | CN | Cl |
| CH | CH | CH | N | i-Pr | Cl | CN | Cl |
| CH | CH | CH | N | t-Bu | Cl | CN | Cl |
| CH | CH | CH | N | i-Pr | Br | CN | Cl |
| CH | CH | CH | N | t-Bu | Br | CN | Cl |
| CH | CH | CH | N | i-Pr | Me | $CF_3$ | Br |
| CH | CH | CH | N | t-Bu | Me | $CF_3$ | Br |
| CH | CH | CH | N | i-Pr | Cl | $CF_3$ | Br |
| CH | CH | CH | N | t-Bu | Cl | $CF_3$ | Br |
| CH | CH | CH | N | i-Pr | Br | $CF_3$ | Br |
| CH | CH | CH | N | t-Bu | Br | $CF_3$ | Br |
| CH | CH | CH | N | i-Pr | Me | Cl | Br |
| CH | CH | CH | N | t-Bu | Me | Cl | Br |
| CH | CH | CH | N | i-Pr | Cl | Cl | Br |
| CH | CH | CH | N | t-Bu | Cl | Cl | Br |
| CH | CH | CH | N | i-Pr | Br | Cl | Br |
| CH | CH | CH | N | t-Bu | Br | Cl | Br |
| CH | CH | CH | N | i-Pr | Me | Br | Br |
| CH | CH | CH | N | t-Bu | Me | Br | Br |
| CH | CH | CH | N | i-Pr | Cl | Br | Br |
| CH | CH | CH | N | t-Bu | Cl | Br | Br |
| CH | CH | CH | N | i-Pr | Br | Br | Br |
| CH | CH | CH | N | t-Bu | Br | Br | Br |
| CH | CH | CH | N | i-Pr | Me | CN | Br |
| CH | CH | CH | N | t-Bu | Me | CN | Br |
| CH | CH | CH | N | i-Pr | Cl | CN | Br |
| CH | CH | CH | N | t-Bu | Cl | CN | Br |
| CH | CH | CH | N | i-Pr | Br | CN | Br |
| CH | CH | CH | N | t-Bu | Br | CN | Br |
| CH | CH | CH | N | i-Pr | Me | $CF_3$ | CN |
| CH | CH | CH | N | t-Bu | Me | $CF_3$ | CN |
| CH | CH | CH | N | i-Pr | Cl | $GE_3$ | CN |
| CH | CH | CH | N | t-Bu | Cl | $CF_3$ | CN |
| CH | CH | CH | N | i-Pr | Br | $CF_3$ | CN |
| CH | CH | CH | N | t-Bu | Br | $CF_3$ | CN |
| CH | CH | CH | N | i-Pr | Me | Cl | CN |
| CH | CH | CH | N | t-Bu | Me | Cl | CN |
| CH | CH | CH | N | i-Pr | Cl | Cl | CN |
| CH | CH | CH | N | t-Bu | Cl | Cl | CN |
| CH | CH | CH | N | i-Pr | Br | Cl | CN |
| CH | CH | CH | N | t-Bu | Br | Cl | CN |
| CH | CH | CH | N | i-Pr | Me | Br | CN |
| CH | CH | CH | N | t-Bu | Me | Br | CN |
| CH | CH | CH | N | i-Pr | Cl | Br | CN |
| CH | CH | CH | N | t-Bu | Cl | Br | CN |
| CH | CH | CH | N | i-Pr | Br | Br | CN |
| CH | CH | CH | N | t-Bu | Br | Br | CN |
| CH | CH | CH | N | i-Pr | Me | CN | CN |
| CH | CH | CH | N | t-Bu | Me | CN | CN |
| CH | CH | CH | N | i-Pr | Cl | CN | CN |
| CH | CH | CH | N | t-Bu | Cl | CN | CN |
| CH | CH | CH | N | i-Pr | Br | CN | CN |

TABLE 9-continued

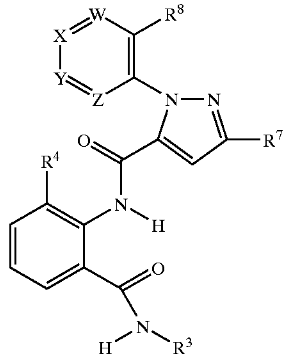

| W | X | Y | Z | $R^3$ | $R^4$ | $R^7$ | $R^8$ |
|---|---|---|---|---|---|---|---|
| CH | CH | CH | N | t-Bu | Br | CN | CN |
| CH | CH | CH | CH | Me | Me | $CF_3$ | F |
| CH | CH | CH | CH | Et | Me | $CF_3$ | F |
| CH | CH | CH | CH | $CH(CH_3)CH_2OCH_3$ | Me | $CF_3$ | F |
| CH | CH | CH | CH | $CH(CH_3)CH_2SCH_3$ | Me | $CF_3$ | F |
| CH | CH | CH | CH | propargyl | Me | $CF_3$ | F |
| CH | CH | CH | CH | Me | Me | $CF_3$ | Cl |
| CH | CH | CH | CH | Et | Me | $CF_3$ | Cl |
| CH | CH | CH | CH | $CH(CH_3)CH_2OCH_3$ | Me | $CF_3$ | Cl |
| CH | CH | CH | CH | $CH(CH_3)CH_2SCH_3$ | Me | $CF_3$ | Cl |
| CH | CH | CH | CH | propargyl | Me | $CF_3$ | Cl |
| CH | CH | CH | CH | Me | Me | Br | F |
| CH | CH | CH | CH | Et | Me | Br | F |
| CH | CH | CH | CH | $CH(CH_3)CH_2OCH_3$ | Me | Br | F |
| CH | CH | CH | CH | $CH(CH_3)CH_2SCH_3$ | Me | Br | F |
| CH | CH | CH | CH | propargyl | Me | Br | F |
| CH | CH | CH | CH | Me | Me | Br | Cl |
| CH | CH | CH | CH | Et | Me | Br | Cl |
| CH | CH | CH | CH | $CH(CH_3)CH_2OCH_3$ | Me | Br | Cl |
| CH | CH | CH | CH | $CH(CH_3)CH_2SCH_3$ | Me | Br | Cl |
| CH | CH | CH | CH | propargyl | Me | Br | Cl |
| CH | CH | CH | CH | Me | Cl | $CF_3$ | F |
| CH | CH | CH | CH | Et | Cl | $CF_3$ | F |
| CH | CH | CH | CH | $CH(CH_3)CH_2OCH_3$ | Cl | $CF_3$ | F |
| CH | CH | CH | CH | $CH(CH_3)CH_2SCH_3$ | Cl | $CF_3$ | F |
| CH | CH | CH | CH | propargyl | Cl | $CF_3$ | F |
| CH | CH | CH | CH | Me | Cl | $CF_3$ | Cl |
| CH | CH | CH | CH | Et | Cl | $CF_3$ | Cl |
| CH | CH | CH | CH | $CH(CH_3)CH_2OCH_3$ | Cl | $CF_3$ | Cl |
| CH | CH | CH | CH | $CH(CH_3)CH_2SCH_3$ | Cl | $CF_3$ | Cl |
| CH | CH | CH | CH | propargyl | Cl | $CF_3$ | Cl |
| CH | CH | CH | CH | Me | Cl | Br | F |
| CH | CH | CH | CH | Et | Cl | Br | F |
| CH | CH | CH | CH | $CH(CH_3)CH_2OCH_3$ | Cl | Br | F |
| CH | CH | CH | CH | $CH(CH_3)CH_2SCH_3$ | Cl | Br | F |
| CH | CH | CH | CH | propargyl | Cl | Br | F |
| CH | CH | CH | CH | Me | Cl | Br | Cl |
| CH | CH | CH | CH | Et | Cl | Br | Cl |
| CH | CH | CH | CH | $CH(CH_3)CH_2OCH_3$ | Cl | Br | Cl |
| CH | CH | CH | CH | $CH(CH_3)CH_2SCH_3$ | Cl | Br | Cl |
| CH | CH | CH | CH | propargyl | Cl | Br | Cl |
| CH | CH | CH | N | Me | Me | $CF_3$ | F |
| CH | CH | CH | N | Et | Me | $CF_3$ | F |
| CH | CH | CH | N | $CH(CH_3)CH_2OCH_3$ | Me | $CF_3$ | F |
| CH | CH | CH | N | $CH(CH_3)CH_2SCH_3$ | Me | $CF_3$ | F |
| CH | CH | CH | N | propargyl | Me | $CF_3$ | F |
| CH | CH | CH | N | Me | Me | $CF_3$ | Cl |
| CH | CH | CH | N | Et | Me | $CF_3$ | Cl |
| CH | CH | CH | N | $CH(CH_3)CH_2OCH_3$ | Me | $CF_3$ | Cl |
| CH | CH | CH | N | $CH(CH_3)CH_2SCH_3$ | Me | $CF_3$ | Cl |
| CH | CH | CH | N | propargyl | Me | $CF_3$ | Cl |
| CH | CH | CH | N | Me | Me | Br | F |
| CH | CH | CH | N | Et | Me | Br | F |
| CH | CH | CH | N | $CH(CH_3)CH_2OCH_3$ | Me | Br | F |
| CH | CH | CH | N | $CH(CH_3)CH_2SCH_3$ | Me | Br | F |
| CH | CH | CH | N | propargyl | Me | Br | F |
| CH | CH | CH | N | Me | Me | Br | Cl |
| CH | CH | CH | N | Et | Me | Br | Cl |
| CH | CH | CH | N | $CH(CH_3)CH_2OCH_3$ | Me | Br | Cl |

TABLE 9-continued

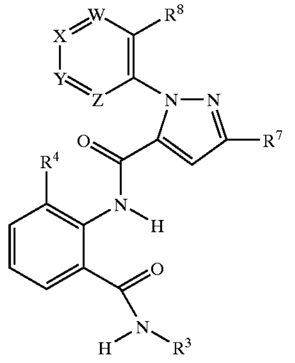

| W | X | Y | Z | $R^3$ | $R^4$ | $R^7$ | $R^8$ |
|---|---|---|---|---|---|---|---|
| CH | CH | CH | N | $CH(CH_3)CH_2SCH_3$ | Me | Br | Cl |
| CH | CH | CH | N | propargyl | Me | Br | Cl |
| CH | CH | CH | N | Me | Cl | $CF_3$ | F |
| CH | CH | CH | N | Et | Cl | $CF_3$ | F |
| CH | CH | CH | N | $CH(CH_3)CH_2OCH_3$ | Cl | $CF_3$ | F |
| CH | CH | CH | N | $CH(CH_3)CH_2SCH_3$ | Cl | $CF_3$ | F |
| CH | CH | CH | N | propargyl | Cl | $CF_3$ | F |
| CH | CH | CH | N | Me | Cl | $CF_3$ | Cl |
| CH | CH | CH | N | Et | Cl | CF3 | Cl |
| CH | CH | CH | N | $CH(CH_3)CH_2OCH_3$ | Cl | $CF_3$ | Cl |
| CH | CH | CH | N | $CH(CH_3)CH_2SCH_3$ | Cl | $CF_3$ | Cl |
| CH | CH | CH | N | propargyl | Cl | $CF_3$ | Cl |
| CH | CH | CH | N | Me | Cl | Br | F |
| CH | CH | CH | N | Et | Cl | Br | F |
| CH | CH | CH | N | $CH(CH_3)CH_2OCH_3$ | Cl | Br | F |
| CH | CH | CH | N | $CH(CH_3)CH_2SCH_3$ | Cl | Br | F |
| CH | CH | CH | N | propargyl | Cl | Br | F |
| CH | CH | CH | N | Me | Cl | Br | Cl |
| CH | CH | CH | N | Et | Cl | Br | Cl |
| CH | CH | CH | N | $CH(CH_3)CH_2OCH_3$ | Cl | Br | Cl |
| CH | CH | CH | N | $CH(CH_3)CH_2SCH_3$ | Cl | Br | Cl |
| CH | CH | CH | N | propargyl | Cl | Br | Cl |
| C-Cl | CH | CH | CH | i-Pr | Me | $CF_3$ | Cl |
| C-F | CH | CH | CH | iPr | Me | $CF_3$ | F |
| CH | CH | CH | CH | i-Pr | Me | $CF_3$ | acetylene |
| CH | CH | CH | CH | i-Pr | Me | $CF_3$ | I |
| CH | CH | CH | CH | i-Pr | Me | $CF_3$ | $SO_2Me$ |
| C-Cl | CH | CH | CH | i-Pr | Cl | $CF_3$ | Cl |
| C-F | CH | CH | CH | i-Pr | Cl | $CF_3$ | F |
| CH | CH | CH | CH | i-Pr | Cl | $CF_3$ | acetylene |
| CH | CH | CH | CH | i-Pr | Cl | $CF_3$ | I |
| CH | CH | CH | CH | i-Pr | Cl | $CF_3$ | $SO_2Me$ |
| C-Cl | CH | CH | CH | i-Pr | Me | Br | Cl |
| C-F | CH | CH | CH | i-Pr | Me | Br | F |
| CH | CH | CH | CH | i-Pr | Me | Br | acetylene |
| CH | CH | CH | CH | i-Pr | Me | Br | I |
| CH | CH | CH | CH | i-Pr | Me | Br | $SO_2Me$ |
| C-Cl | CH | CH | CH | i-Pr | Cl | Br | Cl |
| C-F | CH | CH | CH | i-Pr | Cl | Br | F |
| CH | CH | CH | CH | i-Pr | Cl | Br | acetylene |
| CH | CH | CH | CH | i-Pr | Cl | Br | I |
| CH | CH | CH | CH | i-Pr | Cl | Br | $SO_2Me$ |
| C-Cl | CH | CH | N | i-Pr | Me | $CF_3$ | Cl |
| C-F | CH | CH | N | i-Pr | Me | $CF_3$ | F |
| CH | CH | CH | N | i-Pr | Me | $CF_3$ | acetylene |
| CH | CH | CH | N | i-Pr | Me | $CF_3$ | I |
| CH | CH | CH | N | f-Pr | Me | $CF_3$ | $SO_2Me$ |
| C-Cl | CH | CH | N | i-Pr | Cl | $CF_3$ | Cl |
| C-F | CH | CH | N | i-Pr | Cl | $CF_3$ | F |
| CH | CH | CH | N | i-Pr | Cl | $CF_3$ | acetylene |
| CH | CH | CH | N | i-Pr | Cl | $CF_3$ | I |
| CH | CH | CH | N | i-Pr | Cl | $CF_3$ | $SO_2Me$ |
| C-Cl | CH | CH | N | i-Pr | Me | Br | Cl |
| C-F | CH | CH | N | i-Pr | Me | Br | F |
| CH | CH | CH | N | i-Pr | Me | Br | acetylene |
| CH | CH | CH | N | i-Pr | Me | Br | I |
| CH | CH | CH | N | i-Pr | Me | Br | $SO_2Me$ |
| C-Cl | CH | CH | N | i-Pr | Cl | Br | Cl |
| C-F | CH | CH | N | i-Pr | Cl | Br | F |

TABLE 9-continued

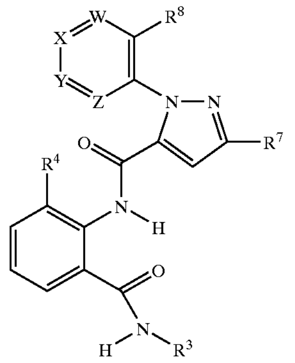

| W | X | Y | Z | $R^3$ | $R^4$ | $R^7$ | $R^8$ |
|---|---|---|---|---|---|---|---|
| CH | CH | CH | N | i-Pr | Cl | Br | acetylene |
| CH | CH | CH | N | i-Pr | Cl | Br | I |
| CH | CH | CH | N | i-Pr | Cl | Br | $SO_2Me$ |
| CH | N | CH | N | i-Pr | Me | $CF_3$ | H |
| CH | N | CH | N | i-Pr | Me | $CF_3$ | Me |
| CH | N | CH | N | i-Pr | Me | $CF_3$ | Cl |
| CH | N | CH | N | i-Pr | Cl | $CF_3$ | H |
| CH | N | CH | N | i-Pr | Cl | $CF_3$ | Me |
| CH | N | CH | N | i-Pr | Cl | $CF_3$ | Cl |
| CH | N | CH | N | i-Pr | Me | CN | H |
| CH | N | CH | N | i-Pr | Me | CN | Me |
| CH | N | CH | N | i-Pr | Me | CN | Cl |
| CH | N | CH | N | i-Pr | Cl | CN | H |
| CH | N | CH | N | i-Pr | Cl | CN | Me |
| CH | N | CH | N | i-Pr | C1 | CN | Cl |
| CH | N | CH | N | i-Pr | Me | Br | H |
| CH | N | CH | N | i-Pr | Me | Br | Me |
| CH | N | CH | N | i-Pr | Me | Br | Cl |
| CH | N | CH | N | i-Pr | Cl | Br | H |
| CH | N | CH | N | i-Pr | Cl | Br | Me |
| CH | N | CH | N | i-Pr | Cl | Br | Cl |
| CH | N | CH | N | t-Bu | Me | $CF_3$ | H |
| CH | N | CH | N | t-Bu | Me | $CF_3$ | Me |
| CH | N | CH | N | t-Bu | Me | $CF_3$ | Cl |
| CH | N | CH | N | t-Bu | Cl | $CF_3$ | H |
| CH | N | CH | N | t-Bu | Cl | $CF_3$ | Me |
| CH | N | CH | N | i-Bu | Cl | $CF_3$ | Cl |
| CH | N | CH | N | t-Bu | Me | CN | H |
| CH | N | CH | N | i-Bu | Me | CN | Me |
| CH | N | CH | N | i-Bu | Me | CN | Cl |
| CH | N | CH | N | t-Bu | Cl | CN | H |
| CH | N | CH | N | t-Bu | Cl | CN | Me |
| CH | N | CH | N | i-Bu | Cl | CN | Cl |
| CH | N | CH | N | i-Bu | Me | Br | H |
| CH | N | CH | N | t-Bu | Me | Br | Me |
| CH | N | CH | N | t-Bu | Me | Br | Cl |
| CH | N | CH | N | t-Bu | Cl | Br | H |
| CH | N | CH | N | t-Bu | Cl | Br | Me |
| CH | N | CH | N | t-Bu | Cl | Br | Cl |
| CH | CH | N | N | i-Pr | Me | $CF_3$ | H |
| CH | CH | N | N | i-Pr | Me | $CF_3$ | Me |
| CH | CH | N | N | i-Pr | Me | $CF_3$ | Cl |
| CH | CH | N | N | i-Pr | Cl | $CF_3$ | H |
| CH | CH | N | N | i-Pr | Cl | $CF_3$ | Me |
| CH | CH | N | N | i-Pr | Cl | $CF_3$ | Cl |
| CH | CH | N | N | i-Pr | Me | CN | H |
| CH | CH | N | N | i-Pr | Me | CN | Me |
| CH | CH | N | N | i-Pr | Me | CN | Cl |
| CH | CH | N | N | i-Pr | Cl | CN | H |
| CH | CH | N | N | i-Pr | Cl | CN | Me |
| CH | CH | N | N | i-Pr | Cl | CH | Cl |
| CH | CH | N | N | i-Pr | Me | Br | H |
| CH | CH | N | N | i-Pr | Me | Br | Me |
| CH | CH | N | N | i-Pr | Me | Br | Cl |
| CH | CH | N | N | i-Pr | Cl | Br | H |
| CH | CH | N | N | i-Pr | Cl | Br | Me |
| CH | CH | N | N | i-Pr | Cl | Br | Cl |
| CH | CH | N | N | i-Pr | Me | $CF_3$ | H |
| CH | CH | N | N | i-Pr | Me | $CF_3$ | Me |

TABLE 9-continued

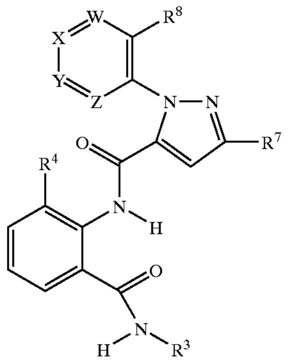

| W | X | Y | Z | $R^3$ | $R^4$ | $R^7$ | $R^8$ |
|---|---|---|---|---|---|---|---|
| CH | CH | N | N | i-Pr | Me | $CF_3$ | Cl |
| CH | CH | N | N | i-Pr | Cl | $CF_3$ | H |
| CH | CH | N | N | i-Pr | Cl | $CF_3$ | Me |
| CH | CH | N | N | i-Pr | Cl | $CF_3$ | Cl |
| CH | CH | N | N | i-Pr | Me | CN | H |
| CH | CH | N | N | i-Pr | Me | CN | Me |
| CH | CH | N | N | i-Pr | Me | CN | Cl |
| CH | CH | N | N | i-Pr | Cl | CN | H |
| CH | CH | N | N | i-Pr | Cl | CN | Me |
| CH | CH | N | N | i-Pr | Cl | CN | Cl |
| CH | CH | N | N | i-Pr | Me | Br | H |
| CH | CH | N | N | i-Pr | Me | Br | Me |
| CH | CH | N | N | i-Pr | Me | Br | Cl |
| CH | CH | N | N | i-Pr | Cl | Br | H |
| CH | CH | N | N | i-Pr | Cl | Br | Me |
| CH | CH | N | N | i-Pr | Cl | Br | Cl |

TABLE 10

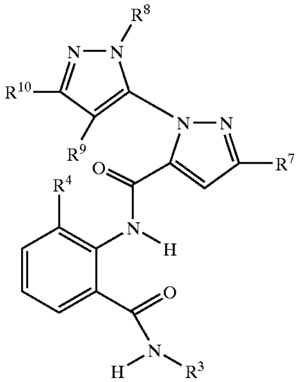

| $R^4$ | $R^7$ | $R^3$ | $R^8$ | $R^9$ | $R^{10}$ |
|---|---|---|---|---|---|
| Me | $CF_3$ | i-Pr | Me | H | H |
| Me | $CF_3$ | i-Pr | Me | H | Me |
| Me | $CF_3$ | i-Pr | Me | Cl | H |
| Me | $CF_3$ | i-Pr | Me | Cl | Me |
| Me | $CF_3$ | i-Pr | Me | Me | Me |
| Cl | $CF_3$ | i-Pr | Me | H | H |
| Cl | $CF_3$ | i-Pr | Me | H | Me |
| Cl | $CF_3$ | i-Pr | Me | Cl | H |
| Cl | $CF_3$ | i-Pr | Me | Cl | Me |
| Cl | $CF_3$ | i-Pr | Me | Me | Me |
| Me | $CF_3$ | t-Bu | Me | H | H |
| Me | $CF_3$ | t-Bu | Me | H | Me |
| Me | $CF_3$ | t-Bu | Me | Cl | H |
| Me | $CF_3$ | t-Bu | Me | Cl | Me |
| Me | $CF_3$ | t-Bu | Me | Me | Me |
| Cl | $CF_3$ | t-Bu | Me | H | H |

TABLE 10-continued

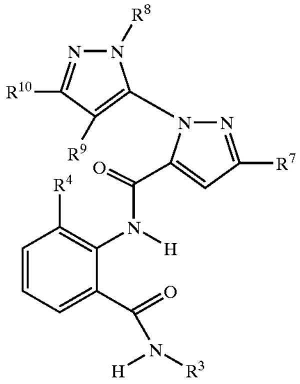

| $R^4$ | $R^7$ | $R^3$ | $R^8$ | $R^9$ | $R^{10}$ |
|---|---|---|---|---|---|
| Cl | $CF_3$ | t-Bu | Me | H | Me |
| Cl | $CF_3$ | t-Bu | Me | Cl | H |
| Cl | $CF_3$ | t-Bu | Me | Cl | Me |
| Cl | $CF_3$ | t-Bu | Me | Me | Me |

TABLE 11

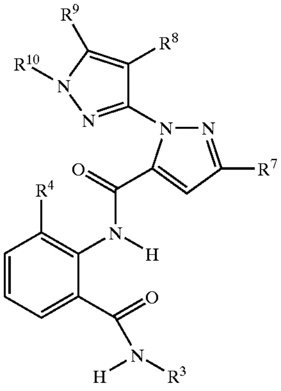

| $R^4$ | $R^7$ | $R^3$ | $R^8$ | $R^9$ | $R^{10}$ |
|---|---|---|---|---|---|
| Me | $CF_3$ | i-Pr | Me | H | Me |
| Me | $CF_3$ | i-Pr | Me | Me | Me |
| Me | $CF_3$ | i-Pr | Cl | H | Me |
| Me | $CF_3$ | i-Pr | Cl | Me | Me |
| Cl | $CF_3$ | i-Pr | Me | H | Me |
| Cl | $CF_3$ | i-Pr | Me | Me | Me |
| Cl | $CF_3$ | i-Pr | Cl | H | Me |
| Cl | $CF_3$ | i-Pr | Cl | Me | Me |
| Me | $CF_3$ | t-Bu | Me | H | Me |
| Me | $CF_3$ | t-Bu | Me | Me | Me |
| Me | $CF_3$ | t-Bu | Cl | H | Me |
| Me | $CF_3$ | t-Bu | Cl | Me | Me |
| Cl | $CF_3$ | t-Bu | Me | H | Me |
| Cl | $CF_3$ | t-Bu | Me | Me | Me |
| Cl | $CF_3$ | t-Bu | Cl | H | Me |
| Cl | $CF_3$ | t-Bu | Cl | Me | Me |

TABLE 12

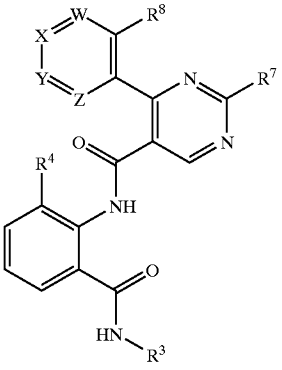

| W | X | Y | Z | $R^3$ | $R^4$ | $R^7$ | $R^8$ |
|---|---|---|---|---|---|---|---|
| CH | CH | CH | CH | Et | Me | $CF_3$ | Cl |
| CH | CH | CH | CH | i-Pr | Me | $CF_3$ | Cl |
| CH | CH | CH | CH | t-Bu | Me | $CF_3$ | Cl |
| CH | CH | CH | CH | Et | Me | $CF_3$ | Br |
| CH | CH | CH | CH | i-Pr | Me | $CF_3$ | Br |
| CH | CH | CH | CH | t-Bu | Me | $CF_3$ | Br |
| CH | CH | CH | CH | Et | Me | $CF_3$ | I |
| CH | CH | CH | CH | i-Pr | Me | $CF_3$ | I |
| CH | CH | CH | CH | t-Bu | Me | $CF_3$ | I |
| CH | CH | CH | CH | Et | Me | $CF_3$ | F |
| CH | CH | CH | CH | i-Pr | Me | $CF_3$ | F |
| CH | CH | CH | CH | t-Bu | Me | $CF_3$ | F |
| CH | CH | CH | CH | Et | Me | $CF_3$ | Me |
| CH | CH | CH | CH | i-Pr | Me | $CF_3$ | Me |
| CH | CH | CH | CH | t-Bu | Me | $CF_3$ | Me |
| CH | CH | CH | CH | Et | Me | $CF_3$ | $CF_3$ |
| CH | CH | CH | CH | i-Pr | Me | $CF_3$ | $CF_3$ |
| CH | CH | CH | CH | t-Bu | Me | $CF_3$ | $CF_3$ |
| CH | CH | CH | CH | Et | Me | $CF_3$ | OMe |
| CH | CH | CH | CH | i-Pr | Me | $CF_3$ | OMe |
| CH | CH | CH | CH | t-Bu | Me | $CF_3$ | OMe |
| CH | CH | CH | CH | Et | Me | $CF_3$ | CN |
| CH | CH | CH | CH | i-Pr | Me | $CF_3$ | CN |
| CH | CH | CH | CH | t-Bu | Me | $CF_3$ | CN |
| CH | CH | CH | CH | Et | Cl | $CF_3$ | Cl |
| CH | CH | CH | CH | i-Pr | Cl | $CF_3$ | Cl |
| CH | CH | CH | CH | t-Bu | Cl | $CF_3$ | Cl |
| CH | CH | CH | CH | Et | Cl | $CF_3$ | Br |
| CH | CH | CH | CH | i-Pr | Cl | $CF_3$ | Br |
| CH | CH | CH | CH | t-Bu | Cl | $CF_3$ | Br |
| CH | CH | CH | CH | Et | Cl | $CF_3$ | I |
| CH | CH | CH | CH | i-Pr | Cl | $CF_3$ | I |
| CH | CH | CH | CH | t-Bu | Cl | $CF_3$ | I |
| CH | CH | CH | CH | Et | Cl | $CF_3$ | F |
| CH | CH | CH | CH | i-Pr | Cl | $CF_3$ | F |
| CH | CH | CH | CH | t-Bu | Cl | $CF_3$ | F |
| CH | CH | CH | CH | Et | Cl | $CF_3$ | Me |
| CH | CH | CH | CH | i-Pr | Cl | $CF_3$ | Me |
| CH | CH | CH | CH | t-Bu | Cl | $CF_3$ | Me |
| CH | CH | CH | CH | Et | Cl | $CF_3$ | $CF_3$ |
| CH | CH | CH | CH | i-Pr | Cl | $CF_3$ | $CF_3$ |
| CH | CH | CH | CH | t-Bu | Cl | $CF_3$ | $CF_3$ |
| CH | CH | CH | CH | Et | Cl | $CF_3$ | OMe |
| CH | CH | CH | CH | i-Pr | Cl | $CF_3$ | OMe |
| CH | CH | CH | CH | t-Bu | Cl | $CF_3$ | OMe |
| CH | CH | CH | CH | Et | Cl | $CF_3$ | CN |
| CH | CH | CH | CH | i-Pr | Cl | $CF_3$ | CN |
| CH | CH | CH | CH | t-Bu | Cl | $CF_3$ | CN |
| CH | CH | CH | N | Et | Me | $CF_3$ | Cl |
| CH | CH | CH | N | i-Pr | Me | $CF_3$ | Cl |
| CH | CH | CH | N | t-Bu | Me | $CF_3$ | Cl |
| CH | CH | CH | N | Et | Me | $CF_3$ | Br |
| CH | CH | CH | N | i-Pr | Me | $CF_3$ | Br |
| CH | CH | CH | N | t-Bu | Me | $CF_3$ | Br |
| CH | CH | CH | N | Et | Me | $CF_3$ | I |
| CH | CH | CH | N | i-Pr | Me | $CF_3$ | I |
| CH | CH | CH | N | t-Bu | Me | $CF_3$ | I |
| CH | CH | CH | N | Et | Me | $CF_3$ | F |

TABLE 12-continued

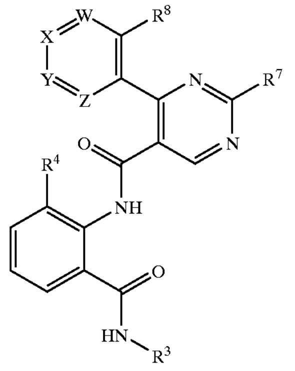

| W | X | Y | Z | $R^3$ | $R^4$ | $R^7$ | $R^8$ |
|---|---|---|---|---|---|---|---|
| CH | CH | CH | N | i-Pr | Me | $CF_3$ | F |
| CH | CH | CH | N | t-Bu | Me | $CF_3$ | F |
| CH | CH | CH | N | Et | Me | $CF_3$ | Me |
| CH | CH | CH | N | i-Pr | Me | $CF_3$ | Me |
| CH | CH | CH | N | t-Bu | Me | $CF_3$ | Me |
| CH | CH | CH | N | Et | Me | $CF_3$ | $CF_3$ |
| CH | CH | CH | N | i-Pr | Me | $CF_3$ | $CF_3$ |
| CH | CH | CH | N | t-Bu | Me | $CF_3$ | $CF_3$ |
| CH | CH | CH | N | Et | Me | $CF_3$ | OMe |
| CH | CH | CH | N | i-Pr | Me | $CF_3$ | OMe |
| CH | CH | CH | N | t-Bu | Me | $CF_3$ | OMe |
| CH | CH | CH | N | Et | Me | $CF_3$ | CN |
| CH | CH | CH | N | i-Pr | Me | $CF_3$ | CN |
| CH | CH | CH | N | t-Bu | Me | $CF_3$ | CN |
| CH | CH | CH | N | Et | Cl | $CF_3$ | Cl |
| CH | CH | CH | N | i-Pr | Cl | $CF_3$ | Cl |
| CH | CH | CH | N | t-Bu | Cl | $CF_3$ | Cl |
| CH | CH | CH | N | Et | Cl | $CF_3$ | Br |
| CH | CH | CH | N | i-Pr | Cl | $CF_3$ | Br |
| CH | CH | CH | N | t-Bu | Cl | $CF_3$ | Br |
| CH | CH | CH | N | Et | Cl | $CF_3$ | I |
| CH | CH | CH | N | i-Pr | Cl | $CF_3$ | I |
| CH | CH | CH | N | t-Bu | Cl | $CF_3$ | I |
| CH | CH | CH | N | Et | Cl | $CF_3$ | F |
| CH | CH | CH | N | i-Pr | Cl | $CF_3$ | F |
| CH | CH | CH | N | t-Bu | Cl | $CF_3$ | F |
| CH | CH | CH | N | Et | Cl | $CF_3$ | Me |
| CH | CH | CH | N | i-Pr | Cl | $CF_3$ | Me |
| CH | CH | CH | N | t-Bu | Cl | $CF_3$ | Me |
| CH | CH | CH | N | Et | Cl | $CF_3$ | $CF_3$ |
| CH | CH | CH | N | i-Pr | Cl | $CF_3$ | $CF_3$ |
| CH | CH | CH | N | t-Bu | Cl | $CF_3$ | $CF_3$ |
| CH | CH | CH | N | Et | Cl | $CF_3$ | OMe |
| CH | CH | CH | N | i-Pr | Cl | $CF_3$ | OMe |
| CH | CH | CH | N | t-Bu | Cl | $CF_3$ | OMe |
| CH | CH | CH | N | Et | Cl | $CF_3$ | CN |
| CH | CH | CH | N | i-Pr | Cl | $CF_3$ | CN |
| CH | CH | CH | N | t-Bu | Cl | $CF_3$ | CN |
| CH | CH | N | CH | Et | Me | $CF_3$ | Cl |
| CH | CH | N | CH | i-Pr | Me | $CF_3$ | Cl |
| CH | CH | N | CH | t-Bu | Me | $CF_3$ | Cl |
| CH | CH | N | CH | Et | Me | $CF_3$ | Br |
| CH | CH | N | CH | i-Pr | Me | $CF_3$ | Br |
| CH | CH | N | CH | t-Bu | Me | $CF_3$ | Br |
| CH | CH | N | CH | Et | Me | $CF_3$ | I |
| CH | CH | N | CH | i-Pr | Me | $CF_3$ | I |
| CH | CH | N | CH | t-Bu | Me | $CF_3$ | I |
| CH | CH | N | CH | Et | Me | $CF_3$ | F |
| CH | CH | N | CH | i-Pr | Me | $CF_3$ | F |
| CH | CH | N | CH | t-Bu | Me | $CF_3$ | F |
| CH | CH | N | CH | Et | Me | $CF_3$ | Me |
| CH | CH | N | CH | i-Pr | Me | $CF_3$ | Me |
| CH | CH | N | CH | t-Bu | Me | $CF_3$ | Me |
| CH | CH | N | CH | Et | Me | $CF_3$ | $CF_3$ |
| CH | CH | N | CH | i-Pr | Me | $CF_3$ | $CF_3$ |
| CH | CH | N | CH | t-Bu | Me | $CF_3$ | $CF_3$ |
| CH | CH | N | CH | Et | Me | $CF_3$ | OMe |
| CH | CH | N | CH | i-Pr | Me | $CF_3$ | OMe |

TABLE 12-continued

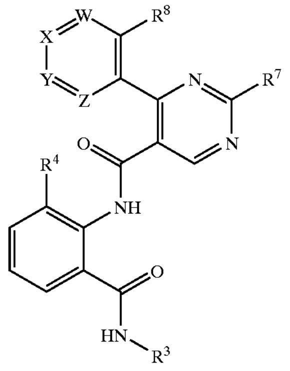

| W | X | Y | Z | $R^3$ | $R^4$ | $R^7$ | $R^8$ |
|---|---|---|---|---|---|---|---|
| CH | CH | N | CH | t-Bu | Me | $CF_3$ | OMe |
| CH | CH | N | CH | Et | Me | $CF_3$ | CN |
| CH | CH | N | CH | i-Pr | Me | $CF_3$ | CN |
| CH | CH | N | CH | t-Bu | Me | $CF_3$ | CN |
| CH | CH | N | CH | Et | Cl | $CF_3$ | Cl |
| CH | CH | N | CH | i-Pr | Cl | $CF_3$ | Cl |
| CH | CH | N | CH | t-Bu | Cl | $CF_3$ | Cl |
| CH | CH | N | CH | Et | Cl | $CF_3$ | Br |
| CH | CH | N | CH | i-Pr | Cl | $CF_3$ | Br |
| CH | CH | N | CH | t-Bu | Cl | $CF_3$ | Br |
| CH | CH | N | CH | Et | Cl | $CF_3$ | I |
| CH | CH | N | CH | i-Pr | Cl | $CF_3$ | I |
| CH | CH | N | CH | t-Bu | Cl | $CF_3$ | I |
| CH | CH | N | CH | Et | Cl | $CF_3$ | F |
| CH | CH | N | CH | i-Pr | Cl | $CF_3$ | F |
| CH | CH | N | CH | t-Bu | Cl | $CF_3$ | F |
| CH | CH | N | CH | Et | Cl | $CF_3$ | Me |
| CH | CH | N | CH | i-Pr | Cl | $CF_3$ | Me |
| CH | CH | N | CH | t-Bu | Cl | $CF_3$ | Me |
| CH | CH | N | CH | Et | Cl | $CF_3$ | $CF_3$ |
| CH | CH | N | CH | i-Pr | Cl | $CF_3$ | $CF_3$ |
| CH | CH | N | CH | t-Bu | Cl | $CF_3$ | $CF_3$ |
| CH | CH | N | CH | Et | Cl | $CF_3$ | OMe |
| CH | CH | N | CH | i-Pr | Cl | $CF_3$ | OMe |
| CH | CH | N | CH | t-Bu | Cl | $CF_3$ | OMe |
| CH | CH | N | CH | Et | Cl | $CF_3$ | CN |
| CH | CH | N | CH | i-Pr | Cl | $CF_3$ | CN |
| CH | CH | N | CH | t-Bu | Cl | $CF_3$ | CN |
| CH | N | CH | CH | Et | Me | $CF_3$ | Cl |
| CH | N | CH | CH | i-Pr | Me | $CF_3$ | Cl |
| CH | N | CH | CH | t-Bu | Me | $CF_3$ | Cl |
| CH | N | CH | CH | Et | Me | $CF_3$ | Br |
| CH | N | CH | CH | i-Pr | Me | $CF_3$ | Br |
| CH | N | CH | CH | t-Bu | Me | $CF_3$ | Br |
| CH | N | CH | CH | Et | Me | $CF_3$ | I |
| CH | N | CH | CH | i-Pr | Me | $CF_3$ | I |
| CH | N | CH | CH | t-Bu | Me | $CF_3$ | I |
| CH | N | CH | CH | Et | Me | $CF_3$ | F |
| CH | N | CH | CH | i-Pr | Me | $CF_3$ | F |
| CH | N | CH | CH | t-Bu | Me | $CF_3$ | F |
| CH | N | CH | CH | Et | Me | $CF_3$ | Me |
| CH | N | CH | CH | i-Pr | Me | $CF_3$ | Me |
| CH | N | CH | CH | t-Bu | Me | $CF_3$ | Me |
| CH | N | CH | CH | Et | Me | $CF_3$ | $CF_3$ |
| CH | N | CH | CH | i-Pr | Me | $CF_3$ | $CF_3$ |
| CH | N | CH | CH | t-Bu | Me | $CF_3$ | $CF_3$ |
| CH | N | CH | CH | Et | Me | $CF_3$ | OMe |
| CH | N | CH | CH | i-Pr | Me | $CF_3$ | OMe |
| CH | N | CH | CH | t-Bu | Me | $CF_3$ | OMe |
| CH | N | CH | CH | Et | Me | $CF_3$ | CN |
| CH | N | CH | CH | i-Pr | Me | $CF_3$ | CN |
| CH | N | CH | CH | t-Bu | Me | $CF_3$ | CN |
| CH | N | CH | CH | Et | Cl | $CF_3$ | Cl |
| CH | N | CH | CH | i-Pr | Cl | $CF_3$ | Cl |
| CH | N | CH | CH | t-Bu | Cl | $CF_3$ | Cl |
| CH | N | CH | CH | Et | Cl | $CF_3$ | Br |
| CH | N | CH | CH | i-Pr | Cl | $CF_3$ | Br |
| CH | N | CH | CH | t-Bu | Cl | $CF_3$ | Br |

TABLE 12-continued

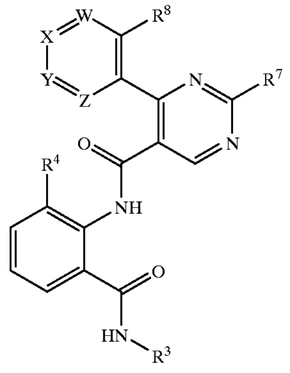

| W | X | Y | Z | $R^3$ | $R^4$ | $R^7$ | $R^8$ |
|---|---|---|---|---|---|---|---|
| CH | N | CH | CH | Et | Cl | $CF_3$ | I |
| CH | N | CH | CH | i-Pr | Cl | $CF_3$ | I |
| CH | N | CH | CH | t-Bu | Cl | $CF_3$ | I |
| CH | N | CH | CH | Et | Cl | $CF_3$ | F |
| CH | N | CH | CH | i-Pr | Cl | $CF_3$ | F |
| CH | N | CH | CH | t-Bu | Cl | $CF_3$ | F |
| CH | N | CH | CH | Et | Cl | $CF_3$ | Me |
| CH | N | CH | CH | i-Pr | Cl | $CF_3$ | Me |
| CH | N | CH | CH | t-Bu | Cl | $CF_3$ | Me |
| CH | N | CH | CH | Et | Cl | $CF_3$ | $CF_3$ |
| CH | N | CH | CH | i-Pr | Cl | $CF_3$ | $CF_3$ |
| CH | N | CH | CH | t-Bu | Cl | $CF_3$ | $CF_3$ |
| CH | N | CH | CH | Et | Cl | $CF_3$ | OMe |
| CH | N | CH | CH | i-Pr | Cl | $CF_3$ | OMe |
| CH | N | CH | CH | t-Bu | Cl | $CF_3$ | OMe |
| CH | N | CH | CH | Et | Cl | $CF_3$ | CN |
| CH | N | CH | CH | i-Pr | Cl | $CF_3$ | CN |
| CH | N | CH | CH | t-Bu | Cl | $CF_3$ | CN |
| N | CH | CH | CH | Et | Me | $CF_3$ | Cl |
| N | CH | CH | CH | i-Pr | Me | $CF_3$ | Cl |
| N | CH | CH | CH | t-Bu | Me | $CF_3$ | Cl |
| N | CH | CH | CH | Et | Me | $CF_3$ | Br |
| N | CH | CH | CH | i-Pr | Me | $CF_3$ | Br |
| N | CH | CH | CH | t-Bu | Me | $CF_3$ | Br |
| N | CH | CH | CH | Et | Me | $CF_3$ | I |
| N | CH | CH | CH | i-Pr | Me | $CF_3$ | I |
| N | CH | CH | CH | t-Bu | Me | $CF_3$ | I |
| N | CH | CH | CH | Et | Me | $CF_3$ | F |
| N | CH | CH | CH | i-Pr | Me | $CF_3$ | F |
| N | CH | CH | CH | t-Bu | Me | $CF_3$ | F |
| N | CH | CH | CH | Et | Me | $CF_3$ | Me |
| N | CH | CH | CH | i-Pr | Me | $CF_3$ | Me |
| N | CH | CH | CH | t-Bu | Me | $CF_3$ | Me |
| N | CH | CH | CH | Et | Me | $CF_3$ | $CF_3$ |
| N | CH | CH | CH | i-Pr | Me | $CF_3$ | $CF_3$ |
| N | CH | CH | CH | t-Bu | Me | $CF_3$ | $CF_3$ |
| N | CH | CH | CH | Et | Me | $CF_3$ | OMe |
| N | CH | CH | CH | i-Pr | Me | $CF_3$ | OMe |
| N | CH | CH | CH | t-Bu | Me | $CF_3$ | OMe |
| N | CH | CH | CH | Et | Me | $CF_3$ | CN |
| N | CH | CH | CH | i-Pr | Me | $CF_3$ | CN |
| N | CH | CH | CH | t-Bu | Me | $CF_3$ | CN |
| N | CH | CH | CH | Et | Cl | $CF_3$ | Cl |
| N | CH | CH | CH | i-Pr | Cl | $CF_3$ | Cl |
| N | CH | CH | CH | t-Bu | Cl | $CF_3$ | Cl |
| N | CH | CH | CH | Et | Cl | $CF_3$ | Br |
| N | CH | CH | CH | i-Pr | Cl | $CF_3$ | Br |
| N | CH | CH | CH | t-Bu | Cl | $CF_3$ | Br |
| N | CH | CH | CH | Et | Cl | $CF_3$ | I |
| N | CH | CH | CH | i-Pr | Cl | $CF_3$ | I |
| N | CH | CH | CH | t-Bu | Cl | $CF_3$ | I |
| N | CH | CH | CH | Et | Cl | $CF_3$ | F |
| N | CH | CH | CH | i-Pr | Cl | $CF_3$ | F |
| N | CH | CH | CH | t-Bu | Cl | $CF_3$ | F |
| N | CH | CH | CH | Et | Cl | $CF_3$ | Me |
| N | CH | CH | CH | i-Pr | Cl | $CF_3$ | Me |
| N | CH | CH | CH | t-Bu | Cl | $CF_3$ | Me |
| N | CH | CH | CH | Et | Cl | $CF_3$ | $CF_3$ |

TABLE 12-continued

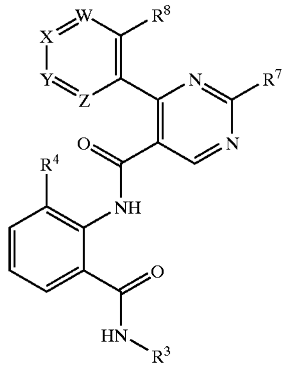

| W | X | Y | Z | $R^3$ | $R^4$ | $R^7$ | $R^8$ |
|---|---|---|---|---|---|---|---|
| N | CH | CH | CH | i-Pr | Cl | $CF_3$ | $CF_3$ |
| N | CH | CH | CH | t-Bu | Cl | $CF_3$ | $CF_3$ |
| N | CH | CH | CH | Et | Cl | $CF_3$ | OMe |
| N | CH | CH | CH | i-Pr | Cl | $CF_3$ | OMe |
| N | CH | CH | CH | t-Bu | Cl | $CF_3$ | OMe |
| N | CH | CH | CH | Et | Cl | $CF_3$ | CN |
| N | CH | CH | CH | i-Pr | Cl | $CF_3$ | CN |
| N | CH | CH | CH | t-Bu | Cl | $CF_3$ | CN |
| CH | N | CH | N | Et | Me | $CF_3$ | Cl |
| CH | N | CH | N | i-Pr | Me | $CF_3$ | Cl |
| CH | N | CH | N | t-Bu | Me | $CF_3$ | Cl |
| CH | N | CH | N | Et | Me | $CF_3$ | Br |
| CH | N | CH | N | i-Pr | Me | $CF_3$ | Br |
| CH | N | CH | N | t-Bu | Me | $CF_3$ | Br |
| CH | N | CH | N | Et | Me | $CF_3$ | I |
| CH | N | CH | N | i-Pr | Me | $CF_3$ | I |
| CH | N | CH | N | t-Bu | Me | $CF_3$ | I |
| CH | N | CH | N | Et | Me | $CF_3$ | F |
| CH | N | CH | N | i-Pr | Me | $CF_3$ | F |
| CH | N | CH | N | t-Bu | Me | $CF_3$ | F |
| CH | N | CH | N | Et | Me | $CF_3$ | Me |
| CH | N | CH | N | i-Pr | Me | $CF_3$ | Me |
| CH | N | CH | N | t-Bu | Me | $CF_3$ | Me |
| CH | N | CH | N | Et | Me | $CF_3$ | $CF_3$ |
| CH | N | CH | N | i-Pr | Me | $CF_3$ | $CF_3$ |
| CH | N | CH | N | t-Bu | Me | $CF_3$ | $CF_3$ |
| CH | N | CH | N | Et | Me | $CF_3$ | OMe |
| CH | N | CH | N | i-Pr | Me | $CF_3$ | OMe |
| CH | N | CH | N | t-Bu | Me | $CF_3$ | OMe |
| CH | N | CH | N | Et | Me | $CF_3$ | CN |
| CH | N | CH | N | i-Pr | Me | $CF_3$ | CN |
| CH | N | CH | N | t-Bu | Me | $CF_3$ | CN |
| CH | N | CH | N | Et | Cl | $CF_3$ | Cl |
| CH | N | CH | N | i-Pr | Cl | $CF_3$ | Cl |
| CH | N | CH | N | t-Bu | Cl | $CF_3$ | Cl |
| CH | N | CH | N | Et | Cl | $CF_3$ | Br |
| CH | N | CH | N | i-Pr | Cl | $CF_3$ | Br |
| CH | N | CH | N | t-Bu | Cl | $CF_3$ | Br |
| CH | N | CH | N | Et | Cl | $CF_3$ | I |
| CH | N | CH | N | i-Pr | Cl | $CF_3$ | I |
| CH | N | CH | N | t-Bu | Cl | $CF_3$ | I |
| CH | N | CH | N | Et | Cl | $CF_3$ | F |
| CH | N | CH | N | i-Pr | Cl | $CF_3$ | F |
| CH | N | CH | N | t-Bu | Cl | $CF_3$ | F |
| CH | N | CH | N | Et | Cl | $CF_3$ | Me |
| CH | N | CH | N | i-Pr | Cl | $CF_3$ | Me |
| CH | N | CH | N | t-Bu | Cl | $CF_3$ | Me |
| CH | N | CH | N | Et | Cl | $CF_3$ | $CF_3$ |
| CH | N | CH | N | i-Pr | Cl | $CF_3$ | $CF_3$ |
| CH | N | CH | N | t-Bu | Cl | $CF_3$ | $CF_3$ |
| CH | N | CH | N | Et | Cl | $CF_3$ | OMe |
| CH | N | CH | N | i-Pr | Cl | $CF_3$ | OMe |
| CH | N | CH | N | t-Bu | Cl | $CF_3$ | OMe |
| CH | N | CH | N | Et | Cl | $CF_3$ | CN |
| CH | N | CH | N | i-Pr | Cl | $CF_3$ | CN |
| CH | N | CH | N | t-Bu | Cl | $CF_3$ | CN |
| CH | CH | CH | CCl | Et | Me | $CF_3$ | Cl |
| CH | CH | CH | CCl | i-Pr | Me | $CF_3$ | Cl |

TABLE 12-continued

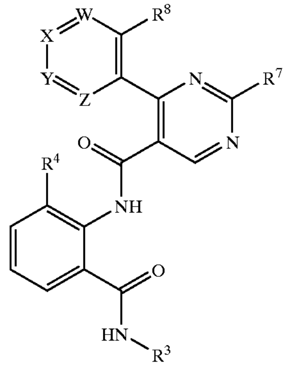

| W | X | Y | Z | $R^3$ | $R^4$ | $R^7$ | $R^8$ |
|---|---|---|---|---|---|---|---|
| CH | CH | CH | CCl | t-Bu | Me | $CF_3$ | Cl |
| CH | CH | CH | CCl | Et | Me | $CF_3$ | Br |
| CH | CH | CH | CCl | i-Pr | Me | $CF_3$ | Br |
| CH | CH | CH | CCl | t-Bu | Me | $CF_3$ | Br |
| CH | CH | CH | CCl | Et | Me | $CF_3$ | I |
| CH | CH | CH | CCl | i-Pr | Me | $CF_3$ | I |
| CH | CH | CH | CCl | t-Bu | Me | $CF_3$ | I |
| CH | CH | CH | CCl | Et | Me | $CF_3$ | F |
| CH | CH | CH | CCl | i-Pr | Me | $CF_3$ | F |
| CH | CH | CH | CCl | t-Bu | Me | $CF_3$ | F |
| CH | CH | CH | CCl | Et | Me | $CF_3$ | Me |
| CH | CH | CH | CCl | i-Pr | Me | $CF_3$ | Me |
| CH | CH | CH | CCl | t-Bu | Me | $CF_3$ | Me |
| CH | CH | CH | CCl | Et | Me | $CF_3$ | $CF_3$ |
| CH | CH | CH | CCl | i-Pr | Me | $CF_3$ | $CF_3$ |
| CH | CH | CH | CCl | t-Bu | Me | $CF_3$ | $CF_3$ |
| CH | CH | CH | CCl | Et | Me | $CF_3$ | OMe |
| CH | CH | CH | CCl | i-Pr | Me | $CF_3$ | OMe |
| CH | CH | CH | CCl | t-Bu | Me | $CF_3$ | OMe |
| CH | CH | CH | CCl | Et | Me | $CF_3$ | CN |
| CH | CH | CH | CCl | i-Pr | Me | $CF_3$ | CN |
| CH | CH | CH | CCl | t-Bu | Me | $CF_3$ | CN |
| CH | CH | CH | CCl | Et | Cl | $CF_3$ | Cl |
| CH | CH | CH | CCl | i-Pr | Cl | $CF_3$ | Cl |
| CH | CH | CH | CCl | t-Bu | Cl | $CF_3$ | Cl |
| CH | CH | CH | CCl | Et | Cl | $CF_3$ | Br |
| CH | CH | CH | CCl | i-Pr | Cl | $CF_3$ | Br |
| CH | CH | CH | CCl | t-Bu | Cl | $CF_3$ | Br |
| CH | CH | CH | CCl | Et | Cl | $CF_3$ | I |
| CH | CH | CH | CCl | i-Pr | Cl | $CF_3$ | I |
| CH | CH | CH | CCl | t-Bu | Cl | $CF_3$ | I |
| CH | CH | CH | CCl | Et | Cl | $CF_3$ | F |
| CH | CH | CH | CCl | i-Pr | Cl | $CF_3$ | F |
| CH | CH | CH | CCl | t-Bu | Cl | $CF_3$ | F |
| CH | CH | CH | CCl | Et | Cl | $CF_3$ | Me |
| CH | CH | CH | CCl | i-Pr | Cl | $CF_3$ | Me |
| CH | CH | CH | CCl | t-Bu | Cl | $CF_3$ | Me |
| CH | CH | CH | CCl | Et | Cl | $CF_3$ | $CF_3$ |
| CH | CH | CH | CCl | i-Pr | Cl | $CF_3$ | $CF_3$ |
| CH | CH | CH | CCl | t-Bu | Cl | $CF_3$ | $CF_3$ |
| CH | CH | CH | CCl | Et | Cl | $CF_3$ | OMe |
| CH | CH | CH | CCl | i-Pr | Cl | $CF_3$ | OMe |
| CH | CH | CH | CCl | t-Bu | Cl | $CF_3$ | OMe |
| CH | CH | CH | CCl | Et | Cl | $CF_3$ | CN |
| CH | CH | CH | CCl | i-Pr | Cl | $CF_3$ | CN |
| CH | CH | CH | CCl | t-Bu | Cl | $CF_3$ | CN |
| CH | CH | CH | CF | Et | Me | $CF_3$ | Cl |
| CH | CH | CH | CF | i-Pr | Me | $CF_3$ | Cl |
| CH | CH | CH | CF | t-Bu | Me | $CF_3$ | Cl |
| CH | CH | CH | CF | Et | Me | $CF_3$ | Br |
| CH | CH | CH | CF | i-Pr | Me | $CF_3$ | Br |
| CH | CH | CH | CF | t-Bu | Me | $CF_3$ | Br |
| CH | CH | CH | CF | Et | Me | $CF_3$ | I |
| CH | CH | CH | CF | i-Pr | Me | $CF_3$ | I |
| CH | CH | CH | CF | t-Bu | Me | $CF_3$ | I |
| CH | CH | CH | CF | Et | Me | $CF_3$ | F |
| CH | CH | CH | CF | i-Pr | Me | $CF_3$ | F |
| CH | CH | CH | CF | t-Bu | Me | $CF_3$ | F |

TABLE 12-continued

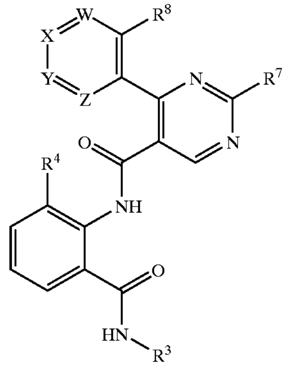

| W | X | Y | Z | $R^3$ | $R^4$ | $R^7$ | $R^8$ |
|---|---|---|---|---|---|---|---|
| CH | CH | CH | CF | Et | Me | $CF_3$ | Me |
| CH | CH | CH | CF | i-Pr | Me | $CF_3$ | Me |
| CH | CH | CH | CF | t-Bu | Me | $CF_3$ | Me |
| CH | CH | CH | CF | Et | Me | $CF_3$ | $CF_3$ |
| CH | CH | CH | CF | i-Pr | Me | $CF_3$ | $CF_3$ |
| CH | CH | CH | CF | t-Bu | Me | $CF_3$ | $CF_3$ |
| CH | CH | CH | CF | Et | Me | $CF_3$ | OMe |
| CH | CH | CH | CF | i-Pr | Me | $CF_3$ | OMe |
| CH | CH | CH | CF | t-Bu | Me | $CF_3$ | OMe |
| CH | CH | CH | CF | Et | Me | $CF_3$ | CN |
| CH | CH | CH | CF | i-Pr | Me | $CF_3$ | CN |
| CH | CH | CH | CF | t-Bu | Me | $CF_3$ | CN |
| CH | CH | CH | CF | Et | Cl | $CF_3$ | Cl |
| CH | CH | CH | CF | i-Pr | Cl | $CF_3$ | Cl |
| CH | CH | CH | CF | t-Bu | Cl | $CF_3$ | Cl |
| CH | CH | CH | CF | Et | Cl | $CF_3$ | Br |
| CH | CH | CH | CF | i-Pr | Cl | $CF_3$ | Br |
| CH | CH | CH | CF | t-Bu | Cl | $CF_3$ | Br |
| CH | CH | CH | CF | Et | Cl | $CF_3$ | I |
| CH | CH | CH | CF | i-Pr | Cl | $CF_3$ | I |
| CH | CH | CH | CF | t-Bu | Cl | $CF_3$ | I |
| CH | CH | CH | CF | i-Pr | Cl | $CF_3$ | F |
| CH | CH | CH | CF | t-Bu | Cl | $CF_3$ | F |
| CH | CH | CH | CF | Et | Cl | $CF_3$ | Me |
| CH | CH | CH | CF | i-Pr | Cl | $CF_3$ | Me |
| CH | CH | CH | CF | t-Bu | Cl | $CF_3$ | Me |
| CH | CH | CH | CF | Et | Cl | $CF_3$ | $CF_3$ |
| CH | CH | CH | CF | i-Pr | Cl | $CF_3$ | $CF_3$ |
| CH | CH | CH | CF | t-Bu | Cl | $CF_3$ | $CF_3$ |
| CH | CH | CH | CF | Et | Cl | $CF_3$ | OMe |
| CH | CH | CH | CF | i-Pr | Cl | $CF_3$ | OMe |
| CH | CH | CH | CF | t-Bu | Cl | $CF_3$ | OMe |
| CH | CH | CH | CF | Et | Cl | $CF_3$ | CN |
| CH | CH | CH | CF | i-Pr | Cl | $CF_3$ | CN |
| CH | CH | CH | CF | t-Bu | Cl | $CF_3$ | CN |
| CH | CH | CH | CH | Et | Me | $C_2F_5$ | Cl |
| CH | CH | CH | CH | i-Pr | Me | $C_2F_5$ | Cl |
| CH | CH | CH | CH | t-Bu | Me | $C_2F_5$ | Cl |
| CH | CH | CH | CH | Et | Me | $C_2F_5$ | Br |
| CH | CH | CH | CH | i-Pr | Me | $C_2F_5$ | Br |
| CH | CH | CH | CH | t-Bu | Me | $C_2F_5$ | Br |
| CH | CH | CH | CH | Et | Me | $C_2F_5$ | I |
| CH | CH | CH | CH | i-Pr | Me | $C_2F_5$ | I |
| CH | CH | CH | CH | t-Bu | Me | $C_2F_5$ | I |
| CH | CH | 0H | CH | Et | Me | $C_2F_5$ | F |
| CH | CH | CH | CH | i-Pr | Me | $C_2F_5$ | F |
| CH | CH | CH | CH | t-Bu | Me | $C_2F_5$ | F |
| CH | CH | CH | CH | Et | Me | $C_2F_5$ | Me |
| CH | CH | CH | CH | i-Pr | Me | $C_2F_5$ | Me |
| CH | CH | CH | CH | t-Bu | Me | $C_2F_5$ | Me |
| CH | CH | CH | CH | Et | Me | $C_2F_5$ | $CF_3$ |
| CH | CH | CH | CH | i-Pr | Me | $C_2F_5$ | $CF_3$ |
| CH | CH | CH | CH | t-Bu | Me | $C_2F_5$ | $CF_3$ |
| CH | CH | CH | CH | Et | Me | $C_2F_5$ | OMe |
| CH | CH | CH | CH | i-Pr | Me | $C_2F_5$ | OMe |
| CH | CH | CH | CH | t-Bu | Me | $C_2F_5$ | OMe |
| CH | CH | CH | CH | Et | Me | $C_2F_5$ | CN |
| CH | CH | CH | CH | i-Pr | Me | $C_2F_5$ | CN |

TABLE 12-continued

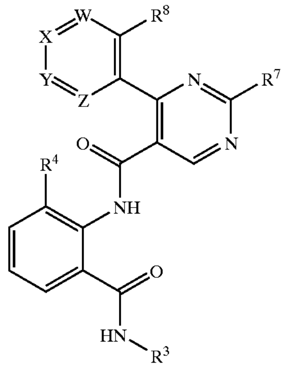

| W | X | Y | Z | $R^3$ | $R^4$ | $R^7$ | $R^8$ |
|---|---|---|---|---|---|---|---|
| CH | CH | CH | CH | t-Bu | Me | $C_2F_5$ | CN |
| CH | CH | CH | CH | Et | Cl | $C_2F_5$ | Cl |
| CH | CH | CH | CH | i-Pr | Cl | $C_2F_5$ | Cl |
| CH | CH | CH | CH | t-Bu | Cl | $C_2F_5$ | Cl |
| CH | CH | CH | CH | Et | Cl | $C_2F_5$ | Br |
| CH | CH | CH | CH | i-Pr | Cl | $C_2F_5$ | Br |
| CH | CH | CH | CH | t-Bu | Cl | $C_2F_5$ | Br |
| CH | CH | CH | CH | Et | Cl | $C_2F_5$ | I |
| CH | CH | CH | CH | i-Pr | Cl | $C_2F_5$ | I |
| CH | CH | CH | CH | t-Bu | Cl | $C_2F_5$ | I |
| CH | CH | CH | CH | Et | Cl | $C_2F_5$ | F |
| CH | CH | CH | CH | i-Pr | Cl | $C_2F_5$ | F |
| CH | CH | CH | CH | t-Bu | Cl | $C_2F_5$ | F |
| CH | CH | CH | CH | Et | Cl | $C_2F_5$ | Me |
| CH | CH | CH | CH | i-Pr | Cl | $C_2F_5$ | Me |
| CH | CH | CH | CH | t-Bu | Cl | $C_2F_5$ | Me |
| CH | CH | CH | CH | Et | Cl | $C_2F_5$ | $CF_3$ |
| CH | CH | CH | CH | i-Pr | Cl | $C_2F_5$ | $CF_3$ |
| CH | CH | CH | CH | t-Bu | Cl | $C_2F_5$ | $CF_3$ |
| CH | CH | CH | CH | Et | Cl | $C_2F_5$ | OMe |
| CH | CH | CH | CH | i-Pr | Cl | $C_2F_5$ | OMe |
| CH | CH | CH | CH | t-Bu | Cl | $C_2F_5$ | OMe |
| CH | CH | CH | CH | Et | Cl | $C_2F_5$ | CN |
| CH | CH | CH | CH | i-Pr | Cl | $C_2F_5$ | CN |
| CH | CH | CH | CH | t-Bu | Cl | $C_2F_5$ | CN |

TABLE 13

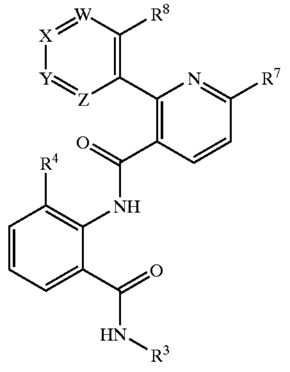

| W | X | Y | Z | $R^3$ | $R^4$ | $R^7$ | $R^8$ |
|---|---|---|---|---|---|---|---|
| CH | CH | CH | CH | Et | Me | $CF_3$ | Cl |
| CH | CH | CH | CH | i-Pr | Me | $CF_3$ | Cl |
| CH | CH | CH | CH | t-Bu | Me | $CF_3$ | Cl |
| CH | CH | CH | CH | Et | Me | $CF_3$ | Br |
| CH | CH | CH | CH | i-Pr | Me | $CF_3$ | Br |
| CH | CH | CH | CH | t-Bu | Me | $CF_3$ | Br |
| CH | CH | CH | CH | Et | Me | $CF_3$ | I |
| CH | CH | CH | CH | i-Pr | Me | $CF_3$ | I |

TABLE 13-continued

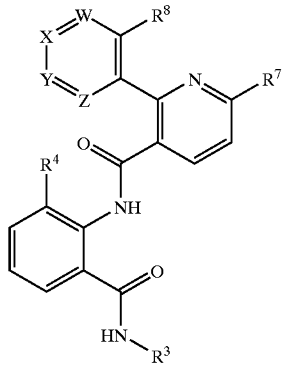

| W | X | Y | Z | $R^3$ | $R^4$ | $R^7$ | $R^8$ |
|---|---|---|---|---|---|---|---|
| CH | CH | CH | CH | t-Bu | Me | $CF_3$ | I |
| CH | CH | CH | CH | Et | Me | $CF_3$ | F |
| CH | CH | CH | CH | i-Pr | Me | $CF_3$ | F |
| CH | CH | CH | CH | t-Bu | Me | $CF_3$ | F |
| CH | CH | CH | CH | Et | Me | $CF_3$ | Me |
| CH | CH | CH | CH | i-Pr | Me | $CF_3$ | Me |
| CH | CH | CH | CH | t-Bu | Me | $CF_3$ | Me |
| CH | CH | CH | CH | Et | Me | $CF_3$ | $CF_3$ |
| CH | CH | CH | CH | i-Pr | Me | $CF_3$ | $CF_3$ |
| CH | CH | CH | CH | t-Bu | Me | $CF_3$ | $CF_3$ |
| CH | CH | CH | CH | Et | Me | $CF_3$ | OMe |
| CH | CH | CH | CH | i-Pr | Me | $CF_3$ | OMe |
| CH | CH | CH | CH | t-Bu | Me | $CF_3$ | OMe |
| CH | CH | CH | CH | Et | Me | $CF_3$ | CN |
| CH | CH | CH | CH | i-Pr | Me | $CF_3$ | CN |
| CH | CH | CH | CH | t-Bu | Me | $CF_3$ | CN |
| CH | CH | CH | CH | Et | Cl | $CF_3$ | Cl |
| CH | CH | CH | CH | i-Pr | Cl | $CF_3$ | Cl |
| CH | CH | CH | CH | t-Bu | Cl | $CF_3$ | Cl |
| CH | CH | CH | CH | Et | Cl | $CF_3$ | Br |
| CH | CH | CH | CH | i-Pr | Cl | $CF_3$ | Br |
| CH | CH | CH | CH | t-Bu | Cl | $CF_3$ | Br |
| CH | CH | CH | CH | Et | Cl | $CF_3$ | I |
| CH | CH | CH | CH | i-Pr | Cl | $CF_3$ | I |
| CH | CH | CH | CH | t-Bu | Cl | $CF_3$ | I |
| CH | CH | CH | CH | Et | Cl | $CF_3$ | F |
| CH | CH | CH | CH | i-Pr | Cl | $CF_3$ | F |
| CH | CH | CH | CH | t-Bu | Cl | $CF_3$ | F |
| CH | CH | CH | CH | Et | Cl | $CF_3$ | Me |
| CH | CH | CH | CH | i-Pr | Cl | $CF_3$ | Me |
| CH | CH | CH | CH | t-Bu | Cl | $CF_3$ | Me |
| CH | CH | CH | CH | Et | Cl | $CF_3$ | $CF_3$ |
| CH | CH | CH | CH | i-Pr | Cl | $CF_3$ | $CF_3$ |
| CH | CH | CH | CH | t-Bu | Cl | $CF_3$ | $CF_3$ |
| CH | CH | CH | CH | Et | Cl | $CF_3$ | OMe |
| CH | CH | CH | CH | i-Pr | Cl | $CF_3$ | OMe |
| CH | CH | CH | CH | t-Bu | Cl | $CF_3$ | OMe |
| CH | CH | CH | CH | Et | Cl | $CF_3$ | CN |
| CH | CH | CH | CH | i-Pr | Cl | $CF_3$ | CN |
| CH | CH | CH | CH | t-Bu | Cl | $CF_3$ | CN |
| CH | CH | CH | N | Et | Me | $CF_3$ | Cl |
| CH | CH | CH | N | i-Pr | Me | $CF_3$ | Cl |
| CH | CH | CH | N | t-Bu | Me | $CF_3$ | Cl |
| CH | CH | CH | N | Et | Me | $CF_3$ | Br |
| CH | CH | CH | N | i-Pr | Me | $CF_3$ | Br |
| CH | CH | CH | N | t-Bu | Me | $CF_3$ | Br |
| CH | CH | CH | N | Et | Me | $CF_3$ | I |
| CH | CH | CH | N | i-Pr | Me | $CF_3$ | I |
| CH | CH | CH | N | t-Bu | Me | $CF_3$ | I |
| CH | CH | CH | N | Et | Me | $CF_3$ | F |
| CH | CH | CH | N | i-Pr | Me | $CF_3$ | F |
| CH | CH | CH | N | t-Bu | Me | $CF_3$ | F |
| CH | CH | CH | N | Et | Me | $CF_3$ | Me |
| CH | CH | CH | N | i-Pr | Me | $CF_3$ | Me |
| CH | CH | CH | N | t-Bu | Me | $CF_3$ | Me |
| CH | CH | CH | N | Et | Me | $CF_3$ | $CF_3$ |
| CH | CH | CH | N | i-Pr | Me | $CF_3$ | $CF_3$ |
| CH | CH | CH | N | t-Bu | Me | $CF_3$ | $CF_3$ |

TABLE 13-continued

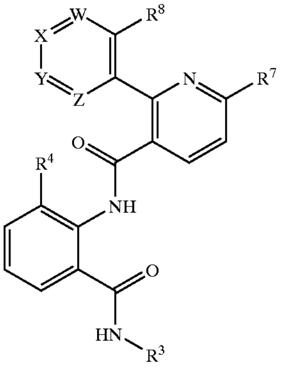

| W | X | Y | Z | $R^3$ | $R^4$ | $R^7$ | $R^8$ |
|---|---|---|---|---|---|---|---|
| CH | CH | CH | N | Et | Me | $CF_3$ | OMe |
| CH | CH | CH | N | i-Pr | Me | $CF_3$ | OMe |
| CH | CH | CH | N | t-Bu | Me | $CF_3$ | OMe |
| CH | CH | CH | N | Et | Me | $CF_3$ | CN |
| CH | CH | CH | N | i-Pr | Me | $CF_3$ | CN |
| CH | CH | CH | N | t-Bu | Me | $CF_3$ | CN |
| CH | CH | CH | N | Et | Cl | $CF_3$ | Cl |
| CH | CH | CH | N | i-Pr | Cl | $CF_3$ | Cl |
| CH | CH | CH | N | t-Bu | Cl | $CF_3$ | Cl |
| CH | CH | CH | N | Et | Cl | $CF_3$ | Br |
| CH | CH | CH | N | i-Pr | Cl | $CF_3$ | Br |
| CH | CH | CH | N | t-Bu | Cl | $CF_3$ | Br |
| CH | CH | CH | N | Et | Cl | $CF_3$ | I |
| CH | CH | CH | N | i-Pr | Cl | $CF_3$ | I |
| CH | CH | CH | N | t-Bu | Cl | $CF_3$ | I |
| CH | CH | CH | N | Et | Cl | $CF_3$ | F |
| CH | CH | CH | N | i-Pr | Cl | $CF_3$ | F |
| CH | CH | CH | N | t-Bu | Cl | $CF_3$ | F |
| CH | CH | CH | N | Et | Cl | $CF_3$ | Me |
| CH | CH | CH | N | i-Pr | Cl | $CF_3$ | Me |
| CH | CH | CH | N | t-Bu | Cl | $CF_3$ | Me |
| CH | CH | CH | N | Et | Cl | $CF_3$ | $CF_3$ |
| CH | CH | CH | N | i-Pr | Cl | $CF_3$ | $CF_3$ |
| CH | CH | CH | N | t-Bu | Cl | $CF_3$ | $CF_3$ |
| CH | CH | CH | N | Et | Cl | $CF_3$ | OMe |
| CH | CH | CH | N | i-Pr | Cl | $CF_3$ | OMe |
| CH | CH | CH | N | t-Bu | Cl | $CF_3$ | OMe |
| CH | CH | CH | N | Et | Cl | $CF_3$ | CN |
| CH | CH | CH | N | i-Pr | Cl | $CF_3$ | CN |
| CH | CH | CH | N | t-Bu | Cl | $CF_3$ | CN |
| CH | CH | N | CH | Et | Me | $CF_3$ | Cl |
| CH | CH | N | CH | i-Pr | Me | $CF_3$ | Cl |
| CH | CH | N | CH | t-Bu | Me | $CF_3$ | Cl |
| CH | CH | N | CH | Et | Me | $CF_3$ | Br |
| CH | CH | N | CH | i-Pr | Me | $CF_3$ | Br |
| CH | CH | N | CH | t-Bu | Me | $CF_3$ | Br |
| CH | CH | N | CH | Et | Me | $CF_3$ | I |
| CH | CH | N | CH | i-Pr | Me | $CF_3$ | I |
| CH | CH | N | CH | t-Bu | Me | $CF_3$ | I |
| CH | CH | N | CH | Et | Me | $CF_3$ | F |
| CH | CH | N | CH | i-Pr | Me | $CF_3$ | F |
| CH | CH | N | CH | t-Bu | Me | $CF_3$ | F |
| CH | CH | N | CH | Et | Me | $CF_3$ | Me |
| CH | CH | N | CH | i-Pr | Me | $CF_3$ | Me |
| CH | CH | N | CH | t-Bu | Me | $CF_3$ | Me |
| CH | CH | N | CH | Et | Me | $CF_3$ | $CF_3$ |
| CH | CH | N | CH | i-Pr | Me | $CF_3$ | $CF_3$ |
| CH | CH | N | CH | t-Bu | Me | $CF_3$ | $CF_3$ |
| CH | CH | N | CH | Et | Me | $CF_3$ | OMe |
| CH | CH | N | CH | i-Pr | Me | $CF_3$ | OMe |
| CH | CH | N | CH | t-Bu | Me | $CF_3$ | OMe |
| CH | CH | N | CH | Et | Me | $CF_3$ | CN |
| CH | CH | N | CH | i-Pr | Me | $CF_3$ | CN |
| CH | CH | N | CH | t-Bu | Me | $CF_3$ | CN |
| CH | CH | N | CH | Et | Cl | $CF_3$ | Cl |
| CH | CH | N | CH | i-Pr | Cl | $CF_3$ | Cl |
| CH | CH | N | CH | t-Bu | Cl | $CF_3$ | Cl |
| CH | CH | N | CH | Et | Cl | $CF_3$ | Br |

TABLE 13-continued

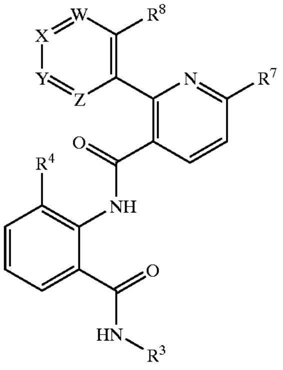

| W | X | Y | Z | $R^3$ | $R^4$ | $R^7$ | $R^8$ |
|---|---|---|---|---|---|---|---|
| CH | CH | N | CH | i-Pr | Cl | $CF_3$ | Br |
| CH | CH | N | CH | t-Bu | Cl | $CF_3$ | Br |
| CH | CH | N | CH | Et | Cl | $CF_3$ | I |
| CH | CH | N | CH | i-Pr | Cl | $CF_3$ | I |
| CH | CH | N | CH | t-Bu | Cl | $CF_3$ | I |
| CH | CH | N | CH | Et | Ci | $CF_3$ | F |
| CH | CH | N | CH | i-Pr | Cl | $CF_3$ | F |
| CH | CH | N | CH | t-Bu | Cl | $CF_3$ | F |
| CH | CH | N | CH | Et | Cl | $CF_3$ | Me |
| CH | CH | N | CH | i-Pr | Cl | $CF_3$ | Me |
| CH | CH | N | CH | t-Bu | Cl | $CF_3$ | Me |
| CH | CH | N | CH | Et | Cl | $CF_3$ | $CF_3$ |
| CH | CH | N | CH | i-Pr | Cl | $CF_3$ | $CF_3$ |
| CH | CH | N | CH | t-Bu | Cl | $CF_3$ | $CF_3$ |
| CH | CH | N | CH | Et | Cl | $CF_3$ | OMe |
| CH | CH | N | CH | i-Pr | Cl | $CF_3$ | OMe |
| CH | CH | N | CH | t-Bu | Cl | $CF_3$ | OMe |
| CH | CH | N | CH | Et | Cl | $CF_3$ | CN |
| CH | CH | N | CH | i-Pr | Cl | $CF_3$ | CN |
| CH | CH | N | CH | t-Bu | Cl | $CF_3$ | CN |
| CH | N | CH | CH | Et | Me | $CF_3$ | Cl |
| CH | N | CH | CH | i-Pr | Me | $CF_3$ | Cl |
| CH | N | CH | CH | t-Bu | Me | $CF_3$ | Cl |
| CH | N | CH | CH | Et | Me | $CF_3$ | Br |
| CH | N | CH | CH | i-Pr | Me | $CF_3$ | Br |
| CH | N | CH | CH | t-Bu | Me | $CF_3$ | Br |
| CH | N | CH | CH | Et | Me | $CF_3$ | I |
| CH | N | CH | CH | i-Pr | Me | $CF_3$ | I |
| CH | N | CH | CH | t-Bu | Me | $CF_3$ | I |
| CH | N | CH | CH | Et | Me | $CF_3$ | F |
| CH | N | CH | CH | i-Pr | Me | $CF_3$ | F |
| CH | N | CH | CH | t-Bu | Me | $CF_3$ | F |
| CH | N | CH | CH | Et | Me | $CF_3$ | Me |
| CH | N | CH | CH | i-Pr | Me | $CF_3$ | Me |
| CH | N | CH | CH | t-Bu | Me | $CF_3$ | Me |
| CH | N | CH | CH | Et | Me | $CF_3$ | $CF_3$ |
| CH | N | CH | CH | i-Pr | Me | $CF_3$ | $CF_3$ |
| CH | N | CH | CH | t-Bu | Me | $CF_3$ | $CF_3$ |
| CH | N | CH | CH | Et | Me | $CF_3$ | OMe |
| CH | N | CH | CH | i-Pr | Me | $CF_3$ | OMe |
| CH | N | CH | CH | t-Bu | Me | $CF_3$ | OMe |
| CH | N | CH | CH | Et | Me | $CF_3$ | CN |
| CH | N | CH | CH | i-Pr | Me | $CF_3$ | CN |
| CH | N | CH | CH | t-Bu | Me | $CF_3$ | CN |
| CH | N | CH | CH | Et | Cl | $CF_3$ | Cl |
| CH | N | CH | CH | i-Pr | Cl | $CF_3$ | Cl |
| CH | N | CH | CH | t-Bu | Cl | $CF_3$ | Cl |
| CH | N | CH | CH | Et | Cl | $CF_3$ | Br |
| CH | N | CH | CH | i-Pr | Cl | $CF_3$ | Br |
| CH | N | CH | CH | t-Bu | Cl | $CF_3$ | Br |
| CH | N | CH | CH | Et | Cl | $CF_3$ | I |
| CH | N | CH | CH | i-Pr | Cl | $CF_3$ | I |
| CH | N | CH | CH | t-Bu | Cl | $CF_3$ | I |
| CH | N | CH | CH | Et | Cl | $CF_3$ | F |
| CH | N | CH | CH | i-Pr | Cl | $CF_3$ | F |
| CH | N | CH | CH | t-Bu | Cl | $CF_3$ | F |
| CH | N | CH | CH | Et | Cl | $CF_3$ | Me |
| CH | N | CH | CH | i-Pr | Cl | $CF_3$ | Me |

TABLE 13-continued

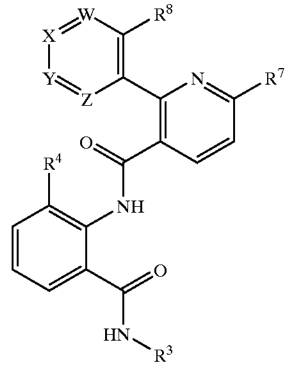

| W | X | Y | Z | $R^3$ | $R^4$ | $R^7$ | $R^8$ |
|---|---|---|---|---|---|---|---|
| CH | N | CH | CH | t-Bu | Cl | $CF_3$ | Me |
| CH | N | CH | CH | Et | Cl | $CF_3$ | $CF_3$ |
| CH | N | CH | CH | i-Pr | Cl | $CF_3$ | $CF_3$ |
| CH | N | CH | CH | t-Bu | Cl | $CF_3$ | $CF_3$ |
| CH | N | CH | CH | Et | Cl | $CF_3$ | OMe |
| CH | N | CH | CH | i-Pr | Cl | $CF_3$ | OMe |
| CH | N | CH | CH | t-Bu | Cl | $CF_3$ | OMe |
| CH | N | CH | CH | Et | Cl | $CF_3$ | CN |
| CH | N | CH | CH | i-Pr | Cl | $CF_3$ | CN |
| CH | N | CH | CH | t-Bu | Cl | $CF_3$ | CN |
| N | CH | CH | CH | Et | Me | $CF_3$ | Cl |
| N | CH | CH | CH | i-Pr | Me | $CF_3$ | Cl |
| N | CH | CH | CH | t-Bu | Me | $CF_3$ | Cl |
| N | CH | CH | CH | Et | Me | $CF_3$ | Br |
| N | CH | CH | CH | i-Pr | Me | $CF_3$ | Br |
| N | CH | CH | CH | t-Bu | Me | $CF_3$ | Br |
| N | CH | CH | CH | Et | Me | $CF_3$ | I |
| N | CH | CH | CH | i-Pr | Me | $CF_3$ | I |
| N | CH | CH | CH | t-Bu | Me | $CF_3$ | I |
| N | CH | CH | CH | Et | Me | $CF_3$ | F |
| N | CH | CH | CH | i-Pr | Me | $CF_3$ | F |
| N | CH | CH | CH | t-Bu | Me | $CF_3$ | F |
| N | CH | CH | CH | Et | Me | $CF_3$ | Me |
| N | CH | CH | CH | i-Pr | Me | $CF_3$ | Me |
| N | CH | CH | CH | t-Bu | Me | $CF_3$ | Me |
| N | CH | CH | CH | Et | Me | $CF_3$ | $CF_3$ |
| N | CH | CH | CH | i-Pr | Me | $CF_3$ | $CF_3$ |
| N | CH | CH | CH | t-Bu | Me | $CF_3$ | $CF_3$ |
| N | CH | CH | CH | Et | Me | $CF_3$ | OMe |
| N | CH | CH | CH | i-Pr | Me | $CF_3$ | OMe |
| N | CH | CH | CH | t-Bu | Me | $CF_3$ | OMe |
| N | CH | CH | CH | Et | Me | $CF_3$ | CN |
| N | CH | CH | CH | i-Pr | Me | $CF_3$ | CN |
| N | CH | CH | CH | t-Bu | Me | $CF_3$ | CN |
| N | CH | CH | CH | Et | Cl | $CF_3$ | Cl |
| N | CH | CH | CH | i-Pr | Cl | $CF_3$ | Cl |
| N | CH | CH | CH | t-Bu | Cl | $CF_3$ | Cl |
| N | CH | CH | CH | Et | Cl | $CF_3$ | Br |
| N | CH | CH | CH | i-Pr | Cl | $CF_3$ | Br |
| N | CH | CH | CH | t-Bu | Cl | $CF_3$ | Br |
| N | CH | CH | CH | Et | Cl | $CF_3$ | I |
| N | CH | CH | CH | i-Pr | Cl | $CF_3$ | I |
| N | CH | CH | CH | t-Bu | Cl | $CF_3$ | I |
| N | CH | CH | CH | Et | Cl | $CF_3$ | F |
| N | CH | CH | CH | i-Pr | Cl | $CF_3$ | F |
| N | CH | CH | CH | t-Bu | Cl | $CF_3$ | F |
| N | CH | CH | CH | Et | Cl | $CF_3$ | Me |
| N | CH | CH | CH | i-Pr | Cl | $CF_3$ | Me |
| N | CH | CH | CH | t-Bu | Cl | $CF_3$ | Me |
| N | CH | CH | CH | Et | Cl | $CF_3$ | $CF_3$ |
| N | CH | CH | CH | i-Pr | Cl | $CF_3$ | $CF_3$ |
| N | CH | CH | CH | t-Bu | Cl | $CF_3$ | $CF_3$ |
| N | CH | CH | CH | Et | Cl | $CF_3$ | OMe |
| N | CH | CH | CH | i-Pr | Cl | $CF_3$ | OMe |
| N | CH | CH | CH | t-Bu | Cl | $CF_3$ | OMe |
| N | CH | CH | CH | Et | Cl | $CF_3$ | CN |
| N | CH | CH | CH | i-Pr | Cl | $CF_3$ | CN |
| N | CH | CH | CH | t-Bu | Cl | $CF_3$ | CN |

TABLE 13-continued

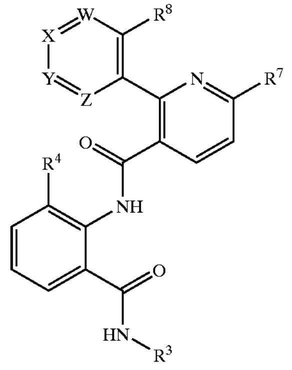

| W | X | Y | Z | $R^3$ | $R^4$ | $R^7$ | $R^8$ |
|---|---|---|---|---|---|---|---|
| CH | N | CH | N | Et | Me | $CF_3$ | Cl |
| CH | N | CH | N | i-Pr | Me | $CF_3$ | Cl |
| CH | N | CH | N | t-Bu | Me | $CF_3$ | Cl |
| CH | N | CH | N | Et | Me | $CF_3$ | Br |
| CH | N | CH | N | i-Pr | Me | $CF_3$ | Br |
| CH | N | CH | N | t-Bu | Me | $CF_3$ | Br |
| CH | N | CH | N | Et | Me | $CF_3$ | I |
| CH | N | CH | N | i-Pr | Me | $CF_3$ | I |
| CH | N | CH | N | t-Bu | Me | $CF_3$ | I |
| CH | N | CH | N | Et | Me | $CF_3$ | F |
| CH | N | CH | N | i-Pr | Me | $CF_3$ | F |
| CH | N | CH | N | t-Bu | Me | $CF_3$ | F |
| CH | N | CH | N | Et | Me | $CF_3$ | Me |
| CH | N | CH | N | i-Pr | Me | $CF_3$ | Me |
| CH | N | CH | N | t-Bu | Me | $CF_3$ | Me |
| CH | N | CH | N | Et | Me | $CF_3$ | $CF_3$ |
| CH | N | CH | N | i-Pr | Me | $CF_3$ | $CF_3$ |
| CH | N | CH | N | t-Bu | Me | $CF_3$ | $CF_3$ |
| CH | N | CH | N | Et | Me | $CF_3$ | OMe |
| CH | N | CH | N | i-Pr | Me | $CF_3$ | OMe |
| CH | N | CH | N | t-Bu | Me | $CF_3$ | OMe |
| CH | N | CH | N | Et | Me | $CF_3$ | CN |
| CH | N | CH | N | i-Pr | Me | $CF_3$ | CN |
| CH | N | CH | N | t-Bu | Me | $CF_3$ | CN |
| CH | N | CH | N | Et | Cl | $CF_3$ | Cl |
| CH | N | CH | N | i-Pr | Cl | $CF_3$ | Cl |
| CH | N | CH | N | t-Bu | Cl | $CF_3$ | Cl |
| CH | N | CH | N | Et | Cl | $CF_3$ | Br |
| CH | N | CH | N | i-Pr | Cl | $CF_3$ | Br |
| CH | N | CH | N | t-Bu | Cl | $CF_3$ | Br |
| CH | N | CH | N | Et | Cl | $CF_3$ | I |
| CH | N | CH | N | i-Pr | Cl | $CF_3$ | I |
| CH | N | CH | N | t-Bu | Cl | $CF_3$ | I |
| CH | N | CH | N | Et | Cl | $CF_3$ | F |
| CH | N | CH | N | i-Pr | Cl | $CF_3$ | F |
| CH | N | CH | N | t-Bu | Cl | $CF_3$ | F |
| CH | N | CH | N | Et | Cl | $CF_3$ | Me |
| CH | N | CH | N | i-Pr | Cl | $CF_3$ | Me |
| CH | N | CH | N | t-Bu | Cl | $CF_3$ | Me |
| CH | N | CH | N | Et | Cl | $CF_3$ | $CF_3$ |
| CH | N | CH | N | i-Pr | Cl | $CF_3$ | $CF_3$ |
| CH | N | CH | N | t-Bu | Cl | $CF_3$ | $CF_3$ |
| CH | N | CH | N | Et | Cl | $CF_3$ | OMe |
| CH | N | CH | N | i-Pr | Cl | $CF_3$ | OMe |
| CH | N | CH | N | t-Bu | Cl | $CF_3$ | OMe |
| CH | N | CH | N | Et | Cl | $CF_3$ | CN |
| CH | N | CH | N | i-Pr | Cl | $CF_3$ | CN |
| CH | N | CH | N | t-Bu | Cl | $CF_3$ | CN |
| CH | CH | CH | CCl | Et | Me | $CF_3$ | Cl |
| CH | CH | CH | CCl | i-Pr | Me | $CF_3$ | Cl |
| CH | CH | CH | CCl | t-Bu | Me | $CF_3$ | Cl |
| CH | CH | CH | CCl | Et | Me | $CF_3$ | Br |
| CH | CH | CH | CCl | i-Pr | Me | $CF_3$ | Br |
| CH | CH | CH | CCl | t-Bu | Me | $CF_3$ | Br |
| CH | CH | CH | CCl | Et | Me | $CF_3$ | I |
| CH | CH | CH | CCl | i-Pr | Me | $CF_3$ | I |
| CH | CH | CH | CCl | t-Bu | Me | $CF_3$ | I |
| CH | CH | CH | CCl | Et | Me | $CF_3$ | F |

TABLE 13-continued

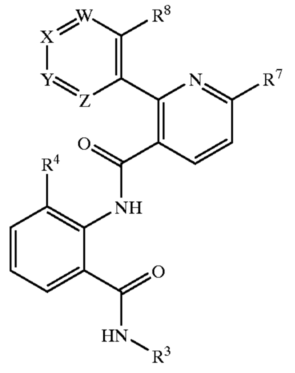

| W | X | Y | Z | $R^3$ | $R^4$ | $R^7$ | $R^8$ |
|---|---|---|---|---|---|---|---|
| CH | CH | CH | CCl | i-Pr | Me | $CF_3$ | F |
| CH | CH | CH | CCl | t-Bu | Me | $CF_3$ | F |
| CH | CH | CH | CCl | Et | Me | $CF_3$ | Me |
| CH | CH | CH | CCl | i-Pr | Me | $CF_3$ | Me |
| CH | CH | CH | CCl | t-Bu | Me | $CF_3$ | Me |
| CH | CH | CH | CCl | Et | Me | $CF_3$ | $CF_3$ |
| CH | CH | CH | CCl | i-Pr | Me | $CF_3$ | $CF_3$ |
| CH | CH | CH | CCl | t-Bu | Me | $CF_3$ | $CF_3$ |
| CH | CH | CH | CCl | Et | Me | $CF_3$ | OMe |
| CH | CH | CH | CCl | i-Pr | Me | $CF_3$ | OMe |
| CH | CH | CH | CCl | t-Bu | Me | $CF_3$ | OMe |
| CH | CH | CH | CCl | Et | Me | $CF_3$ | CN |
| CH | CH | CH | CCl | i-Pr | Me | $CF_3$ | CN |
| CH | CH | CH | CCl | t-Bu | Me | $CF_3$ | CN |
| CH | CH | CH | CCl | Et | Cl | $CF_3$ | Cl |
| CH | CH | CH | CCl | i-Pr | Cl | $CF_3$ | Cl |
| CH | CH | CH | CCl | t-Bu | Cl | $CF_3$ | Cl |
| CH | CH | CH | CCl | Et | Cl | $CF_3$ | Br |
| CH | CH | CH | CCl | i-Pr | Cl | $CF_3$ | Br |
| CH | CH | CH | CCl | t-Bu | Cl | $CF_3$ | Br |
| CH | CH | CH | CCl | Et | Cl | $CF_3$ | I |
| CH | CH | CH | CCl | i-Pr | Cl | $CF_3$ | I |
| CH | CH | CH | CCl | t-Bu | Cl | $CF_3$ | I |
| CH | CH | CH | CCl | Et | Cl | $CF_3$ | F |
| CH | CH | CH | CCl | i-Pr | Cl | $CF_3$ | F |
| CH | CH | CH | CCl | t-Bu | Cl | $CF_3$ | F |
| CH | CH | CH | CCl | Et | Cl | $CF_3$ | Me |
| CH | CH | CH | CCl | i-Pr | Cl | $CF_3$ | Me |
| CH | CH | CH | CCl | t-Bu | Cl | $CF_3$ | Me |
| CH | CH | CH | CCl | Et | Cl | $CF_3$ | $CF_3$ |
| CH | CH | CH | CCl | i-Pr | Cl | $CF_3$ | $CF_3$ |
| CH | CH | CH | CCl | t-Bu | Cl | $CF_3$ | $CF_3$ |
| CH | CH | CH | CCl | Et | Cl | $CF_3$ | OMe |
| CH | CH | CH | CCl | i-Pr | Cl | $CF_3$ | OMe |
| CH | CH | CH | CCl | t-Bu | Cl | $CF_3$ | OMe |
| CH | CH | CH | CCl | Et | Cl | $CF_3$ | CN |
| CH | CH | CH | CCl | i-Pr | Cl | $CF_3$ | CN |
| CH | CH | CH | CCl | t-Bu | Cl | $CF_3$ | CN |
| CH | CH | CH | CF | Et | Me | $CF_3$ | Cl |
| CH | CH | CH | CF | i-Pr | Me | $CF_3$ | Cl |
| CH | CH | CH | CF | t-Bu | Me | $CF_3$ | Cl |
| CH | CH | CH | CF | Et | Me | $CF_3$ | Br |
| CH | CH | CH | CF | i-Pr | Me | $CF_3$ | Br |
| CH | CH | CH | CF | t-Bu | Me | $CF_3$ | Br |
| CH | CH | CH | CF | Et | Me | $CF_3$ | I |
| CH | CH | CH | CF | i-Pr | Me | $CF_3$ | I |
| CH | CH | CH | CF | t-Bu | Me | $CF_3$ | I |
| CH | CH | CH | CF | Et | Me | $CF_3$ | F |
| CH | CH | CH | CF | i-Pr | Me | $CF_3$ | F |
| CH | CH | CH | CF | t-Bu | Me | $CF_3$ | F |
| CH | CH | CH | CF | Et | Me | $CF_3$ | Me |
| CH | CH | CH | CF | i-Pr | Me | $CF_3$ | Me |
| CH | CH | CH | CF | t-Bu | Me | $CF_3$ | Me |
| CH | CH | CH | CF | Et | Me | $CF_3$ | $CF_3$ |
| CH | CH | CH | CF | i-Pr | Me | $CF_3$ | $CF_3$ |
| CH | CH | CH | CF | t-Bu | Me | $CF_3$ | $CF_3$ |
| CH | CH | CH | CF | Et | Me | $CF_3$ | OMe |
| CH | CH | CH | CF | i-Pr | Me | $CF_3$ | OMe |

TABLE 13-continued

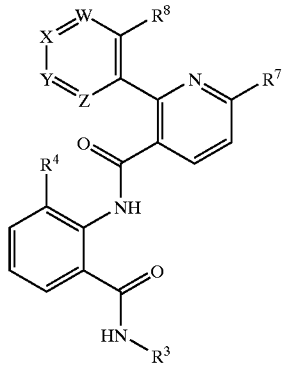

| W | X | Y | Z | $R^3$ | $R^4$ | $R^7$ | $R^8$ |
|---|---|---|---|---|---|---|---|
| CH | CH | CH | CF | t-Bu | Me | $CF_3$ | OMe |
| CH | CH | CH | CF | Et | Me | $CF_3$ | CN |
| CH | CH | CH | CF | i-Pr | Me | $CF_3$ | CN |
| CH | CH | CH | CF | t-Bu | Me | $CF_3$ | CN |
| CH | CH | CH | CF | Et | Cl | $CF_3$ | Cl |
| CH | CH | CH | CF | i-Pr | Cl | $CF_3$ | Cl |
| CH | CH | CH | CF | t-Bu | Cl | $CF_3$ | Cl |
| CH | CH | CH | CF | Et | Cl | $CF_3$ | Br |
| CH | CH | CH | CF | i-Pr | Cl | $CF_3$ | Br |
| CH | CH | CH | CF | t-Bu | Cl | $CF_3$ | Br |
| CH | CH | CH | CF | Et | Cl | $CF_3$ | I |
| CH | CH | CH | CF | i-Pr | Cl | $CF_3$ | I |
| CH | CH | CH | CF | t-Bu | Cl | $CF_3$ | I |
| CH | CH | CH | CF | i-Pr | Cl | $CF_3$ | F |
| CH | CH | CH | CF | t-Bu | Cl | $CF_3$ | F |
| CH | CH | CH | CF | Et | Cl | $CF_3$ | Me |
| CH | CH | CH | CF | i-Pr | Cl | $CF_3$ | Me |
| CH | CH | CH | CF | t-Bu | Cl | $CF_3$ | Me |
| CH | CH | CH | CF | Et | Cl | $CF_3$ | $CF_3$ |
| CH | CH | CH | CF | i-Pr | Cl | $CF_3$ | $CF_3$ |
| CH | CH | CH | CF | t-Bu | Cl | $CF_3$ | $CF_3$ |
| CH | CH | CH | CF | Et | Cl | $CF_3$ | OMe |
| CH | CH | CH | CF | i-Pr | Cl | $CF_3$ | OMe |
| CH | CH | CH | CF | t-Bu | Cl | $CF_3$ | OMe |
| CH | CH | CH | CF | Et | Cl | $CF_3$ | CN |
| CH | CH | CH | CF | i-Pr | Cl | $CF_3$ | CN |
| CH | CH | CH | CF | t-Bu | Cl | $CF_3$ | CN |
| CH | CH | CH | CH | Et | Me | $C_2F_5$ | Cl |
| CH | CH | CH | CH | i-Pr | Me | $C_2F_5$ | Cl |
| CH | CH | CH | CH | t-Bu | Me | $C_2F_5$ | Cl |
| CH | CH | CH | CH | Et | Me | $C_2F_5$ | Br |
| CH | CH | CH | CH | i-Pr | Me | $C_2F_5$ | Br |
| CH | CH | CH | CH | t-Bu | Me | $C_2F_5$ | Br |
| CH | CH | CH | CH | Et | Me | $C_2F_5$ | I |
| CH | CH | CH | CH | i-Pr | Me | $C_2F_5$ | I |
| CH | CH | CH | CH | t-Bu | Me | $C_2F_5$ | I |
| CH | CH | CH | CH | Et | Me | $C_2F_5$ | F |
| CH | CH | CH | CH | i-Pr | Me | $C_2F_5$ | F |
| CH | CH | CH | CH | t-Bu | Me | $C_2F_5$ | F |
| CH | CH | CH | CH | Et | Me | $C_2F_5$ | Me |
| CH | CH | CH | CH | i-Pr | Me | $C_2F_5$ | Me |
| CH | CH | CH | CH | t-Bu | Me | $C_2F_5$ | Me |
| CH | CH | CH | CH | Et | Me | $C_2F_5$ | $CF_3$ |
| CH | CH | CH | CH | i-Pr | Me | $C_2F_5$ | $CF_3$ |
| CH | CH | CH | CH | t-Bu | Me | $C_2F_5$ | $CF_3$ |
| CH | CH | CH | CH | Et | Me | $C_2F_5$ | OMe |
| CH | CH | CH | CH | i-Pr | Me | $C_2F_5$ | OMe |
| CH | CH | CH | CH | t-Bu | Me | $C_2F_5$ | OMe |
| CH | CH | CH | CH | Et | Me | $C_2F_5$ | CN |
| CH | CH | CH | CH | i-Pr | Me | $C_2F_5$ | CN |
| CH | CH | CH | CH | t-Bu | Me | $C_2F_5$ | CN |
| CH | CH | CH | CH | Et | Cl | $C_2F_5$ | Cl |
| CH | CH | CH | CH | i-Pr | Cl | $C_2F_5$ | Cl |
| CH | CH | CH | CH | t-Bu | Cl | $C_2F_5$ | Cl |
| CH | CH | CH | CH | Et | Cl | $C_2F_5$ | Br |
| CH | CH | CH | CH | i-Pr | Cl | $C_2F_5$ | Br |
| CH | CH | CH | CH | t-Bu | Cl | $C_2F_5$ | Br |
| CH | CH | CH | CH | Et | Cl | $C_2F_5$ | I |

TABLE 13-continued

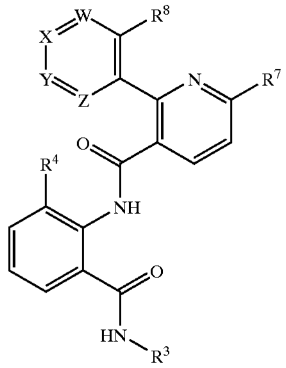

| W | X | Y | Z | $R^3$ | $R^4$ | $R^7$ | $R^8$ |
|---|---|---|---|---|---|---|---|
| CH | CH | CH | CH | i-Pr | Cl | $C_2F_5$ | I |
| CH | CH | CH | CH | t-Bu | Cl | $C_2F_5$ | I |
| CH | CH | CH | CH | Et | Cl | $C_2F_5$ | F |
| CH | CH | CH | CH | i-Pr | Cl | $C_2F_5$ | F |
| CH | CH | CH | CH | t-Bu | Cl | $C_2F_5$ | F |
| CH | CH | CH | CH | Et | Cl | $C_2F_5$ | Me |
| CH | CH | CH | CH | i-Pr | Cl | $C_2F_5$ | Me |
| CH | CH | CH | CH | t-Bu | Cl | $C_2F_5$ | Me |
| CH | CH | CH | CH | Et | Cl | $C_2F_5$ | $CF_3$ |
| CH | CH | CH | CH | i-Pr | Cl | $C_2F_5$ | $CF_3$ |
| CH | CH | CH | CH | t-Bu | Cl | $C_2F_5$ | $CF_3$ |
| CH | CH | CH | CH | Et | Cl | $C_2F_5$ | OMe |
| CH | CH | CH | CH | i-Pr | Cl | $C_2F_5$ | OMe |
| CH | CH | CH | CH | t-Bu | Cl | $C_2F_5$ | OMe |
| CH | CH | CH | CH | Et | Cl | $C_2F_5$ | CN |
| CH | CH | CH | CH | i-Pr | Cl | $C_2F_5$ | CN |
| CH | CH | CH | CH | t-Bu | Cl | $C_2F_5$ | CN |

TABLE 14

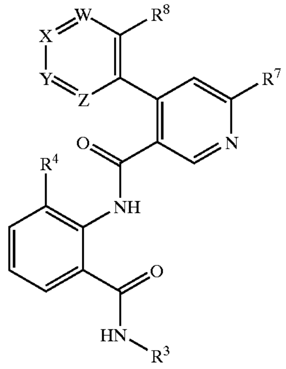

| W | X | Y | Z | $R^3$ | $R^4$ | $R^7$ | $R^8$ |
|---|---|---|---|---|---|---|---|
| CH | CH | CH | CH | Et | Me | $CF_3$ | Cl |
| CH | CH | CH | CH | i-Pr | Me | $CF_3$ | Cl |
| CH | CH | CH | CH | t-Bu | Me | $CF_3$ | Cl |
| CH | CH | CH | CH | Et | Me | $CF_3$ | Br |
| CH | CH | CH | CH | i-Pr | Me | $CF_3$ | Br |
| CH | CH | CH | CH | t-Bu | Me | $CF_3$ | Br |
| CH | CH | CH | CH | Et | Me | $CF_3$ | I |
| CH | CH | CH | CH | i-Pr | Me | $CF_3$ | I |
| CH | CH | CH | CH | t-Bu | Me | $CF_3$ | I |
| CH | CH | CH | CH | Et | Me | $CF_3$ | F |
| CH | CH | CH | CH | i-Pr | Me | $CF_3$ | F |
| CH | CH | CH | CH | t-Bu | Me | $CF_3$ | F |
| CH | CH | CH | CH | Et | Me | $CF_3$ | Me |
| CH | CH | CH | CH | i-Pr | Me | $CF_3$ | Me |
| CH | CH | CH | CH | t-Bu | Me | $CF_3$ | Me |
| CH | CH | CH | CH | Et | Me | $CF_3$ | $CF_3$ |

TABLE 14-continued

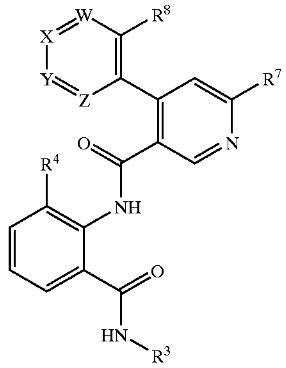

| W | X | Y | Z | $R^3$ | $R^4$ | $R^7$ | $R^8$ |
|---|---|---|---|---|---|---|---|
| CH | CH | CH | CH | i-Pr | Me | $CF_3$ | $CF_3$ |
| CH | CH | CH | CH | t-Bu | Me | $CF_3$ | $CF_3$ |
| CH | CH | CH | CH | Et | Me | $CF_3$ | OMe |
| CH | CH | CH | CH | i-Pr | Me | $CF_3$ | OMe |
| CH | CH | CH | CH | t-Bu | Me | $CF_3$ | OMe |
| CH | CH | CH | CH | Et | Me | $CF_3$ | CN |
| CH | CH | CH | CH | i-Pr | Me | $CF_3$ | CN |
| CH | CH | CH | CH | t-Bu | Me | $CF_3$ | CN |
| CH | CH | CH | CH | Et | Cl | $CF_3$ | Cl |
| CH | CH | CH | CH | i-Pr | Cl | $CF_3$ | Cl |
| CH | CH | CH | CH | t-Bu | Cl | $CF_3$ | Cl |
| CH | CH | CH | CH | Et | Cl | $CF_3$ | Br |
| CH | CH | CH | CH | i-Pr | Cl | $CF_3$ | Br |
| CH | CH | CH | CH | t-Bu | Cl | $CF_3$ | Br |
| CH | CH | CH | CH | Et | Cl | $CF_3$ | I |
| CH | CH | CH | CH | i-Pr | Cl | $CF_3$ | I |
| CH | CH | CH | CH | t-Bu | Cl | $CF_3$ | I |
| CH | CH | CH | CH | Et | Cl | $CF_3$ | F |
| CH | CH | CH | CH | i-Pr | Cl | $CF_3$ | F |
| CH | CH | CH | CH | t-Bu | Cl | $CF_3$ | F |
| CH | CH | CH | CH | Et | Cl | $CF_3$ | Me |
| CH | CH | CH | CH | i-Pr | Cl | $CF_3$ | Me |
| CH | CH | CH | CH | t-Bu | Cl | $GF_3$ | Me |
| CH | CH | CH | CH | Et | Cl | $CF_3$ | $CF_3$ |
| CH | CH | CH | CH | i-Pr | Cl | $CF_3$ | $CF_3$ |
| CH | CH | CH | CH | t-Bu | Cl | $CF_3$ | $CF_3$ |
| CH | CH | CH | CH | Et | Cl | $CF_3$ | OMe |
| CH | CH | CH | CH | i-Pr | Cl | $CF_3$ | OMe |
| CH | CH | CH | CH | t-Bu | Cl | $CF_3$ | OMe |
| CH | CH | CH | CH | Et | Cl | $CF_3$ | CN |
| CH | CH | CH | CH | i-Pr | Cl | $CF_3$ | CN |
| CH | CH | CH | CH | t-Bu | Cl | $CF_3$ | CN |
| CH | CH | CH | N | Et | Me | $CF_3$ | Cl |
| CH | CH | CH | N | i-Pr | Me | $CF_3$ | Cl |
| CH | CH | CH | N | t-Bu | Me | $CF_3$ | Cl |
| CH | CH | CH | N | Et | Me | $CF_3$ | Br |
| CH | CH | CH | N | i-Pr | Me | $CF_3$ | Br |
| CH | CH | CH | N | t-Bu | Me | $CF_3$ | Br |
| CH | CH | CH | N | Et | Me | $CF_3$ | I |
| CH | CH | CH | N | i-Pr | Me | $CF_3$ | I |
| CH | CH | CH | N | t-Bu | Me | $CF_3$ | I |
| CH | CH | CH | N | Et | Me | $CF_3$ | F |
| CH | CH | CH | N | i-Pr | Me | $CF_3$ | F |
| CH | CH | CH | N | t-Bu | Me | $CF_3$ | F |
| CH | CH | CH | N | Et | Me | $CF_3$ | Me |
| CH | CH | CH | N | i-Pr | Me | $CF_3$ | Me |
| CH | CH | CH | N | t-Bu | Me | $CF_3$ | Me |
| CH | CH | CH | N | Et | Me | $CF_3$ | $CF_3$ |
| CH | CH | CH | N | i-Pr | Me | $CF_3$ | $CF_3$ |
| CH | CH | CH | N | t-Bu | Me | $CF_3$ | $CF_3$ |
| CH | CH | CH | N | Et | Me | $CF_3$ | OMe |
| CH | CH | CH | N | i-Pr | Me | $CF_3$ | OMe |
| CH | CH | CH | N | t-Bu | Me | $CF_3$ | OMe |
| CH | CH | CH | N | Et | Me | $CF_3$ | CN |
| CH | CH | CH | N | i-Pr | Me | $CF_3$ | CN |
| CH | CH | CH | N | t-Bu | Me | $CF_3$ | CN |
| CH | CH | CH | N | Et | Cl | $CF_3$ | Cl |
| CH | CH | CH | N | i-Pr | Cl | $CF_3$ | Cl |

TABLE 14-continued

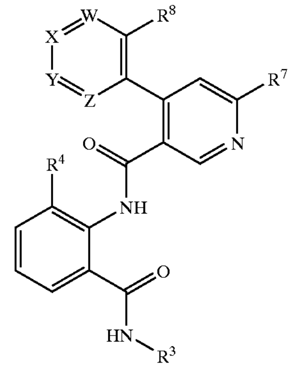

| W | X | Y | Z | $R^3$ | $R^4$ | $R^7$ | $R^8$ |
|---|---|---|---|---|---|---|---|
| CH | CH | CH | N | t-Bu | Cl | $CF_3$ | Cl |
| CH | CH | CH | N | Et | Cl | $CF_3$ | Br |
| CH | CH | CH | N | i-Pr | Cl | $CF_3$ | Br |
| CH | CH | CH | N | t-Bu | Cl | $CF_3$ | Br |
| CH | CH | CH | N | Et | Cl | $CF_3$ | I |
| CH | CH | CH | N | i-Pr | Cl | $CF_3$ | I |
| CH | CH | CH | N | t-Bu | Cl | $CF_3$ | I |
| CH | CH | CH | N | Et | Cl | $CF_3$ | F |
| CH | CH | CH | N | i-Pr | Cl | $CF_3$ | F |
| CH | CH | CH | N | t-Bu | Cl | $CF_3$ | F |
| CH | CH | CH | N | Et | Cl | $CF_3$ | Me |
| CH | CH | CH | N | i-Pr | Cl | $CF_3$ | Me |
| CH | CH | CH | N | t-Bu | Cl | $CF_3$ | Me |
| CH | CH | CH | N | Et | Cl | $CF_3$ | $CF_3$ |
| CH | CH | CH | N | i-Pr | Cl | $CF_3$ | $CF_3$ |
| CH | CH | CH | N | t-Bu | Cl | $CF_3$ | $CF_3$ |
| CH | CH | CH | N | Et | Cl | $CF_3$ | OMe |
| CH | CH | CH | N | i-Pr | Cl | $CF_3$ | OMe |
| CH | CH | CH | N | i-Bu | Cl | $CF_3$ | OMe |
| CH | CH | CH | N | Et | Cl | $CF_3$ | CN |
| CH | CH | CH | N | i-Pr | Cl | $CF_3$ | CN |
| CH | CH | CH | N | t-Bu | Cl | $CF_3$ | CN |
| CH | CH | N | CH | Et | Me | $CF_3$ | Cl |
| CH | CH | N | CH | i-Pr | Me | $CF_3$ | Cl |
| CH | CH | N | CH | t-Bu | Me | $CF_3$ | Cl |
| CH | CH | N | CH | Et | Me | $CF_3$ | Br |
| CH | CH | N | CH | i-Pr | Me | $CF_3$ | Br |
| CH | CH | N | CH | t-Bu | Me | $CF_3$ | Br |
| CH | CH | N | CH | Et | Me | $CF_3$ | I |
| CH | CH | N | CH | i-Pr | Me | $CF_3$ | I |
| CH | CH | N | CH | t-Bu | Me | $CF_3$ | I |
| CH | CH | N | CH | Et | Me | $CF_3$ | F |
| CH | CH | N | CH | i-Pr | Me | $CF_3$ | F |
| CH | CH | N | CH | t-Bu | Me | $CF_3$ | F |
| CH | CH | N | CH | Et | Me | $CF_3$ | Me |
| CH | CH | N | CH | i-Pr | Me | $CF_3$ | Me |
| CH | CH | N | CH | t-Bu | Me | $CF_3$ | Me |
| CH | CH | N | CH | Et | Me | $CF_3$ | $CF_3$ |
| CH | CH | N | CH | i-Pr | Me | $CF_3$ | $CF_3$ |
| CH | CH | N | CH | t-Bu | Me | $CF_3$ | $CF_3$ |
| CH | CH | N | CH | Et | Me | $CF_3$ | OMe |
| CH | CH | N | CH | i-Pr | Me | $CF_3$ | OMe |
| CH | CH | N | CH | t-Bu | Me | $CF_3$ | OMe |
| CH | CH | N | CH | Et | Me | $CF_3$ | CN |
| CH | CH | N | CH | i-Pr | Me | $CF_3$ | CN |
| CH | CH | N | CH | t-Bu | Me | $CF_3$ | CN |
| CH | CH | N | CH | Et | Cl | $CF_3$ | Cl |
| CH | CH | N | CH | i-Pr | Cl | $CF_3$ | Cl |
| CH | CH | N | CH | t-Bu | Cl | $CF_3$ | Cl |
| CH | CH | N | CH | Et | Cl | $CF_3$ | Br |
| CH | CH | N | CH | i-Pr | Cl | $CF_3$ | Br |
| CH | CH | N | CH | t-Bu | Cl | $CF_3$ | Br |
| CH | CH | N | CH | Et | Cl | $CF_3$ | I |
| CH | CH | N | CH | i-Pr | Cl | $CF_3$ | I |
| CH | CH | N | CH | t-Bu | Cl | $CF_3$ | I |
| CH | CH | N | CH | Et | Cl | $CF_3$ | F |
| CH | CH | N | CH | i-Pr | Cl | $CF_3$ | F |
| CH | CH | N | CH | t-Bu | Cl | $CF_3$ | F |

TABLE 14-continued

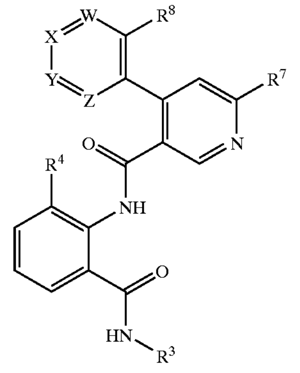

| W | X | Y | Z | $R^3$ | $R^4$ | $R^7$ | $R^8$ |
|---|---|---|---|---|---|---|---|
| CH | CH | N | CH | Et | Cl | $CF_3$ | Me |
| CH | CH | N | CH | i-Pr | Cl | $CF_3$ | Me |
| CH | CH | N | CH | t-Bu | Cl | $CF_3$ | Me |
| CH | CH | N | CH | Et | Cl | $CF_3$ | $CF_3$ |
| CH | CH | N | CH | i-Pr | Cl | $CF_3$ | $CF_3$ |
| CH | CH | N | CH | t-Bu | Cl | $CF_3$ | $CF_3$ |
| CH | CH | N | CH | Et | Cl | $CF_3$ | OMe |
| CH | CH | N | CH | i-Pr | Cl | $CF_3$ | OMe |
| CH | CH | N | CH | t-Bu | Cl | $CF_3$ | OMe |
| CH | CH | N | CH | Et | Cl | $CF_3$ | CN |
| CH | CH | N | CH | i-Pr | Cl | $CF_3$ | CN |
| CH | CH | N | CH | t-Bu | Cl | $CF_3$ | CN |
| CH | N | CH | CH | Et | Me | $CF_3$ | Cl |
| CH | N | CH | CH | i-Pr | Me | $CF_3$ | Cl |
| CH | N | CH | CH | t-Bu | Me | $CF_3$ | Cl |
| CH | N | CH | CH | Et | Me | $CF_3$ | Br |
| CH | N | CH | CH | i-Pr | Me | $CF_3$ | Br |
| CH | N | CH | CH | t-Bu | Me | $CF_3$ | Br |
| CH | N | CH | CH | Et | Me | $CF_3$ | I |
| CH | N | CH | CH | i-Pr | Me | $CF_3$ | I |
| CH | N | CH | CH | t-Bu | Me | $CF_3$ | I |
| CH | N | CH | CH | Et | Me | $CF_3$ | F |
| CH | N | CH | CH | i-Pr | Me | $CF_3$ | F |
| CH | N | CH | CH | t-Bu | Me | $CF_3$ | F |
| CH | N | CH | CH | Et | Me | $CF_3$ | Me |
| CH | N | CH | CH | i-Pr | Me | $CF_3$ | Me |
| CH | N | CH | CH | t-Bu | Me | $CF_3$ | Me |
| CH | N | CH | CH | Et | Me | $CF_3$ | $CF_3$ |
| CH | N | CH | CH | i-Pr | Me | $CF_3$ | $CF_3$ |
| CH | N | CH | CH | t-Bu | Me | $CF_3$ | $CF_3$ |
| CH | N | CH | CH | Et | Me | $CF_3$ | OMe |
| CH | N | CH | CH | i-Pr | Me | $CF_3$ | OMe |
| CH | N | CH | CH | t-Bu | Me | $CF_3$ | OMe |
| CH | N | CH | CH | Et | Me | $CF_3$ | CN |
| CH | N | CH | CH | i-Pr | Me | $CF_3$ | CN |
| CH | N | CH | CH | t-Bu | Me | $CF_3$ | CN |
| CH | N | CH | CH | Et | Cl | $CF_3$ | Cl |
| CH | N | CH | CH | i-Pr | Cl | $CF_3$ | Cl |
| CH | N | CH | CH | t-Bu | Cl | $CF_3$ | Cl |
| CH | N | CH | CH | Et | Cl | $CF_3$ | Br |
| CH | N | CH | CH | i-Pr | Cl | $CF_3$ | Br |
| CH | N | CH | CH | t-Bu | Cl | $CF_3$ | Br |
| CH | N | CH | CH | Et | Cl | $CF_3$ | I |
| CH | N | CH | CH | i-Pr | Cl | $CF_3$ | I |
| CH | N | CH | CH | t-Bu | Cl | $CF_3$ | I |
| CH | N | CH | CH | Et | Cl | $CF_3$ | F |
| CH | N | CH | CH | i-Pr | Cl | $CF_3$ | F |
| CH | N | CH | CH | t-Bu | Cl | $CF_3$ | F |
| CH | N | CH | CH | Et | Cl | $CF_3$ | Me |
| CH | N | CH | CH | i-Pr | Cl | $CF_3$ | Me |
| CH | N | CH | CH | t-Bu | Cl | $CF_3$ | Me |
| CH | N | CH | CH | Et | Cl | $CF_3$ | $CF_3$ |
| CH | N | CH | CH | i-Pr | Cl | $CF_3$ | $CF_3$ |
| CH | N | CH | CH | t-Bu | Cl | $CF_3$ | $CF_3$ |
| CH | N | CH | CH | Et | Cl | $CF_3$ | OMe |
| CH | N | CH | CH | i-Pr | Cl | $CF_3$ | OMe |
| CH | N | CH | CH | t-Bu | Cl | $CF_3$ | OMe |
| CH | N | CH | CH | Et | Cl | $CF_3$ | CN |

TABLE 14-continued

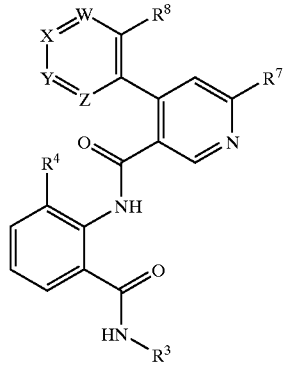

| W | X | Y | Z | $R^3$ | $R^4$ | $R^7$ | $R^8$ |
|---|---|---|---|---|---|---|---|
| CH | N | CH | CH | i-Pr | Cl | $CF_3$ | CN |
| CH | N | CH | CH | t-Bu | Cl | $CF_3$ | CN |
| N | CH | CH | CH | Et | Me | $CF_3$ | Cl |
| N | CH | CH | CH | i-Pr | Me | $CF_3$ | Cl |
| N | CH | CH | CH | t-Bu | Me | $CF_3$ | Cl |
| N | CH | CH | CH | Et | Me | $CF_3$ | Br |
| N | CH | CH | CH | i-Pr | Me | $CF_3$ | Br |
| N | CH | CH | CH | t-Bu | Me | $CF_3$ | Br |
| N | CH | CH | CH | Et | Me | $CF_3$ | I |
| N | CH | CH | CH | i-Pr | Me | $CF_3$ | I |
| N | CH | CH | CH | t-Bu | Me | $CF_3$ | I |
| N | CH | CH | CH | Et | Me | $CF_3$ | F |
| N | CH | CH | CH | i-Pr | Me | $CF_3$ | F |
| N | CH | CH | CH | t-Bu | Me | $CF_3$ | F |
| N | CH | CH | CH | Et | Me | $CF_3$ | Me |
| N | CH | CH | CH | i-Pr | Me | $CF_3$ | Me |
| N | CH | CH | CH | t-Bu | Me | $CF_3$ | Me |
| N | CH | CH | CH | Et | Me | $CF_3$ | $CF_3$ |
| N | CH | CH | CH | i-Pr | Me | $CF_3$ | $CF_3$ |
| N | CH | CH | CH | t-Bu | Me | $CF_3$ | $CF_3$ |
| N | CH | CH | CH | Et | Me | $CF_3$ | OMe |
| N | CH | CH | CH | i-Pr | Me | $CF_3$ | OMe |
| N | CH | CH | CH | t-Bu | Me | $CF_3$ | OMe |
| N | CH | CH | CH | Et | Me | $CF_3$ | CN |
| N | CH | CH | CH | i-Pr | Me | $CF_3$ | CN |
| N | CH | CH | CH | t-Bu | Me | $CF_3$ | CN |
| N | CH | CH | CH | Et | Cl | $CF_3$ | Cl |
| N | CH | CH | CH | i-Pr | Cl | $CF_3$ | Cl |
| N | CH | CH | CH | t-Bu | Cl | $CF_3$ | Cl |
| N | CH | CH | CH | Et | Cl | $CF_3$ | Br |
| N | CH | CH | CH | i-Pr | Cl | $CF_3$ | Br |
| N | CH | CH | CH | t-Bu | Cl | $CF_3$ | Br |
| N | CH | CH | CH | Et | Cl | $CF_3$ | I |
| N | CH | CH | CH | i-Pr | Cl | $CF_3$ | I |
| N | CH | CH | CH | t-Bu | Cl | $CF_3$ | I |
| N | CH | CH | CH | Et | Cl | $CF_3$ | F |
| N | CH | CH | CH | i-Pr | Cl | $CF_3$ | F |
| N | CH | CH | CH | t-Bu | Cl | $CF_3$ | F |
| N | CH | CH | CH | Et | Cl | $CF_3$ | Me |
| N | CH | CH | CH | i-Pr | Cl | $CF_3$ | Me |
| N | CH | CH | CH | t-Bu | Cl | $CF_3$ | Me |
| N | CH | CH | CH | Et | Cl | $CF_3$ | $CF_3$ |
| N | CH | CH | CH | i-Pr | Cl | $CF_3$ | $CF_3$ |
| N | CH | CH | CH | t-Bu | Cl | $CF_3$ | $CF_3$ |
| N | CH | CH | CH | Et | Cl | $CF_3$ | OMe |
| N | CH | CH | CH | i-Pr | Cl | $CF_3$ | OMe |
| N | CH | CH | CH | t-Bu | Cl | $CF_3$ | OMe |
| N | CH | CH | CH | Et | Cl | $CF_3$ | CN |
| N | CH | CH | CH | i-Pr | Cl | $CF_3$ | CN |
| N | CH | CH | CH | t-Bu | Cl | $CF_3$ | CN |
| CH | N | CH | N | Et | Me | $CF_3$ | Cl |
| CH | N | CH | N | i-Pr | Me | $CF_3$ | Cl |
| CH | N | CH | N | t-Bu | Me | $CF_3$ | Cl |
| CH | N | CH | N | Et | Me | $CF_3$ | Br |
| CH | N | CH | N | i-Pr | Me | $CF_3$ | Br |
| CH | N | CH | N | t-Bu | Me | $CF_3$ | Br |
| CH | N | CH | N | Et | Me | $CF_3$ | I |
| CH | N | CH | N | i-Pr | Me | $CF_3$ | I |

TABLE 14-continued

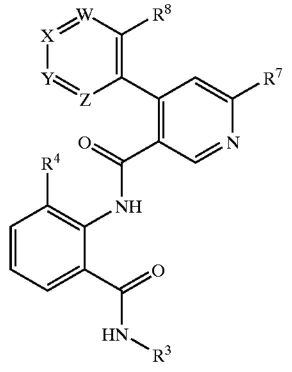

| W | X | Y | Z | $R^3$ | $R^4$ | $R^7$ | $R^8$ |
|---|---|---|---|---|---|---|---|
| CH | N | CH | N | t-Bu | Me | $CF_3$ | I |
| CH | N | CH | N | Et | Me | $CF_3$ | F |
| CH | N | CH | N | i-Pr | Me | $CF_3$ | F |
| CH | N | CH | N | t-Bu | Me | $CF_3$ | F |
| CH | N | CH | N | Et | Me | $CF_3$ | Me |
| CH | N | CH | N | i-Pr | Me | $CF_3$ | Me |
| CH | N | CH | N | t-Bu | Me | $CF_3$ | Me |
| CH | N | CH | N | Et | Me | $CF_3$ | $CF_3$ |
| CH | N | CH | N | i-Pr | Me | $CF_3$ | $CF_3$ |
| CH | N | CH | N | t-Bu | Me | $CF_3$ | $CF_3$ |
| CH | N | CH | N | Et | Me | $CF_3$ | OMe |
| CH | N | CH | N | i-Pr | Me | $CF_3$ | OMe |
| CH | N | CH | N | t-Bu | Me | $CF_3$ | OMe |
| CH | N | CH | N | Et | Me | $CF_3$ | CN |
| CH | N | CH | N | i-Pr | Me | $CF_3$ | CN |
| CH | N | CH | N | t-Bu | Me | $CF_3$ | CN |
| CH | N | CH | N | Et | Cl | $CF_3$ | Cl |
| CH | N | CH | N | i-Pr | Cl | $CF_3$ | Cl |
| CH | N | CH | N | t-Bu | Cl | $CF_3$ | Cl |
| CH | N | CH | N | Et | Cl | $CF_3$ | Br |
| CH | N | CH | N | i-Pr | Cl | $CF_3$ | Br |
| CH | N | CH | N | t-Bu | Cl | $CF_3$ | Br |
| CH | N | CH | N | Et | Cl | $CF_3$ | I |
| CH | N | CH | N | i-Pr | Cl | $CF_3$ | I |
| CH | N | CH | N | t-Bu | C1 | $CF_3$ | I |
| CH | N | CH | N | Et | Cl | $CF_3$ | F |
| CH | N | CH | N | i-Pr | Cl | $CF_3$ | F |
| CH | N | CH | N | t-Bu | Cl | $CF_3$ | F |
| CH | N | CH | N | Et | Cl | $CF_3$ | Me |
| CH | N | CH | N | i-Pr | Cl | $CF_3$ | Me |
| CH | N | CH | N | t-Bu | Cl | $CF_3$ | Me |
| CH | N | CH | N | Et | Cl | $CF_3$ | $CF_3$ |
| CH | N | CH | N | i-Pr | Cl | $CF_3$ | $CF_3$ |
| CH | N | CH | N | t-Bu | Cl | $CF_3$ | $CF_3$ |
| CH | N | CH | N | Et | Cl | $CF_3$ | OMe |
| CH | N | CH | N | i-Pr | Cl | $CF_3$ | OMe |
| CH | N | CH | N | t-Bu | Cl | $CF_3$ | OMe |
| CH | N | CH | N | Et | Cl | $CF_3$ | CN |
| CH | N | CH | N | i-Pr | Cl | $CF_3$ | CN |
| CH | N | CH | N | t-Bu | Cl | $CF_3$ | CN |
| CH | CH | CH | CCl | Et | Me | $CF_3$ | Cl |
| CH | CH | CH | CCl | i-Pr | Me | $CF_3$ | Cl |
| CH | CH | CH | CCl | t-Bu | Me | $CF_3$ | Cl |
| CH | CH | CH | CCl | Et | Me | $CF_3$ | Br |
| CH | CH | CH | CCl | i-Pr | Me | $CF_3$ | Br |
| CH | CH | CH | CCl | t-Bu | Me | $CF_3$ | Br |
| CH | CH | CH | CCl | Et | Me | $CF_3$ | I |
| CH | CH | CH | CCl | i-Pr | Me | $CF_3$ | I |
| CH | CH | CH | CCl | t-Bu | Me | $CF_3$ | I |
| CH | CH | CH | CCl | Et | Me | $CF_3$ | F |
| CH | CH | CH | CCl | i-Pr | Me | $CF_3$ | F |
| CH | CH | CH | CCl | t-Bu | Me | $CF_3$ | F |
| CH | CH | CH | CCl | Et | Me | $CF_3$ | Me |
| CH | CH | CH | CCl | i-Pr | Me | $CF_3$ | Me |
| CH | CH | CH | CCl | t-Bu | Me | $CF_3$ | Me |
| CH | CH | CH | CCl | Et | Me | $CF_3$ | $CF_3$ |
| CH | CH | CH | CCl | i-Pr | Me | $CF_3$ | $CF_3$ |
| CH | CH | CH | CCl | t-Bu | Me | $CF_3$ | $CF_3$ |

TABLE 14-continued

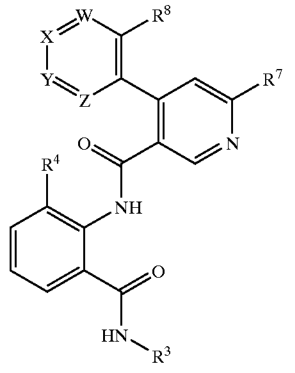

| W | X | Y | Z | $R^3$ | $R^4$ | $R^7$ | $R^8$ |
|---|---|---|---|---|---|---|---|
| CH | CH | CH | CCl | Et | Me | $CF_3$ | OMe |
| CH | CH | CH | CCl | i-Pr | Me | $CF_3$ | OMe |
| CH | CH | CH | CCl | t-Bu | Me | $CF_3$ | OMe |
| CH | CH | CH | CCl | Et | Me | $CF_3$ | CN |
| CH | CH | CH | CCl | i-Pr | Me | $CF_3$ | CN |
| CH | CH | CH | CCl | t-Bu | Me | $CF_3$ | CN |
| CH | CH | CH | CCl | Et | Cl | $CF_3$ | Cl |
| CH | CH | CH | CCl | i-Pr | Cl | $CF_3$ | Cl |
| CH | CH | CH | CCl | t-Bu | Cl | $CF_3$ | Cl |
| CH | CH | CH | CCl | Et | Cl | $CF_3$ | Br |
| CH | CH | CH | CCl | i-Pr | Cl | $CF_3$ | Br |
| CH | CH | CH | CCl | t-Bu | Cl | $CF_3$ | Br |
| CH | CH | CH | CCl | Et | Cl | $CF_3$ | I |
| CH | CH | CH | CCl | i-Pr | Cl | $CF_3$ | I |
| CH | CH | CH | CCl | t-Bu | Cl | $CF_3$ | I |
| CH | CH | CH | CCl | Et | Cl | $CF_3$ | F |
| CH | CH | CH | CCl | i-Pr | Cl | $CF_3$ | F |
| CH | CH | CH | CCl | t-Bu | Cl | $CF_3$ | F |
| CH | CH | CH | CCl | Et | Cl | $CF_3$ | Me |
| CH | CH | CH | CCl | i-Pr | Cl | $CF_3$ | Me |
| CH | CH | CH | CCl | t-Bu | Cl | $CF_3$ | Me |
| CH | CH | CH | CCl | Et | Cl | $CF_3$ | $CF_3$ |
| CH | CH | CH | CCl | i-Pr | Cl | $CF_3$ | $CF_3$ |
| CH | CH | CH | CCl | t-Bu | Cl | $CF_3$ | $CF_3$ |
| CH | CH | CH | CCl | Et | Cl | $CF_3$ | OMe |
| CH | CH | CH | CCl | i-Pr | Cl | $CF_3$ | OMe |
| CH | CH | CH | CCl | t-Bu | Cl | $CF_3$ | OMe |
| CH | CH | CH | CCl | Et | Cl | $CF_3$ | CN |
| CH | CH | CH | CCl | i-Pr | Cl | $CF_3$ | CN |
| CH | CH | CH | CCl | t-Bu | Cl | $CF_3$ | CN |
| CH | CH | CH | CF | Et | Me | $CF_3$ | Cl |
| CH | CH | CH | CF | i-Pr | Me | $CF_3$ | Cl |
| CH | CH | CH | CF | t-Bu | Me | $CF_3$ | Cl |
| CH | CH | CH | CF | Et | Me | $CF_3$ | Br |
| CH | CH | CH | CF | i-Pr | Me | $CF_3$ | Br |
| CH | CH | CH | CF | t-Bu | Me | $CF_3$ | Br |
| CH | CH | CH | CF | Et | Me | $CF_3$ | I |
| CH | CH | CH | CF | i-Pr | Me | $CF_3$ | I |
| CH | CH | CH | CF | t-Bu | Me | $CF_3$ | I |
| CH | CH | CH | CF | Et | Me | $CF_3$ | F |
| CH | CH | CH | CF | i-Pr | Me | $CF_3$ | F |
| CH | CH | CH | CF | t-Bu | Me | $CF_3$ | F |
| CH | CH | CH | CF | Et | Me | $CF_3$ | Me |
| CH | CH | CH | CF | i-Pr | Me | $CF_3$ | Me |
| CH | CH | CH | CF | t-Bu | Me | $CF_3$ | Me |
| CH | CH | CH | CF | Et | Me | $CF_3$ | $CF_3$ |
| CH | CH | CH | CF | i-Pr | Me | $CF_3$ | $CF_3$ |
| CH | CH | CH | CF | t-Bu | Me | $CF_3$ | $CF_3$ |
| CH | CH | CH | CF | Et | Me | $CF_3$ | OMe |
| CH | CH | CH | CF | i-Pr | Me | $CF_3$ | OMe |
| CH | CH | CH | CF | t-Bu | Me | $CF_3$ | OMe |
| CH | CH | CH | CF | Et | Me | $CF_3$ | CN |
| CH | CH | CH | CF | i-Pr | Me | $CF_3$ | CN |
| CH | CH | CH | CF | t-Bu | Me | $CF_3$ | CN |
| CH | CH | CH | CF | Et | Cl | $CF_3$ | Cl |
| CH | CH | CH | CF | i-Pr | Cl | $CF_3$ | Cl |
| CH | CH | CH | CF | t-Bu | Cl | $CF_3$ | Cl |
| CH | CH | CH | CF | Et | Cl | $CF_3$ | Br |

TABLE 14-continued

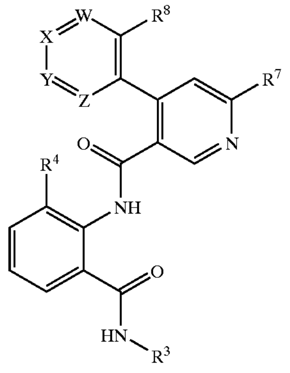

| W | X | Y | Z | $R^3$ | $R^4$ | $R^7$ | $R^8$ |
|---|---|---|---|---|---|---|---|
| CH | CH | CH | CF | i-Pr | Cl | $CF_3$ | Br |
| CH | CH | CH | CF | t-Bu | Cl | $CF_3$ | Br |
| CH | CH | CH | CF | Et | Cl | $CF_3$ | I |
| CH | CH | CH | CF | i-Pr | Cl | $CF_3$ | I |
| CH | CH | CH | CF | t-Bu | Cl | $CF_3$ | I |
| CH | CH | CH | CF | i-Pr | Cl | $CF_3$ | F |
| CH | CH | CH | CF | t-Bu | Cl | $CF_3$ | F |
| CH | CH | CH | CF | Et | Cl | $CF_3$ | Me |
| CH | CH | CH | CF | i-Pr | Cl | $CF_3$ | Me |
| CH | CH | CH | CF | t-Bu | Cl | $CF_3$ | Me |
| CH | CH | CH | CF | Et | Cl | $CF_3$ | $CF_3$ |
| CH | CH | CH | CF | i-Pr | Cl | $CF_3$ | $CF_3$ |
| CH | CH | CH | CF | t-Bu | Cl | $CF_3$ | $CF_3$ |
| CH | CH | CH | CF | Et | Cl | $CF_3$ | OMe |
| CH | CH | CH | CF | i-Pr | Cl | $CF_3$ | OMe |
| CH | CH | CH | CF | t-Bu | Cl | $CF_3$ | OMe |
| CH | CH | CH | CF | Et | Cl | $CF_3$ | CN |
| CH | CH | CH | CF | i-Pr | Cl | $CF_3$ | CN |
| CH | CH | CH | CF | t-Bu | Cl | $CF_3$ | CN |
| CH | CH | CH | CH | Et | Me | $C_2F_5$ | Cl |
| CH | CH | CH | CH | i-Pr | Me | $C_2F_5$ | Cl |
| CH | CH | CH | CH | t-Bu | Me | $C_2F_5$ | Cl |
| CH | CH | CH | CH | Et | Me | $C_2F_5$ | Br |
| CH | CH | CH | CH | i-Pr | Me | $C_2F_5$ | Br |
| CH | CH | CH | CH | t-Bu | Me | $C_2F_5$ | Br |
| CH | CH | CH | CH | Et | Me | $C_2F_5$ | I |
| CH | CH | CH | CH | i-Pr | Me | $C_2F_5$ | I |
| CH | CH | CH | CH | i-Bu | Me | $C_2F_5$ | I |
| CH | CH | CH | CH | Et | Me | $C_2F_5$ | F |
| CH | CH | CH | CH | i-Pr | Me | $C_2F_5$ | F |
| CH | CH | CH | CH | t-Bu | Me | $C_2F_5$ | F |
| CH | CH | CH | CH | Et | Me | $C_2F_5$ | Me |
| CH | CH | CH | CH | i-Pr | Me | $C_2F_5$ | Me |
| CH | CH | CH | CH | t-Bu | Me | $C_2F_5$ | Me |
| CH | CH | CH | CH | Et | Me | $C_2F_5$ | $CF_3$ |
| CH | CH | CH | CH | i-Pr | Me | $C_2F_5$ | $CF_3$ |
| CH | CH | CH | CH | t-Bu | Me | $C_2F_5$ | $CF_3$ |
| CH | CH | CH | CH | Et | Me | $C_2F_5$ | OMe |
| CH | CH | CH | CH | i-Pr | Me | $C_2F_5$ | OMe |
| CH | CH | CH | CH | t-Bu | Me | $C_2F_5$ | OMe |
| CH | CH | CH | CH | Et | Me | $C_2F_5$ | CN |
| CH | CH | CH | CH | i-Pr | Me | $C_2F_5$ | CN |
| CH | CH | CH | CH | t-Bu | Me | $C_2F_5$ | CN |
| CH | CH | CH | CH | Et | Cl | $C_2F_5$ | Cl |
| CH | CH | CH | CH | i-Pr | Cl | $C_2F_5$ | Cl |
| CH | CH | CH | CH | t-Bu | Cl | $C_2F_5$ | Cl |
| CH | CH | CH | CH | Et | Cl | $C_2F_5$ | Br |
| CH | CH | CH | CH | i-Pr | Cl | $C_2F_5$ | Br |
| CH | CH | CH | CH | t-Bu | Cl | $C_2F_5$ | Br |
| CH | CH | CH | CH | Et | Cl | $C_2F_5$ | I |
| CH | CH | CH | CH | i-Pr | Cl | $C_2F_5$ | I |
| CH | CH | CH | CH | t-Bu | Cl | $C_2F_5$ | I |
| CH | CH | CH | CH | Et | Cl | $C_2F_5$ | F |
| CH | CH | CH | CH | i-Pr | Cl | $C_2F_5$ | F |
| CH | CH | CH | CH | t-Bu | Cl | $C_2F_5$ | F |
| CH | CH | CH | CH | Et | Cl | $C_2F_5$ | Me |
| CH | CH | CH | CH | i-Pr | Cl | $C_2F_5$ | Me |
| CH | CH | CH | CH | t-Bu | Cl | $C_2F_5$ | Me |

TABLE 14-continued

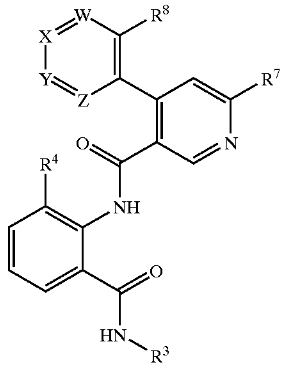

| W | X | Y | Z | $R^3$ | $R^4$ | $R^7$ | $R^8$ |
|---|---|---|---|---|---|---|---|
| CH | CH | CH | CH | Et | Cl | $C_2F_5$ | $CF_3$ |
| CH | CH | CH | CH | i-Pr | Cl | $C_2F_5$ | $CF_3$ |
| CH | CH | CH | CH | t-Bu | Cl | $C_2F_5$ | $CF_3$ |
| CH | CH | CH | CH | Et | Cl | $C_2F_5$ | OMe |
| CH | CH | CH | CH | i-Pr | Cl | $C_2F_5$ | OMe |
| CH | CH | CH | CH | t-Bu | Cl | $C_2F_5$ | OMe |
| CH | CH | CH | CH | Et | Cl | $C_2F_5$ | CN |
| CH | CH | CH | CH | i-Pr | Cl | $C_2F_5$ | CN |
| CH | CH | CH | CH | t-Bu | Cl | $C_2F_5$ | CN |

TABLE 15

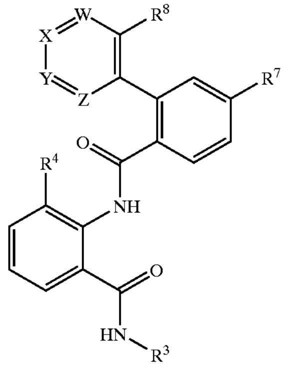

| W | X | Y | Z | $R^3$ | $R^4$ | $R^7$ | $R^8$ |
|---|---|---|---|---|---|---|---|
| CH | CH | CH | CH | Et | Me | $CF_3$ | Cl |
| CH | CH | CH | CH | i-Pr | Me | $CF_3$ | Cl |
| CH | CH | CH | CH | t-Bu | Me | $CF_3$ | Cl |
| CH | CH | CH | CH | Et | Me | $CF_3$ | Br |
| CH | CH | CH | CH | i-Pr | Me | $CF_3$ | Br |
| CH | CH | CH | CH | t-Bu | Me | $CF_3$ | Br |
| CH | CH | CH | CH | Et | Me | $CF_3$ | I |
| CH | CH | CH | CH | i-Pr | Me | $CF_3$ | I |
| CH | CH | CH | CH | t-Bu | Me | $CF_3$ | I |
| CH | CH | CH | CH | Et | Me | $CF_3$ | F |
| CH | CH | CH | CH | i-Pr | Me | $CF_3$ | F |
| CH | CH | CH | CH | t-Bu | Me | $CF_3$ | F |
| CH | CH | CH | CH | Et | Me | $CF_3$ | Me |
| CH | CH | CH | CH | i-Pr | Me | $CF_3$ | Me |
| CH | CH | CH | CH | t-Bu | Me | $CF_3$ | Me |
| CH | CH | CH | CH | Et | Me | $CF_3$ | $CF_3$ |
| CH | CH | CH | CH | i-Pr | Me | $CF_3$ | $CF_3$ |
| CH | CH | CH | CH | t-Bu | Me | $CF_3$ | $CF_3$ |
| CH | CH | CH | CH | Et | Me | $CF_3$ | OMe |
| CH | CH | CH | CH | i-Pr | Me | $CF_3$ | OMe |
| CH | CH | CH | CH | t-Bu | Me | $CF_3$ | OMe |
| CH | CH | CH | CH | Et | Me | $CF_3$ | CN |
| CH | CH | CH | CH | i-Pr | Me | $CF_3$ | CN |
| CH | CH | CH | CH | t-Bu | Me | $CF_3$ | CN |

TABLE 15-continued

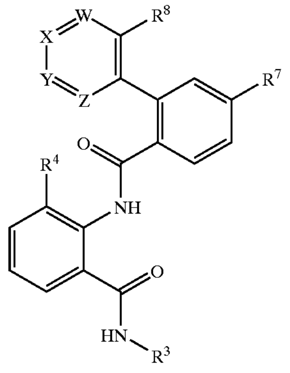

| W | X | Y | Z | $R^3$ | $R^4$ | $R^7$ | $R^8$ |
|---|---|---|---|---|---|---|---|
| CH | CH | CH | CH | Et | Cl | $CF_3$ | Cl |
| CH | CH | CH | CH | i-Pr | Cl | $CF_3$ | Cl |
| CH | CH | CH | CH | t-Bu | Cl | $CF_3$ | Cl |
| CH | CH | CH | CH | Et | Cl | $CF_3$ | Br |
| CH | CH | CH | CH | i-Pr | Cl | $CF_3$ | Br |
| CH | CH | CH | CH | t-Bu | Cl | $CF_3$ | Br |
| CH | CH | CH | CH | Et | Cl | $CF_3$ | I |
| CH | CH | CH | CH | i-Pr | Cl | $CF_3$ | I |
| CH | CH | CH | CH | t-Bu | Cl | $CF_3$ | I |
| CH | CH | CH | CH | Et | Cl | $CF_3$ | F |
| CH | CH | CH | CH | i-Pr | Cl | $CF_3$ | F |
| CH | CH | CH | CH | t-Bu | Cl | $CF_3$ | F |
| CH | CH | CH | CH | Et | Cl | $CF_3$ | Me |
| CH | CH | CH | CH | i-Pr | Cl | $CF_3$ | Me |
| CH | CH | CH | CH | t-Bu | Cl | $CF_3$ | Me |
| CH | CH | CH | CH | Et | Cl | $CF_3$ | $CF_3$ |
| CH | CH | CH | CH | i-Pr | Cl | $CF_3$ | $CF_3$ |
| CH | CH | CH | CH | t-Bu | Cl | $CF_3$ | $CF_3$ |
| CH | CH | CH | CH | Et | Cl | $CF_3$ | OMe |
| CH | CH | CH | CH | i-Pr | Cl | $CF_3$ | OMe |
| CH | CH | CH | CH | t-Bu | Cl | $CF_3$ | OMe |
| CH | CH | CH | CH | Et | Cl | $CF_3$ | CN |
| CH | CH | CH | CH | i-Pr | Cl | $CF_3$ | CN |
| CH | CH | CH | CH | t-Bu | Cl | $CF_3$ | CN |
| CH | CH | CH | N | Et | Me | $CF_3$ | Cl |
| CH | CH | CH | N | i-Pr | Me | $CF_3$ | Cl |
| CH | CH | CH | N | t-Bu | Me | $CF_3$ | Cl |
| CH | CH | CH | N | Et | Me | $CF_3$ | Br |
| CH | CH | CH | N | i-Pr | Me | $CF_3$ | Br |
| CH | CH | CH | N | t-Bu | Me | $CF_3$ | Br |
| CH | CH | CH | N | Et | Me | $CF_3$ | I |
| CH | CH | CH | N | i-Pr | Me | $CF_3$ | I |
| CH | CH | CH | N | t-Bu | Me | $CF_3$ | I |
| CH | CH | CH | N | Et | Me | $CF_3$ | F |
| CH | CH | CH | N | i-Pr | Me | $CF_3$ | F |
| CH | CH | CH | N | t-Bu | Me | $CF_3$ | F |
| CH | CH | CH | N | Et | Me | $CF_3$ | Me |
| CH | CH | CH | N | i-Pr | Me | $CF_3$ | Me |
| CH | CH | CH | N | t-Bu | Me | $CF_3$ | Me |
| CH | CH | CH | N | Et | Me | $CF_3$ | $CF_3$ |
| CH | CH | CH | N | i-Pr | Me | $CF_3$ | $CF_3$ |
| CH | CH | CH | N | t-Bu | Me | $CF_3$ | $CF_3$ |
| CH | CH | CH | N | Et | Me | $CF_3$ | OMe |
| CH | CH | CH | N | i-Pr | Me | $CF_3$ | OMe |
| CH | CH | CH | N | t-Bu | Me | $CF_3$ | OMe |
| CH | CH | CH | N | Et | Me | $CF_3$ | CN |
| CH | CH | CH | N | i-Pr | Me | $CF_3$ | CN |
| CH | CH | CH | N | t-Bu | Me | $CF_3$ | CN |
| CH | CH | CH | N | Et | Cl | $CF_3$ | Cl |
| CH | CH | CH | N | i-Pr | Cl | $CF_3$ | Cl |
| CH | CH | CH | N | t-Bu | Cl | $CF_3$ | Cl |
| CH | CH | CH | N | Et | Cl | $CF_3$ | Br |
| CH | CH | CH | N | i-Pr | Cl | $CF_3$ | Br |
| CH | CH | CH | N | t-Bu | Cl | $CF_3$ | Br |
| CH | CH | CH | N | Et | Cl | $CF_3$ | I |
| CH | CH | CH | N | i-Pr | Cl | $CF_3$ | I |
| CH | CH | CH | N | t-Bu | Cl | $CF_3$ | I |
| CH | CH | CH | N | Et | Cl | $CF_3$ | F |

TABLE 15-continued

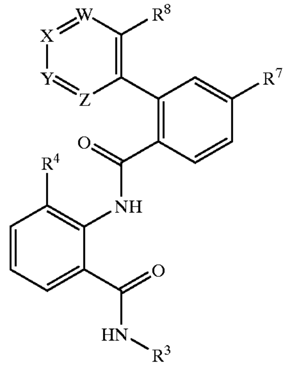

| W | X | Y | Z | $R^3$ | $R^4$ | $R^7$ | $R^8$ |
|---|---|---|---|---|---|---|---|
| CH | CH | CH | N | i-Pr | Cl | $CF_3$ | F |
| CH | CH | CH | N | t-Bu | Cl | $CF_3$ | F |
| CH | CH | CH | N | Et | Cl | $CF_3$ | Me |
| CH | CH | CH | N | i-Pr | Cl | $CF_3$ | Me |
| CH | CH | CH | N | t-Bu | Cl | $CF_3$ | Me |
| CH | CH | CH | N | Et | Cl | $CF_3$ | $CF_3$ |
| CH | CH | CH | N | i-Pr | Cl | $CF_3$ | $CF_3$ |
| CH | CH | CH | N | t-Bu | Cl | $CF_3$ | $CF_3$ |
| CH | CH | CH | N | Et | Cl | $CF_3$ | OMe |
| CH | CH | CH | N | i-Pr | Cl | $CF_3$ | OMe |
| CH | CH | CH | N | t-Bu | Cl | $CF_3$ | OMe |
| CH | CH | CH | N | Et | Cl | $CF_3$ | CN |
| CH | CH | CH | N | i-Pr | Cl | $CF_3$ | CN |
| CH | CH | CH | N | t-Bu | Cl | $CF_3$ | CN |
| CH | CH | N | CH | Et | Me | $CF_3$ | Cl |
| CH | CH | N | CH | i-Pr | Me | $CF_3$ | Cl |
| CH | CH | N | CH | t-Bu | Me | $CF_3$ | Cl |
| CH | CH | N | CH | Et | Me | $CF_3$ | Br |
| CH | CH | N | CH | i-Pr | Me | $CF_3$ | Br |
| CH | CH | N | CH | t-Bu | Me | $CF_3$ | Br |
| CH | CH | N | CH | Et | Me | $CF_3$ | I |
| CH | CH | N | CH | i-Pr | Me | $CF_3$ | I |
| CH | CH | N | CH | t-Bu | Me | $CF_3$ | I |
| CH | CH | N | CH | Et | Me | $CF_3$ | F |
| CH | CH | N | CH | i-Pr | Me | $CF_3$ | F |
| CH | CH | N | CH | t-Bu | Me | $CF_3$ | F |
| CH | CH | N | CH | Et | Me | $CF_3$ | Me |
| CH | CH | N | CH | i-Pr | Me | $CF_3$ | Me |
| CH | CH | N | CH | t-Bu | Me | $CF_3$ | Me |
| CH | CH | N | CH | Et | Me | $CF_3$ | $CF_3$ |
| CH | CH | N | CH | i-Pr | Me | $CF_3$ | $CF_3$ |
| CH | CH | N | CH | t-Bu | Me | $CF_3$ | $CF_3$ |
| CH | CH | N | CH | Et | Me | $CF_3$ | OMe |
| CH | CH | N | CH | i-Pr | Me | $CF_3$ | OMe |
| CH | CH | N | CH | t-Bu | Me | $CF_3$ | OMe |
| CH | CH | N | CH | Et | Me | $CF_3$ | CN |
| CH | CH | N | CH | i-Pr | Me | $CF_3$ | CN |
| CH | CH | N | CH | t-Bu | Me | $CF_3$ | CN |
| CH | CH | N | CH | Et | Cl | $CF_3$ | Cl |
| CH | CH | N | CH | i-Pr | Cl | $CF_3$ | Cl |
| CH | CH | N | CH | t-Bu | Cl | $CF_3$ | Cl |
| CH | CH | N | CH | Et | Cl | $CF_3$ | Br |
| CH | CH | N | CH | i-Pr | Cl | $CF_3$ | Br |
| CH | CH | N | CH | t-Bu | Cl | $CF_3$ | Br |
| CH | CH | N | CH | Et | Cl | $CF_3$ | I |
| CH | CH | N | CH | i-Pr | Cl | $CF_3$ | I |
| CH | CH | N | CH | t-Bu | Cl | $CF_3$ | I |
| CH | CH | N | CH | Et | Cl | $CF_3$ | F |
| CH | CH | N | CH | i-Pr | Cl | $CF_3$ | F |
| CH | CH | N | CH | t-Bu | Cl | $CF_3$ | F |
| CH | CH | N | CH | Et | Cl | $CF_3$ | Me |
| CH | CH | N | CH | i-Pr | Cl | $CF_3$ | Me |
| CH | CH | N | CH | t-Bu | Cl | $CF_3$ | Me |
| CH | CH | N | CH | Et | Cl | $CF_3$ | $CF_3$ |
| CH | CH | N | CH | i-Pr | Cl | $CF_3$ | $CF_3$ |
| CH | CH | N | CH | t-Bu | Cl | $CF_3$ | $CF_3$ |
| CH | CH | N | CH | Et | Cl | $CF_3$ | OMe |
| CH | CH | N | CH | i-Pr | Cl | $CF_3$ | OMe |

TABLE 15-continued

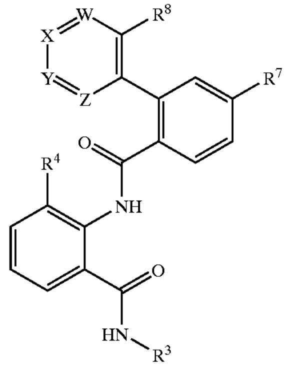

| W | X | Y | Z | $R^3$ | $R^4$ | $R^7$ | $R^8$ |
|---|---|---|---|---|---|---|---|
| CH | CH | N | CH | t-Bu | Cl | $CF_3$ | OMe |
| CH | CH | N | CH | Et | Cl | $CF_3$ | CN |
| CH | CH | N | CH | i-Pr | Cl | $CF_3$ | CN |
| CH | CH | N | CH | t-Bu | Cl | $CF_3$ | CN |
| CH | N | CH | CH | Et | Me | $CF_3$ | Cl |
| CH | N | CH | CH | i-Pr | Me | $CF_3$ | Cl |
| CH | N | CH | CH | t-Bu | Me | $CF_3$ | Cl |
| CH | N | CH | CH | Et | Me | $CF_3$ | Br |
| CH | N | CH | CH | i-Pr | Me | $CF_3$ | Br |
| CH | N | CH | CH | t-Bu | Me | $CF_3$ | Br |
| CH | N | CH | CH | Et | Me | $CF_3$ | I |
| CH | N | CH | CH | i-Pr | Me | $CF_3$ | I |
| CH | N | CH | CH | t-Bu | Me | $CF_3$ | I |
| CH | N | CH | CH | Et | Me | $CF_3$ | F |
| CH | N | CH | CH | i-Pr | Me | $CF_3$ | F |
| CH | N | CH | CH | t-Bu | Me | $CF_3$ | F |
| CH | N | CH | CH | Et | Me | $CF_3$ | Me |
| CH | N | CH | CH | i-Pr | Me | $CF_3$ | Me |
| CH | N | CH | CH | t-Bu | Me | $CF_3$ | Me |
| CH | N | CH | CH | Et | Me | $CF_3$ | $CF_3$ |
| CH | N | CH | CH | i-Pr | Me | $CF_3$ | $CF_3$ |
| CH | N | CH | CH | t-Bu | Me | $CF_3$ | $CF_3$ |
| CH | N | CH | CH | Et | Me | $CF_3$ | OMe |
| CH | N | CH | CH | i-Pr | Me | $CF_3$ | OMe |
| CH | N | CH | CH | t-Bu | Me | $CF_3$ | OMe |
| CH | N | CH | CH | Et | Me | $CF_3$ | CN |
| CH | N | CH | CH | i-Pr | Me | $CF_3$ | CN |
| CH | N | CH | CH | t-Bu | Me | $CF_3$ | CN |
| CH | N | CH | CH | Et | Cl | $CF_3$ | Cl |
| CH | N | CH | CH | i-Pr | Cl | $CF_3$ | Cl |
| CH | N | CH | CH | t-Bu | Cl | $CF_3$ | Cl |
| CH | N | CH | CH | Et | Cl | $CF_3$ | Br |
| CH | N | CH | CH | i-Pr | Cl | $CF_3$ | Br |
| CH | N | CH | CH | t-Bu | Cl | $CF_3$ | Br |
| CH | N | CH | CH | Et | Cl | $CF_3$ | I |
| CH | N | CH | CH | i-Pr | Cl | $CF_3$ | I |
| CH | N | CH | CH | t-Bu | Cl | $CF_3$ | I |
| CH | N | CH | CH | Et | Cl | $CF_3$ | F |
| CH | N | CH | CH | i-Pr | Cl | $CF_3$ | F |
| CH | N | CH | CH | t-Bu | Cl | $CF_3$ | F |
| CH | N | CH | CH | Et | Cl | $CF_3$ | Me |
| CH | N | CH | CH | i-Pr | Cl | $CF_3$ | Me |
| CH | N | CH | CH | t-Bu | Cl | $CF_3$ | Me |
| CH | N | CH | CH | Et | Cl | $CF_3$ | $CF_3$ |
| CH | N | CH | CH | i-Pr | Cl | $CF_3$ | $CF_3$ |
| CH | N | CH | CH | t-Bu | Cl | $CF_3$ | $CF_3$ |
| CH | N | CH | CH | Et | Cl | $CF_3$ | OMe |
| CH | N | CH | CH | i-Pr | Cl | $CF_3$ | OMe |
| CH | N | CH | CH | t-Bu | Cl | $CF_3$ | OMe |
| CH | N | CH | CH | Et | Cl | $CF_3$ | CN |
| CH | N | CH | CH | i-Pr | Cl | $CF_3$ | CN |
| CH | N | CH | CH | t-Bu | Cl | $CF_3$ | CN |
| N | CH | CH | CH | Et | Me | $CF_3$ | Cl |
| N | CH | CH | CH | i-Pr | Me | $CF_3$ | Cl |
| N | CH | CH | CH | t-Bu | Me | $CF_3$ | Cl |
| N | CH | CH | CH | Et | Me | $CF_3$ | Br |
| N | CH | CH | CH | i-Pr | Me | $CF_3$ | Br |
| N | CH | CH | CH | t-Bu | Me | $CF_3$ | Br |

TABLE 15-continued

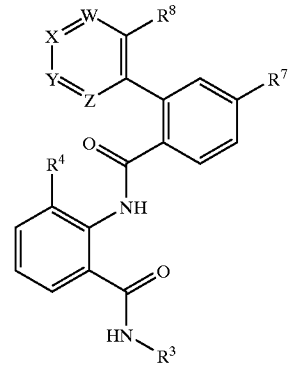

| W | X | Y | Z | $R^3$ | $R^4$ | $R^7$ | $R^8$ |
|---|---|---|---|---|---|---|---|
| N | CH | CH | CH | Et | Me | $CF_3$ | I |
| N | CH | CH | CH | i-Pr | Me | $CF_3$ | I |
| N | CH | CH | CH | t-Bu | Me | $CF_3$ | I |
| N | CH | CH | CH | Et | Me | $CF_3$ | F |
| N | CH | CH | CH | i-Pr | Me | $CF_3$ | F |
| N | CH | CH | CH | t-Bu | Me | $CF_3$ | F |
| N | CH | CH | CH | Et | Me | $CF_3$ | Me |
| N | CH | CH | CH | i-Pr | Me | $CF_3$ | Me |
| N | CH | CH | CH | t-Bu | Me | $CF_3$ | Me |
| N | CH | CH | CH | Et | Me | $CF_3$ | $CF_3$ |
| N | CH | CH | CH | i-Pr | Me | $CF_3$ | $CF_3$ |
| N | CH | CH | CH | t-Bu | Me | $CF_3$ | $CF_3$ |
| N | CH | CH | CH | Et | Me | $CF_3$ | OMe |
| N | CH | CH | CH | i-Pr | Me | $CF_3$ | OMe |
| N | CH | CH | CH | t-Bu | Me | $CF_3$ | OMe |
| N | CH | CH | CH | Et | Me | $CF_3$ | CN |
| N | CH | CH | CH | i-Pr | Me | $CF_3$ | CN |
| N | CH | CH | CH | t-Bu | Me | $CF_3$ | CN |
| N | CH | CH | CH | Et | Cl | $CF_3$ | Cl |
| N | CH | CH | CH | i-Pr | Cl | $CF_3$ | Cl |
| N | CH | CH | CH | t-Bu | Cl | $CF_3$ | Cl |
| N | CH | CH | CH | Et- | Cl | $CF_3$ | Br |
| N | CH | CH | CH | i-Pr | Cl | $CF_3$ | Br |
| N | CH | CH | CH | t-Bu | Cl | $CF_3$ | Br |
| N | CH | CH | CH | Et | Cl | $CF_3$ | I |
| N | CH | CH | CH | i-Pr | Cl | $CF_3$ | I |
| N | CH | CH | CH | t-Bu | Cl | $CF_3$ | I |
| N | CH | CH | CH | Et | Cl | $CF_3$ | F |
| N | CH | CH | CH | i-Pr | Cl | $CF_3$ | F |
| N | CH | CH | CH | t-Bu | Cl | $CF_3$ | F |
| N | CH | CH | CH | Et | Cl | $CF_3$ | Me |
| N | CH | CH | CH | i-Pr | Cl | $CF_3$ | Me |
| N | CH | CH | CH | t-Bu | Cl | $CF_3$ | Me |
| N | CH | CH | CH | Et | Cl | $CF_3$ | $CF_3$ |
| N | CH | CH | CH | i-Pr | Cl | $CF_3$ | $CF_3$ |
| N | CH | CH | CH | t-Bu | Cl | $CF_3$ | $CF_3$ |
| N | CH | CH | CH | Et | Cl | $CF_3$ | OMe |
| N | CH | CH | CH | i-Pr | Cl | $CF_3$ | OMe |
| N | CH | CH | CH | t-Bu | Cl | $CF_3$ | OMe |
| N | CH | CH | CH | Et | Cl | $CF_3$ | CN |
| N | CH | CH | CH | i-Pr | Cl | $CF_3$ | CN |
| N | CH | CH | CH | t-Bu | Cl | $CF_3$ | CN |
| CH | N | CH | N | Et | Me | $CF_3$ | Cl |
| CH | N | CH | N | i-Pr | Me | $CF_3$ | Cl |
| CH | N | CH | N | t-Bu | Me | $CF_3$ | Cl |
| CH | N | CH | N | Et | Me | $CF_3$ | Br |
| CH | N | CH | N | i-Pr | Me | $CF_3$ | Br |
| CH | N | CH | N | t-Bu | Me | $CF_3$ | Br |
| CH | N | CH | N | Et | Me | $CF_3$ | I |
| CH | N | CH | N | i-Pr | Me | $CF_3$ | I |
| CH | N | CH | N | t-Bu | Me | $CF_3$ | I |
| CH | N | CH | N | Et | Me | $CF_3$ | F |
| CH | N | CH | N | i-Pr | Me | $CF_3$ | F |
| CH | N | CH | N | t-Bu | Me | $CF_3$ | F |
| CH | N | CH | N | Et | Me | $CF_3$ | Me |
| CH | N | CH | N | i-Pr | Me | $CF_3$ | Me |
| CH | N | CH | N | t-Bu | Me | $CF_3$ | Me |
| CH | N | CH | N | Et | Me | $CF_3$ | $CF_3$ |

TABLE 15-continued

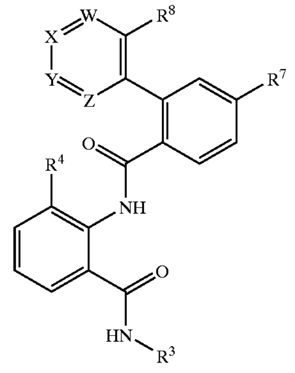

| W | X | Y | Z | $R^3$ | $R^4$ | $R^7$ | $R^8$ |
|---|---|---|---|---|---|---|---|
| CH | N | CH | N | i-Pr | Me | $CF_3$ | $CF_3$ |
| CH | N | CH | N | t-Bu | Me | $CF_3$ | $CF_3$ |
| CH | N | CH | N | Et | Me | $CF_3$ | OMe |
| CH | N | CH | N | i-Pr | Me | $CF_3$ | OMe |
| CH | N | CH | N | t-Bu | Me | $CF_3$ | OMe |
| CH | N | CH | N | Et | Me | $CF_3$ | CN |
| CH | N | CH | N | i-Pr | Me | $CF_3$ | CN |
| CH | N | CH | N | t-Bu | Me | $CF_3$ | CN |
| CH | N | CH | N | Et | Cl | $CF_3$ | Cl |
| CH | N | CH | N | i-Pr | Cl | $CF_3$ | Cl |
| CH | N | CH | N | t-Bu | Cl | $CF_3$ | Cl |
| CH | N | CH | N | Et | Cl | $CF_3$ | Br |
| CH | N | CH | N | i-Pr | Cl | $CF_3$ | Br |
| CH | N | CH | N | t-Bu | Cl | $CF_3$ | Br |
| CH | N | CH | N | Et | Cl | $CF_3$ | I |
| CH | N | CH | N | i-Pr | Cl | $CF_3$ | I |
| CH | N | CH | N | t-Bu | Cl | $CF_3$ | I |
| CH | N | CH | N | Et | Cl | $CF_3$ | F |
| CH | N | CH | N | i-Pr | Cl | $CF_3$ | F |
| CH | N | CH | N | t-Bu | Cl | $CF_3$ | F |
| CH | N | CH | N | Et | Cl | $CF_3$ | Me |
| CH | N | CH | N | i-Pr | Cl | $CF_3$ | Me |
| CH | N | CH | N | t-Bu | Cl | $CF_3$ | Me |
| CH | N | CH | N | Et | Cl | $CF_3$ | $CF_3$ |
| CH | N | CH | N | i-Pr | Cl | $CF_3$ | $CF_3$ |
| CH | N | CH | N | t-Bu | Cl | $CF_3$ | $CF_3$ |
| CH | N | CH | N | Et | Cl | $CF_3$ | OMe |
| CH | N | CH | N | i-Pr | Cl | $CF_3$ | OMe |
| CH | N | CH | N | t-Bu | Cl | $CF_3$ | OMe |
| CH | N | CH | N | Et | Cl | $CF_3$ | CN |
| CH | N | CH | N | i-Pr | Cl | $CF_3$ | CN |
| CH | N | CH | N | t-Bu | Cl | $CF_3$ | CN |
| CH | CH | CH | CCl | Et | Me | $CF_3$ | Cl |
| CH | CH | CH | CCl | i-Pr | Me | $CF_3$ | Cl |
| CH | CH | CH | CCl | t-Bu | Me | $CF_3$ | Cl |
| CH | CH | CH | CCl | Et | Me | $CF_3$ | Br |
| CH | CH | CH | CCl | i-Pr | Me | $CF_3$ | Br |
| CH | CH | CH | CCl | t-Bu | Me | $CF_3$ | Br |
| CH | CH | CH | CCl | Et | Me | $CF_3$ | I |
| CH | CH | CH | CCl | i-Pr | Me | $CF_3$ | I |
| CH | CH | CH | CCl | t-Bu | Me | $CF_3$ | I |
| CH | CH | CH | CCl | Et | Me | $CF_3$ | F |
| CH | CH | CH | CCl | i-Pr | Me | $CF_3$ | F |
| CH | CH | CH | CCl | t-Bu | Me | $CF_3$ | F |
| CH | CH | CH | CCl | Et | Me | $CF_3$ | Me |
| CH | CH | CH | CCl | i-Pr | Me | $CF_3$ | Me |
| CH | CH | CH | CCl | t-Bu | Me | $CF_3$ | Me |
| CH | CH | CH | CCl | Et | Me | $CF_3$ | $CF_3$ |
| CH | CH | CH | CCl | i-Pr | Me | $CF_3$ | $CF_3$ |
| CH | CH | CH | CCl | t-Bu | Me | $CF_3$ | $CF_3$ |
| CH | CH | CH | CCl | Et | Me | $CF_3$ | OMe |
| CH | CH | CH | CCl | i-Pr | Me | $CF_3$ | OMe |
| CH | CH | CH | CCl | t-Bu | Me | $CF_3$ | OMe |
| CH | CH | CH | CCl | Et | Me | $CF_3$ | CN |
| CH | CH | CH | CCl | i-Pr | Me | $CF_3$ | CN |
| CH | CH | CH | CCl | t-Bu | Me | $CF_3$ | CN |
| CH | CH | CH | CCl | Et | Cl | $CF_3$ | Cl |
| CH | CH | CH | CCl | i-Pr | Cl | $CF_3$ | Cl |

TABLE 15-continued

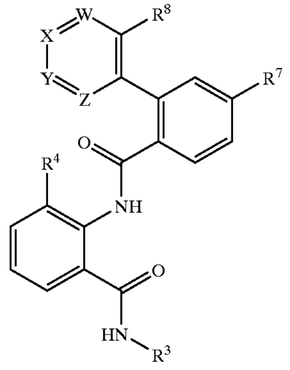

| W | X | Y | Z | $R^3$ | $R^4$ | $R^7$ | $R^8$ |
|---|---|---|---|---|---|---|---|
| CH | CH | CH | CCl | t-Bu | Cl | $CF_3$ | Cl |
| CH | CH | CH | CCl | Et | Cl | $CF_3$ | Br |
| CH | CH | CH | CCl | i-Pr | Cl | $CF_3$ | Br |
| CH | CH | CH | CCl | t-Bu | Cl | $CF_3$ | Br |
| CH | CH | CH | CCl | Et | Cl | $CF_3$ | I |
| CH | CH | CH | CCl | i-Pr | Cl | $CF_3$ | I |
| CH | CH | CH | CCl | t-Bu | Cl | $CF_3$ | I |
| CH | CH | CH | CCl | Et | Cl | $CF_3$ | F |
| CH | CH | CH | CCl | i-Pr | Cl | $CF_3$ | F |
| CH | CH | CH | CCl | t-Bu | Cl | $CF_3$ | F |
| CH | CH | CH | CCl | Et | Cl | $CF_3$ | Me |
| CH | CH | CH | CCl | i-Pr | Cl | $CF_3$ | Me |
| CH | CH | CH | CCl | t-Bu | Cl | $CF_3$ | Me |
| CH | CH | CH | CCl | Et | Cl | $CF_3$ | $CF_3$ |
| CH | CH | CH | CCl | i-Pr | Cl | $CF_3$ | $CF_3$ |
| CH | CH | CH | CCl | t-Bu | Cl | $CF_3$ | $CF_3$ |
| CH | CH | CH | CCl | Et | Cl | $CF_3$ | OMe |
| CH | CH | CH | CCl | i-Pr | Cl | $CF_3$ | OMe |
| CH | CH | CH | CCl | t-Bu | Cl | $CF_3$ | OMe |
| CH | CH | CH | CCl | Et | Cl | $CF_3$ | CN |
| CH | CH | CH | CCl | i-Pr | Cl | $CF_3$ | CN |
| CH | CH | CH | CCl | t-Bu | Cl | $CF_3$ | CN |
| CH | CH | CH | CF | Et | Me | $CF_3$ | Cl |
| CH | CH | CH | CF | i-Pr | Me | $CF_3$ | Cl |
| CH | CH | CH | CF | t-Bu | Me | $CF_3$ | Cl |
| CH | CH | CH | CF | Et | Me | $CF_3$ | Br |
| CH | CH | CH | CF | i-Pr | Me | $CF_3$ | Br |
| CH | CH | CH | CF | t-Bu | Me | $CF_3$ | Br |
| CH | CH | CH | CF | Et | Me | $CF_3$ | I |
| CH | CH | CH | CF | i-Pr | Me | $CF_3$ | I |
| CH | CH | CH | CF | t-Bu | Me | $CF_3$ | I |
| CH | CH | CH | CF | Et | Me | $CF_3$ | F |
| CH | CH | CH | CF | i-Pr | Me | $CF_3$ | F |
| CH | CH | CH | CF | t-Bu | Me | $CF_3$ | F |
| CH | CH | CH | CF | Et | Me | $CF_3$ | Me |
| CH | CH | CH | CF | i-Pr | Me | $CF_3$ | Me |
| CH | CH | CH | CF | t-Bu | Me | $CF_3$ | Me |
| CH | CH | CH | CF | Et | Me | $CF_3$ | $CF_3$ |
| CH | CH | CH | CF | i-Pr | Me | $CF_3$ | $CF_3$ |
| CH | CH | CH | CF | t-Bu | Me | $CF_3$ | $CF_3$ |
| CH | CH | CH | CF | Et | Me | $CF_3$ | OMe |
| CH | CH | CH | CF | i-Pr | Me | $CF_3$ | OMe |
| CH | CH | CH | CF | t-Bu | Me | $CF_3$ | OMe |
| CH | CH | CH | CF | Et | Me | $CF_3$ | CN |
| CH | CH | CH | CF | i-Pr | Me | $CF_3$ | CN |
| CH | CH | CH | CF | t-Bu | Me | $CF_3$ | CN |
| CH | CH | CH | CF | Et | Cl | $CF_3$ | Cl |
| CH | CH | CH | CF | i-Pr | Cl | $CF_3$ | Cl |
| CH | CH | CH | CF | t-Bu | Cl | $CF_3$ | Cl |
| CH | CH | CH | CF | Et | Cl | $CF_3$ | Br |
| CH | CH | CH | CF | i-Pr | Cl | $CF_3$ | Br |
| CH | CH | CH | CF | t-Bu | Cl | $CF_3$ | Br |
| CH | CH | CH | CF | Et | Cl | $CF_3$ | I |
| CH | CH | CH | CF | i-Pr | Cl | $CF_3$ | I |
| CH | CH | CH | CF | t-Bu | Cl | $CF_3$ | I |
| CH | CH | CH | CF | i-Pr | Cl | $CF_3$ | F |
| CH | CH | CH | CF | t-Bu | Cl | $CF_3$ | F |
| CH | CH | CH | CF | Et | Cl | $CF_3$ | Me |

TABLE 15-continued

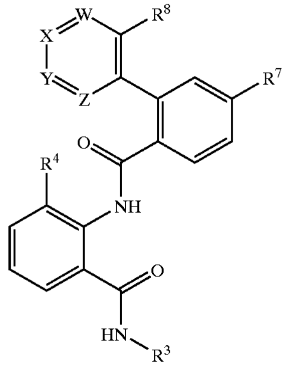

| W | X | Y | Z | $R^3$ | $R^4$ | $R^7$ | $R^8$ |
|---|---|---|---|---|---|---|---|
| CH | CH | CH | CF | i-Pr | Cl | $CF_3$ | Me |
| CH | CH | CH | CF | t-Bu | Cl | $CF_3$ | Me |
| CH | CH | CH | CF | Et | Cl | $CF_3$ | $CF_3$ |
| CH | CH | CH | CF | i-Pr | Cl | $CF_3$ | $CF_3$ |
| CH | CH | CH | CF | t-Bu | Cl | $CF_3$ | $CF_3$ |
| CH | CH | CH | CF | Et | Cl | $CF_3$ | OMe |
| CH | CH | CH | CF | i-Pr | Cl | $CF_3$ | OMe |
| CH | CH | CH | CF | t-Bu | Cl | $CF_3$ | OMe |
| CH | CH | CH | CF | Et | Cl | $CF_3$ | CN |
| CH | CH | CH | CF | i-Pr | Cl | $CF_3$ | CN |
| CH | CH | CH | CF | t-Bu | Cl | $CF_3$ | CN |
| CH | CH | CH | CH | Et | Me | $C_2F_5$ | Cl |
| CH | CH | CH | CH | i-Pr | Me | $C_2F_5$ | Cl |
| CH | CH | CH | CH | t-Bu | Me | $C_2F_5$ | Cl |
| CH | CH | CH | CH | Et | Me | $C_2F_5$ | Br |
| CH | CH | CH | CH | i-Pr | Me | $C_2F_5$ | Br |
| CH | CH | CH | CH | t-Bu | Me | $C_2F_5$ | Br |
| CH | CH | CH | CH | Et | Me | $C_2F_5$ | I |
| CH | CH | CH | CH | i-Pr | Me | $C_2F_5$ | I |
| CH | CH | CH | CH | t-Bu | Me | $C_2F_5$ | I |
| CH | CH | CH | CH | Et | Me | $C_2F_5$ | F |
| CH | CH | CH | CH | i-Pr | Me | $C_2F_5$ | F |
| CH | CH | CH | CH | t-Bu | Me | $C_2F_5$ | F |
| CH | CH | CH | CH | Et | Me | $C_2F_5$ | Me |
| CH | CH | CH | CH | i-Pr | Me | $C_2F_5$ | Me |
| CH | CH | CH | CH | t-Bu | Me | $C_2F_5$ | Me |
| CH | CH | CH | CH | Et | Me | $C_2F_5$ | $CF_3$ |
| CH | CH | CH | CH | i-Pr | Me | $C_2F_5$ | $CF_3$ |
| CH | CH | CH | CH | t-Bu | Me | $C_2F_5$ | $CF_3$ |
| CH | CH | CH | CH | Et | Me | $C_2F_5$ | OMe |
| CH | CH | CH | CH | i-Pr | Me | $C_2F_5$ | OMe |
| CH | CH | CH | CH | t-Bu | Me | $C_2F_5$ | OMe |
| CH | CH | CH | CH | Et | Me | $C_2F_5$ | CN |
| CH | CH | CH | CH | i-Pr | Me | $C_2F_5$ | CN |
| CH | CH | CH | CH | t-Bu | Me | $C_2F_5$ | CN |
| CH | CH | CH | CH | Et | Cl | $C_2F_5$ | Cl |
| CH | CH | CH | CH | i-Pr | Cl | $C_2F_5$ | Cl |
| CH | CH | CH | CH | t-Bu | Cl | $C_2F_5$ | Cl |
| CH | CH | CH | CH | Et | Cl | $C_2F_5$ | Br |
| CH | CH | CH | CH | i-Pr | Cl | $C_2F_5$ | Br |
| CH | CH | CH | CH | t-Bu | Cl | $C_2F_5$ | Br |
| CH | CH | CH | CH | Et | Cl | $C_2F_5$ | I |
| CH | CH | CH | CH | i-Pr | Cl | $C_2F_5$ | I |
| CH | CH | CH | CH | t-Bu | Cl | $C_2F_5$ | I |
| CH | CH | CH | CH | Et | Cl | $C_2F_5$ | F |
| CH | CH | CH | CH | i-Pr | Cl | $C_2F_5$ | F |
| CH | CH | CH | CH | t-Bu | Cl | $C_2F_5$ | F |
| CH | CH | CH | CH | Et | Cl | $C_2F_5$ | Me |
| CH | CH | CH | CH | i-Pr | Cl | $C_2F_5$ | Me |
| CH | CH | CH | CH | t-Bu | Cl | $C_2F_5$ | Me |
| CH | CH | CH | CH | Et | Cl | $C_2F_5$ | $CF_3$ |
| CH | CH | CH | CH | i-Pr | Cl | $C_2F_5$ | $CF_3$ |
| CH | CH | CH | CH | t-Bu | Cl | $C_2F_5$ | $CF_3$ |
| CH | CH | CH | CH | Et | Cl | $C_2F_5$ | OMe |
| CH | CH | CH | CH | i-Pr | Cl | $C_2F_5$ | OMe |
| CH | CH | CH | CH | t-Bu | Cl | $C_2F_5$ | OMe |
| CH | CH | CH | CH | Et | Cl | $C_2F_5$ | CN |

TABLE 15-continued

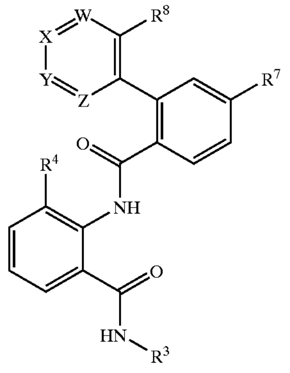

| W | X | Y | Z | $R^3$ | $R^4$ | $R^7$ | $R^8$ |
|---|---|---|---|---|---|---|---|
| CH | CH | CH | CH | i-Pr | Cl | $C_2F_5$ | CN |
| CH | CH | CH | CH | t-Bu | Cl | $C_2F_5$ | CN |

TABLE 16

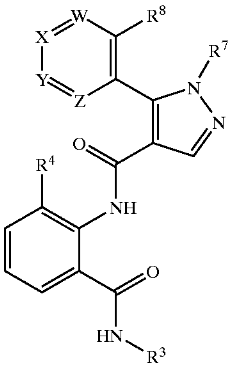

| W | X | Y | Z | $R^3$ | $R^4$ | $R^7$ | $R^8$ |
|---|---|---|---|---|---|---|---|
| CH | CH | CH | CH | Et | Me | $CF_3$ | Cl |
| CH | CH | CH | CH | i-Pr | Me | $CF_3$ | Cl |
| CH | CH | CH | CH | t-Bu | Me | $CF_3$ | Cl |
| CH | CH | CH | CH | Et | Me | $CF_3$ | Br |
| CH | CH | CH | CH | i-Pr | Me | $CF_3$ | Br |
| CH | CH | CH | CH | t-Bu | Me | $CF_3$ | Br |
| CH | CH | CH | CH | Et | Me | $CF_3$ | I |
| CH | CH | CH | CH | i-Pr | Me | $CF_3$ | I |
| CH | CH | CH | CH | t-Bu | Me | $CF_3$ | I |
| CH | CH | CH | CH | Et | Me | $CF_3$ | F |
| CH | CH | CH | CH | i-Pr | Me | $CF_3$ | F |
| CH | CH | CH | CH | t-Bu | Me | $CF_3$ | F |
| CH | CH | CH | CH | Et | Me | $CF_3$ | Me |
| CH | CH | CH | CH | i-Pr | Me | $CF_3$ | Me |
| CH | CH | CH | CH | t-Bu | Me | $CF_3$ | Me |
| CH | CH | CH | CH | Et | Me | $CF_3$ | $CF_3$ |
| CH | CH | CH | CH | i-Pr | Me | $CF_3$ | $CF_3$ |
| CH | CH | CH | CH | t-Bu | Me | $CF_3$ | $CF_3$ |
| CH | CH | CH | CH | Et | Me | $CF_3$ | OMe |
| CH | CH | CH | CH | i-Pr | Me | $CF_3$ | OMe |
| CH | CH | CH | CH | t-Bu | Me | $CF_3$ | OMe |
| CH | CH | CH | CH | Et | Me | $CF_3$ | CN |
| CH | CH | CH | CH | i-Pr | Me | $CF_3$ | CN |
| CH | CH | CH | CH | t-Bu | Me | $CF_3$ | CN |
| CH | CH | CH | CH | Et | Cl | $CF_3$ | Cl |
| CH | CH | CH | CH | i-Pr | Cl | $CF_3$ | Cl |
| CH | CH | CH | CH | t-Bu | Cl | $CF_3$ | Cl |
| CH | CH | CH | CH | Et | Cl | $CF_3$ | Br |
| CH | CH | CH | CH | i-Pr | Cl | $CF_3$ | Br |
| CH | CH | CH | CH | t-Bu | Cl | $CF_3$ | Br |
| CH | CH | CH | CH | Et | Cl | $CF_3$ | I |

TABLE 16-continued

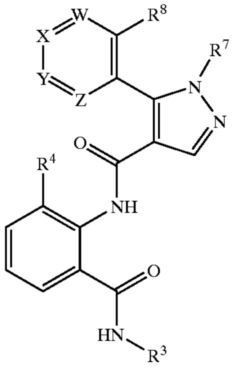

| W | X | Y | Z | $R^3$ | $R^4$ | $R^7$ | $R^8$ |
|---|---|---|---|---|---|---|---|
| CH | CH | CH | CH | i-Pr | Cl | $CF_3$ | I |
| CH | CH | CH | CH | t-Bu | Cl | $CF_3$ | I |
| CH | CH | CH | CH | Et | Cl | $CF_3$ | F |
| CH | CH | CH | CH | i-Pr | Cl | $CF_3$ | F |
| CH | CH | CH | CH | t-Bu | Cl | $CF_3$ | F |
| CH | CH | CH | CH | Et | Cl | $CF_3$ | Me |
| CH | CH | CH | CH | i-Pr | Cl | $CF_3$ | Me |
| CH | CH | CH | CH | t-Bu | Cl | $CF_3$ | Me |
| CH | CH | CH | CH | Et | Cl | $CF_3$ | $CF_3$ |
| CH | CH | CH | CH | i-Pr | Cl | $CF_3$ | $CF_3$ |
| CH | CH | CH | CH | t-Bu | Cl | $CF_3$ | $CF_3$ |
| CH | CH | CH | CH | Et | Cl | $CF_3$ | OMe |
| CH | CH | CH | CH | i-Pr | Cl | $CF_3$ | OMe |
| CH | CH | CH | CH | t-Bu | Cl | $CF_3$ | OMe |
| CH | CH | CH | CH | Et | Cl | $CF_3$ | CN |
| CH | CH | CH | CH | i-Pr | Cl | $CF_3$ | CN |
| CH | CH | CH | CH | t-Bu | Cl | $CF_3$ | CN |
| CH | CH | CH | N | Et | Me | $CF_3$ | Cl |
| CH | CH | CH | N | i-Pr | Me | $CF_3$ | Cl |
| CH | CH | CH | N | t-Bu | Me | $CF_3$ | Cl |
| CH | CH | CH | N | Et | Me | $CF_3$ | Br |
| CH | CH | CH | N | i-Pr | Me | $CF_3$ | Br |
| CH | CH | CH | N | t-Bu | Me | $CF_3$ | Br |
| CH | CH | CH | N | Et | Me | $CF_3$ | I |
| CH | CH | CH | N | i-Pr | Me | $CF_3$ | I |
| CH | CH | CH | N | t-Bu | Me | $CF_3$ | I |
| CH | CH | CH | N | Et | Me | $CF_3$ | F |
| CH | CH | CH | N | i-Pr | Me | $CF_3$ | F |
| CH | CH | CH | N | t-Bu | Me | $CF_3$ | F |
| CH | CH | GE | N | Et | Me | $CF_3$ | Me |
| CH | CH | CH | N | i-Pr | Me | $CF_3$ | Me |
| CH | CH | CH | N | t-Bu | Me | $CF_3$ | Me |
| CH | CH | CH | N | Et | Me | $CF_3$ | $CF_3$ |
| CH | CH | CH | N | i-Pr | Me | $CF_3$ | $CF_3$ |
| CH | CH | CH | N | t-Bu | Me | $CF_3$ | $CF_3$ |
| CH | CH | CH | N | Et | Me | $CF_3$ | OMe |
| CH | CH | CH | N | i-Pr | Me | $CF_3$ | OMe |
| CH | CH | CH | N | t-Bu | Me | $CF_3$ | OMe |
| CH | CH | CH | N | Et | Me | $CF_3$ | CN |
| CH | CH | CH | N | i-Pr | Me | $CF_3$ | CN |
| CH | CH | CH | N | t-Bu | Me | $CF_3$ | CN |
| CH | CH | CH | N | Et | Cl | $CF_3$ | Cl |
| CH | CH | CH | N | i-Pr | Cl | $CF_3$ | Cl |
| CH | CH | CH | N | t-Bu | Cl | $CF_3$ | Cl |
| CH | CH | CH | N | Et | Cl | $CF_3$ | Br |
| CH | CH | CH | N | i-Pr | Cl | $CF_3$ | Br |
| CH | CH | CH | N | t-Bu | Cl | $CF_3$ | Br |
| CH | CH | CH | N | Et | Cl | $CF_3$ | I |
| CH | CH | CH | N | i-Pr | Cl | $CF_3$ | I |
| CH | CH | CH | N | t-Bu | Cl | $CF_3$ | I |
| CH | CH | CH | N | Et | Cl | $CF_3$ | F |
| CH | CH | CH | N | i-Pr | Cl | $CF_3$ | F |
| CH | CH | CH | N | t-Bu | Cl | $CF_3$ | F |
| CH | CH | CH | N | Et | Cl | $CF_3$ | Me |
| CH | CH | CH | N | i-Pr | Cl | $CF_3$ | Me |
| CH | CH | CH | N | t-Bu | Cl | $CF_3$ | Me |
| CH | CH | CH | N | Et | Cl | $CF_3$ | $CF_3$ |
| CH | CH | CH | N | i-Pr | Cl | $CF_3$ | $CF_3$ |

TABLE 16-continued

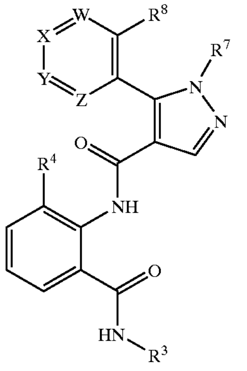

| W | X | Y | Z | $R^3$ | $R^4$ | $R^7$ | $R^8$ |
|---|---|---|---|---|---|---|---|
| CH | CH | CH | N | t-Bu | Cl | $CF_3$ | $CF_3$ |
| CH | CH | CH | N | Et | Cl | $CF_3$ | OMe |
| CH | CH | CH | N | i-Pr | Cl | $CF_3$ | OMe |
| CH | CH | CH | N | t-Bu | Cl | $CF_3$ | OMe |
| CH | CH | CH | N | Et | Cl | $CF_3$ | CN |
| CH | CH | CH | N | i-Pr | Cl | $CF_3$ | CN |
| CH | CH | CH | N | t-Bu | Cl | $CF_3$ | CN |
| CH | CH | N | CH | Et | Me | $CF_3$ | Cl |
| CH | CH | N | CH | i-Pr | Me | $CF_3$ | Cl |
| CH | CH | N | CH | t-Bu | Me | $CF_3$ | Cl |
| CH | CH | N | CH | Et | Me | $CF_3$ | Br |
| CH | CH | N | CH | i-Pr | Me | $CF_3$ | Br |
| CH | CH | N | CH | t-Bu | Me | $CF_3$ | Br |
| CH | CH | N | CH | Et | Me | $CF_3$ | I |
| CH | CH | N | CH | i-Pr | Me | $CF_3$ | I |
| CH | CH | N | CH | t-Bu | Me | $CF_3$ | I |
| CH | CH | N | CH | Et | Me | $CF_3$ | F |
| CH | CH | N | CH | i-Pr | Me | $CF_3$ | F |
| CH | CH | N | CH | t-Bu | Me | $CF_3$ | F |
| CH | CH | N | CH | Et | Me | $CF_3$ | Me |
| CH | CH | N | CH | i-Pr | Me | $CF_3$ | Me |
| CH | CH | N | CH | t-Bu | Me | $CF_3$ | Me |
| CH | CH | N | CH | Et | Me | $CF_3$ | $CF_3$ |
| CH | CH | N | CH | i-Pr | Me | $CF_3$ | $CF_3$ |
| CH | CH | N | CH | t-Bu | Me | $CF_3$ | $CF_3$ |
| CH | CH | N | CH | Et | Me | $CF_3$ | OMe |
| CH | CH | N | CH | i-Pr | Me | $CF_3$ | OMe |
| CH | CH | N | CH | t-Bu | Me | $CF_3$ | OMe |
| CH | CH | N | CH | Et | Me | $CF_3$ | CN |
| CH | CH | N | CH | i-Pr | Me | $CF_3$ | CN |
| CH | CH | N | CH | t-Bu | Me | $CF_3$ | CN |
| CH | CH | N | CH | Et | Cl | $CF_3$ | Cl |
| CH | CH | N | CH | i-Pr | Cl | $CF_3$ | Cl |
| CH | CH | N | CH | t-Bu | Cl | $CF_3$ | Cl |
| CH | CH | N | CH | Et | Cl | $CF_3$ | Br |
| CH | CH | N | CH | i-Pr | Cl | $CF_3$ | Br |
| CH | CH | N | CH | t-Bu | Cl | $CF_3$ | Br |
| CH | CH | N | CH | Et | Cl | $CF_3$ | I |
| CH | CH | N | CH | i-Pr | Cl | $CF_3$ | I |
| CH | CH | N | CH | t-Bu | Cl | $CF_3$ | I |
| CH | CH | N | CH | Et | Cl | $CF_3$ | F |
| CH | CH | N | CH | i-Pr | Cl | $CF_3$ | F |
| CH | CH | N | CH | t-Bu | Cl | $CF_3$ | F |
| CH | CH | N | CH | Et | Cl | $CF_3$ | Me |
| CH | CH | N | CH | i-Pr | Cl | $CF_3$ | Me |
| CH | CH | N | CH | t-Bu | Cl | $CF_3$ | Me |
| CH | CH | N | CH | Et | Cl | $CF_3$ | $CF_3$ |
| CH | CH | N | CH | i-Pr | Cl | $CF_3$ | $CF_3$ |
| CH | CH | N | CH | t-Bu | Cl | $CF_3$ | $CF_3$ |
| CH | CH | N | CH | Et | Cl | $CF_3$ | OMe |
| CH | CH | N | CH | i-Pr | Cl | $CF_3$ | OMe |
| CH | CH | N | CH | t-Bu | Cl | $CF_3$ | OMe |
| CH | CH | N | CH | Et | Cl | $CF_3$ | CN |
| CH | CH | N | CH | i-Pr | Cl | $CF_3$ | CN |
| CH | CH | N | CH | t-Bu | Cl | $CF_3$ | CN |
| CH | N | CH | CH | Et | Me | $CF_3$ | Cl |
| CH | N | CH | CH | i-Pr | Me | $CF_3$ | Cl |
| CH | N | CH | CH | t-Bu | Me | $CF_3$ | Cl |

TABLE 16-continued

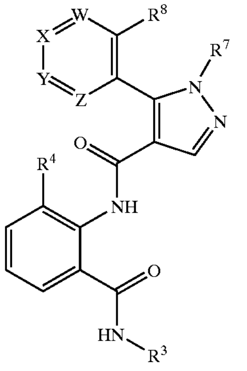

| W | X | Y | Z | $R^3$ | $R^4$ | $R^7$ | $R^8$ |
|---|---|---|---|---|---|---|---|
| CH | N | CH | CH | Et | Me | $CF_3$ | Br |
| CH | N | CH | CH | i-Pr | Me | $CF_3$ | Br |
| CH | N | CH | CH | t-Bu | Me | $CF_3$ | Br |
| CH | N | CH | CH | Et | Me | $CF_3$ | I |
| CH | N | CH | CH | i-Pr | Me | $CF_3$ | I |
| CH | N | CH | CH | t-Bu | Me | $CF_3$ | I |
| CH | N | CH | CH | Et | Me | $CF_3$ | F |
| CH | N | CH | CH | i-Pr | Me | $CF_3$ | F |
| CH | N | CH | CH | t-Bu | Me | $CF_3$ | F |
| CH | N | CH | CH | Et | Me | $CF_3$ | Me |
| CH | N | CH | CH | i-Pr | Me | $CF_3$ | Me |
| CH | N | CH | CH | t-Bu | Me | $CF_3$ | Me |
| CH | N | CH | CH | Et | Me | $CF_3$ | $CF_3$ |
| CH | N | CH | CH | i-Pr | Me | $CF_3$ | $CF_3$ |
| CH | N | CH | CH | t-Bu | Me | $CF_3$ | $CF_3$ |
| CH | N | CH | CH | Et | Me | $CF_3$ | OMe |
| CH | N | CH | CH | i-Pr | Me | $CF_3$ | OMe |
| CH | N | CH | CH | t-Bu | Me | $CF_3$ | OMe |
| CH | N | CH | CH | Bt | Me | $CF_3$ | CN |
| CH | N | CH | CH | i-Pr | Me | $CF_3$ | CN |
| CH | N | CH | CH | t-Bu | Me | $CF_3$ | CN |
| CH | N | CH | CH | Et | Cl | $CF_3$ | Cl |
| CH | N | CH | CH | i-Pr | Cl | $CF_3$ | Cl |
| CH | N | CH | CH | t-Bu | Cl | $CF_3$ | Cl |
| CH | N | CH | CH | Et | Cl | $CF_3$ | Br |
| CH | N | CH | CH | i-Pr | Cl | $CF_3$ | Br |
| CH | N | CH | CH | t-Bu | Cl | $CF_3$ | Br |
| CH | N | CH | CH | Et | Cl | $CF_3$ | I |
| CH | N | CH | CH | i-Pr | Cl | $CF_3$ | I |
| CH | N | CH | CH | t-Bu | Cl | $CF_3$ | I |
| CH | N | CH | CH | Et | Cl | $CF_3$ | F |
| CH | N | CH | CH | i-Pr | Cl | $CF_3$ | F |
| CH | N | CH | CH | t-Bu | Cl | $CF_3$ | F |
| CH | N | CH | CH | Et | Cl | $CF_3$ | Me |
| CH | N | CH | CH | i-Pr | Cl | $CF_3$ | Me |
| CH | N | CH | CH | t-Bu | Cl | $CF_3$ | Me |
| CH | N | CH | CH | Et | Cl | $CF_3$ | $CF_3$ |
| CH | N | CH | CH | i-Pr | Cl | $CF_3$ | $CF_3$ |
| CH | N | CH | CH | t-Bu | Cl | $CF_3$ | $CF_3$ |
| CH | N | CH | CH | Et | Cl | $CF_3$ | OMe |
| CH | N | CH | CH | i-Pr | Cl | $CF_3$ | OMe |
| CH | N | CH | CH | t-Bu | Cl | $CF_3$ | OMe |
| CH | N | CH | CH | Et | Cl | $CF_3$ | CN |
| CH | N | CH | CH | i-Pr | Cl | $CF_3$ | CN |
| CH | N | CH | CH | t-Bu | Cl | $CF_3$ | CN |
| N | CH | CH | CH | Et | Me | $CF_3$ | Cl |
| N | CH | CH | CH | i-Pr | Me | $CF_3$ | Cl |
| N | CH | CH | CH | t-Bu | Me | $CF_3$ | Cl |
| N | CH | CH | CH | Et | Me | $CF_3$ | Br |
| N | CH | CH | CH | i-Pr | Me | $CF_3$ | Br |
| N | CH | CH | CH | t-Bu | Me | $CF_3$ | Br |
| N | CH | CH | CH | Et | Me | $CF_3$ | I |
| N | CH | CH | CH | i-Pr | Me | $CF_3$ | I |
| N | CH | CH | CH | t-Bu | Me | $CF_3$ | I |
| N | CH | CH | CH | Et | Me | $CF_3$ | F |
| N | CH | CH | CH | i-Pr | Me | $CF_3$ | F |
| N | CH | CH | CH | t-Bu | Me | $CF_3$ | F |
| N | CH | CH | CH | Et | Me | $CF_3$ | Me |

TABLE 16-continued

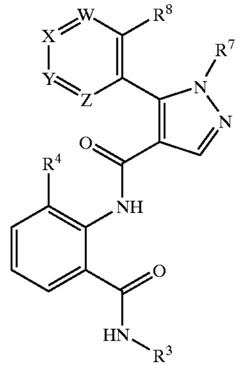

| W | X | Y | Z | $R^3$ | $R^4$ | $R^7$ | $R^8$ |
|---|---|---|---|---|---|---|---|
| N | CH | CH | CH | i-Pr | Me | $CF_3$ | Me |
| N | CH | CH | CH | t-Bu | Me | $CF_3$ | Me |
| N | CH | CH | CH | Et | Me | $CF_3$ | $CF_3$ |
| N | CH | CH | CH | i-Pr | Me | $CF_3$ | $CF_3$ |
| N | CH | CH | CH | t-Bu | Me | $CF_3$ | $CF_3$ |
| N | CH | CH | CH | Et | Me | $CF_3$ | OMe |
| N | CH | CH | CH | i-Pr | Me | $CF_3$ | OMe |
| N | CH | CH | CH | t-Bu | Me | $CF_3$ | OMe |
| N | CH | CH | CH | Et | Me | $CF_3$ | CN |
| N | CH | CH | CH | i-Pr | Me | $CF_3$ | CN |
| N | CH | CH | CH | t-Bu | Me | $CF_3$ | CN |
| N | CH | CH | CH | Et | Cl | $CF_3$ | Cl |
| N | CH | CH | CH | i-Pr | Cl | $CF_3$ | Cl |
| N | CH | CH | CH | t-Bu | Cl | $CF_3$ | Cl |
| N | CH | CH | CH | Et | Cl | $CF_3$ | Br |
| N | CH | CH | CH | i-Pr | Cl | $CF_3$ | Br |
| N | CH | CH | CH | t-Bu | Cl | $CF_3$ | Br |
| N | CH | CH | CH | Et | Cl | $CF_3$ | I |
| N | CH | CH | CH | i-Pr | Cl | $CF_3$ | I |
| N | CH | CH | CH | t-Bu | Cl | $CF_3$ | I |
| N | CH | CH | CH | Et | Cl | $CF_3$ | F |
| N | CH | CH | CH | i-Pr | Cl | $CF_3$ | F |
| N | CH | CH | CH | t-Bu | Cl | $CF_3$ | F |
| N | CH | CH | CH | Et | Cl | $CF_3$ | Me |
| N | CH | CH | CH | i-Pr | Cl | $CF_3$ | Me |
| N | CH | CH | CH | t-Bu | Cl | $CF_3$ | Me |
| N | CH | CH | CH | Et | Cl | $CF_3$ | $CF_3$ |
| N | CH | CH | CH | i-Pr | Cl | $CF_3$ | $CF_3$ |
| N | CH | CH | CH | t-Bu | Cl | $CF_3$ | $CF_3$ |
| N | CH | CH | CH | Et | Cl | $CF_3$ | OMe |
| N | CH | CH | CH | i-Pr | Cl | $CF_3$ | OMe |
| N | CH | CH | CH | t-Bu | Cl | $CF_3$ | OMe |
| N | CH | CH | CH | Et | Cl | $CF_3$ | CN |
| N | CH | CH | CH | i-Pr | Cl | $CF_3$ | CN |
| N | CH | CH | CH | t-Bu | Cl | $CF_3$ | CN |
| CH | N | CH | N | Et | Me | $CF_3$ | Cl |
| CH | N | CH | N | i-Pr | Me | $CF_3$ | Cl |
| CH | N | CH | N | t-Bu | Me | $CF_3$ | Cl |
| CH | N | CH | N | Et | Me | $CF_3$ | Br |
| CH | N | CH | N | i-Pr | Me | $CF_3$ | Br |
| CH | N | CH | N | t-Bu | Me | $CF_3$ | Br |
| CH | N | CH | N | Et | Me | $CF_3$ | I |
| CH | N | CH | N | i-Pr | Me | $CF_3$ | I |
| CH | N | CH | N | t-Bu | Me | $CF_3$ | I |
| CH | N | CH | N | Et | Me | $CF_3$ | F |
| CH | N | CH | N | i-Pr | Me | $CF_3$ | F |
| CH | N | CH | N | t-Bu | Me | $CF_3$ | F |
| CH | N | CH | N | Et | Me | $CF_3$ | Me |
| CH | N | CH | N | i-Pr | Me | $CF_3$ | Me |
| CH | N | CH | N | t-Bu | Me | $CF_3$ | Me |
| CH | N | CH | N | Et | Me | $CF_3$ | $CF_3$ |
| CH | N | CH | N | i-Pr | Me | $CF_3$ | $CF_3$ |
| CH | N | CH | N | t-Bu | Me | $CF_3$ | $CF_3$ |
| CH | N | CH | N | Et | Me | $CF_3$ | OMe |
| CH | N | CH | N | i-Pr | Me | $CF_3$ | OMe |
| CH | N | CH | N | t-Bu | Me | $CF_3$ | OMe |
| CH | N | CH | N | Et | Me | $CF_3$ | CN |
| CH | N | CH | N | i-Pr | Me | $CF_3$ | CN |

TABLE 16-continued

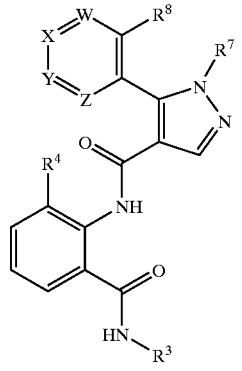

| W | X | Y | Z | $R^3$ | $R^4$ | $R^7$ | $R^8$ |
|---|---|---|---|---|---|---|---|
| CH | N | CH | N | t-Bu | Me | $CF_3$ | CN |
| CH | N | CH | N | Et | Cl | $CF_3$ | Cl |
| CH | N | CH | N | i-Pr | Cl | $CF_3$ | Cl |
| CH | N | CH | N | t-Bu | Cl | $CF_3$ | Cl |
| CH | N | CH | N | Et | Cl | $CF_3$ | Br |
| CH | N | CH | N | i-Pr | Cl | $CF_3$ | Br |
| CH | N | CH | N | t-Bu | Cl | $CF_3$ | Br |
| CH | N | CH | N | Et | Cl | $CF_3$ | I |
| CH | N | CH | N | i-Pr | Cl | $CF_3$ | I |
| CH | N | CH | N | t-Bu | Cl | $CF_3$ | I |
| CH | N | CH | N | Et | Cl | $CF_3$ | F |
| CH | N | CH | N | i-Pr | Cl | $CF_3$ | F |
| CH | N | CH | N | t-Bu | Cl | $CF_3$ | F |
| CH | N | CH | N | Et | Cl | $CF_3$ | Me |
| CH | N | CH | N | i-Pr | Cl | $CF_3$ | Me |
| CH | N | CH | N | t-Bu | Cl | $CF_3$ | Me |
| CH | N | CH | N | Et | Cl | $CF_3$ | $CF_3$ |
| CH | N | CH | N | i-Pr | Cl | $CF_3$ | $CF_3$ |
| CH | N | CH | N | t-Bu | Cl | $CF_3$ | $CF_3$ |
| CH | N | CH | N | Et | Cl | $CF_3$ | OMe |
| CH | N | CH | N | i-Pr | Cl | $CF_3$ | OMe |
| CH | N | CH | N | t-Bu | Cl | $CF_3$ | OMe |
| CH | N | CH | N | Et | Cl | $CF_3$ | CN |
| CH | N | CH | N | i-Pr | Cl | $CF_3$ | CN |
| CH | N | CH | N | t-Bu | Cl | $CF_3$ | CN |
| CH | CH | CH | CCl | Et | Me | $CF_3$ | Cl |
| CH | CH | CH | CCl | i-Pr | Me | $CF_3$ | Cl |
| CH | CH | CH | CCl | t-Bu | Me | $CF_3$ | Cl |
| CH | CH | CH | CCl | Et | Me | $CF_3$ | Br |
| CH | CH | CH | CCl | i-Pr | Me | $CF_3$ | Br |
| CH | CH | CH | CCl | t-Bu | Me | $CF_3$ | Br |
| CH | CH | CH | CCl | Et | Me | $CF_3$ | I |
| CH | CH | CH | CCl | i-Pr | Me | $CF_3$ | I |
| CH | CH | CH | CCl | t-Bu | Me | $CF_3$ | I |
| CH | CH | CH | CCl | Et | Me | $CF_3$ | F |
| CH | CH | CH | CCl | i-Pr | Me | $CF_3$ | F |
| CH | CH | CH | CCl | t-Bu | Me | $CF_3$ | F |
| CH | CH | CH | CCl | Et | Me | $CF_3$ | Me |
| CH | CH | CH | CCl | i-Pr | Me | $CF_3$ | Me |
| CH | CH | CH | CCl | t-Bu | Me | $CF_3$ | Me |
| CH | CH | CH | CCl | Et | Me | $CF_3$ | $CF_3$ |
| CH | CH | CH | CCl | i-Pr | Me | $CF_3$ | $CF_3$ |
| CH | CH | CH | CCl | t-Bu | Me | $CF_3$ | $CF_3$ |
| CH | CH | CH | CCl | Et | Me | $CF_3$ | OMe |
| CH | CH | CH | CCl | i-Pr | Me | $CF_3$ | OMe |
| CH | CH | CH | CCl | t-Bu | Me | $CF_3$ | OMe |
| CH | CH | CH | CCl | Et | Me | $CF_3$ | CN |
| CH | CH | CH | CCl | i-Pr | Me | $CF_3$ | CN |
| CH | CH | CH | CCl | t-Bu | Me | $CF_3$ | CN |
| CH | CH | CH | CCl | Et | Cl | $CF_3$ | Cl |
| CH | CH | CH | CCl | i-Pr | Cl | $CF_3$ | Cl |
| CH | CH | CH | CCl | t-Bu | Cl | $CF_3$ | Cl |
| CH | CH | CH | CCl | Et | Cl | $CF_3$ | Br |
| CH | CH | CH | CCl | i-Pr | Cl | $CF_3$ | Br |
| CH | CH | CH | CCl | t-Bu | Cl | $CF_3$ | Br |
| CH | CH | CH | CCl | Et | Cl | $CF_3$ | I |
| CH | CH | CH | CCl | i-Pr | Cl | $CF_3$ | I |
| CH | CH | CH | CCl | t-Bu | Cl | $CF_3$ | I |

TABLE 16-continued

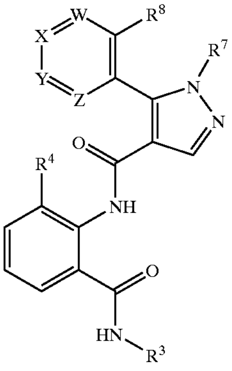

| W | X | Y | Z | $R^3$ | $R^4$ | $R^7$ | $R^8$ |
|---|---|---|---|---|---|---|---|
| CH | CH | CH | CCl | Et | Cl | $CF_3$ | F |
| CH | CH | CH | CCl | i-Pr | Cl | $CF_3$ | F |
| CH | CH | CH | CCl | t-Bu | Cl | $CF_3$ | F |
| CH | CH | CH | CCl | Et | Cl | $CF_3$ | Me |
| CH | CH | CH | CCl | i-Pr | Cl | $CF_3$ | Me |
| CH | CH | CH | CCl | t-Bu | Cl | $CF_3$ | Me |
| CH | CH | CH | CCl | Et | Cl | $CF_3$ | $CF_3$ |
| CH | CH | CH | CCl | i-Pr | Cl | $CF_3$ | $CF_3$ |
| CH | CH | CH | CCl | t-Bu | Cl | $CF_3$ | $CF_3$ |
| CH | CH | CH | CCl | Et | Cl | $CF_3$ | OMe |
| CH | CH | CH | CCl | i-Pr | Cl | $CF_3$ | OMe |
| CH | CH | CH | CCl | t-Bu | Cl | $CF_3$ | OMe |
| CH | CH | CH | CCl | Et | Cl | $CF_3$ | CN |
| CH | CH | CH | CCl | i-Pr | Cl | $CF_3$ | CN |
| CH | CH | CH | CCl | t-Bu | Cl | $CF_3$ | CN |
| CH | CH | CH | CF | Et | Me | $CF_3$ | Cl |
| CH | CH | CH | CF | i-Pr | Me | $CF_3$ | Cl |
| CH | CH | CH | CF | t-Bu | Me | $CF_3$ | Cl |
| CH | CH | CH | CF | Et | Me | $CF_3$ | Br |
| CH | CH | CH | CF | i-Pr | Me | $CF_3$ | Br |
| CH | CH | CH | CF | t-Bu | Me | $CF_3$ | Br |
| CH | CH | CH | CF | Et | Me | $CF_3$ | I |
| CH | CH | CH | CF | i-Pr | Me | $CF_3$ | I |
| CH | CH | CH | CF | t-Bu | Me | $CF_3$ | I |
| CH | CH | CH | CF | Et | Me | $CF_3$ | F |
| CH | CH | CH | CF | i-Pr | Me | $CF_3$ | F |
| CH | CH | CH | CF | t-Bu | Me | $CF_3$ | F |
| CH | CH | CH | CF | Et | Me | $CF_3$ | Me |
| CH | CH | CH | CF | i-Pr | Me | $CF_3$ | Me |
| CH | CH | CH | CF | t-Bu | Me | $CF_3$ | Me |
| CH | CH | CH | CF | Et | Me | $CF_3$ | $CF_3$ |
| CH | CH | CH | CF | i-Pr | Me | $CF_3$ | $CF_3$ |
| CH | CH | CH | CF | t-Bu | Me | $CF_3$ | $CF_3$ |
| CH | CH | CH | CF | Et | Me | $CF_3$ | OMe |
| CH | CH | CH | CF | i-Pr | Me | $CF_3$ | OMe |
| CH | CH | CH | CF | t-Bu | Me | $CF_3$ | OMe |
| CH | CH | CH | CF | Et | Me | $CF_3$ | CN |
| CH | CH | CH | CF | i-Pr | Me | $CF_3$ | CN |
| CH | CH | CH | CF | t-Bu | Me | $CF_3$ | CN |
| CH | CH | CH | CF | Et | Cl | $CF_3$ | Cl |
| CH | CH | CH | CF | i-Pr | Cl | $CF_3$ | Cl |
| CH | CH | CH | CF | t-Bu | Cl | $CF_3$ | Cl |
| CH | CH | CH | CF | Et | Cl | $CF_3$ | Br |
| CH | CH | CH | CF | i-Pr | Cl | $CF_3$ | Br |
| CH | CH | CH | CF | t-Bu | Cl | $CF_3$ | Br |
| CH | CH | CH | CF | Et | Cl | $CF_3$ | I |
| CH | CH | CH | CF | i-Pr | Cl | $CF_3$ | I |
| CH | CH | CH | CF | t-Bu | Cl | $CF_3$ | I |
| CH | CH | CH | CF | i-Pr | Cl | $CF_3$ | F |
| CH | CH | CH | CF | t-Bu | Cl | $CF_3$ | F |
| CH | CH | CH | CF | Et | Cl | $CF_3$ | Me |
| CH | CH | CH | CF | i-Pr | Cl | $CF_3$ | Me |
| CH | CH | CH | CF | t-Bu | Cl | $CF_3$ | Me |
| CH | CH | CH | CF | Et | Cl | $CF_3$ | $CF_3$ |
| CH | CH | CH | CF | i-Pr | Cl | $CF_3$ | $CF_3$ |
| CH | CH | CH | CF | t-Bu | Cl | $CF_3$ | $CF_3$ |
| CH | CH | CH | CF | Et | Cl | $CF_3$ | OMe |
| CH | CH | CH | CF | i-Pr | Cl | $CF_3$ | OMe |

TABLE 16-continued

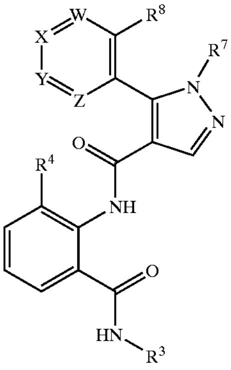

| W | X | Y | Z | $R^3$ | $R^4$ | $R^7$ | $R^8$ |
|---|---|---|---|---|---|---|---|
| CH | CH | CH | CF | t-Bu | Cl | $CF_3$ | OMe |
| CH | CH | CH | CF | Et | Cl | $CF_3$ | CN |
| CH | CH | CH | CF | i-Pr | Cl | $CF_3$ | CN |
| CH | CH | CH | CF | t-Bu | Cl | $CF_3$ | CN |
| CH | CH | CH | CH | Et | Me | $C_2F_5$ | Cl |
| CH | CH | CH | CH | i-Pr | Me | $C_2F_5$ | Cl |
| CH | CH | CH | CH | t-Bu | Me | $C_2F_5$ | Cl |
| CH | CH | CH | CH | Et | Me | $C_2F_5$ | Br |
| CH | CH | CH | CH | i-Pr | Me | $C_2F_5$ | Br |
| CH | CH | CH | CH | t-Bu | Me | $C_2F_5$ | Br |
| CH | CH | CH | CH | Et | Me | $C_2F_5$ | I |
| CH | CH | CH | CH | i-Pr | Me | $C_2F_5$ | I |
| CH | CH | CH | CH | t-Bu | Me | $C_2F_5$ | I |
| CH | CH | CH | CH | Et | Me | $C_2F_5$ | F |
| CH | CH | CH | CH | i-Pr | Me | $C_2F_5$ | F |
| CH | CH | CH | CH | t-Bu | Me | $C_2F_5$ | F |
| CH | CH | CH | CH | Et | Me | $C_2F_5$ | Me |
| CH | CH | CH | CH | i-Pr | Me | $C_2F_5$ | Me |
| CH | CH | CH | CH | t-Bu | Me | $C_2F_5$ | Me |
| CH | CH | CH | CH | Et | Me | $C_2F_5$ | $CF_3$ |
| CH | CH | CH | CH | i-Pr | Me | $C_2F_5$ | $CF_3$ |
| CH | CH | CH | CH | t-Bu | Me | $C_2F_5$ | $CF_3$ |
| CH | CH | CH | CH | Et | Me | $C_2F_5$ | OMe |
| CH | CH | CH | CH | i-Pr | Me | $C_2F_5$ | OMe |
| CH | CH | CH | CH | t-Bu | Me | $C_2F_5$ | OMe |
| CH | CH | CH | CH | Et | Me | $C_2F_5$ | CN |
| CH | CH | CH | CH | i-Pr | Me | $C_2F_5$ | CN |
| CH | CH | CH | CH | t-Bu | Me | $C_2F_5$ | CN |
| CH | CH | CH | CH | Et | Cl | $C_2F_5$ | Cl |
| CH | CH | CH | CH | i-Pr | Cl | $C_2F_5$ | Cl |
| CH | CH | CH | CH | t-Bu | Cl | $C_2F_5$ | Cl |
| CH | CH | CH | CH | Et | Cl | $C_2F_5$ | Br |
| CH | CH | CH | CH | i-Pr | Cl | $C_2F_5$ | Br |
| CH | CH | CH | CH | t-Bu | Cl | $C_2F_5$ | Br |
| CH | CH | CH | CH | Et | Cl | $C_2F_5$ | I |
| CH | CH | CH | CH | i-Pr | Cl | $C_2F_5$ | I |
| CH | CH | CH | CH | t-Bu | Cl | $C_2F_5$ | I |
| CH | CH | CH | CH | Et | Cl | $C_2F_5$ | F |
| CH | CH | CH | CH | i-Pr | Cl | $C_2F_5$ | F |
| CH | CH | CH | CH | t-Bu | Cl | $C_2F_5$ | F |
| CH | CH | CH | CH | Et | Cl | $C_2F_5$ | Me |
| CH | CH | CH | CH | i-Pr | Cl | $C_2F_5$ | Me |
| CH | CH | CH | CH | t-Bu | Cl | $C_2F_5$ | Me |
| CH | CH | CH | CH | Et | Cl | $C_2F_5$ | $CF_3$ |
| CH | CH | CH | CH | i-Pr | Cl | $C_2F_5$ | $CF_3$ |
| CH | CH | CH | CH | t-Bu | Cl | $C_2F_5$ | $CF_3$ |
| CH | CH | CH | CH | Et | Cl | $C_2F_5$ | OMe |
| CH | CH | CH | CH | i-Pr | Cl | $C_2F_5$ | OMe |
| CH | CH | CH | CH | t-Bu | Cl | $C_2F_5$ | OMe |
| CH | CH | CH | CH | Et | Cl | $C_2F_5$ | CN |
| CH | CH | CH | CH | i-Pr | Cl | $C_2F_5$ | CN |
| CH | CH | CH | CH | t-Bu | Cl | $C_2F_5$ | CN |

TABLE 17

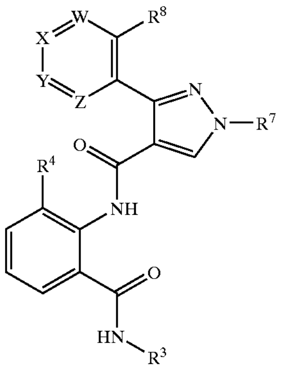

| W | X | Y | Z | $R^3$ | $R^4$ | $R^7$ | $R^8$ |
|---|---|---|---|---|---|---|---|
| CH | CH | CH | CH | Et | Me | $CF_3$ | Cl |
| CH | CH | CH | CH | i-Pr | Me | $CF_3$ | Cl |
| CH | CH | CH | CH | t-Bu | Me | $CF_3$ | Cl |
| CH | CH | CH | CH | Et | Me | $CF_3$ | Br |
| CH | CH | CH | CH | i-Pr | Me | $CF_3$ | Br |
| CH | CH | CH | CH | t-Bu | Me | $CF_3$ | Br |
| CH | CH | CH | CH | Et | Me | $CF_3$ | I |
| CH | CH | CH | CH | i-Pr | Me | $CF_3$ | I |
| CH | CH | CH | CH | t-Bu | Me | $CF_3$ | I |
| CH | CH | CH | CH | Et | Me | $CF_3$ | F |
| CH | CH | CH | CH | i-Pr | Me | $CF_3$ | F |
| CH | CH | CH | CH | t-Bu | Me | $CF_3$ | F |
| CH | CH | CH | CH | Et | Me | $CF_3$ | Me |
| CH | CH | CH | CH | i-Pr | Me | $CF_3$ | Me |
| CH | CH | CH | CH | t-Bu | Me | $CF_3$ | Me |
| CH | CH | CH | CH | Et | Me | $CF_3$ | $CF_3$ |
| CH | CH | CH | CH | i-Pr | Me | $CF_3$ | $CF_3$ |
| CH | CH | CH | CH | t-Bu | Me | $CF_3$ | $CF_3$ |
| CH | CH | CH | CH | Et | Me | $CF_3$ | OMe |
| CH | CH | CH | CH | i-Pr | Me | $CF_3$ | OMe |
| CH | CH | CH | CH | t-Bu | Me | $CF_3$ | OMe |
| CH | CH | CH | CH | Et | Me | $CF_3$ | CN |
| CH | CH | CH | CH | i-Pr | Me | $CF_3$ | CN |
| CH | CH | CH | CH | t-Bu | Me | $CF_3$ | CN |
| CH | CH | CH | CH | Et | Cl | $CF_3$ | Cl |
| CH | CH | CH | CH | i-Pr | Cl | $CF_3$ | Cl |
| CH | CH | CH | CH | t-Bu | Cl | $CF_3$ | Cl |
| CH | CH | CH | CH | Et | Cl | $CF_3$ | Br |
| CH | CH | CH | CH | i-Pr | Cl | $CF_3$ | Br |
| CH | CH | CH | CH | t-Bu | Cl | $CF_3$ | Br |
| CH | CH | CH | CH | Et | Cl | $CF_3$ | I |
| CH | CH | CH | CH | i-Pr | Cl | $CF_3$ | I |
| CH | CH | CH | CH | t-Bu | Cl | $CF_3$ | I |
| CH | CH | CH | CH | Et | Cl | $CF_3$ | F |
| CH | CH | CH | CH | i-Pr | Cl | $CF_3$ | F |
| CH | CH | CH | CH | t-Bu | Cl | $CF_3$ | F |
| CH | CH | CH | CH | Et | Cl | $CF_3$ | Me |
| CH | CH | CH | CH | i-Pr | Cl | $CF_3$ | Me |
| CH | CH | CH | CH | t-Bu | Cl | $CF_3$ | Me |
| CH | CH | CH | CH | Et | Cl | $CF_3$ | $CF_3$ |
| CH | CH | CH | CH | i-Pr | Cl | $CF_3$ | $CF_3$ |
| CH | CH | CH | CH | t-Bu | Cl | $CF_3$ | $CF_3$ |
| CH | CH | CH | CH | Et | Cl | $CF_3$ | OMe |
| CH | CH | CH | CH | i-Pr | Cl | $CF_3$ | OMe |
| CH | CH | CH | CH | t-Bu | Cl | $CF_3$ | OMe |
| CH | CH | CH | CH | Et | Cl | $CF_3$ | CN |
| CH | CH | CH | CH | i-Pr | Cl | $CF_3$ | CN |
| CH | CH | CH | CH | t-Bu | Cl | $CF_3$ | CN |
| CH | CH | CH | N | Et | Me | $CF_3$ | Cl |
| CH | CH | CH | N | i-Pr | Me | $CF_3$ | Cl |
| CH | CH | CH | N | t-Bu | Me | $CF_3$ | Cl |
| CH | CH | CH | N | Et | Me | $CF_3$ | Br |
| CH | CH | CH | N | i-Pr | Me | $CF_3$ | Br |
| CH | CH | CH | N | t-Bu | Me | $CF_3$ | Br |
| CH | CH | CH | N | Et | Me | $CF_3$ | I |
| CH | CH | CH | N | i-Pr | Me | $CF_3$ | I |
| CH | CH | CH | N | t-Bu | Me | $CF_3$ | I |
| CH | CH | CH | N | Et | Me | $CF_3$ | F |

TABLE 17-continued

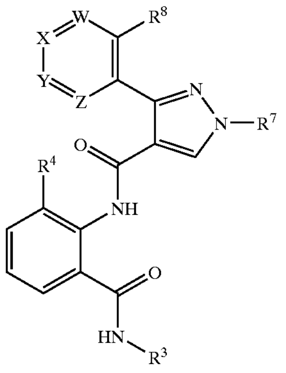

| W | X | Y | Z | $R^3$ | $R^4$ | $R^7$ | $R^8$ |
|---|---|---|---|---|---|---|---|
| CH | CH | CH | N | i-Pr | Me | $CF_3$ | F |
| CH | CH | CH | N | i-Bu | Me | $CF_3$ | F |
| CH | CH | CH | N | Et | Me | $CF_3$ | Me |
| CH | CH | CH | N | i-Pr | Me | $CF_3$ | Me |
| CH | CH | CH | N | t-Bu | Me | $CF_3$ | Me |
| CH | CH | CH | N | Et | Me | $CF_3$ | $CF_3$ |
| CH | CH | CH | N | i-Pr | Me | $CF_3$ | $CF_3$ |
| CH | CH | CH | N | t-Bu | Me | $CF_3$ | $CF_3$ |
| CH | CH | CH | N | Et | Me | $CF_3$ | OMe |
| CH | CH | CH | N | i-Pr | Me | $CF_3$ | OMe |
| CH | CH | CH | N | t-Bu | Me | $CF_3$ | OMe |
| CH | CH | CH | N | Et | Me | $CF_3$ | CN |
| CH | CH | CH | N | i-Pr | Me | $CF_3$ | CN |
| CH | CH | CH | N | t-Bu | Me | $CF_3$ | CN |
| CH | CH | CH | N | Et | Cl | $CF_3$ | Cl |
| CH | CH | CH | N | i-Pr | Cl | $CF_3$ | Cl |
| CH | CH | CH | N | t-Bu | Cl | $CF_3$ | Cl |
| CH | CH | CH | N | Et | Cl | $CF_3$ | Br |
| CH | CH | CH | N | i-Pr | Cl | $CF_3$ | Br |
| CH | CH | CH | N | i-Bu | Cl | $CF_3$ | Br |
| CH | CH | CH | N | Et | Cl | $CF_3$ | I |
| CH | CH | CH | N | i-Pr | Cl | $CF_3$ | I |
| CH | CH | CH | N | t-Bu | Cl | $CF_3$ | I |
| CH | CH | CH | N | Et | Cl | $CF_3$ | F |
| CH | CH | CH | N | i-Pr | Cl | $CF_3$ | F |
| CH | CH | CH | N | t-Bu | Cl | $CF_3$ | F |
| CH | CH | CH | N | Et | Cl | $CF_3$ | Me |
| CH | CH | CH | N | i-Pr | Cl | $CF_3$ | Me |
| CH | CH | CH | N | t-Bu | Cl | $CF_3$ | Me |
| CH | CH | CH | N | Et | Cl | $CF_3$ | $CF_3$ |
| CH | CH | CH | N | i-Pr | Cl | $CF_3$ | $CF_3$ |
| CH | CH | CH | N | i-Bu | Cl | $CF_3$ | $CF_3$ |
| CH | CH | CH | N | Et | Cl | $CF_3$ | OMe |
| CH | CH | CH | N | i-Pr | Cl | $CF_3$ | OMe |
| CH | CH | CH | N | t-Bu | Cl | $CF_3$ | OMe |
| CH | CH | CH | N | Et | Cl | $CF_3$ | CN |
| CH | CH | CH | N | i-Pr | Cl | $CF_3$ | CN |
| CH | CH | CH | N | t-Bu | Cl | $CF_3$ | CN |
| CH | CH | N | CH | Et | Me | $CF_3$ | Cl |
| CH | CH | N | CH | i-Pr | Me | $CF_3$ | Cl |
| CH | CH | N | CH | t-Bu | Me | $CF_3$ | Cl |
| CH | CH | N | CH | Et | Me | $CF_3$ | Br |
| CH | CH | N | CH | i-Pr | Me | $CF_3$ | Br |
| CH | CH | N | CH | t-Bu | Me | $CF_3$ | Br |
| CH | CH | N | CH | Et | Me | $CF_3$ | I |
| CH | CH | N | CH | i-Pr | Me | $CF_3$ | I |
| CH | CH | N | CH | t-Bu | Me | $CF_3$ | I |
| CH | CH | N | CH | Et | Me | $CF_3$ | F |
| CH | CH | N | CH | i-Pr | Me | $CF_3$ | F |
| CH | CH | N | CH | t-Bu | Me | $CF_3$ | F |
| CH | CH | N | CH | Et | Me | $CF_3$ | Me |
| CH | CH | N | CH | i-Pr | Me | $CF_3$ | Me |
| CH | CH | N | CH | r-Bu | Me | $CF_3$ | Me |
| CH | CH | N | CH | Et | Me | $CF_3$ | $CF_3$ |
| CH | CH | N | CH | i-Pr | Me | $CF_3$ | $CF_3$ |
| CH | CH | N | CH | t-Bu | Me | $CF_3$ | $CF_3$ |
| CH | CH | N | CH | Et | Me | $CF_3$ | OMe |
| CH | CH | N | CH | i-Pr | Me | $CF_3$ | OMe |

TABLE 17-continued

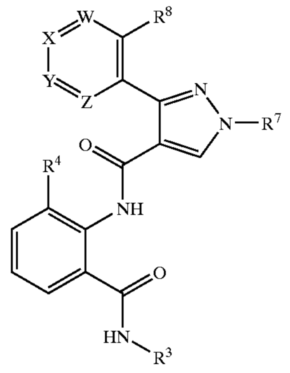

| W | X | Y | Z | $R^3$ | $R^4$ | $R^7$ | $R^8$ |
|---|---|---|---|---|---|---|---|
| CH | CH | N | CH | t-Bu | Me | $CF_3$ | OMe |
| CH | CH | N | CH | Et | Me | $CF_3$ | CN |
| CH | CH | N | CH | i-Pr | Me | $CF_3$ | CN |
| CH | CH | N | CH | t-Bu | Me | $CF_3$ | CN |
| CH | CH | N | CH | Et | Cl | $CF_3$ | Cl |
| CH | CH | N | CH | i-Pr | Cl | $CF_3$ | Cl |
| CH | CH | N | CH | t-Bu | Cl | $CF_3$ | Cl |
| CH | CH | N | CH | Et | Cl | $CF_3$ | Br |
| CH | CH | N | CH | i-Pr | Cl | $CF_3$ | Br |
| CH | CH | N | CH | t-Bu | Cl | $CF_3$ | Br |
| CH | CH | N | CH | Et | Cl | $CF_3$ | I |
| CH | CH | N | CH | i-Pr | Cl | $CF_3$ | I |
| CH | CH | N | CH | t-Bu | Cl | $CF_3$ | I |
| CH | CH | N | CH | Et | Cl | $CF_3$ | F |
| CH | CH | N | CH | i-Pr | Cl | $CF_3$ | F |
| CH | CH | N | CH | t-Bu | Cl | $CF_3$ | F |
| CH | CH | N | CH | Et | Cl | $CF_3$ | Me |
| CH | CH | N | CH | i-Pr | Cl | $CF_3$ | Me |
| CH | CH | N | CH | t-Bu | Cl | $CF_3$ | Me |
| CH | CH | N | CH | Et | Cl | $CF_3$ | $CF_3$ |
| CH | CH | N | CH | i-Pr | Cl | $CF_3$ | $CF_3$ |
| CH | CH | N | CH | t-Bu | Cl | $CF_3$ | $CF_3$ |
| CH | CH | N | CH | Et | Cl | $CF_3$ | OMe |
| CH | CH | N | CH | i-Pr | Cl | $CF_3$ | OMe |
| CH | CH | N | CH | t-Bu | Cl | $CF_3$ | OMe |
| CH | CH | N | CH | Et | Cl | $CF_3$ | CN |
| CH | CH | N | CH | i-Pr | Cl | $CF_3$ | CN |
| CH | CH | N | CH | t-Bu | Cl | $CF_3$ | CN |
| CH | N | CH | CH | Et | Me | $CF_3$ | Cl |
| CH | N | CH | CH | i-Pr | Me | $CF_3$ | Cl |
| CH | N | CH | CH | t-Bu | Me | $CF_3$ | Cl |
| CH | N | CH | CH | Et | Me | $CF_3$ | Br |
| CH | N | CH | CH | i-Pr | Me | $CF_3$ | Br |
| CH | N | CH | CH | t-Bu | Me | $CF_3$ | Br |
| CH | N | CH | CH | Et | Me | $CF_3$ | I |
| CH | N | CH | CH | i-Pr | Me | $CF_3$ | I |
| CH | N | CH | CH | t-Bu | Me | $CF_3$ | I |
| CH | N | CH | CH | Et | Me | $CF_3$ | F |
| CH | N | CH | CH | i-Pr | Me | $CF_3$ | F |
| CH | N | CH | CH | t-Bu | Me | $CF_3$ | F |
| CH | N | CH | CH | Et | Me | $CF_3$ | Me |
| CH | N | CH | CH | i-Pr | Me | $CF_3$ | Me |
| CH | N | CH | CH | t-Bu | Me | $CF_3$ | Me |
| CH | N | CH | CH | Et | Me | $CF_3$ | $CF_3$ |
| CH | N | CH | CH | i-Pr | Me | $CF_3$ | $CF_3$ |
| CH | N | CH | CH | t-Bu | Me | $CF_3$ | $CF_3$ |
| CH | N | CH | CH | Et | Me | $CF_3$ | OMe |
| CH | N | CH | CH | i-Pr | Me | $CF_3$ | OMe |
| CH | N | CH | CH | t-Bu | Me | $CF_3$ | OMe |
| CH | N | CH | CH | Et | Me | $CF_3$ | CN |
| CH | N | CH | CH | i-Pr | Me | $CF_3$ | CN |
| CH | N | CH | CH | t-Bu | Me | $CF_3$ | CN |
| CH | N | CH | CH | Et | Cl | $CF_3$ | Cl |
| CH | N | CH | CH | i-Pr | Cl | $CF_3$ | Cl |
| CH | N | CH | CH | t-Bu | Cl | $CF_3$ | Cl |
| CH | N | CH | CH | Et | Cl | $CF_3$ | Br |
| CH | N | CH | CH | i-Pr | Cl | $CF_3$ | Br |
| CH | N | CH | CH | t-Bu | Cl | $CF_3$ | Br |

TABLE 17-continued

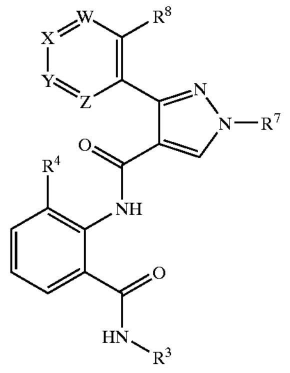

| W | X | Y | Z | $R^3$ | $R^4$ | $R^7$ | $R^8$ |
|---|---|---|---|---|---|---|---|
| CH | N | CH | CH | Et | Cl | $CF_3$ | I |
| CH | N | CH | CH | i-Pr | Cl | $CF_3$ | I |
| CH | N | CH | CH | t-Bu | Cl | $CF_3$ | I |
| CH | N | CH | CH | Et | Cl | $CF_3$ | F |
| CH | N | CH | CH | i-Pr | Cl | $CF_3$ | F |
| CH | N | CH | CH | t-Bu | Cl | $CF_3$ | F |
| CH | N | CH | CH | Et | Cl | $CF_3$ | Me |
| CH | N | CH | CH | i-Pr | Cl | $CF_3$ | Me |
| CH | N | CH | CH | t-Bu | Cl | $CF_3$ | Me |
| CH | N | CH | CH | Et | Cl | $CF_3$ | $CF_3$ |
| CH | N | CH | CH | i-Pr | Cl | $CF_3$ | $CF_3$ |
| CH | N | CH | CH | t-Bu | Cl | $CF_3$ | $CF_3$ |
| CH | N | CH | CH | Et | Cl | $CF_3$ | OMe |
| CH | N | CH | CH | i-Pr | Cl | $CF_3$ | OMe |
| CH | N | CH | CH | t-Bu | Cl | $CF_3$ | OMe |
| CH | N | CH | CH | Et | Cl | $CF_3$ | CN |
| CH | N | CH | CH | i-Pr | Cl | $CF_3$ | CN |
| CH | N | CH | CH | t-Bu | Cl | $CF_3$ | CN |
| N | CH | CH | CH | Et | Me | $CF_3$ | Cl |
| N | CH | CH | CH | i-Pr | Me | $CF_3$ | Cl |
| N | CH | CH | CH | t-Bu | Me | $CF_3$ | Cl |
| N | CH | CH | CH | Et | Me | $CF_3$ | Br |
| N | CH | CH | CH | i-Pr | Me | $CF_3$ | Br |
| N | CH | CH | CH | t-Bu | Me | $CF_3$ | Br |
| N | CH | CH | CH | Et | Me | $CF_3$ | I |
| N | CH | CH | CH | i-Pr | Me | $CF_3$ | I |
| N | CH | CH | CH | t-Bu | Me | $CF_3$ | I |
| N | CH | CH | CH | Et | Me | $CF_3$ | F |
| N | CH | CH | CH | i-Pr | Me | $CF_3$ | F |
| N | CH | CH | CH | t-Bu | Me | $CF_3$ | F |
| N | CH | CH | CH | Et | Me | $CF_3$ | Me |
| N | CH | CH | CH | i-Pr | Me | $CF_3$ | Me |
| N | CH | CH | CH | t-Bu | Me | $CF_3$ | Me |
| N | CH | CH | CH | Et | Me | $CF_3$ | $CF_3$ |
| N | CH | CH | CH | i-Pr | Me | $CF_3$ | $CF_3$ |
| N | CH | CH | CH | t-Bu | Me | $CF_3$ | $CF_3$ |
| N | CH | CH | CH | Et | Me | $CF_3$ | OMe |
| N | CH | CH | CH | i-Pr | Me | $CF_3$ | OMe |
| N | CH | CH | CH | t-Bu | Me | $CF_3$ | OMe |
| N | CH | CH | CH | Et | Me | $CF_3$ | CN |
| N | CH | CH | CH | i-Pr | Me | $CF_3$ | CN |
| N | CH | CH | CH | t-Bu | Me | $CF_3$ | CN |
| N | CH | CH | CH | Et | Cl | $CF_3$ | Cl |
| N | CH | CH | CH | i-Pr | Cl | $CF_3$ | Cl |
| N | CH | CH | CH | t-Bu | Cl | $CF_3$ | Cl |
| N | CH | CH | CH | Et | Cl | $CF_3$ | Br |
| N | CH | CH | CH | i-Pr | Cl | $CF_3$ | Br |
| N | CH | CH | CH | t-Bu | Cl | $CF_3$ | Br |
| N | CH | CH | CH | Et | Cl | $CF_3$ | I |
| N | CH | CH | CH | i-Pr | Cl | $CF_3$ | I |
| N | CH | CH | CH | t-Bu | Cl | $CF_3$ | I |
| N | CH | CH | CH | Et | Cl | $CF_3$ | F |
| N | CH | CH | CH | i-Pr | Cl | $CF_3$ | F |
| N | CH | CH | CH | t-Bu | Cl | $CF_3$ | F |
| N | CH | CH | CH | Et | Cl | $CF_3$ | Me |
| N | CH | CH | CH | i-Pr | Cl | $CF_3$ | Me |
| N | CH | CH | CH | t-Bu | Cl | $CF_3$ | Me |
| N | CH | CH | CH | Et | Cl | $CF_3$ | $CF_3$ |

TABLE 17-continued

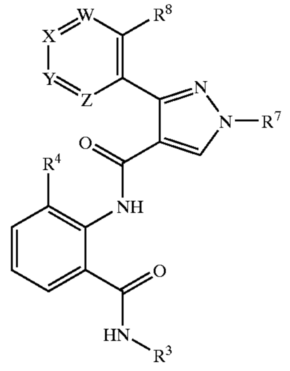

| W | X | Y | Z | $R^3$ | $R^4$ | $R^7$ | $R^8$ |
|---|---|---|---|---|---|---|---|
| N | CH | CH | CH | i-Pr | Cl | $CF_3$ | $CF_3$ |
| N | CH | CH | CH | t-Bu | Cl | $CF_3$ | $CF_3$ |
| N | CH | CH | CH | Et | Cl | $CF_3$ | OMe |
| N | CH | CH | CH | i-Pr | Cl | $CF_3$ | OMe |
| N | CH | CH | CH | t-Bu | Cl | $CF_3$ | OMe |
| N | CH | CH | CH | Et | Cl | $CF_3$ | CN |
| N | CH | CH | CH | i-Pr | Cl | $CF_3$ | CN |
| N | CH | CH | CH | t-Bu | Cl | $CF_3$ | CN |
| CH | N | CH | N | Et | Me | $CF_3$ | Cl |
| CH | N | CH | N | i-Pr | Me | $CF_3$ | Cl |
| CH | N | CH | N | t-Bu | Me | $CF_3$ | Cl |
| CH | N | CH | N | Et | Me | $CF_3$ | Br |
| CH | N | CH | N | i-Pr | Me | $CF_3$ | Br |
| CH | N | CH | N | t-Bu | Me | $CF_3$ | Br |
| CH | N | CH | N | Et | Me | $CF_3$ | I |
| CH | N | CH | N | i-Pr | Me | $CF_3$ | I |
| CH | N | CH | N | t-Bu | Me | $CF_3$ | I |
| CH | N | CH | N | Et | Me | $CF_3$ | F |
| CH | N | CH | N | i-Pr | Me | $CF_3$ | F |
| CH | N | CH | N | t-Bu | Me | $CF_3$ | F |
| CH | N | CH | N | Et | Me | $CF_3$ | Me |
| CH | N | CH | N | i-Pr | Me | $CF_3$ | Me |
| CH | N | CH | N | t-Bu | Me | $CF_3$ | Me |
| CH | N | CH | N | Et | Me | $CF_3$ | $CF_3$ |
| CH | N | CH | N | i-Pr | Me | $CF_3$ | $CF_3$ |
| CH | N | CH | N | t-Bu | Me | $CF_3$ | $CF_3$ |
| CH | N | CH | N | Et | Me | $CF_3$ | OMe |
| CH | N | CH | N | i-Pr | Me | $CF_3$ | OMe |
| CH | N | CH | N | t-Bu | Me | $CF_3$ | OMe |
| CH | N | CH | N | Et | Me | $CF_3$ | CN |
| CH | N | CH | N | i-Pr | Me | $CF_3$ | CN |
| CH | N | CH | N | t-Bu | Me | $CF_3$ | CN |
| CH | N | CH | N | Et | Cl | $CF_3$ | Cl |
| CH | N | CH | N | i-Pr | Cl | $CF_3$ | Cl |
| CH | N | CH | N | t-Bu | Cl | $CF_3$ | Cl |
| CH | N | CH | N | Et | Cl | $CF_3$ | Br |
| CH | N | CH | N | i-Pr | Cl | $CF_3$ | Br |
| CH | N | CH | N | t-Bu | Cl | $CF_3$ | Br |
| CH | N | CH | N | Et | Cl | $CF_3$ | I |
| CH | N | CH | N | i-Pr | Cl | $CF_3$ | I |
| CH | N | CH | N | t-Bu | Cl | $CF_3$ | I |
| CH | N | CH | N | Et | Cl | $CF_3$ | F |
| CH | N | CH | N | i-Pr | Cl | $CF_3$ | F |
| CH | N | CH | N | t-Bu | Cl | $CF_3$ | F |
| CH | N | CH | N | Et | Cl | $CF_3$ | Me |
| CH | N | CH | N | i-Pr | Cl | $CF_3$ | Me |
| CH | N | CH | N | t-Bu | Cl | $CF_3$ | Me |
| CH | N | CH | N | Et | Cl | $CF_3$ | $CF_3$ |
| CH | N | CH | N | i-Pr | Cl | $CF_3$ | $CF_3$ |
| CH | N | CH | N | t-Bu | Cl | $CF_3$ | $CF_3$ |
| CH | N | CH | N | Et | Cl | $CF_3$ | OMe |
| CH | N | CH | N | i-Pr | Cl | $CF_3$ | OMe |
| CH | N | CH | N | t-Bu | Cl | $CF_3$ | OMe |
| CH | N | CH | N | Et | Cl | $CF_3$ | CN |
| CH | N | CH | N | i-Pr | Cl | $CF_3$ | CN |
| CH | N | CH | N | t-Bu | Cl | $CF_3$ | CN |
| CH | CH | CH | CCl | Et | Me | $CF_3$ | Cl |
| CH | CH | CH | CCl | i-Pr | Me | $CF_3$ | Cl |

TABLE 17-continued

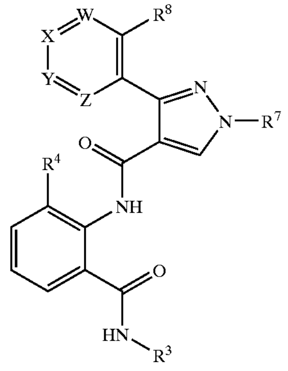

| W | X | Y | Z | $R^3$ | $R^4$ | $R^7$ | $R^8$ |
|---|---|---|---|---|---|---|---|
| CH | CH | CH | CCl | t-Bu | Me | $CF_3$ | Cl |
| CH | CH | CH | CCl | Et | Me | $CF_3$ | Br |
| CH | CH | CH | CCl | i-Pr | Me | $CF_3$ | Br |
| CH | CH | CH | CCl | t-Bu | Me | $CF_3$ | Br |
| CH | CH | CH | CCl | Et | Me | $CF_3$ | I |
| CH | CH | CH | CCl | i-Pr | Me | $CF_3$ | I |
| CH | CH | CH | CCl | t-Bu | Me | $CF_3$ | I |
| CH | CH | CH | CCl | Et | Me | $CF_3$ | F |
| CH | CH | CH | CCl | i-Pr | Me | $CF_3$ | F |
| CH | CH | CH | CCl | t-Bu | Me | $CF_3$ | F |
| CH | CH | CH | CCl | Et | Me | $CF_3$ | Me |
| CH | CH | CH | CCl | i-Pr | Me | $CF_3$ | Me |
| CH | CH | CH | CCl | t-Bu | Me | $CF_3$ | Me |
| CH | CH | CH | CCl | Et | Me | $CF_3$ | $CF_3$ |
| CH | CH | CH | CCl | i-Pr | Me | $CF_3$ | $CF_3$ |
| CH | CH | CH | CCl | t-Bu | Me | $CF_3$ | $CF_3$ |
| CH | CH | CH | CCl | Et | Me | $CF_3$ | OMe |
| CH | CH | CH | CCl | i-Pr | Me | $CF_3$ | OMe |
| CH | CH | CH | CCl | t-Bu | Me | $CF_3$ | OMe |
| CH | CH | CH | CCl | Et | Me | $CF_3$ | CN |
| CH | CH | CH | CCl | i-Pr | Me | $CF_3$ | CN |
| CH | CH | CH | CCl | t-Bu | Me | $CF_3$ | CN |
| CH | CH | CH | CCl | Et | Cl | $CF_3$ | Cl |
| CH | CH | CH | CCl | i-Pr | Cl | $CF_3$ | Cl |
| CH | CH | CH | CCl | t-Bu | Cl | $CF_3$ | Cl |
| CH | CH | CH | CCl | Et | Cl | $CF_3$ | Br |
| CH | CH | CH | CCl | i-Pr | Cl | $CF_3$ | Br |
| CH | CH | CH | CCl | t-Bu | Cl | $CF_3$ | Br |
| CH | CH | CH | CCl | Et | Cl | $CF_3$ | I |
| CH | CH | CH | CCl | i-Pr | Cl | $CF_3$ | I |
| CH | CH | CH | CCl | t-Bu | Cl | $CF_3$ | I |
| CH | CH | CH | CCl | Et | Cl | $CF_3$ | F |
| CH | CH | CH | CCl | i-Pr | Cl | $CF_3$ | F |
| CH | CH | CH | CCl | t-Bu | Cl | $CF_3$ | F |
| CH | CH | CH | CCl | Et | Cl | $CF_3$ | Me |
| CH | CH | CH | CCl | i-Pr | Cl | $CF_3$ | Me |
| CH | CH | CH | CCl | t-Bu | Cl | $CF_3$ | Me |
| CH | CH | CH | CCl | Et | Cl | $CF_3$ | $CF_3$ |
| CH | CH | CH | CCl | i-Pr | Cl | $CF_3$ | $CF_3$ |
| CH | CH | CH | CCl | t-Bu | Cl | $CF_3$ | $CF_3$ |
| CH | CH | CH | CCl | Et | Cl | $CF_3$ | OMe |
| CH | CH | CH | CCl | i-Pr | Cl | $CF_3$ | OMe |
| CH | CH | CH | CCl | t-Bu | Cl | $CF_3$ | OMe |
| CH | CH | CH | CCl | Et | Cl | $CF_3$ | CN |
| CH | CH | CH | CCl | i-Pr | Cl | $CF_3$ | CN |
| CH | CH | CH | CCl | t-Bu | Cl | $CF_3$ | CN |
| CH | CH | CH | CF | Et | Me | $CF_3$ | Cl |
| CH | CH | CH | CF | i-Pr | Me | $CF_3$ | Cl |
| CH | CH | CH | CF | t-Bu | Me | $CF_3$ | Cl |
| CH | CH | CH | CF | Et | Me | $CF_3$ | Br |
| CH | CH | CH | CF | i-Pr | Me | $CF_3$ | Br |
| CH | CH | CH | CF | t-Bu | Me | $CF_3$ | Br |
| CH | CH | CH | CF | Et | Me | $CF_3$ | I |
| CH | CH | CH | CF | i-Pr | Me | $CF_3$ | I |
| CH | CH | CH | CF | t-Bu | Me | $CF_3$ | I |
| CH | CH | CH | CF | Et | Me | $CF_3$ | F |
| CH | CH | CH | CF | i-Pr | Me | $CF_3$ | F |
| CH | CH | CH | CF | t-Bu | Me | $CF_3$ | F |

TABLE 17-continued

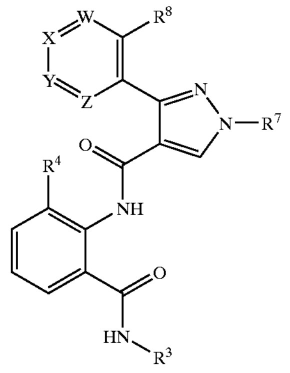

| W | X | Y | Z | $R^3$ | $R^4$ | $R^7$ | $R^8$ |
|---|---|---|---|---|---|---|---|
| CH | CH | CH | CF | Et | Me | $CF_3$ | Me |
| CH | CH | CH | CF | i-Pr | Me | $CF_3$ | Me |
| CH | CH | CH | CF | t-Bu | Me | $CF_3$ | Me |
| CH | CH | CH | CF | Et | Me | $CF_3$ | $CF_3$ |
| CH | CH | CH | CF | i-Pr | Me | $CF_3$ | $CF_3$ |
| CH | CH | CH | CF | t-Bu | Me | $CF_3$ | $CF_3$ |
| CH | CH | CH | CF | Et | Me | $CF_3$ | OMe |
| CH | CH | CH | CF | i-Pr | Me | $CF_3$ | OMe |
| CH | CH | CH | CF | t-Bu | Me | $CF_3$ | OMe |
| CH | CH | CH | CF | Et | Me | $CF_3$ | CN |
| CH | CH | CH | CF | i-Pr | Me | $CF_3$ | CN |
| CH | CH | CH | CF | t-Bu | Me | $CF_3$ | CN |
| CH | CH | CH | CF | Et | Cl | $CF_3$ | Cl |
| CH | CH | CH | CF | i-Pr | Cl | $CF_3$ | Cl |
| CH | CH | CH | CF | t-Bu | Cl | $CF_3$ | Cl |
| CH | CH | CH | CF | Et | Cl | $CF_3$ | Br |
| CH | CH | CH | CF | i-Pr | Cl | $CF_3$ | Br |
| CH | CH | CH | CF | t-Bu | Cl | $CF_3$ | Br |
| CH | CH | CH | CF | Et | Cl | $CF_3$ | I |
| CH | CH | CH | CF | i-Pr | Cl | $CF_3$ | I |
| CH | CH | CH | CF | t-Bu | Cl | $CF_3$ | I |
| CH | CH | CH | CF | i-Pr | Cl | $CF_3$ | F |
| CH | CH | CH | CF | t-Bu | Cl | $CF_3$ | F |
| CH | CH | CH | CF | Et | Cl | $CF_3$ | Me |
| CH | CH | CH | CF | i-Pr | Cl | $CF_3$ | Me |
| CH | CH | CH | CF | t-Bu | Cl | $CF_3$ | Me |
| CH | CH | CH | CF | Et | Cl | $CF_3$ | $CF_3$ |
| CH | CH | CH | CF | i-Pr | Cl | $CF_3$ | $CF_3$ |
| CH | CH | CH | CF | t-Bu | Cl | $CF_3$ | $CF_3$ |
| CH | CH | CH | CF | Et | Cl | $CF_3$ | OMe |
| CH | CH | CH | CF | i-Pr | Cl | $CF_3$ | OMe |
| CH | CH | CH | CF | t-Bu | Cl | $CF_3$ | OMe |
| CH | CH | CH | CF | Et | Cl | $CF_3$ | CN |
| CH | CH | CH | CF | i-Pr | Cl | $CF_3$ | CN |
| CH | CH | CH | CF | t-Bu | Cl | $CF_3$ | CN |
| CH | CH | CH | CH | Et | Me | $C_2F_5$ | Cl |
| CH | CH | CH | CH | i-Pr | Me | $C_2F_5$ | Cl |
| CH | CH | CH | CH | t-Bu | Me | $C_2F_5$ | Cl |
| CH | CH | CH | CH | Et | Me | $C_2F_5$ | Br |
| CH | CH | CH | CH | i-Pr | Me | $C_2F_5$ | Br |
| CH | CH | CH | CH | t-Bu | Me | $C_2F_5$ | Br |
| CH | CH | CH | CH | Et | Me | $C_2F_5$ | I |
| CH | CH | CH | CH | i-Pr | Me | $C_2F_5$ | I |
| CH | CH | CH | CH | t-Bu | Me | $C_2F_5$ | I |
| CH | CH | CH | CH | Et | Me | $C_2F_5$ | F |
| CH | CH | CH | CH | i-Pr | Me | $C_2F_5$ | F |
| CH | CH | CH | CH | t-Bu | Me | $C_2F_5$ | F |
| CH | CH | CH | CH | Et | Me | $C_2F_5$ | Me |
| CH | CH | CH | CH | i-Pr | Me | $C_2F_5$ | Me |
| CH | CH | CH | CH | t-Bu | Me | $C_2F_5$ | Me |
| CH | CH | CH | CH | Et | Me | $C_2F_5$ | $CF_3$ |
| CH | CH | CH | CH | i-Pr | Me | $C_2F_5$ | $CF_3$ |
| CH | CH | CH | CH | t-Bu | Me | $C_2F_5$ | $CF_3$ |
| CH | CH | CH | CH | Et | Me | $C_2F_5$ | OMe |
| CH | CH | CH | CH | i-Pr | Me | $C_2F_5$ | OMe |
| CH | CH | CH | CH | t-Bu | Me | $C_2F_5$ | OMe |
| CH | CH | CH | CH | Et | Me | $C_2F_5$ | CN |
| CH | CH | CH | CH | i-Pr | Me | $C_2F_5$ | CN |

TABLE 17-continued

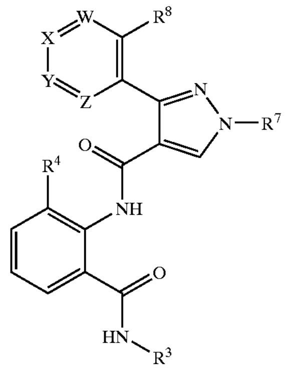

| W | X | Y | Z | $R^3$ | $R^4$ | $R^7$ | $R^8$ |
|---|---|---|---|---|---|---|---|
| CH | CH | CH | CH | t-Bu | Me | $C_2F_5$ | CN |
| CH | CH | CH | CH | Et | Cl | $C_2F_5$ | Cl |
| CH | CH | CH | CH | i-Pr | Cl | $C_2F_5$ | Cl |
| CH | CH | CH | CH | t-Bu | Cl | $C_2F_5$ | Cl |
| CH | CH | CH | CH | Et | Cl | $C_2F_5$ | Br |
| CH | CH | CH | CH | i-Pr | Cl | $C_2F_5$ | Br |
| CH | CH | CH | CH | t-Bu | Cl | $C_2F_5$ | Br |
| CH | CH | CH | CH | Et | Cl | $C_2F_5$ | I |
| CH | CH | CH | CH | i-Pr | Cl | $C_2F_5$ | I |
| CH | CH | CH | CH | t-Bu | Cl | $C_2F_5$ | I |
| CH | CH | CH | CH | Et | Cl | $C_2F_5$ | F |
| CH | CH | CH | CH | i-Pr | Cl | $C_2F_5$ | F |
| CH | CH | CH | CH | t-Bu | Cl | $C_2F_5$ | F |
| CH | CH | CH | CH | Et | Cl | $C_2F_5$ | Me |
| CH | CH | CH | CH | i-Pr | Cl | $C_2F_5$ | Me |
| CH | CH | CH | CH | t-Bu | Cl | $C_2F_5$ | Me |
| CH | CH | CH | CH | Et | Cl | $C_2F_5$ | $CF_3$ |
| CH | CH | CH | CH | i-Pr | Cl | $C_2F_5$ | $CF_3$ |
| CH | CH | CH | CH | t-Bu | Cl | $C_2F_5$ | $CF_3$ |
| CH | CH | CH | CH | Et | Cl | $C_2F_5$ | OMe |
| CH | CH | CH | CH | i-Pr | Cl | $C_2F_5$ | OMe |
| CH | CH | CH | CH | t-Bu | Cl | $C_2F_5$ | OMe |
| CH | CH | CH | CH | Et | Cl | $C_2F_5$ | CN |
| CH | CH | CH | CH | i-Pr | Cl | $C_2F_5$ | CN |
| CH | CH | CH | CH | t-Bu | Cl | $C_2F_5$ | CN |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, N.Y., 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnapthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, N.Y., 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A.

EXAMPLE A

| Wettable Powder | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

| Granule | |
|---|---|
| Compound 1 | 10.0% |
| attapulgite granules (low volatile matter, 0.71/0.30 mm; U.S.S. No. 25–50 sieves) | 90.0%. |

EXAMPLE C

| Extruded Pellet | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

Emulsifiable Concentrate

| Emulsifiable Concentrate | |
|---|---|
| Compound 1 | 20.0% |
| blend of oil soluble sulfonates and polyoxyethylene ethers | 10.0% |
| isophorone | 70.0%. |

The compounds of this invention exhibit activity against a wide spectrum of foliar-feeding, fruit-feeding, stem or root feeding, seed-feeding, aquatic and soil-inhabiting arthropods (term "arthropods" includes insects, mites and nematodes) which are pests of growing and stored agronomic crops, forestry, greenhouse crops, ornamentals, nursery crops, stored food and fiber products, livestock, household, and public and animal health. Those skilled in the art will appreciate that not all compounds are equally effective against all growth stages of all pests. Nevertheless, all of the compounds of this invention display activity against pests that include: eggs, larvae and adults of the Order Lepidoptera; eggs, foliar-feeding, fruit-feeding, root-feeding, seed-feeding larvae and adults of the Order Coleoptera; eggs, immatures and adults of the Orders Hemiptera and Homoptera, eggs, larvae, nymphs and adults of the Order Acari; eggs, immatures and adults of the Orders Thysanoptera, Orthoptera and Dermaptera; eggs, immatures and adults of the Order Diptera; and eggs, juveniles and adults of the Phylum Nematoda. The compounds of this invention are also active against pests of the Orders Hymenoptera, Isoptera, Siphonaptera, Blattaria, Thysanura and Psocoptera; pests belonging to the Class Arachnida and Phylum Platyhelminthes. Specifically, the compounds are active against southern corn rootworm (*Diabrotica undecimpunctata howardi*), aster leafhopper (*Mascrosteles fascifrons*), boll weevil (*Anthonomus grandis*), two-spotted spider mite (*Tetranychus urticae*), fall armyworm (*Spodoptera frugiperda*), black bean aphid (*Aphis fabae*), green peach aphid (*Myzus persica*), cotton aphid (*Aphis gossypii*), Russian wheat aphid (*Diuraphis noxia*), English grain aphid (*Sitobion avenae*), whitefly (*Bemisia tabacii*), tobacco budworm (*Heliothis virescens*), rice water weevil (*Lissorhoptrus oryzophilus*), rice leaf beetle (*Oulema oryzae*), whitebacked planthopper (*Sogatella furcifera*), green leafhopper (*Nephotettix cincticeps*), brown planthopper (*Nilaparvata lugens*), small brown planthopper (*Laodelphax striatellus*), rice stem borer (*Chilo suppressalis*), rice leafroller (*Cnaphalocrocis medinalis*), black rice stink bug (*Scotinophara lurida*), rice stink bug (*Oebalus pugnax*), rice bug (*Leptocorisa chinensis*), slender rice bug (*Cletus puntiger*), southern green stink bug (*Nezara viridula*) and german cockroach (*Blatella germanica*). The compounds are active on mites, demonstrating ovicidal, larvicidal and chemosterilant activity against such families as Tetranychidae including *Tetranychus urticae, Tetranychus cinnabarinus, Tetranychus mcdanieli, Tetranychus pacificus, Tetranychus turkestani, Byrobia rubrioculus, Panonychus ulmi, Panonychius citri, Eotetranychus carpini borealis, Eotetranychus, hicoriae, Eotetranychus sexmaculatus, Eotetranychus yumensis, Eotetranychus banksi* and *Oligonychus pratensis*; Tenuipalpidae including *Brevipalpus lewisi, Brevipalpus phoenicis, Brevipalpus californicus* and *Brevipalpus obovatus*, Eriophyidae including *Phyllocoptruta oleivora, Eriophyes sheldoni, Aculus cornutus, Epitrimerus pyri* and *Eriophyes mangiferae*. See WO 90/10623 and WO 92/00673 for more detailed pest descriptions.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, avermectin, azinphos-methyl, bifenthrin, buprofezin, carbofuran, chlorfenapyr, chlorpyrifos, chlorpyrifos-methyl, clothianidin, cyfluthrin, beta-cyfluthrin, cyhalothrin, lambda-cyhalothrin, cypermethrin, deltamethrin, diafenthiuron, diazion, diflubenzuron, dimethoate, diofenolan, emamectin, endosulfan, esfenvalerate, fenothicarb, fenoxycarb, fenpropathrin, fenvalerate, fipronil, flucythrinate, tau-fluvalinate, flufenoxuron, fonophos, imidacloprid, isofenphos, malathion, metaldehyde, methamidophos, methidathion, methomyl, methoprene, methoxychlor, methyl, 7-chloro-2,5-dihydro-2-[[N-(methoxycarbonyl)-N-[4-(trifluoromethoxy)phenyl]amino]carbonyl]indeno[1,2-e][1,3,4]oxadiazine-4a(3H)-carboxylate (indoxacarb), monocrotophos, oxamyl, parathion, parathion-methyl, permethrin, phorate, phosalone, phosmet, phosphamidon, pirimicarb, profenofos, pymetrozine, pyriproxyphen, rotenone, spionsad, sulprofos, tebufenozide, tefluthrin, terbufos, tetrachlorvinphos, thiacloprid, thiodicarb, tralomethrin, trichlorfon and triflumuron; fungicides such as acibenzolar, azoxystrobin, benomyl, blasticidin-S, Bordeaux mixture (Tribasic copper sulfate), bromuconazole, carpropamid (KTU 3616), captafol, captan, carbendazim, chloroneb, cblorothalonil, copper oxychloride, copper salts, cymoxanil, cyproconazole, cyprodinil (CGA 219417),(S)-3,5-dichloro-N-(3-chloro-1-ethyl-1-methyl-2-oxopropyl)-4-methylbenzamide (RH 7281), diclocymet (S-2900), diclomezine, dicloran, difenoconazole,(S)-3,5-dihydro-5-methyl-2-(methylthio)-5-phenyl-3-(phenylamino)-4H-imidazol-4-one (RP 407213), dimethomorph, diniconazole, diniconazole-M, dodine, edifenphos, epoxiconazole (BAS 480F), famoxadone, fenamidone, fenarimol, fenbuconazole, fencaramid (SZX0722), fenpiclonil fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasigamycin, kresoxim-methyl, mancozeb, maneb, mefenoxam, mepronil, metalaxyl, metconazole, metominostrobin/fenominostrobin (SSF-126), myclobutanil, neo-asozin (ferric methanearsonate), oxadixyl, penconazole, pencycuron, probenazole, prochloraz, propamocarb, propiconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thurnigiensis, Bacillus thuringiensis* delta endotoxin, baculovirus, and entomopathogenic bacteria, virus and fungi.

Preferred insecticides and acaricides for mixing with compounds of this invention include pyrethroids such as cypermethrin, cyhalothrin, cyfluthrin and beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid, neuronal sodium channel blockers such as indoxacarb, insecticidal macrocyclic lactones such as spinosad, abamectin, avermectin and emamectin; GABA antagonists such as endosulfan and fipronil; insecticidal ureas such as flufenoxuron and triflumuron, juvenile hormone mimics such as diofenolan and pyriproxyphen; pymetrozine; and amitraz. Preferred biological agents for mixing with compounds of this invention include *Bacillus thuringiensis* and *Bacillus thuringiensis* delta endotoxin.

Most preferred mixtures include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with fipronil; a mixture of a compound of this invention with flufenoxuron; a mixture of a compound of this invention with pyriproxyphen; a mixture of a compound of this invention with; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

In certain instances, combinations with other arthropodicides having a similar spectrum of control but a different mode of action will be particularly advantageous for resistance management.

Arthropod pests are controlled and protection of agronomic, horticultural and specialty crops, animal and human health is achieved by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of foliar and soil inhabiting arthropods and nematode pests and protection of agronomic and/or nonagronomic crops, comprising applying one or more of the compounds of the invention, or compositions containing at least one such compound, in an effective amount, to the environment of the pests including the agronomic and/or nonagronomic locus of infestation, to the area to be protected, or directly on the pests to be controlled. A preferred method of application is by spraying. Alternatively, granular formulations of these compounds can be applied to the plant foliage or the soil. Other methods of application include direct and residual sprays, aerial sprays, seed coats, microencapsulations, systemic uptake, baits, eartags, boluses, foggers, fumigants, aerosols, dusts and many others. The compounds can be incorporated into baits that are consumed by the arthropods or in devices such as traps and the like.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy.

The rate of application required for effective control will depend on such factors as the species of arthropod to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required.

The following TEST demonstrates the control efficacy of compounds of this invention on specific pests. "Control efficacy" represents inhibition of arthropod development (including mortality) that causes significantly reduced feeding. The pest control protection afforded by the compounds is not limited, however, to these species. See Index Tables A through Q for compound descriptions. The following abbreviations are used in the Index Tables which follow: t is tertiary, n is normal, i is iso, c is cyclo, s is secondary, Me is methyl, Et is ethyl, Pr is propyl, i-Pr is isopropyl, c-Pr is cyclopropyl, Bu is butyl, s-Bu is secondary butyl, Pent is pentyl, OMe is methoxy, OEt is ethoxy, SMe is methylthio, SEt is ethylthio, CN is cyano, $NO_2$ is nitro, and Het is heterocycle. The abbreviation "Ex." stands for "Example" and is followed by a number indicating in which example the compound is prepared.

INDEX TABLE A

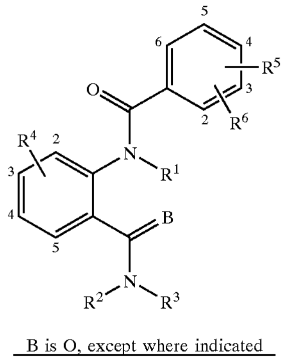

B is O, except where indicated

| Compound | $R^1$ | $R^2$ | $R^3$ | $R^4$ | $R^5$ and/or $R^6$ | m.p. ° C. |
|---|---|---|---|---|---|---|
| 1 (Ex 1) | H | i-Pr | H | 2-Me | 4-$OCF_3$ | 207–209 |
| 2 | H | i-Pr | H | 5-Cl | 2-$CF_3$ | 195–196 |
| 3 | H | i-Pr | H | 5-Cl | 2-Me-4-$CF_3$ | 182–184 |
| 4 | H | i-Pr | H | 2-Me | 4-$CF_3$ | 238–240 |
| 5 | H | i-Pr | H | 2-Me | 4-$CO_2$Me | 216–217 |
| 6 | H | i-Pr | H | 2-Me | 3-$NO_2$ | 230–233 |
| 7 | H | i-Pr | H | 2-Me | 3-$CF_3$-4-F | 223–225 |

INDEX TABLE A-continued

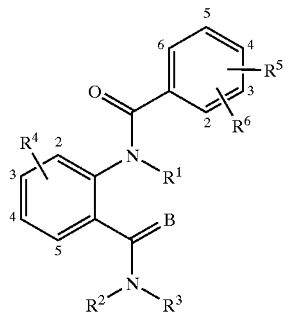

B is O, except where indicated

| Compound | $R^1$ | $R^2$ | $R^3$ | $R^4$ | $R^5$ and/or $R^6$ | m.p. ° C. |
|---|---|---|---|---|---|---|
| 8 | H | i-Pr | H | 2-Me | 3-CN | 237–239 |
| 9 | H | i-Pr | H | 2-Me | 2-$OCF_3$ | 191–193 |
| 10 | H | t-Bu | H | 2-Me | 4-$OCF_3$ | 163–167 |
| 11 | H | t-Bu | H | 2-Me | 4-$CO_2Me$ | 164–169 |
| 12 | H | i-Pr | H | 2-Cl | 4-$CO_2Me$ | 224–225 |
| 13 | H | t-Bu | H | 2-Me | 2-$OCF_3$ | 203–204 |
| 14 | H | t-Bu | H | 2-Me | 3-$NO_2$ | 193–195 |
| 15 | H | t-Bu | H | 2-Me | 3-$CF_3$-4-F | 198–199 |
| 16 | H | i-Pr | H | 2-OMe | 4-$OCF_3$ | 178–181 |
| 17 | H | i-Pr | H | 2-Me | 2-$OCF_3$ | 170–172 |
| 18 | H | i-Pr | H | 2-OMe | 3-$CF_3$-4-F | 209–211 |
| 19 | H | i-Pr | H | 2-Cl | 4-$OCF_3$ | 215–216 |
| 20 | H | i-Pr | Me | 2-Me | 2-$OCF_3$ | 153–155 |
| 21 | H | i-Pr | H | 5-Me | 4-$OCF_3$ | 173–175 |
| 22 | H | i-Pr | H | 5-Me | 2-$OCF_3$ | 180–185 |
| 23 | H | i-Pr | H | 5-Me | 4-$CO_2Me$ | 182–184 |
| 24 | H | i-Pr | Me | 2-Me | 4-$OCF_3$ | Glass |
| 25 | H | i-Pr | Me | 2-Me | 4-$CO_2Me$ | 67–73 |
| 26 | H | (1,2-di-Me)—Pr | H | 2-Me | 4-$OCF_3$ | 189–191 |
| 27 | H | $CH(CH_3)CH_2OCH_3$ | H | 2-Me | 4-$OCF_3$ | 147–148 |
| 28 | H | $CH_2CH_2OCH_3$ | H | 2-Me | 4-$OCF_3$ | 153–155 |
| 29 | H | 2-Pent | H | 2-Me | 4-$OCF_3$ | 165–168 |
| 30 | H | s-Bu | H | 2-Me | 4-$OCF_3$ | 181–183 |
| 31 | H | propargyl | H | 2-Me | 4-$OCF_3$ | 190–192 |
| 32 | H | n-Pr | H | 2-Me | 4-$OCF_3$ | 189–191 |
| 33 | H | allyl | H | 2-Me | 4-$OCF_3$ | 185–187 |
| 34 | H | $Me_2NCH_2CH_2$ | H | 2-Me | 4-$OCF_3$ | 168–170 |
| 35 | H | propargyl | H | 2-Me | 4-$OCF_3$ | 202–204 |
| 36 | H | i-Bu | H | 2-Me | 4-$OCF_3$ | 182–183 |
| 37 | H | i-Pr | H | 2,4-di-Me | 4-$OCF_3$ | 205–208 |
| 38 | H | i-Pr | H | 2,4-di-Me | 4-$CF_3$ | >230 |
| 39 | H | i-Pr | H | 2,4-di-Me | 2-OCF3 | 231–232 |
| 40 | H | i-Pr | H | 2,4-di-Me | 4-$CO_2Me$ | 219–221 |
| 41 | H | i-Pr | H | 2,4-di-Me | 3-$CF_3$-4-F | 222–224 |
| 42 | H | t-Bu | H | 2-OMe | 4-$CF_3$ | 210–214 |
| 43 | H | t-Bu | H | 2-OMe | 4-$OCF_3$ | 170–173 |
| 44 | H | i-Pr | Me | 2-Me | 3-$NO_2$ | Oil |
| 45 | H | i-Pr | H | 2-Cl | 4-$OCF_3$ | 187–194 |
| 46 | H | t-Bu | H | 2-Cl | 4-$OCF_3$ | 205–207 |
| 47 | H | allyl | H | 2-Cl | 4-$OCF_3$ | 188–189 |
| 48 | H | s-Bu | H | 2-Cl | 4-$OCF_3$ | 192–193 |
| 49 | H | —$CH_2CH_2CH_2CH_2$— | | 2-Me | 4-$OCF_3$ | 138–142 |
| 50 | H | $CH_2CF_3$ | H | 2-Me | 4-$OCF_3$ | >230 |
| 51 | H | c-Bu | H | 2-Me | 4-$OCF_3$ | 218–220 |
| 52 (Ex 3) | H | i-Pr | H | 2-Me | 2-Me-4-$CF_3$ | 247–248 |
| 53 | H | i-Pr | H | 5-Me | 2-Me-4-$CF_3$ | 186–188 |
| 54 | H | i-Pr | H | H | 4-$OCF_3$ | 185–187 |
| 55 | H | i-Pr | H | H | 3-$NO_2$ | 199–200 |
| 56 | H | i-Pr | H | H | 2-$OCF_3$ | 118–122 |
| 57 | Me | i-Pr | H | H | 4-$OCF_3$ | 117–118 |
| 58 | Me | i-Pr | H | H | 3-$NO_2$ | 134–136 |
| 59 | Me | i-Pr | H | H | 2-$OCF_3$ | 128–130 |
| 60 | H | i-Pr | H | H | 3-$CF_3$ | 176–177 |
| 61 | H | i-Pr | H | H | 2-Me-4-$CF_3$ | 100–106 |
| 62 | H | Me | H | 2-Me | 4-$OCF_3$ | 204–206 |
| 63 | H | Et | H | 2-Me | 4-$OCF_3$ | 198–200 |
| 64 | H | H | NHi-Pr | 2-Me | 4-$OCF_3$ | 126–128 |
| 65 | H | i-Pr | H | 2-Me | 3-$CF_3$ | 198–200 |

INDEX TABLE A-continued

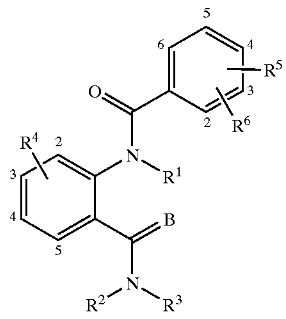

B is O, except where indicated

| Compound | $R^1$ | $R^2$ | $R^3$ | $R^4$ | $R^5$ and/or $R^6$ | m.p. ° C. |
|---|---|---|---|---|---|---|
| 66 | H | i-Pr | H | 2-Me | 4-CN | >230 |
| 67 | H | i-Pr | H | 2-Me | 2-$NO_2$ | >230 |
| 68 | H | i-Pr | H | 2-Me | 3,5-di-$CF_3$ | >230 |
| 69 | H | i-Pr | H | 2-Me | 4-$NO_2$ | 227–230 |
| 70 | H | i-Pr | H | 2-Me | 2-$CF_3$ | 227–230 |
| 71 | H | i-Pr | H | H | 2-Me-4-$OCF_3$ | 118–124 |
| 72 | H | i-Pr | H | H | 4-$CF_3$ | 196–198 |
| 73 | H | i-Pr | H | 2-Me | 2-Me-4-$SCF_2H$ | 212–213 |
| 74 | H | t-Bu | H | 2-Me | 2-Me-4-$SCF_2H$ | 193–195 |
| 75 | H | i-Pr | H | 2-Me | 2-Me-4-$OCF_3$ | 221–222 |
| 76 | H | t-Bu | H | 2-Me | 4-$CF_3$ | 217–219 |
| 77 | H | t-Bu | H | 2-Me | 3-$CF_3$ | 197–198 |
| 78 | H | t-Bu | H | 2-Me | 3,5-di-$CF_3$ | 206–207 |
| 79 | H | t-Bu | H | 2-Me | 4-CN | >230 |
| 80 | H | t-Bu | H | 2-Me | 4-$NO_2$ | >230 |
| 81 | Me | i-Pr | H | 2-Me | 2-$CF_3$ | oil |
| 82 | Me | i-Pr | H | 2-Me | 4-$OCF_3$ | 151–157 |
| 83 | Me | i-Pr | H | H | 2-Me-4-$OCF_3$ | 103–107 |
| 84 | Me | t-Bu | H | 2-Me | 2-Me-4-$CF_3$ | 233–234 |
| 85 | H | t-Bu | H | 2-Me | 2-Me-4-$OCF_3$ | 207–209 |
| 86 | H | t-Bu | H | 2-Me | 2,5-di-$CF_3$ | 199–201 |
| 87 | H | i-Pr | H | 2-$CF_3$ | 4-$OCF_3$ | 183–185 |
| 88 | H | i-Pr | H | 2-$CF_3$ | 4-$CF_3$ | 211–212 |
| 89 | H | t-Bu | H | 2-$CF_3$ | 4-$CF_3$ | 191–192 |
| 90 | H | R-(−)-s-Bu | H | 2-Me | 4-$OCF_3$ | 170–172 |
| 91 | H | S-(+)-s-Bu | H | 2-Me | 4-$OCF_3$ | 177–179 |
| 92 | Me | i-Pr | H | H | 4-$CF_3$ | oil |
| 93 | Me | i-Pr | H | 2-$OCF_2H$ | 4-$OCF_3$ | 162–164 |
| 94 | H | t-Bu | H | 2-$CF_3$ | 4-$OCF_3$ | 145–148 |
| 95 | H | i-Pr | Me | 2-$CF_3$ | 4-$CF_3$ | 151–154 |
| 96 | H | i-Pr | Me | 2-$CF_3$ | 4-$OCF_3$ | 140–144 |
| 97 | H | i-Pr | H | 2-$OCF_2H$ | 4-$CF_3$ | 224–227 |
| 98 | H | i-Pr | H | 2,4-di-Me | 2-Me-4-$CF_3$ | >230 |
| 99 | H | i-Pr | H | 2-Cl | 2-Me-4-$CF_3$ | >230 |
| 100 | H | $CH(CH_3)CH_2OCH_3$ | H | 2-Cl | 2-Me-4-$CF_3$ | 194–197 |
| 101 | H | s-Bu | H | 2-Cl | 2-Me-4-$CF_3$ | 212–214 |
| 102 | H | c-Pr | H | 2-Me | 4-$OCF_3$ | 208–210 |
| 103 | H | $CH(CH_3)CH_2OCH_3$ | H | 2,4-di-Me | 4-$OCF_3$ | 166–168 |
| 104 | H | $CH(CH_3)CH_2OCH_3$ | H | 2,4-di-Me | 4-$CF_3$ | 192–194 |
| 105 | H | i-Pr | H | 4-Me | 4-$CF_3$ | 212–213 |
| 106 | H | i-Pr | H | 4-Me | 4-$OCF_3$ | 204–205 |
| 107 | H | i-Pr | H | 2-Br-4-Me | 4-$OCF_3$ | >230 |
| 108 | H | t-Bu | H | 2-Br-4-Me | 4-$OCF_3$ | 118–121 |
| 109 | H | i-Pr | H | 2-$NO_2$ | 4-$CF_3$ | 203–204 |
| 110 | H | t-Bu | H | 2-$NO_2$ | 4-$CF_3$ | 199–200 |
| 111 | H | i-Pr | H | 2-$NO_2$ | 4-$OCF_3$ | 204–205 |
| 112 | H | t-Bu | H | 2-$NO_2$ | 4-$OCF_3$ | 181–183 |
| 113 | H | i-Pr | H | 2-Me | 2-Me-4-$S(O)_2CF_2H$ | 218–221 |
| 114 | H | i-Pr | H | 2-Me | 2-Me-4-$S(O)CF_2H$ | 203–206 |
| 115 | H | $CH(CH_3)CH_2OCH_3$ | H | 3-Cl | 4-$CF_3$ | 158–161 |
| 116 | H | i-Pr | H | 4-Br | 4-$CF_3$ | 232–234 |
| 117 | H | t-Bu | H | 4-Br | 4-$CF_3$ | 204–206 |
| 118 | H | $CH(CH_3)CH_2OCH_3$ | H | 4-Br | 4-$CF_3$ | 157–158 |
| 119 | H | i-Pr | H | 4-Br | 4-$OCF_3$ | 221–222 |
| 120 | H | t-Bu | H | 4-Br | 4-$OCF_3$ | 173–175 |
| 121 | H | $CH(CH_3)CH_2OCH_3$ | H | 4-Br | 4-$OCF_3$ | 153–155 |
| 122 | H | $CH(CH_3)CH_2OCH_3$ | H | 3-Cl | 4-$OCF_3$ | 137–140 |
| 123 | H | i-Pr | H | 4-F | 4-$CF_3$ | 205–206 |
| 124 | H | t-Bu | H | 2-Cl | 2-Me-4-$CF_3$ | 237–240 |

INDEX TABLE A-continued

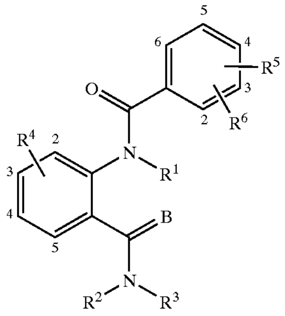

B is O, except where indicated

| Compound | $R^1$ | $R^2$ | $R^3$ | $R^4$ | $R^5$ and/or $R^6$ | m.p. ° C. |
| --- | --- | --- | --- | --- | --- | --- |
| 125 | H | 2-Pent | H | 2-Me | 4-$CF_3$ | 194–196 |
| 126 | H | s-Bu | H | 2-Me | 4-$CF_3$ | 207–210 |
| 127 | H | Et | H | 2-Me | 4-$CF_3$ | >240 |
| 128 | H | Me | H | 2-Me | 4-$CF_3$ | 236–237 |
| 129 | H | i-Pr | H | 4-F | 4-$OCF_3$ | 208–209 |
| 130 | H | $CH(CH_3)CH_2OCH_3$ | H | 4-F | 4-$OCF_3$ | 151–152 |
| 131 | H | $CH(CH_3)CH_2OCH_3$ | H | 2-Me | 4-$CF_3$ | 188–190 |
| 132 | $CH_2CO_2Me$ | i-Pr | H | H | 4-$CF_3$ | oil |
| 133 | $CH_2CO_2Me$ | i-Pr | H | H | 4-$OCF_3$ | oil |
| 134 | Me | Et | H | 2-Me | 4-$CF_3$ | oil |
| 135 | Me | Et | H | 2-Me | 4-$OCF_3$ | oil |
| 136 | Me | Et | H | 2-Me | 2-Me-4-$SCF_2H$ | 132–136 |
| 137 | H | $CH(CH_3)CH_2OCH_3$ | H | 2-Me-4-Br | 4-$CF_3$ | 197–199 |
| 138 | H | $CH(CH_3)CH_2OCH_3$ | H | 2-Me-4-Br | 4-$OCF_3$ | 188–190 |
| 139 | H | i-Pr | H | 3-Cl | 4-$CF_3$ | 201–202 |
| 140 | H | t-Bu | H | 3-Cl | 4-$CF_3$ | 159–161 |
| 141 | H | i-Pr | H | 3-Cl | 4-$OCF_3$ | 190–192 |
| 142 | H | t-Bu | H | 3-Cl | 4-$OCF_3$ | 150–152 |
| 143 | H | i-Pr | H | 2-Br-4-Me | 4-$CF_3$ | >230 |
| 144 | H | t-Bu | H | 2-Br-4-Me | 4-$CF_3$ | 213–215 |
| 145 | H | $CH(CH_3)CH_2OCH_3$ | H | 5-F | 4-$CF_3$ | 145–147 |
| 146 | H | 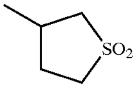 | H | 2-Me | 4-$CF_3$ | >230 |
| 147 | H | i-Pr | H | 2-Me | 2-F-4-$CF_3$ | 224–226 |
| 148 | H | i-Pr | H | 2-Me | 2-$CF_3$-4-F | 223–225 |
| 149 | H | t-Bu | H | 4-F | 4-$OCF_3$ | 180–187 |
| 150 | H | $CH(CH_3)CH_2OCH_3$ | H | 2-Me | 2-Me-4-$CF_3$ | 194–197 |
| 151 | H | Me | H | 2-Me | 2-Me-4-$CF_3$ | >230 |
| 152 | H | Et | H | 2-Me | 2-Me-4-$CF_3$ | 243–245 |
| 153 | H | 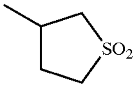 | H | 2-Me | 2-Me-4-$CF_3$ | >230 |
| 154 | H | i-Pr | H | 3-$NO_2$ | 4-$CF_3$ | 244–246 |
| 155 | H | i-Pr | H | 3-$NO_2$ | 4-$OCF_3$ | 239–240 |
| 156 | H | t-Bu | H | 3-$NO_2$ | 4-$OCF_3$ | 180–184 |
| 157 | H | $CH(CH_3)CH_2OCH_3$ | H | 3-$NO_2$ | 4-$OCF_3$ | 172–175 |
| 158 | H | t-Bu | H | 3-$NO_2$ | 4-$CF_3$ | 194–196 |
| 159 | H | $CH(CH_3)CH_2OCH_3$ | H | 3-$NO_2$ | 4-$CF_3$ | 178–179 |
| 160 | H | i-Pr | H | 2-Cl | 4-$CF_3$ | >230 |
| 161 | H | $CH(CH_3)CH_2OCH_3$ | H | 2-Cl | 4-$CF_3$ | 182–185 |
| 162 | H | t-Bu | H | 5-Cl | 2-Me-4-$CF_3$ | 203–205 |
| 163 | H | $CH(CH_3)CH_2OCH_3$ | H | 5-Cl | 2-Me-4-$CF_3$ | 154–155 |
| 164 | H | i-Pr | H | 2-Me | 2,4-$(CF_3)_2$ | >230 |
| 165 | H | i-Pr | H | 2-Me | 3,4-$OCF_2O$— | 199–200 |
| 166 | H | $CH_2CN$ | H | 2-Me | 4-$CF_3$ | 218–223 |
| 167 | H | $CH(CH_3)Ph$ | H | 2-Me | 4-$CF_3$ | 225–228 |
| 168 | H | $CH(CH_3)Ph$ | H | 2-Me | 4-$OCF_3$ | 208–210 |
| 169 | H | t-Bu | H | 2-Cl | 4-$CF_3$ | 191–193 |
| 170 | H | i-Pr | Me | 2-Cl | 4-$CF_3$ | 136–140 |
| 171 | H | i-Pr | H | 2-Me | 4-$SO_2CH_3$ | >250 |
| 172 | H | i-Pr | H | 5-Cl | 4-$CF_3$ | 217–218 |
| 173 | H | t-Bu | H | 5-Cl | 4-$CF_3$ | 231–235 |

INDEX TABLE A-continued

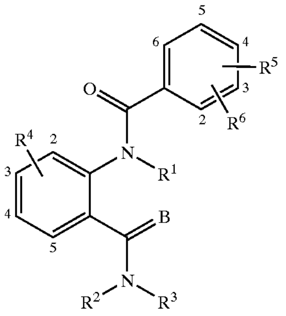

B is O, except where indicated

| Compound | $R^1$ | $R^2$ | $R^3$ | $R^4$ | $R^5$ and/or $R^6$ | m.p. ° C. |
|---|---|---|---|---|---|---|
| 174 | H | $CH(CH_3)CH_2OCH_3$ | H | 5-Cl | 4-$CF_3$ | 175–177 |
| 175 | H | i-Pr | H | 4-I | 4-$CF_3$ | >230 |
| 176 | H | t-Bu | H | 4-I | 4-$CF_3$ | 215–219 |
| 177 | H | $CH(CH_3)CH_2OCH_3$ | H | 4-I | 4-$CF_3$ | 173–178 |
| 178 | H | i-Pr | H | 4-I | 4-$OCF_3$ | >230 |
| 179 | H | t-Bu | H | 4-I | 4-$OCF_3$ | 192–194 |
| 180 | H | $CH(CH_3)CH_2OCH_3$ | H | 4-I | 4-$OCF_3$ | 178–180 |
| 181 | H | $CH_2$(3-pyridinyl) | H | 2-Me | 4-$CF_3$ | 198–199 |
| 182 | H | $CH_2CN$ | H | 2-Me | 2-Me-4-$CF_3$ | >230 |
| 183 | H | $CH(CH_3)CO_2CH_3$ | H | 2-Me | 4-$CF_3$ | 223–225 |
| 184 | H | i-Pr | H | 2-F | 4-$CF_3$ | 228–229 |
| 185 | H | i-Pr | H | 5-F | 4-$CF_3$ | 169–170 |
| 186 | H | i-Pr | H | 2-F | 2-Me-4-$OCF_3$ | 206–208 |
| 187 | H | i-Pr | H | 5-F | 2-Me-4-$OCF_3$ | 125–126 |
| 188 | H | i-Pr | H | 2-F | 2-Me-4-$CF_3$ | 234–235 |
| 189 | H | i-Pr | H | 5-F | 2-Me-4-$CF_3$ | 133–135 |
| 190 | H | $CH_2$(3-pyridinyl) | H | 2-Me | 4-$OCF_3$ | 201–202 |
| 191 | H | $CH_2CH_2SCH_3$ | H | 2-Me | 4-$CF_3$ | 187–188 |
| 192 | H | $CH_2CH_2SCH_3$ | H | 2-Me | 2-Me-4-$CF_3$ | 250–251 |
| 193 | H | $CH_2CH_2SEt$ | H | 2-Me | 4-$CF_3$ | 190–191 |
| 194 | H | $CH_2CH_2SEt$ | H | 2-Me | 2-Me-4-$CF_3$ | 228–230 |
| 195 | H | $CH(CH_3)CH{=}CH_2$ | H | 2-Me | 2-Me-4-$CF_3$ | 211–214 |
| 196 | H | i-Pr | H | 2-Et | 4-$CF_3$ | 228–230 |
| 197 | H | $CH(CH_3)CH_2OCH_3$ | H | 2-Et | 4-$CF_3$ | 176–177 |
| 198 | H | i-Pr | H | 2-Me | 3-4-$OCF_2CF_2O$— | 218–220 |
| 199 | H | i-Pr | H | 2-Me | 2-($CONMe_2$)-4,5-$Cl_2$ | 229–230 |
| 200 | H | i-Pr | H | 2-Me | 2-(CO-1-piperidinyl)-4,5-$Cl_2$ | 202–205 |
| 201 | H | t-Bu | H | 2-Et | 4-$CF_3$ | 187–191 |
| 202 | H | $CH(CH_3)CH_2SCH_3$ | H | 2-Et | 2-Me-4-$CF_3$ | 206–208 |
| 203 | H | i-Pr | H | 2-Me | 2-($CONMe_2$)-4-Br | 191–194 |
| 204 | H | i-Pr | H | 2-Me | 2-($CONMe_2$)-5-Br | 190–194 |
| 205 | H | $CH(CH_3)CH_2SO_2CH_3$ | H | 2-Me | 2-Me-4-$CF_3$ | 231–233 |
| 206 | H | c-Pr | H | 2-Me | 2-Me-4-$CF_3$ | 258–261 |
| 207 | H | c-Pr | H | 2-Cl | 2-Me-4-$CF_3$ | >260 |
| 208 | H | i-Pr | H | 2-I | 2-Me-4-$OCF_3$ | 241–242 |
| 209 | H | i-Pr | H | 2-I | 2-Me-4-$CF_3$ | 260–262 |
| 210 | H | i-Pr | H | 2-Me | 2-($CONMe_2$)-4-F | 164–170 |
| 211 | H | i-Pr | H | 2-Me | 2-($CONMe_2$)-5-F | 167–171 |
| 212 | H | i-Pr | H | 2-Me | 2-(CO-1-piperidinyl)-4-Br | 105–117 |
| 213 | H | $CH(CH_3)CH_2OH$ | H | 2-Me | 2-Me-4-$CF_3$ | 179–180 |
| 214 | H | $CH(CH_3)CH_2OH$ | H | 2-Cl | 2-Me-4-$CF_3$ | 183–185 |
| 215 | H | i-Pr | H | 2-Cl | 2-($CONMe_2$)-4-Br | 165–170 |
| 216 | H | i-Pr | H | 2-Cl | 2-($CONMe_2$)-5-Br | 179–181 |
| 217 | H | i-Pr | H | 2-Me | 2-(3-$CF_3$-1-pyrazolyl)-4-$CF_3$ | 243–244 |
| 218 | H | i-Pr | H | 2-Me | 2-(1-(1,2,4-triazolyl))-4-$CF_3$ | 238–240 |
| 219 | H | i-Pr | H | 2-Me | 2-(3-Br-1-pyrazolyl)-4-$CF_3$ | >250 |
| 220 | H | i-Pr | H | 2-Me | 2-(3-CN-l-pyrazolyl)-4-$CF_3$ | >250 |
| 221 | H | i-Pr | H | 2-Me | 2-(4-$CF_3$-1-imidazolyl)-4-$CF_3$ | >250 |
| 222 | H | i-Pr | H | 2-Me | 2-(3-$CH_3$-1-pyrazolyl)-4-$CF_3$ | 248–250 |
| 223 | H | i-Pr | H | 2-Me | 2-(2-$CH_3$-1-imidazolyl)-4-$CF_3$ | 186–188 |

INDEX TABLE A-continued

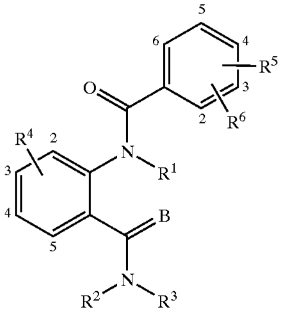

B is O, except where indicated

| Compound | $R^1$ | $R^2$ | $R^3$ | $R^4$ | $R^5$ and/or $R^6$ | m.p. ° C. |
|---|---|---|---|---|---|---|
| 224 | H | i-Pr | H | 2-Me | 2-(3-CF3-1-(1,2,4-triazolyl))-4-$CF_3$ | 254–256 |
| 225 | H | i-Pr | H | 2-Me | 2-(1-pyrazolyl)-4-$CF_3$ | 246–248 |
| 226 | H | i-Pr | H | 2-Me | 2-(3-$CO_2$Et-5-Me-1-pyrazolyl)-4-$CF_3$ | 224–225 |
| 227 | H | i-Pr | H | 2-Me | 2-(1-imidazolyl)-4-$CF_3$ | 240–241 |
| 228 | H | i-Pr | H | 2-Me | 2-(3-$CF_3$-5-Me-1-pyrazolyl)-4-$CF_3$ | 229–231 |
| 229 | H | i-Pr | H | 2-Me | 2-(3,5-$Me_2$-1-pyrazolyl)-4-$CF_3$ | 214–218 |
| 230 | H | i-Pr | H | 2-Me | 2-(2,4-$Me_2$-1-imidazolyl)-4-$CF_3$ | 246–248 |
| 231 | H | i-Pr | H | 2-Me | 2-(4-Me-1-imidazolyl)-4-$CF_3$ | 223–225 |
| 232 | H | i-Pr | H | 2-Cl | 2-(3-$CF_3$-1-pyrazolyl)-4-$CF_3$ | >250 |
| 233 | H | i-Pr | H | 2-Cl | 2-(1-(1,2,4-triazolyl))-4-$CF_3$ | 252–254 |
| 234 | H | i-Pr | H | 2-Cl | 2-(3-Br-1-pyrazolyl)-4-$CF_3$ | >250 |
| 235 | H | i-Pr | H | 2-Cl | 2-(3-$CO_2$Et-5-Me-l-pyrazolyl)-4-$CF_3$ | 220–221 |
| 236 | H | i-Pr | H | 2-Cl | 2-(4-$CO_2$Me-1-imidazolyl)-4-$CF_3$ | 255–257 |
| 237 | H | i-Pr | H | 2-Cl | 2-(3-CN-1-pyrazolyl)-4-$CF_3$ | >250 |
| 238 | H | i-Pr | H | 2-Cl | 2-(1-imidazolyl)-4-$CF_3$ | 248–249 |
| 239 | H | i-Pr | H | 2-Me | 2-(4-$CO_2$Me-1-imidazolyl)-4-$CF_3$ | 219–222 |
| 240 | H | i-Pr | H | 2-Me | 2-(2-thienyl)-4-$CF_3$ | 241–243 |
| 241 | H | i-Pr | H | 2-Me | 2-(3-thienyl)-4-$CF_3$ | 229–231 |
| 242 | H | i-Pr | H | 2-Me | 2-(2-furanyl)-4-$CF_3$ | 246–247 |
| 243 | H | i-Pr | H | 2-Me | 2-(3-t-Bu-1-pyrazolyl)-4-$CF_3$ | 247–249 |
| 244 | H | i-Pr | H | 2-Me | 2-(3-s-Bu-1-pyrazolyl)-4-$CF_3$ | 224–225 |
| 245 | H | i-Pr | H | 2-Me | 2-(3-c-Pr-1-pyrazolyl)-4-$CF_3$ | 220–221 |
| 246 | H | i-Pr | H | 2-Me | 2-(3-Me-5-isoxazolyl)-4-$CF_3$ | 233–234 |
| 247 | H | i-Pr | H | 2-Me | 2- 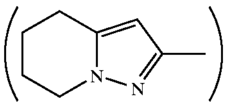 -4-$CF_3$ | >250 |
| 248 | H | i-Pr | H | 2-Me | 2-($CONMe_2$)-4-$CF_3$ | 188–192 |
| 249 | H | i-Pr | H | 2-Me | 2-($CONMe_2$)-5-$CF_3$ | 194–196 |
| 250 | H | i-Pr | H | 2-Me | 2-(CO-1-pyrrolidinyl)-4-$CF_3$ | 201–204 |
| 251 | H | i-Pr | H | 2-Me | 2-(CO-1-pyrrolidinyl)-5-$CF_3$ | 221–223 |
| 252 | H | i-Pr | H | 2-Me | 2-$OCH_3$-4-$CF_3$ | 188–189 |
| 253 | H | i-Pr | H | 2-Me | 2-(3-Cl-5-isoxazolyl)-4-$CF_3$ | 247–248 |
| 254 | H | i-Pr | H | 2-Me | 2-Oi-Pr-4-$CF_3$ | 158–159 |

INDEX TABLE A-continued

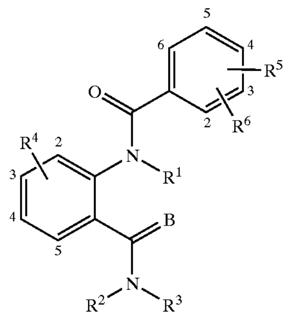

B is O, except where indicated

| Compound | $R^1$ | $R^2$ | $R^3$ | $R^4$ | $R^5$ and/or $R^6$ | m.p. ° C. |
|---|---|---|---|---|---|---|
| 255 | H | i-Pr | H | 2-Cl | 2-(4-Me-1-pyrazolyl)-4-$CF_3$ | 252–253 |
| 256 | H | i-Pr | H | 2-Me | 2-(4-Me-1-pyrazolyl)-4-$CF_3$ | 226–227 |
| 257 | H | i-Pr | H | 2,5-$Cl_2$ | 2-Me-4-$CF_3$ | 235–237 |
| 258 | H | i-Pr | H | 2-Me | 4-Ph | 221–224 |
| 259 | H | i-Pr | H | 2-Me | 4-(4-$OCH_3$)Ph | >230 |
| 260 | H | i-Pr | H | 2-Me | 4-(2-Me)Ph | 156–158 |
| 261 | H | i-Pr | H | 2-Me | 4-(3-$CH_3$)Ph | 225–226 |
| 262 | H | i-Pr | H | 2-Me | 4-(3-$CF_3$)Ph | 214–215 |
| 263 | H | i-Pr | H | 2-Me | 4-(4-F)Ph | >230 |
| 264 | H | —$CH_2CH_2CH_2CH_2$— | | 2-Cl | 3-Cl | 158–161 |
| 265 | H | 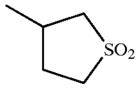 | H | 2-Me | 4-$OCF_3$ | >230 |
| 266 | H | i-Pr | H | 2-$CF_3$ | 2-Me-4-Br | >230 |
| 267 | H | t-Bu | H | 2-$CF_3$ | 2-Me-4-Br | 234–236 |
| 268 | H | i-Pr | Me | 2-$CF_3$ | 2-Me-4-Br | 154–158 |
| 269 | H | $CH(CH_3)CH_2OCH_3$ | H | 2-$CF_3$ | 2-Me-4-Br | 202–204 |
| 270 | H | s-Bu | H | 2-$CF_3$ | 2-Me-4-Br | >230 |
| 271 | H | s-pentyl | H | 2-$CF_3$ | 2-Me-4-Br | 215–217 |
| 272 | H | i-Pr | H | 2-$CH_3$ | 2-Me-4-$CF_3$ | >230 |
| 273 | H | i-Pr | Me | 2-$OCHF_2$ | 2-Me-4-Br | 224–227 |
| 274 | H | i-Pr | H | 2-$CH_3$ | 2-($CONMe_2$)-4-$CF_3$ | 130–137 |
| 275 | B is S H | i-Pr | H | 2-Me | 2-Me-4-$CF_3$ | 193–195 |
| 276 | H | i-Pr | H | 2-Cl | 2-(1-pyrazolyl)-4-$CF_3$ | 249–250 |
| 277 | B is S H | i-Pr | H | 2-Me | 4-$OCF_3$ | 169–171 |
| 278 | B is S H | i-Pr | H | 2-Me | 4-$CF_3$Ph | 204–206 |

INDEX TABLE B

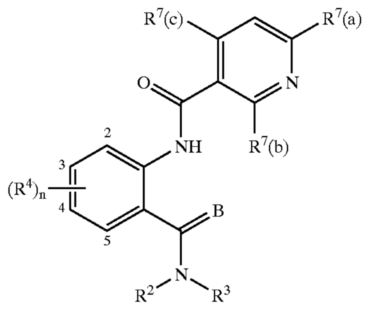

$R^7$(c) is H, except where indicated and B is O, except where indicated

| Compound | $R^3$ | $R^2$ | $(R^4)_n$ | $R^7$(a) | $R^7$(b) | m.p. ° C. |
|---|---|---|---|---|---|---|
| B1 (Ex. 4) | i-Pr | H | 2-Me | $CF_3$ | $CH_3$ | 247–248 |
| B2 | i-Pr | H | 2-Me | $OCH_2CF_3$ | H | 188–191 |

INDEX TABLE B-continued

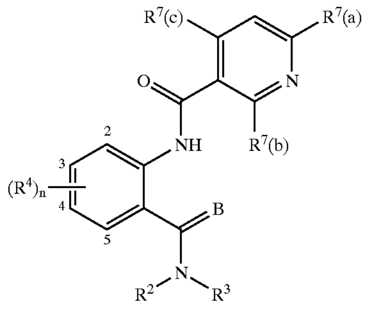

$R^7$(c) is H, except where indicated
and B is O, except where indicated

| Compound | $R^3$ | $R^2$ | $(R^4)_n$ | $R^7$(a) | $R^7$(b) | m.p. ° C. |
|---|---|---|---|---|---|---|
| B3 | i-Pr | H | 2-Cl | $CF_3$ | $CH_3$ | 234–236 |
| B4 | t-Bu | H | 2-Cl | $CF_3$ | $CH_3$ | 243–245 |
| B5 | $CH(CH_3)CH_2OCH_3$ | H | 2-Cl | $CF_3$ | $CH_3$ | 198–201 |
| B6 | $CH(CH_3)CH{=}CH_2$ | H | 2-Me | $CF_3$ | $CH_3$ | 226–227 |
| B7 | i-Pr | H | 2-Cl | $OCH_2CF_3$ | H | 208–210 |
| B8 | t-Bu | H | 2-Cl | $OCH_2CF_3$ | H | 174–175 |
| B9 | $CH(CH_3)CH_2OCH_3$ | H | 2-Cl | $OCH_2CF_3$ | H | 163–165 |
| B10 | i-Pr | H | 2-Me | $CF_3$ | H | 208–211 |
| B11 | $CH(CH_3)CH_2OCH_3$ | H | 2-Me | $CF_3$ | $CH_3$ | 187–191 |
| B12 | s-Bu | H | 2-Me | $CF_3$ | $CH_3$ | 215–218 |
| B13 | 2-pentyl | H | 2-Me | $CF_3$ | $CH_3$ | 213–215 |
| B14 | i-Pr | H | 2-Me | Cl | H | 235–237 |
| B15 | i-Pr | H | 2-Me | H | Cl | 235–237 |
| B16 | i-Pr | H | $2\text{-}OCHF_2$ | $CF_3$ | $CH_3$ | 221–224 |
| B17 | i-Pr | H | 2-Me | $CF_2CF_3$ | $CH_3$ | 208–209 |
| B18 | t-Bu | H | 2-Me | $CF_2CF_3$ | $CH_3$ | 211–212 |
| B19 | $CH(CH_3)CH_2OCH_3$ | H | 2-Me | $CF_2CF_3$ | $CH_3$ | 193–196 |
| B20 | t-Bu | H | $2\text{-}CF_3$ | $CF_3$ | $CH_3$ | >250 |
| B21 | t-Bu | H | $2\text{-}CF_3$ | $CF_3$ | $CH_3$ | 218–222 |
| B22 | $CH(CH_3)CH_2OCH_3$ | H | $2\text{-}CF_3$ | $CF_3$ | $CH_3$ | 200–202 |
| B23 | i-Pr | H | 2-Me | $CF_3$ | Br | 253–255 |
| B24 | $CH(CH_3)CH_2SCH_3$ | H | 2-Me | $CF_3$ | $CH_3$ | 222–223 |
| B25 | $CH(CH_3)CH_2CN$ | H | 2-Me | $CF_3$ | $CH_3$ | 230–232 |
| B26 | $CH_2CH_2CN$ | H | 2-Me | $CF_3$ | $CH_3$ | >260 |
| B27 | c-Pr | H | 2-Me | $CF_3$ | $CH_3$ | >260 |
| B28 | i-Pr | H | 2-Me | $CF_3$ | $OCH_3$ | 181–183 |
| B29 | i-Pr | H | 2-Me | Cl | $CH_3$ | 246–247 |
| B30 | i-Pr | H | 2-Me | $CF_3$ | Ph | >250 |
| B31 | i-Pr | H | 2-I | $CF_3$ | $CH_3$ | 256–257 |
| B32 | i-Pr | H | 2-F | $CF_3$ | $CH_3$ | 218–220 |
| B33 | i-Pr | H | 5-F | $CF_3$ | $CH_3$ | 144–146 |
| B34 | $CH(CH_3)CH_2SO_2CH_3$ | H | 2-Me | $CF_3$ | $CH_3$ | 243–245 |
| B35 | $CH(CH_3)CH_2OH$ | H | 2-Me | $CF_3$ | $CH_3$ | 222–223 |
| B36 | $CH(CH_3)CH_2CO_2CH_3$ | H | 2-Me | $CF_3$ | $CH_3$ | 204–206 |
| B37 | i-Pr | H | 2-Me | $CF_3$ | $CH_2OCH_3$ | 241–242 |
| B38 | i-Pr | H | 2-Me | $CF_3$ | $CH_2CH_3$ | 229–231 |
| B39 | i-Pr | H | 2-Me | $CH_3$ | Cl | 236–237 |
| B40 | i-Pr | H | 2-Me | $CH_3$ | 2-pyridinyl | 278–281 |
| B41 | t-Bu | H | 2-Me | $CF_3$ | $CH_3$ | 234–236 |
| B42 | i-Pr | H | 2-Me | $CF_3$ | n-Pr | 224–226 |
| B43 | i-Pr | Me | 2-Me | $CF_3$ | $CH_3$ | 202–205 |
| B44 | i-Pr | H | 2-Me | c-Pr | $CH_3$ | 226–229 |
| B45 | i-Pr | H | 2-Me | c-Pr | $CH_3$, HCl salt | >230 |
| B46 | i-Pr | H | 2-Me | $CF_3$ | Cl | 248–254 |
| B47 | i-Pr | H | 2-Me | $CF_3$ | i-Pr | 235–237 |
| B48 | i-Pr | H | 2-Me | $CF_3$ | 1-(1,2,4-triazolyl) | >260 |
| B49 | i-Pr | H | 2-Br | $CF_3$ | $CH_3$ | 247–248 |
| B50 | i-Pr | H | 2-Me | $OCH_2CF_3$ | $CH_3$ | 150–160 |
| B51 | i-Pr | H | 2-Me | $CF_3$ | 2-phenoxy | 231–232 |
| B52 | i-Pr | H | 2-Me | $CF_3$ | 1-morpholinyl | >250 |
| B53 | i-Pr | H | 2-Me | $CF_3$ | 1-(3-$CF_3$-imidazolyl) | 247–250 |
| B54 | i-Pr | H | 2-Me | $CF_3$ | 1-(3-Br-pyrazolyl) | >260 |
| B55 | i-Pr | H | 2-Me | $CF_3$ | 1-(3-$CF_3$-pyrazolyl) | >260 |
| B56 | i-Pr | H | 2-Me | $CF_3$ | 1-((3-$CF_3$)-1,2,4-triazolyl) | >260 |
| B57 | i-Pr | H | 2-Me | $CF_3$ | 1-((3-CN)-1,2,4-triazolyl) | >260 |
| B58 | i-Pr | H | 2-Me | i-Bu | Cl | 185–190 |
| B59 | i-Pr | H | 2-Me | $CF_3$ | 2-MePh | 200–203 |
| B60 | i-Pr | H | 2-Me | i-Pr | $CH_3$ | 186–190 |

INDEX TABLE B-continued

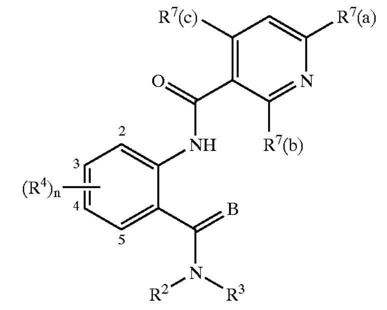

$R^7$(c) is H, except where indicated
and B is O, except where indicated

| Compound | $R^3$ | $R^2$ | $(R^4)_n$ | $R^7$(a) | $R^7$(b) | m.p. ° C. |
|---|---|---|---|---|---|---|
| B61 | i-Pr | H | 2-Me | Ph | Cl | 229–234 |
| B62 | i-Pr | H | 2-Me | $CF_3$ | $SCH_2CH(CH_3)_2$ | 230–231 |
| B63 | i-Pr | H | 2-Me | $CF_2CF_3$ | $CH_2CH_3$ | 209–211 |
| B64 | i-Pr | H | 2-Me | $CF_3$ | 1-pyrazoly1 | >250 |
| B65 | i-Pr | H | 2-Me | $CF_2CF_3$ | H | >250 |
| B66 | i-Pr | H | 2-Me | $CF_2CF_3$ | i-Pr | 209–212 |
| B67 | i-Pr | H | 2-Me-4-Br | $CF_3$ | $CH_3$ | >250 |
| B68 | i-Pr | H | 2-Me | $OCH_2CF_3$ | n-Pr | 165–169 |
| B69 | i-Pr | H | 2-Me | Cl | n-Pr | 200–205 |
| B70 | i-Pr | H | 2-Me | Cl | Et | 200–205 |
| B71 | i-Pr | H | 2-Me | $CF_3$ | CN | 214–215 |
| B72 | i-Pr | H | 2,5-$Cl_2$ | $CF_3$ | $CH_3$ | >240 |
| B73 | i-Pr | H | 2-Me | H | H, $R^7$(c) is SPh | 223–225 |
| B74 | B is S, i-Pr | H | 2-Me | $CF_3$ | $CH_3$ | 201–203 |
| B75 | B is S, i-Pr | H | 2-Me | $CF_3$ | Et | 173–175 |
| B76 | B is S, i-Pr | H | 2-Me | $CF_2CF_3$ | $CH_3$ | 156–158 |
| B77 | i-Pr | H | 2-Me | H | 1-((3-$CF_3$)-pyrazolyl) | 224–225 |
| B78 | i-Pr | H | 2-Me | $CF_3$ | 2-ClPh | 223–225 |

INDEX TABLE C

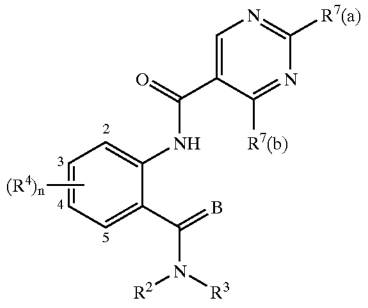

B is O, except where indicated

| Compound | $R^3$ | $R^2$ | $(R^4)_n$ | $R^7$(a) | $R^7$(b) | m.p. ° C. |
|---|---|---|---|---|---|---|
| C1 (Ex. 5) | i-Pr | H | 2-Me | $CF_3$ | $CH_3$ | 252–253 |
| C2 | i-Pr | H | 2-Cl | $CF_3$ | $CH_3$ | 260–262 |
| C3 | i-Pr | H | 2-Me | $CF_3$ | $OCH_3$ | 195–196 |
| C4 | i-Pr | H | 2-Me | $CF_3$ | $N(CH_3)_2$ | 270–272 |
| C5 | i-Pr | H | 2-Me | $CF_3$ | Et | 246–248 |
| C6 | i-Pr | H | 2-Me | $CF_3$ | Ph | 175–177 |
| C7 | i-Pr | H | 2-Me | i-Pr | Et | 179–182 |
| C8 | i-Pr | H | 2-Me | c-Pr | Et | 202–204 |
| C9 | i-Pr | H | 2-Me | i-Pr | $CH_3$ | 206–209 |
| C10 | i-Pr | H | 2-Me | c-Pr | $CH_3$ | 222–225 |
| C11 | i-Pr | H | 2-Me | c-Pr | Ph | 236–239 |
| C12 | i-Pr | H | 2-Me | $CF_3$ | $SCH_3$ | 244–247 |
| C13 | i-Pr | H | 2-Me | $CF_3$ | 1-pyrrolidinyl | 272–273 |

INDEX TABLE C-continued

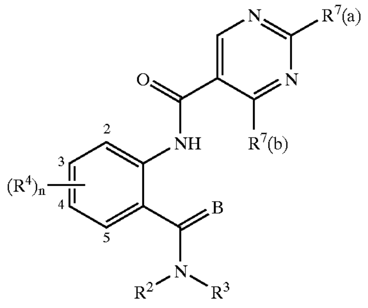

B is O, except where indicated

| Compound | $R^3$ | $R^2$ | $(R^4)_n$ | $R^7$(a) | $R^7$(b) | m.p. ° C. |
|---|---|---|---|---|---|---|
| C14 | i-Pr | H | 2-Me | $CF_3$ | $OCH_2C(Cl){=}CH_{q2}$ | 142–144 |
| C15 | Et | R | 2-Me | $CF_3$ | 2-MePh | 253–256 |
| C16 | i-Pr | H | 2-Me | $CF_3$ | 2-MePh | 244–246 |
| C17 | t-Bu | H | 2-Me | $CF_3$ | 2-MePh | 251–253 |
| C18 | Et | H | 2-Cl | $CF_3$ | 2-MePh | 242–243 |
| C19 | i-Pr | H | 2-Cl | $CF_3$ | 2-MePh | 237–240 |
| C20 | t-Bu | H | 2-Cl | $CF_3$ | 2-MePh | 253–255 |
| C21 | Et | H | 2-Me | $CF_3$ | 2-ClPh | 251–252 |
| C22 | i-Pr | H | 2-Me | $CF_3$ | 2-ClPh | 246–248 |
| C23 | t-Bu | H | 2-Me | $CF_3$ | 2-ClPh | 238–239 |
| C24 | Et | H | 2-Cl | $CF_3$ | 2-ClPh | 248–249 |
| C25 | i-Pr | H | 2-Cl | $CF_3$ | 2-ClPh | 254–255 |
| C26 | t-Bu | H | 2-Cl | $CF_3$ | 2-ClPh | 240–242 |
| C27 | Et | H | 2-Me | $CF_3$ | c-Pr | 236–238 |

INDEX TABLE C-continued

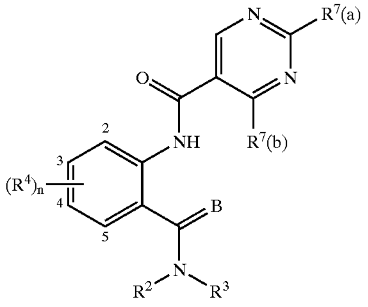

B is O, except where indicated

| Compound | $R^3$ | $R^2$ | $(R^4)_n$ | $R^7$(a) | $R^7$(b) | m.p. ° C. |
|---|---|---|---|---|---|---|
| C28 | i-Pr | H | 2-Me | $CF_3$ | c-Pr | 240–241 |
| C29 | t-Bu | H | 2-Me | $CF_3$ | c-Pr | 246–248 |
| C30 | Et | H | 2-Cl | $CF_3$ | c-Pr | 240–242 |
| C31 | i-Pr | H | 2-Cl | $CF_3$ | c-Pr | 232–235 |
| C32 | t-Bu | H | 2-Cl | $CF_3$ | c-Pr | 266–268 |
| C33 | Et | H | 2-Me | $CF_3$ | i-Pr | 230–231 |
| C34 | i-Pr | H | 2-Me | $CF_3$ | i-Pr | 211–214 |
| C35 | t-Bu | H | 2-Me | $CF_3$ | i-Pr | 210–213 |
| C36 | Et | H | 2-Cl | $CF_3$ | i-Pr | 247–249 |
| C37 | i-Pr | H | 2-Cl | $CF_3$ | i-Pr | 236–239 |
| C38 | t-Bu | H | 2-Cl | $CF_3$ | i-Pr | 235–238 |
| C39 | Et | H | 2-Me | $CF_2CF_3$ | 2-MePh | 247 |
| C40 | i-Pr | H | 2-Me | $CF_2CF_3$ | 2-MePh | 218–220 |
| C41 | t-Bu | H | 2-Me | $CF_2CF_3$ | 2-MePh | 224–226 |
| C42 | Et | H | 2-Cl | $CF_2CF_3$ | 2-MePh | 241–243 |
| C43 | i-Pr | H | 2-Cl | $CF_2CF_3$ | 2-MePh | 232–234 |
| C44 | t-Bu | H | 2-Cl | $CF_2CF_3$ | 2-MePh | 237–239 |
| C45 | Et | H | 2-Me | $CF_2CF_3$ | 2-ClPh | 255–257 |
| C46 | i-Pr | H | 2-Me | $CF_2CF_3$ | 2-ClPh | 224 |
| C47 | t-Bu | H | 2-Me | $CF_2CF_3$ | 2-ClPh | 215 |
| C48 | Et | H | 2-Cl | $CF_2CF_3$ | 2-ClPh | 248–250 |
| C49 | i-Pr | H | 2-Cl | $CF_2CF_3$ | 2-ClPh | 222–224 |
| C50 | t-Bu | H | 2-Cl | $CF_2CF_3$ | 2-ClPh | 242 |
| C51 | Et | H | 2-Me | $CF_2CF_3$ | Ph | 246–248 |
| C52 | i-Pr | H | 2-Me | $CF_2CF_3$ | Ph | 220 |
| C53 | t-Bu | H | 2-Me | $CF_2CF_3$ | Ph | 242 |
| C54 | Et | H | 2-Cl | $CF_2CF_3$ | Ph | 238–240 |
| C55 | i-Pr | H | 2-Cl | $CF_2CF_3$ | Ph | 260 |
| C56 | t-Bu | H | 2-Cl | $CF_2CF_3$ | Ph | 231–232 |
| C57 | i-Pr | H | 2-Me | $CF_2CF_3$ | $CH_3$ | 208 |

INDEX TABLE C-continued

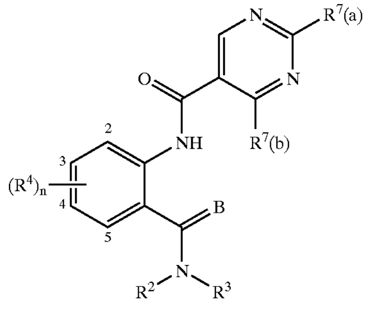

B is O, except where indicated

| Compound | $R^3$ | $R^2$ | $(R^4)_n$ | $R^7$(a) | $R^7$(b) | m.p. ° C. |
|---|---|---|---|---|---|---|
| C58 | t-Bu | H | 2-Me | $CF_2CF_3$ | $CH_3$ | 242–244 |
| C59 | Et | H | 2-Cl | $CF_2CF_3$ | $CH_3$ | 210–212 |
| C60 | i-Pr | H | 2-Cl | $CF_2CF_3$ | $CH_3$ | 195 |
| C61 | t-Bu | H | 2-Cl | $CF_2CF_3$ | $CH_3$ | 246–248 |
| C62 | Et | H | 2-Me | $CF_2CF_3$ | c-Pr | 224–225 |
| C63 | i-Pr | H | 2-Me | $CF_2CF_3$ | c-Pr | 232–234 |
| C64 | Et | H | 2-Cl | $CF_2CF_3$ | c-Pr | 216–218 |
| C65 | i-Pr | H | 2-Cl | $CF_2CF_3$ | c-Pr | 218–220 |
| C66 | t-Bu | H | 2-Cl | $CF_2CF_3$ | c-Pr | 210–212 |
| C67 | Et | H | 2-Me | $CF_2CF_3$ | i-Pr | 218–220 |
| C68 | i-Pr | H | 2-Me | $CF_2CF_3$ | i-Pr | 196–198 |
| C69 | t-Bu | H | 2-Me | $CF_2CF_3$ | i-Pr | 212–214 |
| C70 | Et | H | 2-Cl | $CF_2CF_3$ | i-Pr | 216–220 |
| C71 | i-Pr | H | 2-Cl | $CF_2CF_3$ | i-Pr | 215–218 |
| C72 | t-Bu | H | 2-Cl | $CF_2CF_3$ | i-Pr | 240–244 |
| C73 | i-Pr | H | 2-Me | $CF_2CF_3$ | Et | 210–212 |
| C74 | Et | H | 2-Me | $CF_2CF_3$ | Et | 230–232 |
| C75 | Et | H | 2-Cl | $CF_2CF_3$ | Et | 210–213 |
| C76 | i-Pr | H | 2-Cl | $CF_2CF_3$ | Et | 203–204 |
| C77 | t-Bu | H | 2-Cl | $CF_2CF_3$ | Et | 230–232 |
| C78 | Et | H | 2-Me | $CF_2CF_3$ | $CH_3$ | 238–240 |
| C79 | B is S i-Pr | H | 2-Me | $CF_3$ | Et | 190–193 |
| C80 | i-Pr | H | 2-Me | $CF_3$ | 2-$CF_3$Ph | 255–258 |

INDEX TABLE D

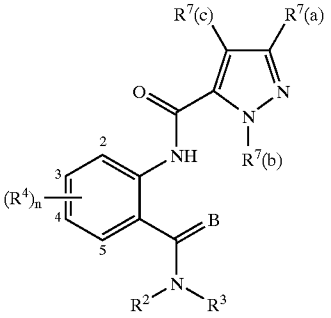

$R^7$(c) is H, except where indicated and B is O, except where indicated

| Compound | $R^3$ | $R^2$ | $(R^4)_n$ | $R^7$(a) | $R^7$(b) | m.p. ° C. |
|---|---|---|---|---|---|---|
| D1 | i-Pr | H | 2-Me | $CF_3$ | $CH_3$ | 200–204 |
| D2 (Ex. 2) | i-Pr | H | 2-Me | $CF_3$ | Et | 123–126 |

INDEX TABLE D-continued

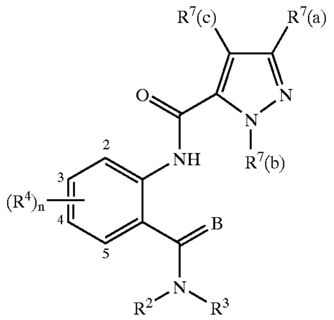

$R^7$(c) is H, except where indicated
and B is O, except where indicated

| Compound | $R^3$ | $R^2$ | $(R^4)_n$ | $R^7$(a) | $R^7$(b) | m.p. ° C. |
|---|---|---|---|---|---|---|
| D3 | i-Pr | H | 2-Cl | $CF_3$ | $CH_3$ | 233–235 |
| D4 | t-Bu | H | 2-Me | $CF_3$ | Et | 215–218 |
| D5 | i-Pr | H | 2-Me | $CH_3$ | Ph | 238–239 |
| D6 | i-Pr | H | 2-Me | $CH_3$ | $CH_3$ | 206–208 |
| D7 | i-Pr | H | 2-Me | $CH_3$ | $CH_2CF_3$ | 246–248 |
| D8 | i-Pr | H | 2-Cl | Et | $CF_3$ | 235–237 |
| D9 | i-Pr | H | 2-Me | $CH_3$ | $CH_3$, $R^7$(c) is Cl | 205–207 |
| D10 | i-Pr | H | 2-Me | $CH_3$ | 4-$CF_3$Ph | 256–258 |
| D11 | i-Pr | H | 2-Me | $CH_3$ | 2-$CF_3$Ph | 204–206 |
| D12 | t-Bu | H | 2-Me | $CH_3$ | Ph | 236–238 |
| D13 | i-Pr | H | 2-F | $CH_3$ | Ph | 227–229 |
| D14 | i-Pr | H | 5-F | $CH_3$ | Ph | 209–211 |
| D15 | i-Pr | H | 2-Cl | $CH_3$ | Ph | 233–234 |
| D16 | i-Pr | H | H | $CH_3$ | Ph | 215–217 |
| D17 | i-Pr | H | 2-$NO_2$ | $CH_3$ | Ph | 236–237 |
| D18 | i-Pr | H | 2-Cl | $CF_3$ | Ph | 240–242 |
| D19 (Ex. 6) | i-Pr | H | 2-Me | $CF_3$ | Ph | 260–262 |
| D20 | i-Pr | H | 2-I | $CH_3$ | Ph | 250–251 |
| D21 | i-Pr | H | 2-I | $CH_3$ | 2-$CF_3$Ph | 251–253 |
| D22 | H | H | 2-Me | $CH_3$ | Ph | 253–255 |
| D23 | Et | Et | 2-Me | $CH_3$ | Ph | 182–184 |
| D24 | t-Bu | H | 2-Cl | $CF_3$ | Ph | 232–234 |
| D25 | i-Pr | H | 2-I | $CF_3$ | Ph | 271–273 |
| D26 | t-Bu | H | 2-I | $CF_3$ | Ph | 249–250 |
| D27 | i-Pr | H | 2-Me | $CH_3$ | t-Bu | 210–211 |
| D28 | i-Pr | H | 2-Br | $CF_3$ | Ph | 257–259 |
| D29 | i-Pr | H | 2-Br | $CH_3$ | Ph | 246–247 |
| D30 | i-Pr | H | 2-Me | $CF_3$ | 2-pyridinyl | 237–238 |
| D31 | i-Pr | H | 2,5-$Cl_2$ | $CF_3$ | Ph | >250 |
| D32 | B is S, i-Pr | H | 2-Me | $CF_3$ | Ph | 169–172 |
| D33 | i-Pr | H | 2-Me | $CF_3$ | 2-ClPh | 208–209 |
| D34 | i-Pr | H | 2-Cl | $CF_3$ | 2-ClPh | 234–235 |
| D35 | i-Pr | H | 2-Me | $CF_3$ | 4-ClPh | 289–290 |
| D36 | i-Pr | H | 2-Cl | $CF_3$ | 4-ClPh | 276–278 |
| D37 | i-Pr | H | 2-Cl | $CF_3$ | 2-pyridinyl | 239–240 |
| D38 | i-Pr | H | 2-Me | $CF_3$ | 2-pyrimidinyl | 205–208 |
| D39 | i-Pr | H | 2-Me | $CF_3$ | 2-(3-$CH_3$-pyridinyl) | 183–187 |
| D40 | i-Pr | H | 2-Me | $CF_2CF_3$ | Ph | 231–232 |
| D41 | i-Pr | H | 2-Cl | $CF_2CF_3$ | Ph | 206–207 |
| D42 | t-Bu | H | 2-Cl | $CF_2CF_3$ | Ph | 212–213 |
| D43 | i-Pr | H | 2-Br | $CF_2CF_3$ | Ph | 219–222 |
| D44 | i-Pr | H | 2-Me | $CF_3$ | 3-ClPh | 278–280 |
| D45 | i-Pr | H | 2-Cl | $CF_3$ | 3-ClPh | 272–273 |
| D46 | i-Pr | H | 2-Me | $CF_3$ | 2-FPh | 217–218 |
| D47 | i-Pr | H | 2-Cl | $CF_3$ | 2-FPh | 220–221 |
| D48 | i-Pr | H | 2-Me | $CF_3$ | 4-FPh | 269–270 |
| D49 | i-Pr | H | 2-Cl | $CF_3$ | 4-EPh | 279–280 |
| D50 | i-Pr | H | 2-I | C-Pr | $CH_3$ | 222–224 |
| D51 | i-Pr | H | 5-I | c-Pr | $CH_3$ | 215–217 |
| D52 | i-Pr | H | 2-$CF_3$ | $CF_3$ | Ph | 247–249 |
| D53 | i-Pr | H | 2-Cl | $CF_3$ | i-Pr | 255–258 |
| D54 | i-Pr | H | 2-Me | $CF_3$ | 3-EPh | 277–278 |
| D55 | i-Pt | H | 2-Cl | $CF_3$ | 3-FPh | 256–257 |
| D56 | i-Pr | H | 2-Me | $CF_3$ | 2-$CF_3$Ph | 215–216 |
| D57 | i-Pr | H | 2-Cl | $CF_3$ | 2-$CF_3$Ph | 230–231 |
| D58 | i-Pr | H | 2-Me | $CF_3$ | 2-BrPh | 207–208 |
| D59 | i-Pt | H | 2-Cl | $CF_3$ | 2-BrPh | 239–240 |
| D60 | i-Pr | H | 2-$OCH_3$ | $CF_3$ | Ph | 215–216 |

INDEX TABLE D-continued

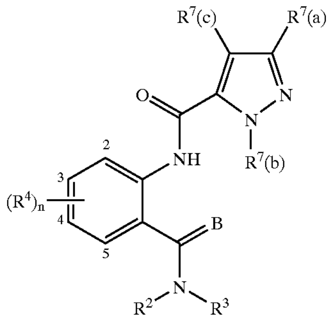

$R^7$(c) is H, except where indicated
and B is O, except where indicated

| Compound | $R^3$ | $R^2$ | $(R^4)_n$ | $R^7$(a) | $R^7$(b) | m.p. ° C. |
|---|---|---|---|---|---|---|
| D61 | i-Pr | H | 5-Cl | $CF_3$ | 2-(3-$CH_3$-pyridinyl) | 224–225 |
| D62 | i-Pr | H | 5-Me | $CF_3$ | 2-(3-Cl-pyridinyl) | 179–181 |
| D63 | s-Bu | H | 2-Cl | $CF_3$ | Ph | >240 |
| D64 | c-Pr | H | 2-Cl | $CF_3$ | Ph | >240 |
| D65 | Et | H | 2-Cl | $CF_3$ | Ph | >240 |
| D66 | t-Bu | H | 2-$CF_3$ | $CF_3$ | Ph | 230–233 |
| D67 | Et | H | 2-$CF_3$ | $CF_3$ | Ph | 246–249 |
| D68 | $CH(CH_3)CH_2SCH_3$ | H | 2-$CF_3$ | $CF_3$ | Ph | 215–217 |
| D69 | $CH(CH_3)CH_2OCH_3$ | H | 2-$CF_3$ | $CF_3$ | Ph | 220–223 |
| D70 | i-Pr | H | 5-Cl | $CF_3$ | 2-(3-Cl-pyridinyl) | 230–233 |
| D71 | i-Pr | H | 5-Me | $CF_3$ | 2-thiazolyl | 201–203 |
| D72 | i-Pr | H | 5-Me | $CF_3$ | 2-pyrazinyl | 252–253 |
| D73 | i-Pr | H | 5-Me | $CF_3$ | 4-pyridinyl | 224–228 |
| D74 | i-Pr | H | 2-Me | $CF_3$ | i-Pr | 236–243 |
| D75 | i-Pr | H | 2-Me | $CF_3$ | 2-$CH_3$Ph | 211–212 |
| D76 | i-Pr | H | 2-Cl | $CF_3$ | 2-$CH_3$Ph | 232–234 |
| D77 | i-Pr | H | 2-Br | $CF_3$ | 2-ClPh | 247–248 |
| D78 | t-Bu | H | 2-Me | $CF_3$ | 2-ClPh | 216–217 |
| D79 (Ex. 7) | i-Pr | H | 2-Me | $CF_3$ | 2-(3-$CF_3$-pyridinyl) | 227–230 |
| D80 | $CH_2CH_2Cl$ | H | 2-Cl | $CF_3$ | Ph | 237–242 |
| D81 | $CH_2CH_2CH_2Cl$ | H | 2-Cl | $CF_3$ | Ph | 233–239 |
| D82 | $CH(CH_3)CO_2CH_3$ | H | 2-Cl | $CF_3$ | Ph | 221–222 |
| D83 | S-CH(i-Pr)$CO_2CH_3$ | H | 2-Cl | $CF_3$ | Ph | 212–213 |
| D84 | i-Pr | H | 2-Me | $CF_3$ | 2,6-$C1_2$-Ph | 267–268 |
| D85 | i-Pr | H | 2-Cl | $CF_3$ | 2,6-$C1_2$-Ph | 286–287 |
| D86 | i-Pr | H | 2-Me | Br | Ph | 253–255 |
| D87 | i-Pr | H | 2-Cl | Br | Ph | 247–248 |
| D88 | i-Pr | H | 2-Me | $CF_3$ | i-Bu | 205–210 |
| D89 | i-Pr | H | 2-Me | $CF_3$ | $CH_2$Ph | 235–237 |
| D90 | i-Pr | H | 2-Me | $CF_3$ | 2-(3-$OCH_3$-pyridinyl) | 221–222 |
| D91 | i-Pr | H | 2-Me | $CF_3$ | 3-pyridinyl | 260–261 |
| D92 | i-Pr | H | 2-Me | $CF_3$ | 4-quinolinyl | >260 |
| D93 | i-Pr | H | 2-Me | CN | 2-(3-Cl-pyridinyl) | 203–204 |
| D94 | i-Pr | H | 2-Me | $CF_3$ | 2-4-F2-Ph | 245–246 |
| D95 | i-Pr | H | 2-Cl | $CF_3$ | 2,4-F2-Ph | 252–253 |
| D96 | i-Pr | H | 2-Me | $CF_3$ | 2-Et-Ph | 207–209 |
| D97 | i-Pr | H | 2-Cl | $CF_3$ | 2-Et-Ph | 221–222 |
| D98 | i-Pr | H | H | $CF_3$ | 2-ClPh | 206–207 |
| D99 | t-Bu | H | H | $CF_3$ | 2-ClPh | 197–198 |
| D100 | $CH(CH_3)CH_2OCH_3$ | H | H | $CF_3$ | 2-ClPh | 145–148 |
| D101 | $CH(CH_3)CH_2SCH_3$ | H | H | $CF_3$ | 2-ClPh | 158–160 |
| D102 | $CH(CH_3)CH_2SCH_3$ | H | 2-Cl | $CF_3$ | Ph | 184–186 |
| D103 | $CH(CH_3)CH_2OCH_3$ | H | 2-Cl | $CF_3$ | Ph | 217–218 |
| D104 | n-Pr | H | 2-Cl | $CF_3$ | Ph | 247–248 |
| D105 | i-Bu | H | 2-Cl | $CF_3$ | Ph | 244–245 |
| D106 | $CH_3$ | H | 2-Cl | $CF_3$ | Ph | >250 |
| D107 | i-Pr | Me | 2-Cl | $CF_3$ | Ph | 193–194 |
| D108 | $CH_2C{\equiv}CH$ | H | 2-Cl | $CF_3$ | Ph | >250 |
| D109 | $CH_2CH{=}CH_2$ | H | 2-Cl | $CF_3$ | Ph | 248–249 |
| D110 | $CH_2$(2-furanyl) | H | 2-Cl | $CF_3$ | Ph | 246–247 |
| D111 | i-Pr | H | 2-Me | Ph | 2-ClPh | 133–136 |
| D112 | i-Pr | H | 2-Cl | Ph | 2-ClPh | 220–221 |
| D113 | i-Pr | H | 2-Me | $CF_3$ | 4-(3,5-$C1_2$-pyridinyl) | 239–242 |
| D114 | i-Pr | H | 2-Cl | $CF_3$ | 4-(3,5-$C1_2$-pyridinyl) | 229–231 |
| D115 | $CH(CH_3)CH_2SCH_3$ | H | 2-Me | $CF_3$ | 2-ClPh | 194–195 |
| D116 | $CH(CH_3)CH_2OCH_3$ | H | 2-Me | $CF_3$ | 2-ClPh | 181–183 |
| D117 | s-Bu | H | 2-Me | $CF_3$ | 2-ClPh | 199–200 |
| D118 | c-Pr | H | 2-Me | $CF_3$ | 2-ClPh | 234–235 |

INDEX TABLE D-continued

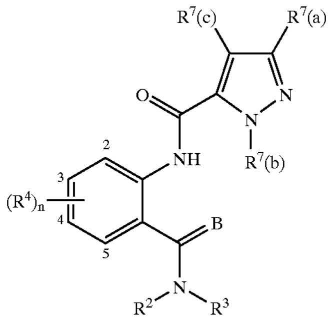

$R^7$(c) is H, except where indicated
and B is O, except where indicated

| Compound | $R^3$ | $R^2$ | $(R^4)_n$ | $R^7$(a) | $R^7$(b) | m.p. ° C. |
|---|---|---|---|---|---|---|
| D119 | n-Pr | H | 2-Me | $CF_3$ | 2-ClPh | 222–223 |
| D120 | i-Bu | H | 2-Me | $CF_3$ | 2-ClPh | 235–237 |
| D121 | Me | H | 2-Me | $CF_3$ | 2-ClPh | 242–243 |
| D122 | i-Pr | Me | 2-Me | $CF_3$ | 2-ClPh | 90–93 |
| D123 | $CH_2C{=}CH$ | H | 2-Me | $CF_3$ | 2-ClPh | 215–216 |
| D124 | Et | H | 2-Me | $CF_3$ | 2-ClPh | 228–229 |
| D125 | $CH_2CH{=}CH_2$ | H | 2-Me | $CF_3$ | 2-ClPh | 227–228 |
| D126 | $CH_2$(2-furanyl) | H | 2-Me | $CF_3$ | 2-ClPh | 218–219 |
| D127 | $CH(CH_3)CH_2SCH_3$ | H | 2-Me | $CF_3$ | Ph | 179–180 |
| D128 | $CH(CH_3)CH_2OCH_3$ | H | 2-Me | $CF_3$ | Ph | 219–220 |
| D129 | s-Bu | H | 2-Me | $CF_3$ | Ph | 244–245 |
| D130 | c-Pr | H | 2-Me | $CF_3$ | Ph | >250 |
| D131 | n-Pr | H | 2-Me | $CF_3$ | Ph | 238–239 |
| D132 | i-Bu | H | 2-Me | $CF_3$ | Ph | 237–238 |
| D133 | Me | H | 2-Me | $CF_3$ | Ph | 263–265 |
| D134 | i-Pr | Me | 2-Me | $CF_3$ | Ph | 178–179 |
| D135 | $CH_2C{=}CH$ | H | 2-Me | $CF_3$ | Ph | 253–254 |
| D136 | Et | H | 2-Me | $CF_3$ | Ph | 244–245 |
| D137 | $CH(2-CH{=}CH_2$ | H | 2-Me | $CF_3$ | Ph | 240–241 |
| D138 | $CH_2$(2-furanyl) | H | 2-Me | $CF_3$ | Ph | 245–246 |
| D139 | i-Pr | H | 2-$OCHF_2$ | $CF_3$ | 2-ClPh | 200–201 |
| D140 | i-Pr | H | 2-$OCH_3$ | $CF_3$ | 2-ClPh | 206–207 |
| D141 | i-Pr | H | 2-I | $CF_3$ | 2-ClPh | 253–256 |
| D142 | i-Pr | H | 2-Me | Br | 2-ClPh | 147–150 |
| D143 | i-Pr | H | 2-Cl | Br | 2-ClPh | 246–247 |
| D144 | i-Pr | H | 2-Me | $CF_3$ | 2-$OCH_3$Ph | 218–219 |
| D145 | i-Pr | H | 2-Cl | $CF_3$ | 2-$OCH_3$Ph | 243–244 |
| D146 | i-Pr | H | 2-Me | $CF_3$ | 1-isoquinolinyl | 252–253 |
| D147 | $CH(CH_3)CH_2SCH_3$ | H | 2-Cl | $CF_3$ | 2-ClPh | 217–218 |
| D148 | $CH(CH_3)CH_2OCH_3$ | H | 2-Cl | $CF_3$ | 2-ClPh | 207–208 |
| D149 | s-Bu | H | 2-Cl | $CF_3$ | 2-ClPh | 216–217 |
| D150 | c-Pr | H | 2-Cl | $CF_3$ | 2-ClPh | 261–262 |
| D151 | n-Pr | H | 2-Cl | $CF_3$ | 2-ClPh | 231–232 |
| D152 | i-Bn | H | 2-Cl | $CF_3$ | 2-ClPh | 255–256 |
| D153 | Me | H | 2-Cl | $CF_3$ | 2-ClPh | 233–235 |
| D154 | i-Pr | Me | 2-Cl | $CF_3$ | 2-ClPh | 127–128 |
| D155 | $CH_2C{=}CH$ | H | 2-Cl | $CF_3$ | 2-ClPh | 226–227 |
| D156 | Et | H | 2-Cl | $CF_3$ | 2-ClPh | 244–246 |
| D157 | $CH_2CH{=}CH_2$ | H | 2-Cl | $CF_3$ | 2-ClPh | 235–236 |
| D158 | $CH_2$(2-furanyl) | H | 2-Cl | $CF_3$ | 2-ClPh | 207–208 |
| D159 | i-Pr | H | $C{=}CSi(CH_3)_3$ | $CF_3$ | 2-ClPh | 256–258 |
| D160 | i-Pr | H | $C{=}CH$ | $CF_3$ | 2-ClPh | 228–230 |
| D161 | i-Pr | H | 2-Cl | $C{\equiv}CH$ | 2-ClPh | 219–222 |
| D162 | i-Pr | H | 2-Me | H | H, $R^7$(c) is $CH_3$ | 220–223 |
| D163 | i-Pr | H | 2-Me | $CH_3$ | Ph, $R^7$(c) is Cl | 209–210 |
| Dl64 | B is S i-Pr | H | 2-Cl | $CF_3$ | Ph | 169–174 |
| D165 | i-Pr | H | 2-Me | $CF_3$ | 2,6-$F_2$Ph | 223–225 |
| D166 | i-Pr | H | 2-Me | $CF_3$ | 2-C1-6-FPh | 203–206 |
| D167 | i-Pr | H | 2-Cl | $CF_3$ | 2-C1-6-FPh | 218–221 |
| D168 | i-Pr | H | 2-Me-4-Br | $CF_3$ | 2-EPh | 232–233 |
| D169 | t-Bu | H | 2-Cl | $CF_3$ | 2-(3-Cl-pyridinyl) | 250–251 |
| D170 | 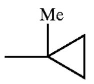 | H | 2-Cl | $CF_3$ | 2-(3-Cl-pyridinyl) | >250 |
| D171 | Et | Et | 2-Cl | $CF_3$ | 2-ClPh | 243–247 |

INDEX TABLE D-continued

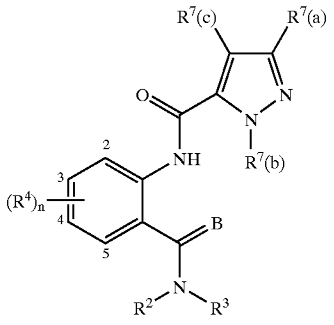

$R^7$(c) is H, except where indicated
and B is O, except where indicated

| Compound | $R^3$ | $R^2$ | $(R^4)_n$ | $R^7$(a) | $R^7$(b) | m.p. ° C. |
|---|---|---|---|---|---|---|
| D172 | Me | Me | 2-Cl | $CF_3$ | 2-ClPh | 234–235 |
| D173 | Et | Et | 2-Me | $CF_3$ | 2-ClPh | 237–238 |
| D174 | Me | Me | 2-Me | $CF_3$ | 2-ClPh | 225–226 |
| D175 | $CH_2CH_2N(Me)_2$ | H | 2-Me | $CF_3$ | 2-ClPh | 188–190 |
| D176 | i-Pr | H | 2-Cl | $CF_3$ | 2-pyrazinyl | 242–243 |
| D177 | t-Bu | H | 2-Me-4-Br | $CF_3$ | 2-ClPh | >260 |
| D178 | $CH(CH_3)CH_2OCH_3$ | H | 2-Me | $CF_3$ | 2-(3-Cl-pyridinyl) | 176–177 |
| D179 | $CH(CH_3)CH_2SCH_3$ | H | 2-Me | $CF_3$ | 2-(3-Cl-pyridinyl) | 196–197 |
| D180 | $CH(CH_3)CH_2OCH_3$ | H | 2-Cl | $CF_3$ | 2-(3-Cl-pyridinyl) | 197–198 |
| D181 | $CH(CH_3)CH_2SCH_3$ | H | 2-Cl | $CF_3$ | 2-(3-Cl-pyridinyl) | 202–203 |
| D182 | i-Pr | H | 2-Me | $CF_3$ | 2-IPh | 221–222 |
| D183 | i-Pr | H | 2-Cl | $CF_3$ | 2-IPh | 238–240 |
| D184 | i-Pr | H | 2-Me | $CF_3$ | 2-(C≡CH)-Ph | 215–217 |
| D185 | i-Pr | H | 2-Cl | $CF_3$ | 2-(C≡CH)-Ph | 244–246 |
| D186 | t-Bu | H | 2-Cl | $CF_3$ | 2-(3-Cl-pyridinyl) | 250–251 |
| D187 | 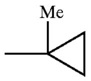 | H | 2-Cl | $CF_3$ | 2-(3-Cl-pyridinyl) | >250 |
| D188 | i-Pr | H | 2-Me | $CF_3$ | 2-Cl-4-FPh | 203–265 |
| D189 | i-Pr | H | 2-Cl | $CF_3$ | 2-Cl-4-FPh | 218–219 |
| D190 | Me | Me | 2-Me | $CF_3$ | 2-ClPh | 225–226 |
| D191 | Et | Et | 2-Me | $CF_3$ | 2-ClPh | 243–247 |
| D192 | i-Pr | H | 2-Me | $CF_3$ | 2,6-$Me_2$Ph | 259–260 |
| D193 | i-Pr | H | 2-Cl | $CF_3$ | 2,6-$Me_2$Ph | 268–269 |
| D194 | i-Pr | H | 2-Me | $CF_3$ | 2,6-$Cl_2$-CNPh | * |
| D195 | i-Pr | H | 2-Me | $CF_3$ | 2-CNPh | 225–235 |
| D196 | i-Pr | H | 2-Me | $CF_3$ | 2-($OCF_3$)Ph | 214–215 |
| D197 | i-Pr | H | 2-Cl | $CF_3$ | 2-($OCF_3$)Ph | 223–224 |
| D198 | i-Pr | H | 2-Me | $CF_3$ | 2-Br-4-FPh | 202–203 |
| D199 | i-Pr | H | 2-Cl | $CF_3$ | 2-Br-4-FPh | 222–223 |
| D200 | i-Pr | H | 2-Me | $CF_3$ | 2-(3-Me-pyrazinyl) | 205–207 |
| D201 | Me | H | 2-Cl | $CF_3$ | 2-(3-Cl-pyridinyl) | 215–220 |
| D202 | $CH_2C≡CH$ | H | 2-Cl | $CF_3$ | 2-(3-Cl-pyridinyl) | 197–198 |
| D203 | Me | H | 2-Me | $CF_3$ | 2-(3-Cl-pyridinyl) | 193–196 |
| D204 | Et | H | 2-Me | $CF_3$ | 2-(3-Cl-pyridinyl) | 204–206 |
| D205 | $CH_2C≡CH$ | H | 2-Me | $CF_3$ | 2-(3-Cl-pyridinyl) | 177–178 |
| D206 | i-Pr | H | 2-Me | $CF_3$ | 4-(8-Cl-quinolinyl) | >250 |
| D207 | i-Pr | H | 2-Me | $CF_3$ | 4-(2-Me-quinolinyl) | >250 |
| D208 | i-Pr | H | 2-Cl | $CF_3$ | 4-(2-Me-quinolinyl) | >250 |
| D209 | i-Pr | H | 2-Me | $CF_3$ | 4-(7-Cl-quinolinyl) | >250 |
| D210 | i-Pr | H | 2,4-$Br_2$ | $CF_3$ | 2-ClPh | 233–234 |
| D211 | i-Pr | H | 2-Br | Br | 2-ClPh | 255–258 |
| D212 | Me | H | 2-Me | Br | 2-ClPh | 236–237 |
| D213 | t-Bu | H | 2-Cl | Br | 2-ClPh | 260–261 |
| D214 | Et | H | 2-Me | Br | 2-ClPh | 254–255 |
| D215 | t-Bu | H | 2-Me | Br | 2-ClPh | 259–260 |
| D216 | c-Bu | H | 2-Cl | CN | 2-(3-Cl-pyridinyl) | 177–180 |
| D217 | i-Pr | H | 2-Me | $CF_3$ | 2-(3-Cl-pyridinyl) | 237–239 |
| D218 | i-Pr | H | 2-Me | $CF_3$ | 4-(6-Cl-quinolinyl) | >250 |
| D219 | Me | Me | 2-Me | $CF_3$ | 4-(6-Cl-quinolinyl) | >250 |
| D220 | H | O-i-Pr | 2-Cl | $CF_3$ | 2-ClPh | 218–219 |
| D221 | i-Pr | H | 2-Cl | CN | 2-(3-Cl-pyridinyl) | 195–200 |
| D222 | t-Bu | H | 2-Cl | CN | 2-(3-Cl-pyridinyl) | >250 |

INDEX TABLE D-continued

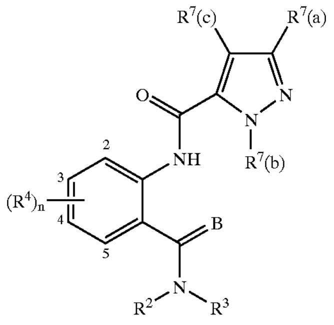

$R^7$(c) is H, except where indicated
and B is O, except where indicated

| Compound | $R^3$ | $R^2$ | $(R^4)_n$ | $R^7$(a) | $R^7$(b) | m.p. ° C. |
|---|---|---|---|---|---|---|
| D223 | Et | H | 2-Cl | CN | 2-(3-Cl-pyridinyl) | 200–205 |
| D224 | i-Pr | H | 2-Cl | $CF_3$ | 2-(3-Me-pyrazinyl) | 225–230 |
| D225 | t-Bu | H | 2-Cl | $CF_3$ | 2-(3-Me-pyrazinyl) | 235–240 |
| D226 | Et | H | 2-CL | $CF_3$ | 2-(3-Me-pyrazinyl) | 210–220 |
| D227 | i-Pr | H | 2-Me | $CF_3$ | 3-(2-Cl-pyridinyl) | * |
| D228 | i-Pr | H | 2-Cl | $CF_3$ | 2,3-$Cl_2$Ph | 217–219 |
| D229 | t-Bu | H | 2-Cl | $CF_3$ | 2,3-$Cl_2$Ph | 254–256 |
| D230 | i-Pr | H | 2-Me | $CF_3$ | 2,3-$Cl_2$Ph | 208–209 |
| D231 | t-Bu | H | 2-Me | $CF_3$ | 2,3-$Cl_2$Ph | 232–233 |
| D232 | t-Bu | H | 2-Me-4-Br | Br | 2-ClPh | 239–241 |
| D233 | Me | H | 2-Me-4-Br | Br | 2-ClPh | 150–152 |
| D234 | Et | H | 2-Me-4-Br | Br | 2-ClPh | 223–225 |
| D235 | i-Pr | H | 2-Me-4-Br | Br | 2-ClPh | 197–198 |
| D236 | Me | H | 2-Me | $CF_3$ | 2-FPh | 245–247 |
| D237 | $CH_2C{\equiv}CH$ | H | 2-Me | $CF_3$ | 2-FPh | 222–227 |
| D238 | H | O-i Pr | 2-Cl | CN | 2-(3-Cl-pyridinyl) | 205–206 |
| D239 | H | O-i Pr | 2-Me | CN | 2-(3-Cl-pyridinyl) | 210–211 |
| D240 | Me | Me | 2-Cl | $CF_3$ | 2-ClPh | 234–236 |
| D241 | $CH_2C{\equiv}CH$ | H | 2-Me-4-Br | Br | 2-ClPh | 187–188 |

*See Index Table Q for $^1$H NMR data

INDEX TABLE E

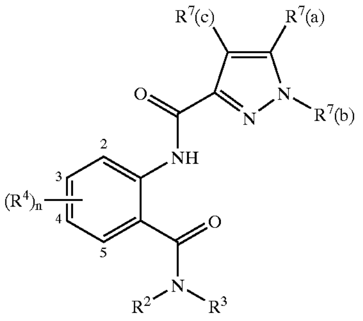

| Compound | $R^3$ | $R^2$ | $(R^4)_n$ | $R^7$(a) | $R^7$(b) | $R^7$(c) | m.p. ° C. |
|---|---|---|---|---|---|---|---|
| E1 | i-Pr | H | 2-Me | $CH_3$ | $CH_3$ | H | 143–145 |
| E2 | i-Pr | H | 2-Me | $CH_3$ | $CH_2CF_3$ | H | 198–199 |
| E3 | i-Pr | H | 2-Me | $CH_3$ | $CH_3$ | Cl | 188–190 |
| E4 | i-Pr | H | 2-Me | $CH_3$ | 4-$CF_3$-Ph | H | 198–199 |
| E5 | i-Pr | H | 2-Me | $CH_3$ | 2-$CF_3$-Ph | H | 211–213 |
| E6 | i-Pr | H | 2-Me | $CH_3$ | t-Bu | H | 125–127 |
| E7 | i-Pr | H | 2-Me | $CF_3$ | $CH_2$Ph | H | 130–135 |
| E8 | i-Pr | H | 2-Me | H | Ph | $CH_3$ | 249–250 |
| E9 | i-Pr | H | 2-Me | H | $CH_3$ | Ph | 268–270 |
| E10 | i-Pr | H | 2-Cl | H | Ph | $CH_3$ | 260–261 |

INDEX TABLE E-continued

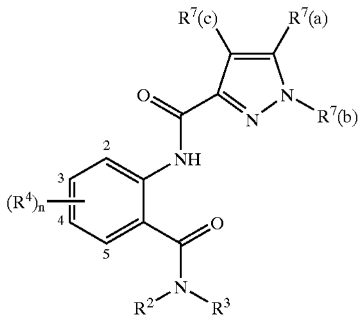

| Compound | $R^3$ | $R^2$ | $(R^4)_n$ | $R^7$(a) | $R^7$(b) | $R^7$(c) | m.p. ° C. |
|---|---|---|---|---|---|---|---|
| E11 | i-Pr | H | 2-Me | H | $CH_2CF_3$ | Ph | 213–215 |
| E12 | i-Pr | H | 2-Cl | H | $CH_2CF_3$ | Ph | 208–209 |
| E13 | i-Pr | H | 2-Me | H | $CHF_2$ | Ph | * |
| E14 | i-Pr | H | 2-Me | $CF_3$ | 2-(3-Cl-pyridinyl) | H | 249–250 |

*See Index Table Q for $^1$H NMR data

INDEX TABLE F

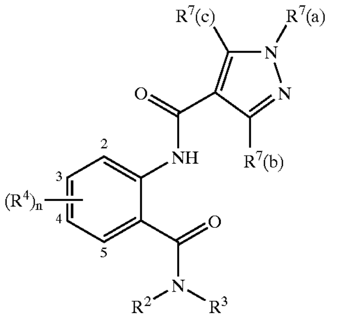

| Compound | $R^3$ | $R^2$ | $(R^4)_n$ | $R^7(a)$ | $R^7(b)$ | $R^{\&}(c)$ | m.p. ° C. |
|---|---|---|---|---|---|---|---|
| F1 | i-Pr | H | 2-Me | $CH_2CF_3$ | $CH_3$ | H | 254–255 |
| F2 | i-Pr | H | 2-Me | $CH_2CF_3$ | H | $CH_3$ | 200–205 |
| F3 | i-Pr | H | 2-Me | $CH_2(3\text{-}CF_3)Ph$ | H | $CH_3$ | 212–215 |
| F4 | i-Pr | H | 2-Cl | $CH_2CF_3$ | H | $CH_3$ | 215–217 |
| F5 | i-Pr | H | 2-Me | Ph | H | $CF_3$ | 223–224 |
| F6 | i-Pr | H | 2-Cl | Ph | H | $CF_3$ | 206–208 |
| F7 | i-Pr | H | 2-Me | $CH_2CF_3$ | H | Ph | 156–158 |
| F8 | i-Pr | H | 2-Cl | $CH_2CF_3$ | H | Ph | 162–164 |

INDEX TABLE G

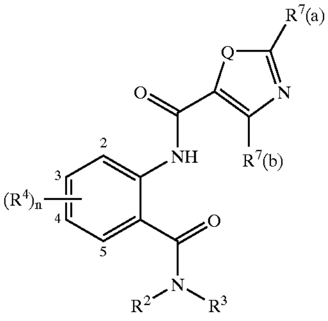

| Compound | Q | $R^3$ | $R^2$ | $(R^4)_n$ | $R^7(a)$ | $R^7(b)$ | m.p. ° C. |
|---|---|---|---|---|---|---|---|
| G1 | S | i-Pr | H | 2-Me | $4\text{-}OCF_3Ph$ | $CH_3$ | 233–234 |
| G2 | S | i-Pr | H | 2-Me | $OCH_2CF_2CF_3$ | $CH_3$ | 170–173 |
| G3 | S | i-Pr | H | 2-Me | Cl | $CH_3$ | 164–167 |
| G4 | S | i-Pr | H | 2-Me | $CH_3$ | Ph | 216–219 |
| G5 | S | i-Pr | H | 2-Me | $C(CH_3)_2OH$ | $CH_3$ | * |
| G6 | S | i-Pr | H | 2-Me | i-Pr | $CH_3$ | 180–181 |
| G7 | S | i-Pr | H | 2-Me | i-Pr | Ph | 182–183 |
| G8 | O | i-Pr | H | 2-Me | i-Pr | $CH_3$ | 163–164 |

*See Index Table Q for $^1H$ NMR data

INDEX TABLE H

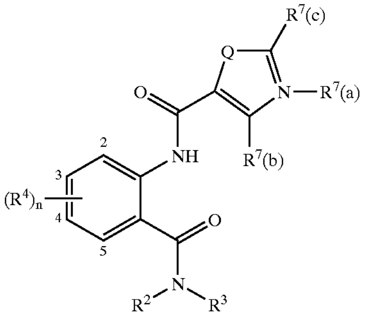

| Compound | Q | $R^3$ | $R^2$ | $(R^4)_n$ | $R^7(a)$ | $R^7(b)$ | $R^7(c)$ | m.p. ° C. |
|---|---|---|---|---|---|---|---|---|
| H1 | S | i-Pr | H | 2-Me | H | H | H | 192–195 |
| H2 | S | $CH(CH_3)CH_2OCH_3$ | H | 2-Me | H | H | H | 120–123 |
| H3 | S | t-Bu | H | 2-Me | H | H | H | 120–123 |
| H4 | NMe | i-Pr | H | 2-Me | Me | H | H | 193–195 |
| H5 | NPh | i-Pr | H | 2-Me | H | Me | H | 188–192 |
| H6 | NPh | i-Pr | H | 2-Me | Br | H | H | 176–179 |
| H7 | NPh | i-Pr | H | 2-Me | Br | H | Br | 215–216 |
| H8 | NPh | i-Pr | H | 2-Me | H | H | Br | 150–154 |
| H9 | NPh | i-Pr | H | 2-Me | $CF_3$ | H | H | 182–184 |
| H10 | N(2-ClPh) | i-Pr | H | 2-Me | Br | H | H | 100–110 |
| H11 | N(2-FPh) | i-Pr | H | 2-Me | Br | H | H | 178–179 |
| H12 | N(2-FPh) | t-Bu | H | 2-Me | Br | H | H | 186–188 |
| H13 | N(2-ClPh) | t-Bu | H | 2-Me | Br | H | H | 225–229 |

INDEX TABLE J

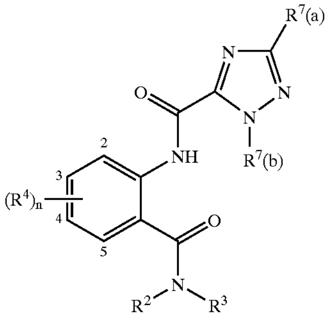

| Compound | $R^3$ | $R^2$ | $(R^4)_n$ | $R^7$(a) | $R^7$(b) | m.p. ° C. |
|---|---|---|---|---|---|---|
| J1 | i-Pr | H | 2-Me | Me | Me | 221–222 |
| J2 | i-Pr | H | H | $CF_3$ | Ph | 279–281 |
| J3 | i-Pr | H | 2-Me | $CF_3$ | Ph | 263–268 |
| J4 | i-Pr | H | 2-Cl | $CF_3$ | 2-ClPh | 235–238 |
| J5 | i-Pr | H | 2-Cl | $CF_3$ | Ph | 245–246 |
| J6 | i-Pr | H | 2-Me | $CF_3$ | 2-ClPh | 240–242 |
| J7 | i-Pr | H | 2-Cl | $CF_3$ | 2-F-4-ClPh | 246–247 |
| J8 | i-Pr | H | 2-Me | $CF_3$ | 2-F-4-ClPh | 266–268 |
| J9 | i-Pr | H | 2-Me | $CF_3$ | 2-pyridinyl | 258–260 |

INDEX TABLE K

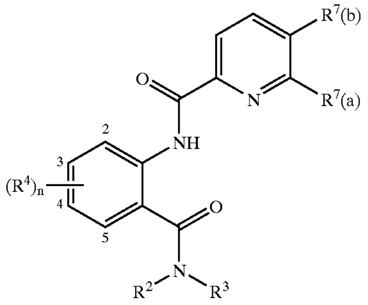

| Compound | $R^3$ | $R^2$ | $(R^4)_n$ | $R^7$(a) | $R^7$(b) | m.p. ° C. |
|---|---|---|---|---|---|---|
| K1 | i-Pr | H | 2-Me | Br | H | 177–180 |
| K2 | t-Bu | H | 2-Me | Br | H | 188–194 |

INDEX TABLE L

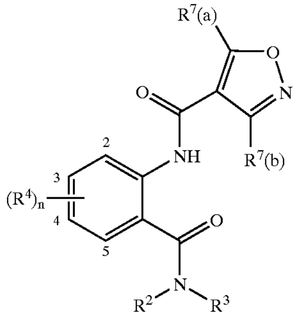

| Compound | $R^3$ | $R^2$ | $(R^4)_n$ | $R^7$(a) | $R^7$(b) | m.p. ° C. |
|---|---|---|---|---|---|---|
| L1 | i-Pr | H | 2-Me | Me | Me | 203–205 |
| L2 | i-Pr | H | 2-Me | Me | 2,6-$Cl_2$Ph | 218–223 |

INDEX TABLE M

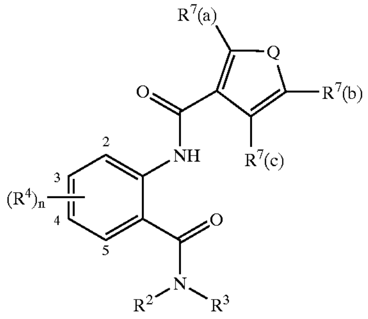

| Compound | Q | $R^3$ | $R^2$ | $(R^4)_n$ | $R^7$(a) | $R^7$(b) | $R^7$(c) | m.p. ° C. |
|---|---|---|---|---|---|---|---|---|
| M1 | S | i-Pr | H | 2-Me | Cl | Me | H | 203–205 |
| M2 | S | i-Pr | H | 2-Cl | Cl | Me | H | 210–213 |
| M3 | $NCHF_2$ | t-Bu | H | 2-Me | H | H | Ph | 165–166 |
| M4 | NH | i-Pr | H | 2-Me | $CF_3$ | Ph | H | 118–120 |
| M5 | NMe | i-Pr | H | 2-Me | $CF_3$ | Ph | H | 110–112 |
| M6 | $NCHF_2$ | i-Pr | H | 2-Me | 2-FPh | H | H | 143–144 |

INDEX TABLE M-continued
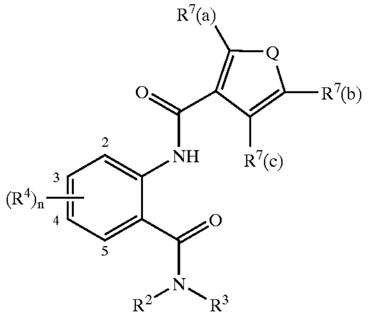
| Compound | Q | $R^3$ | $R^2$ | $(R^4)_n$ | $R^7$(a) | $R^7$(b) | $R^7$(c) | m.p. ° C. |
|---|---|---|---|---|---|---|---|---|
| M7 | $NCHF_2$ | t-Bu | H | 2-Me | 2-FPh | H | H | 120–123 |
| M8 | $NCH_2CF_3$ | i-Pr | H | 2-Me | 2-FPh | H | H | 235–237 |
INDEX TABLE N
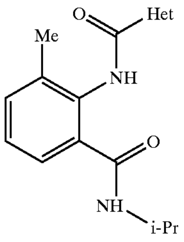
| Compound | Het | m.p. ° C. |
|---|---|---|
| N1 | 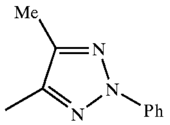 | 169–171 |
| N2 | 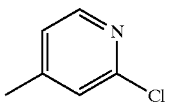 | 227–230 |
INDEX TABLE N-continued
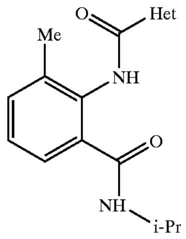
| Compound | Het | m.p. ° C. |
|---|---|---|
| N3 | 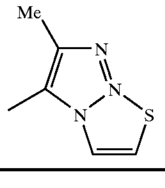 | 243–246 |
INDEX TABLE P
| Compound | | m.p. ° C. |
|---|---|---|
| P1 | 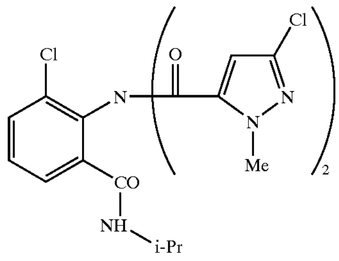 | 178–179 |
INDEX TABLE Q
| Compd. No. | $^1H$ NMR Data ($CDCl_3$ solution unless indicated otherwise)[a] |
|---|---|
| D194 | (DMSO-d6) δ 1.03 (d, 6H), 2.18 (s, 3H), 3.92 (m, 1H), 7.22–7.30 (m, 2H), 7.35 (m, 1H), 7.62 (dd, 1H), 7.81 (s, 1H), 8.02 (d, 1H), 8.15 (dd, 1H), 8.55 (dd, 1H), 10.34 (s, 1H). |

INDEX TABLE Q-continued

| Compd. No. | $^1$H NMR Data ($CDCl_3$ solution unless indicated otherwise)[a] |
|---|---|
| D227 | (DMSO-d6) δ 1.01 (d, 6H), 2.16 (s, 3H), 3.92 (m, 1H), 7.27 (m, 2H), 7.35 (m, 1H), 7.89 (s, 1H), 7.96 (m, 1H), 8.37 (s, 2H), 10.42 (s, 1H). |
| G5 | δ 1.22 (d, 6H), 2.05 (s, 6H), 2.31 (s, 3H), 2.76 (s, 3H), 4.18 (m, 1H), 5.94 (d, 1H), 7.20 (dd, 1H), 7.29 (d, 1H), 7.38 (d, 1H), 9.83 (br s, 1H). |
| E13 | δ 1.12 (d, 6H), 2.32 (s, 1H), 4.14 (m 1H), 4.95 (d, 1H), 7.19 (dd, 1H), 7.28 (t, 1H), 7.32 (m, 5H), 7.59 (dd, 2H), 7.92 (s, 1H), 9.51 (br s, 1H). |

[a] $^1$H NMR data are in ppm downfield from teframethylsilane. Couplings are designated by (s)-singlet, (d)-doublet, (t)-triplet, (q)-quartet, (m)-multiplet, (dd)-doublet of doublets, (dt)-doublet of triplets, (br s)-broad singlet.

BIOLOGICAL EXAMPLES OF THE INVENTION TEST

Application: Compounds are formulated in a10% acetone, 90% water and 300 ppm X-77 surfactant solution, unless otherwise indicated. The formulated compounds are applied with a SUJ2 atomizer nozzle with ⅛ JJ custom body (Spraying Systems) positioned ½" above the top of each test unit. There are 6 of these nozzles that make up the spray boom and this is fixed in a belt sprayer. A rack (or carrier) of 6 different insect test units is placed on the conveyor belt and stops so that each unit is centered under a nozzle. Once the rack is centered, 1 mL of liquid is sprayed into each test unit; the rack then continues down the belt to the end of the sprayer to be off-loaded. All experimental compounds in this screen are sprayed at 250 ppm and replicated three times.

Diamondback Moth (DBM)—*Plutella Xylostella*: The test unit consists of a small self-contained unit with a 12–14 day old radish plant inside. These are pre-infested (using a core sampler) with 10–15 neonate larvae on a piece of insect diet. Once 1 mL of formulated compound has been sprayed into each test unit, the test units are allowed to dry for 1 hour before a black, screened cap is placed on the top of the cylinder. They are held for 6 days in a growth chamber at 25° C. and 70% relative humidity.

Plant feeding damage was visually assessed on a scale of 0–10 where 0 is no feeding, 1 is 10% or less feeding, 2 is 20% or less feeding, 3 is 30% or less feeding through a maximum score of 10 where 10 is 100% of foliage consumed. Of the compounds tested the following provided excellent levels of plant protection (ratings of 0–1, 10% or less feeding dimage): 1, 2, 3, 4, 6, 7, 9, 10, 13, 14, 15, 19, 20, 24, 27, 28, 29, 30, 31, 32, 33, 35, 37, 38, 39, 51, 52, 53, 60, 61, 62, 63, 64, 65, 66, 68, 69, 72, 73, 74, 75, 76, 79, 80, 84, 86, 88, 89, 90, 92, 96, 97, 98, 99, 100, 101, 102, 103, 107, 113, 124, 126, 127, 143, 144, 146, 147, 148, 150, 151, 152, 153, 158, 159, 160, 161, 162, 163, 164, 165, 166, 167, 169, 170, 171, 174, 183, 184, 185, 186, 187, 188, 189, 190, 191, 193, 194, 195, 196, 198, 202, 203, 204, 205, 206, 207, 208, 209, 210, 211, 212, 213, 214, 215, 216, 217, 218, 219, 220, 222, 223, 225, 227, 228, 229, 230, 231, 232, 233, 235, 238, 239, 240, 244, 245, 246, 248, 249, 250, 251, 252, 253, 256, 257, 275, 276, 277, 278, B2, B4, B5, B6, B7, B8, B9, B10, B11, B12, B13, B14, B15, B16, B17, B18, B19, B20, B21, B23, B24, B25, B28, B29, B30, B31, B32, B33, B35, B37, B38, B39, B40, B42, B43, B44, B45, B46, B47, B48, B49, B50, B53, B55, B57, B58, B59, B60, B61, B62, B63, B64, B66, B67, B68, B69, B70, B71, B72, B74, B75, B76, C1, C2, C3, C4, C5, C7, C8, C9, C10, C11, C12, C79, D2, D3, D4, D5, D6, D7, D8, D11, D12, D13, D14, D15, D16, D18, D19, D20, D23, D24, D25, D26, D27, D28, D29, D30, D32, D33, D34, D37, D38, D39, D40, D41, D42, D45, D46, D47, D48, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D81, D83, D84, D85, D86, D87, D88, D89, D91, D92, D93, D94, D95, D96, D97, D111, D113, D114, D115, D116, D117, D118, D119, D120, D121, D122, D123, D124, D125, D126, D162, D164, E4, F2, F5, F6, F7, F8, G2, G3, G5, H1, H2, H3, H4, J3, J4, J6, M1, M3, N2 and P1.

What is claimed is:

1. A method for controlling arthropods comprising contacting the arthropods or their environment with an arthropodicidally effective amount of a compound of Formula 1, its N-oxide or agriculturally suitable salts

1

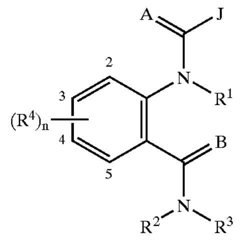

wherein

A and B are independently O or S;

J is a 6- membered heteroaromatic ring optionally substituted with 1 to 4 $R^7$;

n is 1 to 4;

$R^1$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or $R^1$ is $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl or C(=A)J;

$R^2$ is H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^3$ is H; G; $C_1$–$C_6$ alkyl, $C_2$–$C_6$ alkenyl, $C_2$–$C_6$ alkynyl, $C_3$–$C_6$ cycloalkyl, each optionally substituted with one or more substituents selected from the group consisting of halogen, G, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_2$–$C_6$ alkoxycarbonyl, $C_2$–$C_6$ alkylcarbonyl, $C_3$–$C_6$ trialkylsilyl, and a phenyl, phenoxy or 5- or 6-membered heteroaromatic ring, each ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl and $C_3$–$C_6$ trialkylsilyl; $C_1$–$C_4$ alkoxy; $C_1$–$C_4$ alkylamino; $C_2$–$C_8$ dialkylamino; $C_3$–$C_6$ cycloalkylamino; $C_2$–$C_6$ alkoxycarbonyl or $C_2$–$C_6$ alkylcarbonyl; or $R^2$ and $R^3$ can be taken together with the nitrogen to which they are attached to form a ring containing 2 to 6 atoms of carbon and optionally one additional atom of nitrogen, sulfur or oxygen, said ring may be optionally substituted with 1 to 4 substituents selected from the group consisting of $C_1$–$C_2$ alkyl, halogen, CN, $NO_2$ and $C_1$–$C_2$ alkoxy;

G is a 5- or 6-membered nonaromatic carbocyclic or heterocyclic ring, optionally including one or two ring members selected from the group consisting of C(═O), SO or $S(O)_2$ and optionally substituted with 1 to 4 substituents selected from the group consisting of $C_1$–$C_2$ alkyl, halogen, CN, $NO_2$ and $C_1$–$C_2$ alkoxy;

each $R^4$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, or $C_3$–$C_6$ trialkylsilyl; or each $R^4$ is independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_{1-C4}$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

each $R^7$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, or $C_3$–$C_6$ trialkylsilyl; or each $R^7$ is independently a phenyl, benzyl, benzoyl, phenoxy, 5- or 6-membered heteroaromatic ring or an aromatic 8-, 9- or 10-membered fused heterobicyclic ring system, each ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl and $C_3$–$C_6$ trialkylsilyl.

2. The method of claim 1 wherein

J is a 6-membered heteroaromatic ring selected from the group consisting of J-4 and J-5

J-4

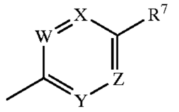

and

J-5

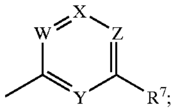

and

W, X, Y and Z are independently N or $CR^7$, provided that at least one of W, X, Y or Z is N.

3. The method of claim 2 wherein

A and B are O;

n is 1 to 2;

$R^1$ is H, $C_1$–$C_4$ alkyl, $C_2$–$C_4$ alkenyl, $C_2$–$C_4$ alkynyl, $C_2$–$C_6$ alkylcarbonyl or $C_2$–$C_6$ alkoxycarbonyl;

$R^2$ is H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;

$R^3$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $C_1$–$C_2$ alkoxy, $C_1$–$C_2$ alkylthio, $C_1$–$C_2$ alkylsulfinyl and $C_1$–$C_2$ alkylsulfonyl;

one of the $R^4$ groups is attached to the phenyl ring at the 2-position, and said $R^4$ is $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl or $C_1$–$C_4$ haloalkylsulfonyl; and each $R^7$ is independently H, $C_1$–$C_4$ alkyl, $C_1$–$C_4$ haloalkyl, halogen, CN, $NO_2$, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl or $C_2$–$C_4$ alkoxycarbonyl; or a phenyl or a 5- or 6-membered heteroaromatic ring, each ring optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

4. The method of claim 3 wherein J is selected from the group consisting of pyridine and pyrimidine, each optionally substituted with 1 to 3 $R^7$.

5. The method of claim 4 wherein $R^1$ and $R^2$ are both H;

$R^3$ is $C_1$–$C_4$ alkyl optionally substituted with halogen, CN, $OCH_3$, $S(O)_pCH_3$;

each $R^4$ is independently H, $CH_3$, $CF_3$, $OCF_3$, $OCHF_2$, $S(O)_pCF_3$, $S(O)_pCHF_2$, CN or halogen;

each $R^7$ is independently H, halogen, $CH_3$, $CF_3$, $OCHF_2$, $S(O)_pCF_3$, $S(O)_pCHF_2$, $OCH_2CF_3$, $OCF_2CHF_2$, $S(O)_pCH_2CF_3$, $S(O)_pCF_2CHF_2$; or phenyl, pyrazole, imidazole, triazole, pyridine or pyrimidine, each ring optionally substituted with $C_1$–$C_4$ alkyl, $C_1$–$C_4$ haloalkyl, $C_1$–$C_4$ alkoxy, $C_1$–$C_4$ haloalkoxy, $C_{-C4}$ alkylthio, $C_1$–$C_4$ alkylsulfinyl, $C_1$–$C_4$ alkylsulfonyl, halogen or CN; and p is 0, 1 or 2.

6. The method of claim 5 wherein J is a pyridine optionally substituted with 1 to 3 $R^7$.

7. The method of claim 6 wherein one $R^7$ is a phenyl optionally substituted with $C_1$–$C_4$ alkyl, $C_1$–$C_4$ haloalkyl, halogen or CN.

8. The method of claim 6 wherein one $R^7$ is a pyrazole, imidazole, triazole, pyridine or pyrimidine, each ring optionally substituted with $C_1$–$C_4$ alkyl, $C_1$–$C_4$ haloalkyl, halogen or CN.

9. The method of claim 5 wherein J is a pyrimidine optionally substituted with 1 to 3 $R^7$.

10. The method of claim 9 wherein one $R^7$ is a phenyl optionally substituted with $C_1$–$C_4$ alkyl, $C_1$–$C_4$ haloalkyl, halogen or CN.

11. The method of claim 9 wherein one $R^7$ is a pyrazole, imidazole, triazole, pyridine or pyrimidine, each ring optionally substituted with $C_1$–$C_4$ alkyl, $C_1$–$C_4$ haloalkyl, halogen or CN.

12. The method of claim 1 comprising a compound of Formula 1 which is 2-methyl-N-[2-methyl-6-[[(1-methylethyl)amino]carbonyl]phenyl]-6-(trifluoromethyl)-3-pyridinecarboxamide.

13. A compound of Formula 1, its N-oxides and agriculturally suitable salts

1

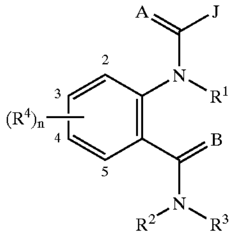

wherein

A and B are independently O or S;

J is a 6-membered heteroaromatic ring optionally substituted with 1 to 4 $R^7$;

n is 1 to 4;

$R^1$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or $R^1$ is $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl or C(=A)J;

$R^2$ is H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^3$ is H; $C_1$–$C_6$ alkyl, $C_2$–$C_6$ alkenyl, $C_2$–$C_6$ alkynyl, $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_2$–$C_6$ alkoxycarbonyl, $C_2$–$C_6$ alkylcarbonyl, $C_3$–$C_6$ trialkylsilyl, and a phenoxy ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl and $C_3$–$C_6$ trialkylsilyl; $C_1$–$C_4$ alkoxy; $C_1$–$C_4$ alkylamino; $C_2$–$C_8$ dialkylamino; $C_3$–$C_6$ cycloalkylamino; $C_2$–$C_6$ alkoxycarbonyl or $C_2$–$C_6$ alkylcarbonyl; or $R^2$ and $R^3$ can be taken together with the nitrogen to which they are attached to form a ring containing 2 to 6 atoms of carbon and optionally one additional atom of nitrogen, sulfur or oxygen, said ring may be optionally substituted with 1 to 4 substituents selected from the group consisting of $C_1$–$C_2$ alkyl, halogen, CN, $NO_2$ and $C_1$–$C_2$ alkoxy;

each $R^4$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, or $C_3$–$C_6$ trialkylsilyl; or each $R^4$ is independently phenyl, benzyl or phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

each $R^7$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, or $C_3$–$C_6$ trialkylsilyl; or each $R^7$ is independently a phenyl, benzyl, benzoyl, phenoxy or 5- or 6-membered heteroaromatic ring 8-, 9- or 10-membered fused heterobicyclic ring system, each ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl and $C_3$–$C_6$ trialkylsilyl;

provided that (i) at least one $R^4$ and at least one $R^7$ are other than H;

(ii) when J is an optionally substituted pyridine and $R^2$ is H, $R^3$ is other than H or $CH_3$;

(iii) when J is an optionally substituted pyridine, then $R^7$ cannot be $CONH_2$, $C_2$–$C_6$ alkylaminocarbonyl or $C_3$–$C_8$ dialkylaminocarbonyl; and (iv) when J is an optionally substituted pyrimidine, then $R^2$ and $R^3$ cannot both be hydrogen.

14. The compound of claim 13 wherein

J is a 6-membered heteroaromatic ring selected from the group consisting of J-4 and J-5

J-4

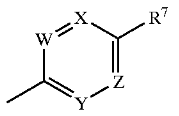

and

J-5

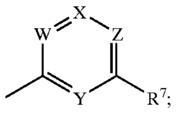

and

W, X, Y and Z are independently N or $CR^7$, provided that at least one of W, X, Y or Z is N.

15. The compound of claim 14 wherein

A and B are O;

n is 1 to 2;

$R^1$ is H, $C_1$–$C_4$ alkyl, $C_2$–$C_4$ alkenyl, $C_2$–$C_4$ alkynyl, $C_2$–$C_6$ alkylcarbonyl or $C_2$–$C_6$ alkoxycarbonyl;

$R^2$ is H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;

$R^3$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $C_1$–$C_2$ alkoxy, $C_1$–$C_2$ alkylthio, $C_1$–$C_2$ alkylsulfinyl and $C_1$–$C_2$ alkylsulfonyl;

one of the $R^4$ groups is attached to the phenyl ring at the 2-position, and said $R^4$ is $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl or $C_1$–$C_4$ haloalkylsulfonyl; and each $R^7$ is independently H, $C_1$–$C_4$ alkyl, $C_1$–$C_4$ haloalkyl, halogen, CN, $NO_2$, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl or $C_2$–$C_4$ alkoxycarbonyl; or a phenyl or a 5- or 6-membered heteroaromatic ring, each ring optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

16. The compound of claim 15 wherein J is selected from the group consisting of pyridine and pyrimidine, each optionally substituted with 1 to 3 $R^7$.

17. The compound of claim 16 wherein $R^1$ and $R^2$ are both H;

$R^3$ is $C_1$–$C_4$ alkyl optionally substituted with halogen, CN, $OCH_3$, $S(O)_pCH_3$;

each $R^4$ is independently H, $CH_3$, $CF_3$, $OCF_3$, $OCHF_2$, $S(O)_pCF_3$, $S(O)_pCHF_2$, CN or halogen;

each $R^7$ is independently H, halogen, $CH_3$, $CF_3$, $OCHF_2$, $S(O)_pCF_3$, $S(O)_pCHF_2$, $OCH_2CF_3$, $OCF_2CHF_2$, $S(O)_pCH_2CF_3$, $S(O)_pCF_2CHF_2$; or phenyl, pyrazole, imidazole, triazole, pyridine or pyrimidine, each ring optionally substituted with $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, halogen or CN; and p is 0, 1 or 2.

18. The compound of claim 17 wherein J is a pyridine optionally substituted with 1 to 3 $R^7$.

19. The compound of claim 18 wherein one $R^7$ is a phenyl optionally substituted with $C_1$–$C_4$ alkyl, $C_1$–$C_4$ haloalkyl, halogen or CN.

20. The compound of claim 18 wherein one $R^7$ is a pyrazole, imidazole, triazole, pyridine or pyrimidine, each ring optionally substituted with $C_1$–$C_4$ alkyl, $C_1$–$C_4$ haloalkyl, halogen or CN.

21. The compound of claim 17 wherein J is a pyrimidine optionally substituted with 1 to 3 $R^7$.

22. The compound of claim 21 wherein one $R^7$ is a phenyl optionally substituted with $C_1$–$C_4$ alkyl, $C_1$–$C_4$ haloalkyl, halogen or CN.

23. The compound of claim 21 wherein one $R^7$ is a pyrazole, imidazole, triazole, pyridine or pyrimidine, each ring optionally substituted with $C_1$–$C_4$ alkyl, $C_1$–$C_4$ haloalkyl, halogen or CN.

24. The compound of claim 13 which is 2-methyl-N-[2-methyl-6-[[(1-methylethyl)amino]carbonyl]phenyl]-6-(trifluoromethyl)-3-pyridinecarboxamide.

25. An arthropodicidal composition comprising an arthropodicidally effective amount of a compound of Formula 1 as described in claim 1 and at least one additional component selected from the group consisting of surfactants, solid diluents and liquid diluents.

* * * * *